US007582455B2

(12) United States Patent
Brazeau et al.

(10) Patent No.: US 7,582,455 B2
(45) Date of Patent: Sep. 1, 2009

(54) POLYPEPTIDES AND BIOSYNTHETIC PATHWAYS FOR THE PRODUCTION OF STEREOISOMERS OF MONATIN AND THEIR PRECURSORS

(75) Inventors: Brian J. Brazeau, Oskaloosa, IA (US); Ellen Burke, San Diego, CA (US); Mervyn DeSouza, Plymouth, MN (US); Steven J. Gort, Brooklyn Center, MN (US); Paula M. Hicks, Eden Prairie, MN (US); Sherry R. Kollmann, Maple Grove, MN (US); Peter Luginbuhl, San Diego, CA (US); Sara C. McFarlan, St. Paul, MN (US); Toby Richardson, San Diego, CA (US); Fernando A. Sanchez-Riera, Eden Prairie, MN (US); Christopher Solheid, Minneapolis, MN (US); David Weiner, Del Mar, CA (US); Lishan Zhao, Carlsbad, CA (US)

(73) Assignee: Cargill, Incorporated, Wayzata, MN (US)

( * ) Notice: Subject to any disclaimer, the term of this patent is extended or adjusted under 35 U.S.C. 154(b) by 191 days.

(21) Appl. No.: 11/411,229

(22) Filed: Apr. 26, 2006

(65) Prior Publication Data

US 2006/0252135 A1 Nov. 9, 2006

Related U.S. Application Data

(60) Provisional application No. 60/674,932, filed on Apr. 26, 2005.

(51) Int. Cl.
*C12P 17/10* (2006.01)

(52) U.S. Cl. ...................................................... 435/121

(58) Field of Classification Search .................. 435/121
See application file for complete search history.

(56) References Cited

U.S. PATENT DOCUMENTS 3,002,889 A 10/1961 Kinoshita et al.
3,128,237 A 4/1964 Motozaki et al.
3,399,114 A 8/1968 Ohsawa et al.
4,371,614 A 2/1983 Anderson et al.
4,975,298 A 12/1990 Van Wyk et al.
5,128,164 A 7/1992 Van Wyk et al.
5,128,482 A 7/1992 Olivier et al.
5,300,437 A 4/1994 Stirling et al.
5,360,724 A 11/1994 Matcham et al.
5,985,617 A 11/1999 Liao
5,994,559 A 11/1999 Abushanab et al.
6,207,427 B1 3/2001 Hashimoto et al.
6,264,999 B1 7/2001 Yatka et al.
6,489,100 B1 12/2002 Liao
7,064,219 B2 6/2006 Kawahara et al.
2003/0228403 A1 12/2003 Amino et al.
2005/0004394 A1 1/2005 Kawahara et al.
2005/0009153 A1 1/2005 Sugiyama et al.
2005/0020508 A1 1/2005 Amino et al.
2005/0095670 A1 5/2005 Ikeda et al.
2005/0106305 A1 5/2005 Abraham et al.
2005/0112260 A1 5/2005 Abraham et al.
2005/0118317 A1 6/2005 Amino et al.
2005/0137246 A1 6/2005 Amino et al.
2005/0153405 A1 7/2005 Sugiyama et al.
2005/0170041 A1 8/2005 Abraham et al.
2005/0221453 A1 10/2005 Takagi et al.
2005/0221455 A1 10/2005 McFarlan et al.
2005/0244937 A1 11/2005 Abraham et al.
2005/0244939 A1 11/2005 Sugiyama et al.
2005/0272939 A1 12/2005 Amino et al.
2005/0282260 A1 12/2005 Hicks et al.
2006/0003411 A1 1/2006 Sugiyama et al.
2006/0003426 A1 1/2006 Sugiyama et al.
2006/0009394 A1 1/2006 Sugiyama et al.
2006/0014819 A1 1/2006 Mori et al.
2006/0074249 A1 4/2006 Kawahara et al.
2006/0083695 A1 4/2006 Mori et al.
2006/0154343 A1 7/2006 Mori et al.
2006/0172396 A1 8/2006 Sugiyama et al.
2007/0099277 A1 5/2007 Anderson et al.
2007/0105938 A1 5/2007 Anderson et al.
2008/0020434 A1 1/2008 Brazeau et al.
2008/0020435 A1 1/2008 Burke et al.

FOREIGN PATENT DOCUMENTS

EP 0 438 314 4/1994

(Continued)

OTHER PUBLICATIONS

Ackerman (Louis Gabriel Jouza Ackerman), "Structure elucidation of and synthetic approaches to monatin, a metabolite from schlerochiton ilicifolius," PhD dissertation, University of Stellenbosch, Jul. 1990.

(Continued)

*Primary Examiner*—Tekchand Saidha

(57) ABSTRACT

Monatin and certain stereoisomers of monatin, such as R,R monatin and S,R monatin, as well as salts thereof, are produced using polypeptides and biosynthetic pathways. These polypeptides and biosynthetic pathways are also useful in the production of R-2-hydroxy-2-(indoly-3-ylmethyl)-4-keto glutaric acid, an intermediate that is formed in certain monatin synthesis pathways, including some biosynthetic pathways.

3 Claims, 12 Drawing Sheets

FOREIGN PATENT DOCUMENTS

| | | |
|---|---|---|
| EP | 1 045 029 | 10/2000 |
| EP | 1 445 323 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 350 791 | 9/2006 |
| EP | 1 719 758 | 11/2006 |
| JP | 2002-060382 | 8/2000 |
| JP | 2003-171365 | 11/2001 |
| JP | 2004-222657 | 1/2003 |
| JP | 2004-331644 | 11/2003 |
| JP | 2004-331650 | 3/2004 |
| WO | WO 87/01130 | 2/1987 |
| WO | WO 89/11212 | 11/1989 |
| WO | WO 99/55877 | 11/1999 |
| WO | WO 03/000913 | 1/2003 |
| WO | WO 03/045914 | 6/2003 |
| WO | WO 03/056026 | 7/2003 |
| WO | WO 03/059865 | 7/2003 |
| WO | WO 03/091396 | 11/2003 |
| WO | WO 2004/018672 | 3/2004 |
| WO | WO 2004/053125 | 6/2004 |
| WO | WO 2005/001105 | 1/2005 |
| WO | WO 2005/014839 | 2/2005 |
| WO | WO 2005/016022 | 2/2005 |
| WO | WO 2005/020721 | 3/2005 |
| WO | WO 2005/042756 | 5/2005 |
| WO | WO 2005/082850 | 9/2005 |
| WO | WO 2006/011613 | 2/2006 |
| WO | WO 2006/113897 | 10/2006 |
| WO | WO 2006/116487 | 11/2006 |
| WO | WO 2007/103389 | 9/2007 |

OTHER PUBLICATIONS

Ager et al., "Commercial, Synthetic Nonnutritive Sweeteners," *Agnew. Chem. Int. Ed.*, 1998, 37:1802-1817.

Ager et al., "Novel biosynthetic routes to non-proteinogenic amino acids as chiral pharmaceutical intermediates," *Journal of Molecular Catalysis B: Enzymatic*, 2001, 11:199-205.

Azuma et al., "Hyper-production of L-tryptophan via fermentation with crystallization," *Appl. Microbiol. Biotechnol.*, 1993, 39:471-476.

Bae et al., "Production of aromatic D-amino acids from α-keto acids and ammonia by coupling of four enzyme reactions," *Journal of Molecular Catalysis B: Enzymatic*, 1999, 6:241-247.

Bassoli, "'Chemistry-Nature,' still an open match for the discovery of new intensive sweeteners," *Agro Food industry hi-tech*, 2004, 15(4):27-29.

Bassoli et al., "Design and synthesis of new monatin derivatives," Abstracts, *13th International Symposium on Olfaction and Taste (ISOTXIII), 14th. European Chemoreception Research Organization Congress (ECRO XIV)* Jul. 20-24, 2000, p. 162.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of Neisseria gonorrhoeae: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Bongaerts et al., "Metabolic Engineering for Microbial Production of Aromatic Amino Acids and Derived Compounds," *Metabolic Engineering*, 2001, 3:289-300.

Brandl and Lindow, "Cloning and characterization of a locus encoding an indolepyruvate decarboxylase involved in indole-3-acetic acid synthesis in Erwinia herbicola," *Appl. Environ. Microbiol.*, 1996, 62:4121-4128.

Camargo (Ediclea Cristina Fregonese Camargo), "Preparation of amino acids not proteinogênicos, structurally related to adoçante natural Monatina" [tranlated by Google], Jan. 2003, Universidade Estadual de Campinas Instituto de Quimica, Dissertation of Masters.

DeLuna et al., "NADP-Glutamate Dehydrogenase Isoenzymes of Saccharomyces cerevisiae: Purification, Kinetic Properties, and Physiological Roles," *J. Biol. Chem.*, 2001, 276(47):43775-43783.

Eggeling and Sahm, "Amino-acid production: principles of metabolic engineering," *Metabolic Engineering*, 1999, Lee & Papoutsakis (eds.), Marcel Dekker, Inc., New York.

Eikmanns et al., "Cloning, sequence analysis, and inactivation of the Corynebacterium glutamicum icd gene encoding isocitrate dehydrogenase and biochemical characterization of the enzyme," *J. Bacteriol.*, 1995, 177:774-782.

El-Abyad and Farid, "Optimization of culture conditions for indole-3-pyruvic acid production by *Streptomyces griseoflavus*," *Can. J. Microbiol.*, 1994, 40:754-760.

Flores et al., "Pathway engineering for the production of aromatic compounds in *Escherichia coli*," *Nat. Biotechnol.*, 1996, 14:620-623.

Floyd et al., "A Simple Strategy for obtaining both Enantiomers from an Aldolase Reaction: Preparation of L- and D-4-Hydroxy-2-ketoglutarate," *J. Chem. Soc. Perkin Trans. 1*, 1992, 1085-1086.

Fotheringham et al., "The cloning and sequence analysis of the aspC and tyrB genes from *Escherichia coli* K12," *Biochem. J.*, 1986, 234:593-604.

Furuya et al., "A Novel Enzyme, L-Tryptophan Oxidase, from a Basidiomycete, Coprinus sp. SF-1: Purification and Characterization," *Biosci. Biotechnol. Biochem.*, 2000, 64(7):1486-1493.

Galkin et al., "Synthesis of optically active amino acids from alpha-keto acids with *Escherichia coli* cells expressing heterologous genes," *Appl. Environ. Microbiol.*, 1997, 63(12):4651-4656.

Gosset et al., "A direct comparison of approaches for increasing carbon flow to aromatic biosynthesis in *Escherichia coli*," *Journal of Industrial Microbiology*, 1996, 17:47-52.

Hayashi et al., "*Escherichia coli* Aromatic Amino Acid Aminotransferase: Characterization and Comparison with Aspartate Aminotransferase," *Biochemistry*, 1993, 32:12229-12239.

Holzapfel et al., "A simple cycloaddition approach to a racemase of the natural sweetener monatin," *Synthetic Communications*, 1994, 24(22):3197-3211.

Holzapfel et al., "The synthesis of a gamma-keto-alpha-amino acid, a key intermediate in the synthesis of monatin, a new natural sweetener," *Synthetic Communications*, 1993, 23(18):2511-2526.

Izumi, "Introduction," *Synthetic Production and Utilization of Amino Acids*, 1974, Kankeko et al. (eds.), Halstad Press, Chapter 1, pp. 3-16.

Jetten et al., "Metabolic Engineering of Corynebacterium glutamicum," *Ann. N.Y. Acad. Sci.*, 1994, 721:12-29.

Jetten et al., "Recent advances in the physiology and genetics of amino acid-producing bacteria," *Critical Reviews in Biotechnology*, 1995, 15:73-103.

Juhl et al., "Catalytic asymmetric homo-aldol reaction of pyruvate—a chiral Lewis acid catalyst that mimics aldolase enzymes," *Chem. Commun.*, 2000, 2211-2212.

Katsumata et al., "Hyperproduction of Tryptophan in Corynebacterium glutamicum by Pathway Engineering," *Bio/Technology*, 1993, 11:921-925.

Kawasaki et al., "L-Tryptophan Production by Pyruvic Acid-Producing *Escherichia coli* Strain Carrying the Enterobacter aerogenes Tryptophanase Gene," *Journal of Fermentation and Bioengineering*, 1996, 82(6):604-606.

Kino et al., "Synthesis of DL-tryptophan by modified broad specificity amino acid racemase from Pseudomonas putida IFO 12996," *Applied Microbiology and Biotechnology*, 2007, 73(6):1299-1305.

Koeller et al., "Enzymes for chemical synthesis," *Nature*, 2001, 409:232-240.

Koffas et al., "Engineering metabolism and product formation in Corynebacterium glutamicum by coordinated gene overexpression," *Metabolic Engineering*, 2003, 5:32-41.

Koga et al., "Involvement of L-tryptophan aminotransferase in indole-3-acetic acid biosynthesis in Enterobacter cloacae," *Biochim. Biophys. Acta*, 1994, 1209:241-247.
Kogiso et al., "Control of Lactamization during the Synthesis of the Monatin Analogue," *Peptide Science*, 2003, pp. 195-198.
Labrou et al., "Oxaloacetate Decarboxylase from Pseudomonas stutzeri: Purification and Characterization," *Archives of Biochemistry and Biophysics*, 1999, 365(1):17-24.
Li et al., "Nonproteinogenic alpha-Amino Acid Preparation Using Equilibrium Shifted Transamination," *Organic Process Research & Development*, 2002, 6:533-538.
Liao et al., "Pathway Analysis, Engineering, and Physiological Considerations for Redirecting Central Metabolism," *Biotechnology and Bioengineering*, 1996, 52:129-140.
Nakamura et al., "Total Synthesis of Monatin," *Organic Letters*, 2000, 2(19):2967-2970.
Nakamura et al., "Total Synthesis of Monatin and the Taste Experience," *Peptide Science*, 2003, pp. 61-64.
Nishihara and Dekker, "A stereospecific 2-keto-4-hydroxyglutarate aldolase from *Escherichia coli*," *Biochim. Biophys. Acta*, 1969, 185(1):255-257.
Oliveira et al., "Highly diastereoselective alkylation of a pyroglutamate derivative with an electrophile obtained from indole. Synthesis of a potential intermediate for the preparation of the natural sweetener (−)-monatin," *Synthetic Communications*, 2000, 30(12):2143-2159.
Oliveira et al., "Diastereoselective formation of a quaternary center in a pyroglutamate derivative. Formal synthesis of Monatin," *Tetrahedron Letters*, 2001,42:6793-6796.
Passerat et al., "Large-scale enzymatic synthesis of diastereoisomeric y-hydroxy 1-glutamic acids," *Tetrahedron Letters*, 1987, 28(12):1277-1280.
Patil et al., "Cloning, nucleotide sequence, overexpression, and inactivation of the *Escherichia coli* 2-keto-4-hydroxyglutarate aldolase gene," *J. Bacteriol.*, 1992, 174(1):102-107.
Patnaik et al., "Engineering of *Escherichia coli* Central Metabolism for Aromatic Metabolite Production with Near Theoretical Yield," *Applied and Environmental Microbiology*, 1994, 60(11):3903-3908.
Rijnen et al., "Genetic Characterization of the Major Lactococcal Aromatic Aminotransferase and Its Involvement in Conversion of Amino Acis to Aroma Compounds," *Applied Environmental Biology*, 1999, 65(11):4873-4880.
Ro et al., "Site-directed mutagenesis of the amino acid residues in beta-strand III [Va130-Va136] of D-amino acid aminotransferase of Bacillus sp. YM-1," *FEBS Lett.*, 1996, 398:141-145.
Roise et al., "Inactivation of the Pseudomonas striata broad specificity amino acid racemase by D and L isomers of beta-substituted alanines: kinetics, stoichiometry, active site peptide, and mechanistic studies," *Biochemistry*, 1984, 23:5195-5201.
Shelton et al., "2-Keto-3-deoxy-6-phosphogluconate Aldolases as Catalysts for Stereocontrolled Carbon—Carbon Bond Formation," *J. Am. Chem. Soc.*, 1996, 118(9):2117-2125.
Sugio et al, "Crystal structure of a D-amino acid aminotransferase: how the protein controls stereoselectivity," *Biochemistry*, 1995, 34:9661-9669.
Tamura et al., "Highly stereoselective synthesis of (−)-monatin, a high-intensity sweetener, using chelation-controlled nitrone cycloaddition," *Chemical Communications*, 2003, 21:2678-2679.
Tamura et al., "Stereoselective Synthesis of 4-Hydroxy 4-Substituted Glutamic Acids," *J. Org. Chem.*, 2005, 70(12):4569-77.
Tanizawa et al., "Thermostable D-amino acid aminotransferase from a thermophilic Bacillus species. Purification, characterization, and active site sequence determination," *J. Biol. Chem.*, 1989, 264:2445-2449.
Vleggaar et al., "Structure elucidation of monatin, a high-intensity sweetener isolated from the plant Schlerochiton ilicifolius," *J. Chem. Soc. Perkin Transactions 1: Organic and Bio-Organic Chemistry*, 1992, 22:3095-3098.
Wolf et al., "A Biocatalytic Route to Enantiomerically Pure Unsaturated -H—Amino Acids," *Adv. Synth. & Catalysis*, 2001, 343:662-674.
Yonaha et al., "D-Amino Acid Aminotransferase of *Bacillus sphaericus*," *J. Biol. Chem.*, 1975, 250(17):6983-6989.
Yoshimura et al., "Unique stereospecificity of D-amino acid aminotransferase and branched-chain L-amino acid aminotransferase for C-4' hydrogen transfer of the coenzyme," *J. Am. Chem. Soc.*, 1993, 115:3897-3900.
Yoshimura and Esaki, "Amino Acid Racemases: Functions and Mechanisms," *J. Biosci. Bioeng.*, 2003, 96:103-109.
Zeman et al., "Enzyme Synthesis of L-Tryptophan," *Folia Microbiol.*, 1990, 35:200-204.
Buldain et al., "Carbon-13 Nuclear Magnetic Resnoance Spectra of the Hydrate, Keto, and Enol Forms of Oxalacetic Acid," *Magnetic Resonance Chemistry*, 1985, 23(6):478-481.
Guo et al., "Protein tolerance to random amino acid charge," *Proc. Natl. Acad. Sci. USA*, 2004, 101(25):9205-9210.
Seffernick et al., "Melamine deaminase and atrazine chlorohydrolase: 98 percent identical but functionally different," *J. Bacteriology*, 2001, 183(8):2405-2410.
Seo Jeong-Sun et al., "The genome sequence of the ethanologenic bacterium Zymomonas mobilis ZM4," *Nature Biotechnology*, 2005, 23(1):63-68.
Whisstock et al., "Prediction of protein function from protein sequence," *Q. Rev. Biophysis*, 2003, 36(3):307-340.
Witkowski et al., "Conversion of b-ketoacyl synthase to a malonyl decarboxylase by replacement of the active-site cysteine with glutamine," *Biochemistry*, 1999, 38:11643-11650.

FIG. 9A

```
                                                    F1       F2
                                                    ------→-----→
BsphDATgene        1   mays---lwndqive--egsitispedrgyqfgdgiyevikvynghmfta
B. halodurans      1   mdyc---lyqdqlvp--reqlkidpedrgyhfgdgiyevvhvyhgkafal
GsteDATgene        1   mgyt---lwndqivk--deevkidkedrgyqfgdgvyevvkvyngemftv
B.cereus 145       1   layekfvlwndevidttkqqtyieleergsqfgdgvyevirlykgnfhll
BsubDAT            1   -mkv---lvngrlig--rseasidledrgyqfgdgiyevirvykgvlfgl
B.lichenifomis     1   -mkv---lfngrlme--rsecavdiedrgyqfgdgvyeviriyngilftl
BsphDATgene      136   qehidrfyasaekirlvipytkdvlhkllhdlieknnlnt-ghvyfqitr
B. halodurans    136   sdhltrfkesaekldlpmlystdklgelvqqlieknkleh-gmvyfqmtr
GsteDATgene      136   nehidrlyasaekiritipytkdkfhqllhelveknelnt-ghiyfqvtr
B.cereus 145     151   dphitrlyrsmeevelslpfskaelitllykliernhfhedgtiylqvsr
BsubDAT           45   rehaerffrsaaeigislpfsiedlewdlqklvqenavse-gavyiqttr
B.lichenifomis   133   dehiarlyksaaeigidlsfseaelksqlkelvdinqrrd-gglylqvtr
                                                                        ←
BsphDATgene      283   gttsrnhifpdasvpavl--tgnvktgersienfekgvkatlvedvrwlr
B. halodurans    283   gisprnhlytrnetp-vl--tgfskp---lpdekresvrlyltddirwlr
GsteDATgene      283   gtsprahqfpentvkpvi--igytkenprplenlekgvkatfvedirwlr
B.cereus 145     301   gvqarthvf-sydtppti--yayitkkerpalwieygiraisepdtrwlr
BsubDAT           94   gvaprkhqy-eaglepqt--taytftvkkpeqeqaygvaaitdedlrwlr
B.lichenifomis   280   gkaprkhqygagltpqvtaytfpiqkpekeqqn---gvsaitaddmrwlr

                        R1
                       -----   R2
                        ←------                                         ←
BsphDATgene      427   cdikslnllgavlakqeasekgcyeailhrgdiitecssanvygikdgkl
B. halodurans    415   cdiktinllgnvlakreatdhqcdeallhrdgtvtegsssnvfliknetl
GsteDATgene      427   cdikslnllgavlakqeahekgcyeailhrnntvtegsssnvfgikdgil
B.cereus 145     442   cdikslnllpnvlaatkaerkgckeallvrngivtegshsnffliknqtl
BsubDAT          141   cdikslnllynvmtkqrayeagafeaillrdgvvtegtssnvyavingtv
B.lichenifomis   421   cdikslnllynvmikqkaqeasafeailirdglvtegtssnvyvakqnvi
```

FIG. 9B

```
                    R3
                    ------
BsphDATgene     577 ythpannyilngitrqvilkcaaeinlpvieepmtkgdlltmdeiivssv
B. halodurans   565 ythpatnlilngitrqitirlakakgytvveepfpkevikdadeafitst
GsteDATgene     577 ythpannmilkgitrdvviacaneinmpvkeipftthealkmdelfvtst
B.cereus 145    592 ythpanhlilngiirqyvlslantlhipvqeelfsvrdvyqadecfftgt
BsubDAT         191 rthpanrlilngitrmnilgliekngikldetpvseeelkqaeeifisst
B.lichenifomis  571 ythpvttlilngitrmkvlqlceenglnyeekavtkdellnadevfitst

BsphDATgene     727 ssevtpvidvdgqqigagvpgewtrklqkafeaklp--isina*----
B. halodurans   715 iheitpvtevigdetahfpvgpvtkmlqqafaeeia--khsqtamkq*
GsteDATgene     727 tseitpvieidgklirdgkvgewtrklqkqfetkip--kplhi*----
B.cereus 145    742 tieilpmthldgtaiqdgqvgaitkklqksfn-kil--lqsnmsss*-
BsubDAT         241 taeiipvvtldgqsigsgkpgpvtkqlqaafqesiqqaasis------
B.lichenifomis  721 taevipvtsidgqtigsgapgpltknvqtalqnsi---lsetaktv*-
```

FIG. 10A

**Alignment of *B. sphaericus* with ATCC 4978 (*B. rotans*) sequence (72% homology)**

```
BsphDATgene      1 mayslwndqiveegsitispedrgyqfgdgiyevikvynghmftaqehid
ATCC4978DAAT     1 msyslwndqivndeevvvdkedrgyqfgdgvyevvkvyngelftaeehvd

BsphDATgene    151 rfyasaekirlvipytkdvlhkllhdlieknnlntghvyfqitrgttsrn
ATCC4978DAAT   151 rfyasaekirvtipytkdklhqllhqlvemnkvqtghiyfqitrgagprn

BsphDATgene    301 hifpdasvpavltgnvktgersienfekgvkatlvedvrwlrcdikslnl
ATCC4978DAAT   301 hifpgdevkpvltgntkenprpvanfekgvkatfvedirwlrcdikslnl

BsphDATgene    451 lgavlakqeasekgcyeailhrgdiitecssanvygikdgklythpanny
ATCC4978DAAT   451 lgavlakqeahekgcyeavlhrdeivtegsssniygikdgvlythpannf

BsphDATgene    601 ilngitrqvilkcaaeinlpvieepmtkgdlltmdeiivssvssevtpvi
ATCC4978DAAT   601 ilngitrqviikcaaeiglpvkeeamtktqllamdevivssttsevtpii

BsphDATgene    751 dvdgqqigagvpgewtrklqkafeaklpisina*
ATCC4978DAAT   751 didgtvigagkpgdwtrklqaqfdtkipkgira*
```

FIG. 10B

**Alignment of *B. sphaericus* with ATCC 7063 (*B. serositidis*) sequence (67% homology)**

```
BsphDAATpep      1 mayslwndqiveegsitispedrgyqfgdgiyevikvynghmftaqehid
ATCC7063DAAT     1 msytlwndkivddnqvfinkedrgyqfgdgvyevikvydgemftatehid

BsphDAATpep     51 rfyasaekirlvipytkdvlhkllhdlieknnlntghvyfqitrgttsrn
ATCC7063DAAT   151 rfyasaekikltvpytkhklhqllhelveanelktgnlyfqitrgasprn

BsphDAATpep    101 hifpdasvpavltgnvktgersienfekgvkatlvedvrwlrcdikslnl
ATCC7063DAAT   301 hlfpgddvlpvltgnvkeaprsienaqkgvkatfaedirwlrcdikslnl

BsphDAATpep    151 lgavlakqeasekgcyeailhrgdiitecssanvygikdgklythpanny
ATCC7063DAAT   451 lgavlakqeahekgcyeailhrgetitegsstnvfgikngvlythpadnf

BsphDAATpep    201 ilngitrqvilkcaaeinlpvieepmtkgdlltmdeiivssvssevtpvi
ATCC7063DAAT   601 ilsgitrgvvlacaneiglpvkqeaftkdkalqmdemfvssttseitpvi

BsphDAATpep    251 dvdgqqigagvpgewtrklqkafeaklpis--ina-----
ATCC7063DAAT   751 dldgvainggeigewtrklqkqfatklpgspaynlteyk*
```

POLYPEPTIDES AND BIOSYNTHETIC PATHWAYS FOR THE PRODUCTION OF STEREOISOMERS OF MONATIN AND THEIR PRECURSORS

BACKGROUND OF THE INVENTION

1. Field of the Invention

This disclosure provides polypeptides and biosynthetic pathways that are useful in the production of D-tryptophan, indole-3-pyruvate, R-2-hydroxy-2-(indol-3ylmethyl)-4-keto glutaric acid (R-MP) and certain stereoisomers of monatin, such as R,R and S,R monatin, and salts thereof.

2. Background Art

Monatin is a high-intensity sweetener having the chemical formula:

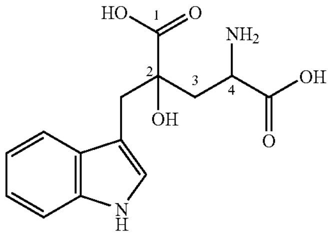

Monatin includes two chiral centers leading to four potential stereoisomeric configurations. The R,R configuration (the "R,R stereoisomer" or "R,R monatin"); the S,S configuration (the "S,S stereoisomer" or "S,S monatin"); the R,S configuration (the "R,S stereoisomer" or "R,S monatin"); and the S,R configuration (the "S,R stereoisomer" or "S,R monatin"). As used herein, unless stated otherwise, the term "monatin" is used to refer to compositions including all four stereoisomers of monatin, compositions including any combination of monatin stereoisomers, (e.g., a composition including only the R,R and S,S, stereoisomers of monatin), as well as a single isomeric form.

For purposes of this disclosure, the monatin carbon backbone will be numbered as illustrated above, with the carbon directly covalently attached to the alcohol group being identified as the 2-position carbon and the carbon directly covalently attached to the amino group being identified as the 4-position carbon. Consequently, references herein to R,R monatin, S,S monatin, R,S monatin, and S,R monatin mean: 2R,4R monatin, 2S,4S monatin, 2R,4S monatin, and 2S,4R monatin, respectively, unless otherwise indicated.

It should be noted that in the literature, the monatin carbon backbone has also been numbered using an alternative convention, with the carbon attached to the alcohol group being the 4-position carbon, and the carbon attached to the amino group being the 2-position carbon. Accordingly, for example, references to 2S,4R monatin in this disclosure would be the same as references to 2R,4S monatin in literature using the alternative numbering convention.

Furthermore, because of various naming conventions, monatin is known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxybut-4-yl)indole.

Certain isomeric forms of monatin can be found in the bark of roots of the *Schlerochiton ilicifolius* plant located in the Transvaal Region of South Africa. U.S. patent application Ser. No. 10/422,366 ("the '366 application"), Ser. No. 10/979,821 ("the '821 application"), and Ser. No. 11/114,922 ("the '922 application), which are hereby incorporated by reference, discloses, inter alia, polypeptides, pathways, and microorganisms for in vitro and in vivo production of monatin.

BRIEF SUMMARY OF THE INVENTION

This disclosure provides, among other things, polypeptides and biosynthetic pathways that are useful in the production of D-tryptophan, indole-3-pyruvate, R-2-hydroxy 2-(indol-3ylmethyl)-4-keto glutaric acid (also referred to as R-alpha keto acid monatin, R-monatin precursor, R-MP, and the alpha keto form of monatin) and certain stereoisomers of monatin, such as R,R and S,R monatin, and salts thereof. The methods include the use of one or more polypeptides, and in particular, enzymes, such as racemases (e.g., glutamate racemases, aspartate racemases and alanine racemases), broad specificity D-aminotransferases (also called D-alanine aminotransferases, D-amino acid aminotransferases and D-aspartate aminotransferases), L-aminotransferases (including L-tryptophan-aminotransferases, L-aromatic aminotransferases, L-aspartate aminotransferases, and L-alanine-aminotransferases), aldolases (e.g., R-specific aldolases), D-phenylglycine aminotransferases (also called D-4-hydroxyphenylglycine aminotransferase), D-methionine aminotransferases, glutamate decarboxylases, aspartate decarboxylases and aspartate-4-decarboxylases to produce monatin compositions enriched with the 4-R isomer forms and/or to produce R,R monatin without having to use stoichiometric amounts of D-amino acid substrate as the amino acid donor for MP amination.

In an effort to be concise, where ever intermediates/products are identified in the specification and claims (e.g. monatin or monatin precursor) as being formed, the term "and/or salts thereof" should be understood to be included where applicable. In other words, for example, the phrase "indole-3-pyruvate is converted to MP" should be understood to read "indole-3-pyruvic acid is converted to MP and and/or salts thereof." A person of ordinary skill, in fact, would appreciate that under reaction conditions shown the salts of the intermediates/products are in fact present or also present.

According to some embodiments, the method produces a monatin composition wherein the monatin component of the composition includes only the R,R and S,R form of monatin. The term "only," when used to indicate that only certain isomers are formed, unless otherwise stated means that the pathway would produce only the identified isomers if racemization did not occur. Consequently, the term "only" should not be taken to mean absence of other isomers, but rather a person of ordinary skill would understand that other isomeric forms may be present in a relatively small amount due to racemization which may occur. According to some embodiments, the method produces a monatin composition wherein the monatin component of the composition includes only the R,R form of monatin (thus meaning except to the extent racemization occurs resulting in other isomeric forms).

As used herein, the phrase "monatin composition" means a composition including one or more isomers of monatin; the term can also mean a composition including only a single isomeric form of monatin and nothing else, depending on the context.

In some embodiments, in accordance with the present invention, a process for producing a monatin composition is provided, which includes producing indole-3-pyruvate from L-tryptophan, producing 2-hydroxy 2-(indol-3ylmethyl)-4- keto glutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan as a substrate than for R-MP, R,R monatin, or both. According to certain embodiments, the reaction of indole-3-pyruvate is facilitated by an enzyme having R-specific aldolase activity and consequently produces R-MP. According to certain embodiments, a racemase enzyme is provided that can facilitate epimerization of the amino acid that is formed as a byproduct of the L-tryptophan transamination reaction (or that is formed from another amino acid that is a byproduct of the tryptophan reaction) from one isomeric form to another isomeric form.

In some embodiments according to the invention, a process for producing a monatin composition is provided, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan as a substrate than for R-MP, R,R monatin, or both, and the reaction of MP to form monatin is facilitated by an enzyme, which is stereoselective for R-MP.

It should be noted that, where references are made to a series of reactions such as in the preceding paragraphs, the invention does not require each step to be explicitly performed; it is sufficient that the steps may be implicitly performed. In other words, for example, the process for producing a monatin composition, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP, wherein each reaction is facilitated by an appropriate enzyme, can be performed by combining L-tryptophan with the enzymes and setting conditions so that the enumerated reactions could occur. In such an instance L-tryptophan could react to produce indole-3-pyruvate, the indole-3-pyruvate produced from the L-tryptophan reaction could react to form MP, and the MP produced from the indole-3-pyruvate reaction could react to form monatin. The process could also be performed, by way of example, by providing a compound that can produce L-tryptophan, under conditions suitable for L-tryptophan production to occur and combining that compound with enzymes capable of facilitating the series of reactions set forth under conditions which would be suitable for those reactions to occur. As yet another example, the process could be performed by providing a microorganism genetically engineered to produce monatin according to the described pathway, and providing appropriate conditions for the fermentation process to occur. For example, a microorganism, which naturally produces large amounts of L-tryptophan (or D-tryptophan) could be genetically engineered to produce or over-produce one or more of the enzymes used to facilitate reactions in the pathway to monatin, and appropriate conditions could be provided so that the microorganism would thereby produce monatin.

In other embodiments according to the invention, a process for producing monatin is provided, in which an α-keto acid substrate forms an L-amino acid when L-tryptophan is converted to indole-3-pyruvate, indole-3-pyruvate reacts to form MP (which can include both R-MP and S-MP though preferably includes only or predominately R-MP), and the L-amino acid reacts to regenerate (also referred to as "recycle") the α-keto acid substrate when R-MP is converted to R,R monatin. The reaction of R-MP to form R,R monatin is facilitated by a stereoinverting aminotransferase such as D-methionine aminotransferase (EC 2.6.1.41) or an enzyme derived from a D-phenylglycine aminotransferase.

In other embodiments according to the invention, a process for producing a monatin composition is provided, which includes producing D-tryptophan from L-tryptophan, producing indole-3-pyruvate from D-tryptophan, producing R-MP from indole-3-pyruvate, and producing R,R monatin from R-MP. The production of the D-tryptophan from the L-tryptophan is facilitated by a tryptophan racemase and functional equivalents thereof. In certain further embodiments, the reactions of D-tryptophan to form indole-3-pyruvate and of MP to form monatin are facilitated by the same enzyme. In yet other further embodiments, the reaction of indole-3-pyruvate is facilitated by an enzyme having R-specific aldolase activity and consequently R-MP is formed, and the reactions of D-tryptophan to form indole-3-pyruvate and of R-MP to form R,R monatin are facilitated by the same enzyme.

In other embodiments according to the invention, a method for producing R,R-monatin, or a salt thereof, comprising, or consisting essentially of, (a) producing D-tryptophan from L-tryptophan utilizing a tryptophan racemase (the racemase should have limited or no activity on monatin), (b) producing indole-3-pyruvate from D-tryptophan, (c) producing R-monatin precursor from indole-3-pyruvate, and (d) producing R,R-monatin from R-monatin precursor is disclosed herein.

While multiple embodiments are disclosed, still other embodiments of the present invention may become apparent to those skilled in the art from the specification. As should be realized from the description herein, the invention is capable of modifications in various aspects, all without departing from the spirit and scope of the present invention. Accordingly, the drawings and detailed description are to be regarded as illustrative in nature and not restrictive.

BRIEF DESCRIPTION OF THE FIGURES

FIGS. 9(A and B) show the amino acid sequence alignment of various published *Bacillus* D-amino acid aminotransferases ("DAATs") from *B. sphaericus* (BsphDATgene SEQ ID NO:103), *B. halodurans* (SEQ ID NO:104), *G. stearothermophilus* (GstepATgene SEQ ID NO:105), *B. cereus* (SEQ ID NO:106), *B. subtilis* (BsubDAE SEQ ID NO:107), and *B. lichenifomis* (SEQ ID NO: 108). Underlined amino acids indicate the regions of homology. Five PCR primers were designed based on the conserved regions. The PCR primers are as follows: 5' GAAGACCGTGGTTATCAATTT 3' (SEQ ID NO:65) (forward primer, F1 as indicated in FIG. 9A), 5' GATGGTATTTACGAAGTAATC 3' (SEQ ID NO:66) (forward primer, F2 as indicated in FIG. 9A), 5' AGATTTAATATCACAACGTAAC 3' (SEQ ID NO:67) (reverse primer, R1 as indicated in FIG. 9A), 5' GCCAAGTAAAATTTAAGATTTA 3' (SEQ ID NO:68) (reverse primer, R2 as indicated in FIG. 9A), 5' ATTTGCTGGGTGCGTATAAAG 3' (SEQ ID NO:69) (reverse primer, R3 as indicated in FIG. 9B).

FIGS. 10(A and B) show the amino acid sequence alignment of the two novel DAATs from ATCC 4978 (SEQ ID NO:86) and ATCC 7063 (SEQ ID NO:87) with the *B. sphaericus* DAAT (cloned in Example 18 SEQ ID NO:103). Non-homologous amino acids are underlined.

DETAILED DESCRIPTION OF THE INVENTION

Abbreviations and Terms

Figure 1:
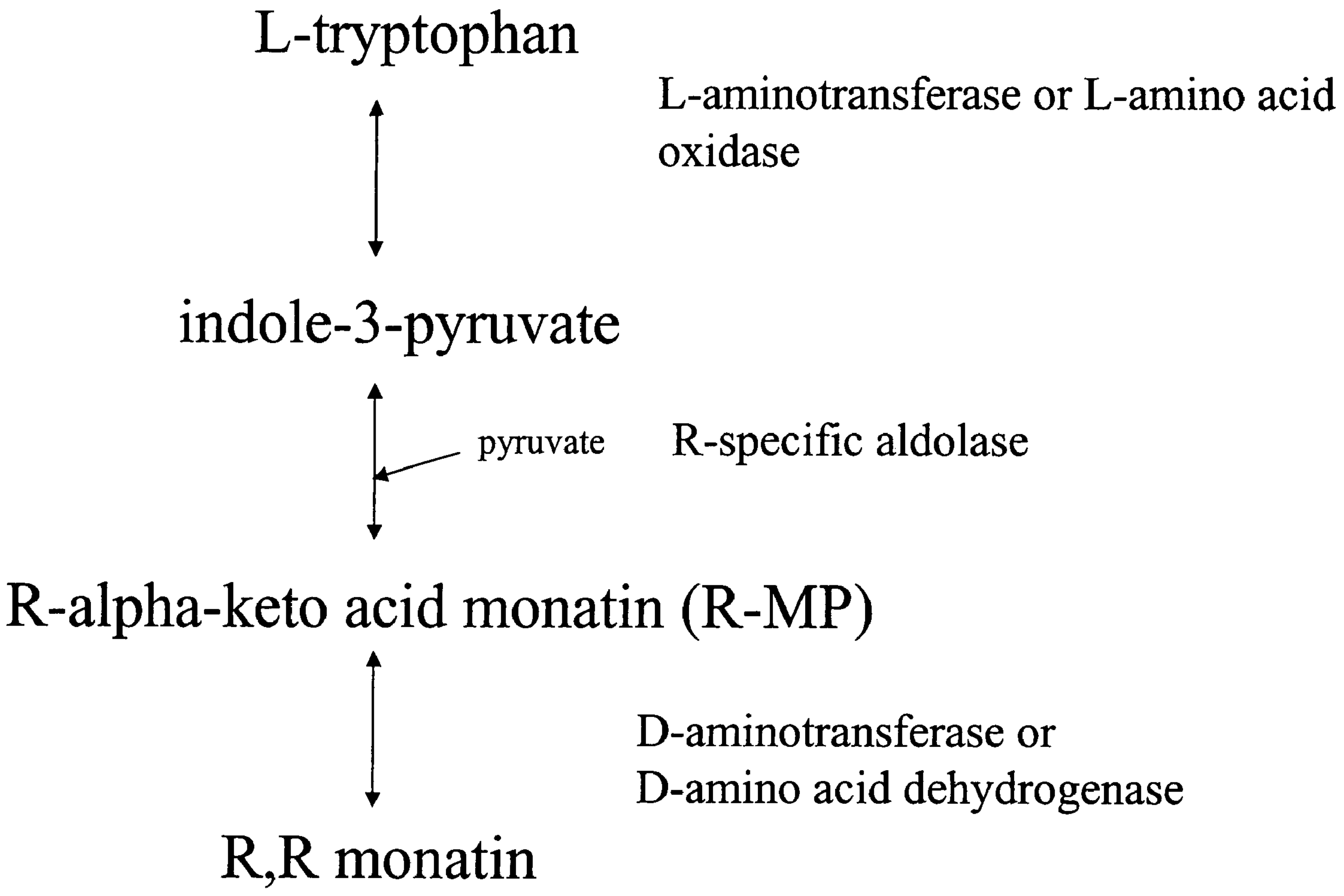
FIG. 1 is a flow chart that shows an example of an enzymatic process for producing R,R monatin from L-tryptophan in accordance with the invention. In this example, the process includes using an L-aminotransferase (examples of which include an L-tryptophan aminotransferase, an L-aromatic aminotransferase, an L-aspartate aminotransferase, and an L-alanine aminotransferase) in the reaction of L-tryptophan that has greater specificity and/or selectivity for L-tryptophan as a substrate than for R-MP and/or an L-amino acid oxidase with limited activity and/or specificity for R,R monatin as a substrate.

The following explanations of terms and methods are provided to better describe the present disclosure and to guide those of ordinary skill in the art in the practice of the present disclosure. As used herein, "including" means "comprising." Wherever the term "includes" is used, it should be understood that "includes but is not limited to" is meant, whether or not "is limited to" is explicitly stated. In addition, the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth. The term "about" encompasses the range of experimental error that occurs in any measurement. Unless otherwise stated, all measurement numbers are presumed to have the word "about" in front of them even if the word "about" is not expressly used.

Conservative substitution: a substitution of one amino acid for another amino acid in a polypeptide, which substitution has little to no impact on the activity of the polypeptide. The substitution is considered conservative independent of whether the exchanged amino acids appear structurally or functionally similar. For example, ideally, a tryptophan aminotransferase polypeptide including one or more conservative substitutions retains tryptophan aminotransferase activity. A polypeptide can be produced to contain one or more conservative substitutions by manipulating the nucleotide sequence that encodes that polypeptide using, for example, standard procedures such as site-directed mutagenesis or PCR or other methods known to those in the art.

Non-limiting examples of amino acids that may be substituted for an original amino acid in a protein and that may be regarded as conservative substitutions if there is little to no impact on the activity of the polypeptide include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

Further information about conservative substitutions can be found in, among other locations, Ben-Bassat et al., *J. Bacteriol.* 169:751-757, (1987); O'Regan et al., *Gene* 77:237-251, (1989); Sahin-Toth et al., *Protein Sci.* 3:240-247, (1994); Hochuli et al., *Bio/Technology* 6:1321-1325, (1988); WO 00/67796 (Curd et al.) and in standard textbooks of genetics and molecular biology.

Derived: For purposes of the specification and claims, a substance is "derived" from organism or source if any one or more of the following are true: 1) the substance is present in the organism/source; 2) the substance is removed from the native host; or, 3) the substance is removed from the native host and is evolved, for example, by mutagenesis.

Isolated: The term "isolated" as used herein refers to any substance removed from its native host; the substance need not exhibit any specific degree of purity. For example "isolated nucleic acid" refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid because non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

A nucleic acid existing among hundreds to millions of other nucleic acid molecules within, for example, cDNA or genomic libraries, or gel slices containing a genomic DNA restriction digest is not to be considered an isolated nucleic acid.

Purified: The term "purified" as used herein indicates that contaminants have been removed from the sample of interest. The term "purified" does not require absolute purity, but rather is intended as a relative term, unless otherwise indicated by the context. Thus, for example, a purified polypeptide or nucleic acid preparation can be one in which the subject polypeptide or nucleic acid is at a higher concentration than the polypeptide or nucleic acid would be in its natural environment within an organism or at a higher concentration than in the environment from which it was removed.

Stereoinverting aminotransferase: A "stereoinverting aminotransferase" is a polypeptide capable of preferentially or selectively producing a chiral amino acid product (such as monatin) while using an opposite chirality substrate as the amino donor. For example, a stereoinverting aminotransferase may be a D-phenylglycine aminotransferase (also called D-4-hydroxyphenylglycine aminotransferase) that preferentially or selectively uses L-glutamate as a substrate to produce R,R monatin. Non-limiting examples of stereoinverting aminotransferases include D-methionine aminotransferase (EC 2.6.1.41) and enzymes having D-phenylglycine aminotransferase activity or D-4-hydroxyphenylglycine aminotransferase activity.

Complementing Gene: A "complementing gene" is a gene that, when expressed, nullifies a mutation in an organism. For example, if an organism has a null mutation in one of the genes required for synthesis of tryptophan by the cell, a complementing gene could be one that, when expressed, allows the strain to grow on minimal medium (i.e., without tryptophan).

Stereoselective Enzyme: A "stereoselective enzyme" is an enzyme that has greater specificity and/or greater activity for one isomer, as compared to the specificity and/or activity for another isomer. For example, a stereoselective enzyme is one that has greater specificity and/or activity for R-MP than for S-MP. In preferred embodiments, a stereoselective enzyme has limited activity for one isomer as compared to another. "Limited" activity means activity that is minimally or not perceptible, for example as determined according to experiments provided herein. Example 6, for example, identifies HEXAspCP9T/R122G as an enzyme with limited activity on S,S monatin. Example 8 identifies the *S. meliloti* TatA as another enzyme with limited activity for S-MP. In Example 18, the *B. halodurans* D-aminotransferase had higher selectivity for R-MP as compared with S-MP, resulting in higher stereopurity of R,R monatin. Also, Example 19 indicates that the hybrid DAT has limited activity on S-MP compared to R-MP.

Homologous: The term "homologous" as used herein indicates that a protein or a nucleic acid exhibits a relatively high degree of sequence identity to a sequence of another protein or nucleic acid when the two sequences are aligned using standard methods. For example, an R-specific aldolase is homologous to the aldolase of SEQ ID NO:22 if the R-specific aldolase contains at least about 50% sequence identity to the aldolase of SEQ ID NO:22 when the two sequences are aligned using standard methods.

EC number: The enzyme classification number as assigned by the International Union of Biochemistry and Molecular Biology.

Biosynthetic Pathways to Produce R,R and Other Stereoisomers of Monatin

As described, inter alia, in WO 03/091396 A2 (see, e.g., FIGS. 1-3 and 11-13), monatin can be produced from tryptophan through a multi-step pathway involving biological conversions (i.e. facilitating the reaction of a substrate to a product with a polypeptide). A pathway described involves biologically converting tryptophan to indole-3-pyruvate, biologically converting indole-3-pyruvate to 2-hydroxy 2-(indol-3-ylmethyl)-4-keto glutaric acid ("MP"), and biologically converting MP to monatin. The biosynthesis pathway of the present invention that is used to produce monatin may comprise, or consist essentially of, one or more of the following steps, mechanisms and/or pathways. The steps, mechanisms, and/or pathways described below are simply intended to be exemplary.

One method of producing monatin, or a salt thereof, comprises (a) producing indole-3-pyruvate from L-tryptophan, (b) producing monatin precursor from the indole-3-pyruvate, and (c) producing monatin from the monatin precursor.

Enzymes useful for converting tryptophan to indole-3-pyruvate include members of the enzyme classifications ("EC") 2.6.1.27, 1.4.1.19, 1.4.99.1, 2.6.1.28, 1.4.3.2, 1.4.3.3, 2.6.1.5, 2.6.1.-, 2.6.1.1, 2.6.1.21 and 3.5.1.-. These classes include polypeptides such as: tryptophan aminotransferase, which converts L-tryptophan and α-KG (i.e., α-ketoglutarate, also called 2-oxoglutarate) to indole-3-pyruvate and L-glutamate; D-tryptophan aminotransferase, which converts D-tryptophan and a 2-oxo acid to indole-3-pyruvate and an amino acid; tryptophan dehydrogenase, which converts L-tryptophan and NAD(P) to indole-3-pyruvate and $NH_3$ and NAD(P)H; D-amino acid dehydrogenase, which converts D-amino acids and FAD to indole-3-pyruvate and $NH_3$ and $FADH_2$; tryptophan-phenylpyruvate transaminase, which converts L-tryptophan and phenylpyruvate to indole-3-pyruvate and L-phenylalanine; L-amino acid oxidase, which converts an L-amino acid and $H_2O$ and $O_2$ to a 2-oxo acid and $NH_3$ and $H_2O_2$; D-amino acid oxidase, which converts a D-amino acid and $H_2O$ and $O_2$ to a 2-oxo acid and $NH_3$ and $H_2O_2$; and tryptophan oxidase, which converts L-tryptophan and $H_2O$ and $O_2$ to indole-3-pyruvate and $NH_3$ and $H_2O_2$.

These classes also contain tyrosine (aromatic) aminotransferase, aspartate aminotransferase, D-amino acid (or D-alanine) aminotransferase, and broad (multiple substrate) aminotransferase which have multiple aminotransferase activities, some of which can convert tryptophan and a 2-oxo acid to indole-3-pyruvate and an amino acid. In addition, these classes include phenylalanine deaminases, which can convert tryptophan to indole-3-pyruvate and ammonium in the presence of water.

The production of indole-3-pyruvate from L-tryptophan can also be facilitated by one or more enzymes having greater activity, greater specificity, or both, for L-tryptophan as a substrate than for either MP or monatin. Examples of enzymes having greater activity and/or greater specificity for L-tryptophan as a substrate than for either MP or monatin include, but is not limited to L-tryptophan aminotransferases, L-aromatic aminotransferases, L-aspartate aminotransferases, and L-amino acid oxidases.

Enzymes useful for converting indole-3-pyruvate to MP include members of enzyme classes EC 4.1.3.-, 4.1.3.16, 4.1.3.17, and 4.1.2.-. These classes include carbon-carbon synthases/lyases, such as aldolases that catalyze the condensation of two carboxylic acid substrates. Enzyme class EC 4.1.3.- are those synthases/lyases that form carbon-carbon bonds utilizing oxo-acid substrates (such as indole-3-pyruvate) as the electrophile, while EC 4.1.2.- are synthases/lyases that form carbon-carbon bonds utilizing aldehyde substrates (such as benzaldehyde) as the electrophile. For example, KHG aldolase (EC 4.1.3.16) and ProA aldolase (EC 4.1.3.17), are known to convert indole-3-pyruvate and pyruvate to MP. Although ProA aldolase can be thought to identify only the 4-hydroxy-4-methyl-2-oxoglutarate aldolase derived from *Comamonas testosteroni*, herein the term ProA aldolase is used to mean any polypeptide with 4-hydroxy-4-methyl-2-oxoglutarate aldolase activity unless otherwise stated. Suitable examples of Pro aldolases include *Comamonas testosteroni* ProA (SEQ ID NO:1 (nucleic acid sequence), SEQ ID NO:2 (amino acid sequence)) and *Sinorhizobium meliloti* ProA (NCBI Accession No.: CAC46344), or enzymes that display homology to *Comamonas testosteroni* ProA (SEQ ID NO:1 (nucleic acid sequence), SEQ ID NO:2 (amino acid sequence)) and/or *Sinorhizobium meliloti* ProA (NCBI Accession No.: CAC46344). For example, suitable enzymes may have at least about 40%, 50%, 60%, 70%, 80%, 90%, 95%, and/or 99% amino acid sequence identity with *Comamonas testosteroni* ProA (SEQ ID NO: 2) and/or *Sinorhizobium meliloti* ProA (NCBI Accession No.: CAC46344). MP can also be generated using chemical reactions, such as the aldol condensations.

Figure 2:
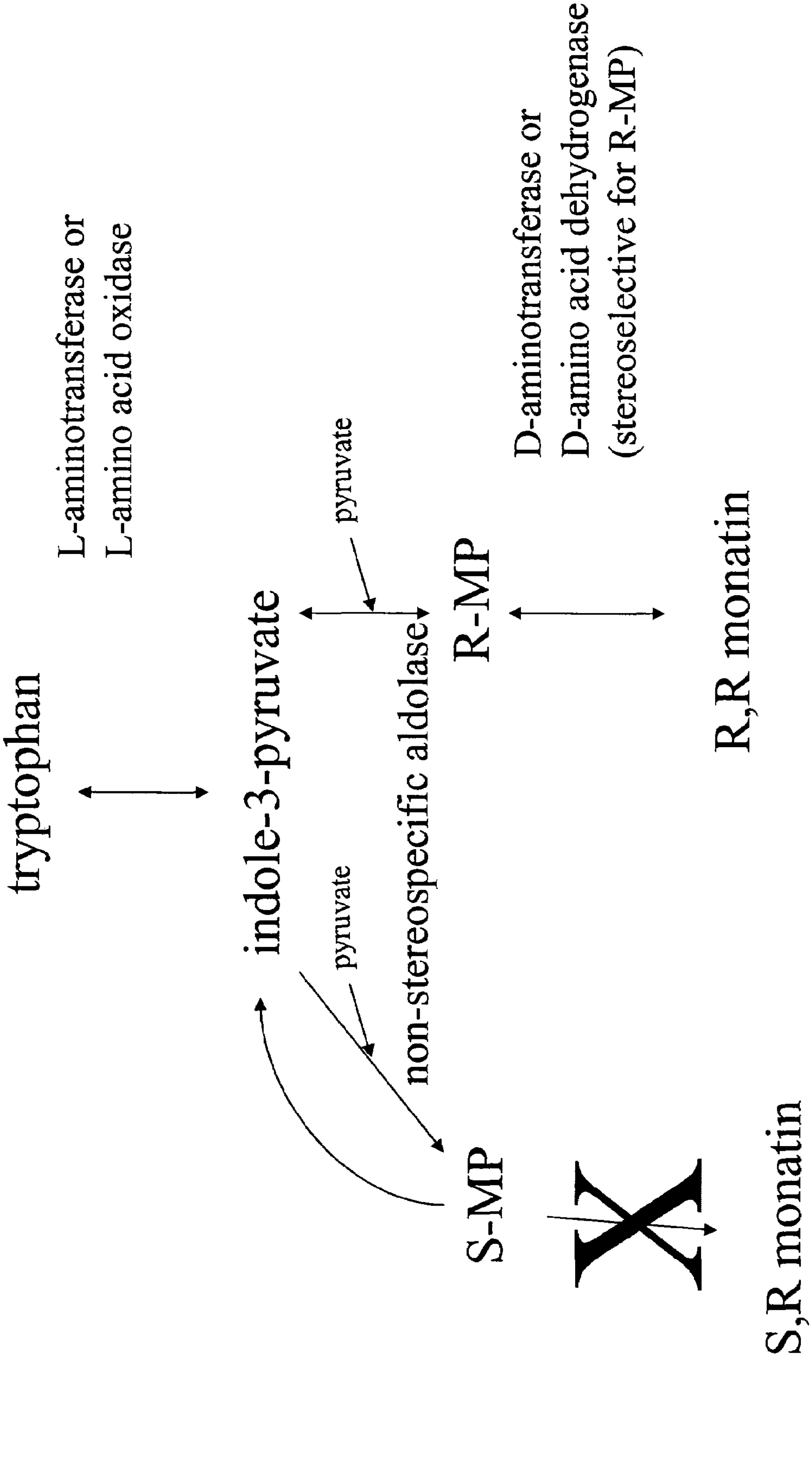
FIG. 2 is a flow chart that shows an example of another process for producing R,R monatin in accordance with the invention. In this example, the process includes using an enzyme to convert R-MP to monatin which is stereoselective for R-MP.

Enzymes useful for the conversion of MP to monatin include members of the enzyme classes (EC): tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (1.4.1.20), tryptophan-phenylpyruvate transaminases (2.6.1.28), or more generally members of the aminotransferase family (2.6.1.-) such as aspartate aminotransferase (EC 2.6.1.1), tyrosine (aromatic) aminotransferase (2.6.1.5), D-tryptophan aminotransferase, or D-alanine (2.6.1.21) aminotransferase (see FIG. 2 of WO 03/091396 A2). This reaction can also be performed using chemical reactions. Amination of the keto acid (MP) is performed by reductive amination using ammonia and sodium cyanoborohydride. FIGS. 11-13 of WO 03/091396 A2 show additional polypeptides that can be used to convert MP to monatin, as well as providing increased yields of monatin from indole-3-pyruvate or tryptophan.

The taste profile of a monatin composition can be altered by controlling the relative amount of the various stereoisomers of monatin in the composition. The present disclosure provides pathways and substances for producing monatin compositions with a desired percentage of R,R monatin and/or S,R monatin.

The chirality of the monatin compounds that is produced by pathways such as those exemplified herein can be altered both by pH and by the polypeptides used for the biological conversions. When monatin is formed using a biosynthetic pathway, the following can be considered. In a biocatalytic reaction, the chirality of the monatin carbon-2 (see chemical structure above) is determined by the enzyme that converts indole-3-pyruvate to MP. Multiple enzymes (e.g., from EC 4.1.2.-, 4.1.3.-) can convert indole-3-pyruvate to MP. Thus, one can choose the enzyme that forms the desired isomer. Alternatively, the enantiospecificity of the enzyme that converts indole-3-pyruvate to MP can be modified through the use of directed evolution or catalytic antibodies can be engineered to catalyze the desired reaction. Once MP is produced (either enzymatically or by chemical condensation), the amino group can be added stereospecifically. Either the R or S configuration of carbon-4 (see previous chemical structure) can be generated depending on whether a D- or L-aromatic acid aminotransferase is used. Many aminotransferases are specific for the L-isomer, however, D-tryptophan aminotransferases exist in certain plants (Kohiba and Mito, Proceedings of the 8th International Symposium on Vitamin $B_6$ and Carbonyl Catalysis, Osaka, Japan 1990). Moreover, D-alanine aminotransferases (EC 2.6.1.21), D-methionine-pyruvate aminotransferases (EC 2.6.1.41) and both (R)-3-amino-2-methylpropanoate aminotransferase (EC 2.6.1.61), (S)-3-amino-2-methylpropanoate aminotransferase (EC 2.6.1.22), and D-phenylglycine aminotransferase have been identified. Certain aminotransferases may only accept the substrate for this reaction with a particular configuration at the C2 carbon. Therefore, even if the conversion to MP is not stereospecific, the stereochemistry of the final product can be controlled through the appropriate selection of an aminotransferase. Because the reaction is reversible, the unreacted MP (undesired isomer) can be recycled back to its constituents and a racemic mixture of MP can be reformed.

Referring now to the figures, the following should be noted. The flow charts identify examples of pathways for producing monatin, but the pathways shown on the figures, and the methods of the invention, are not limited to any particular method for practicing the pathways, unless otherwise stated. For example, the pathways may be practiced in vivo, in vitro, or a combination thereof.

Furthermore, practice of a method of the invention utilizing one or more of the pathways disclosed herein does not require that each of the identified components (e.g. reactants and enzymes) is explicitly provided by the practitioner; rather, it is sufficient that the components, (or sources of components), and reaction conditions are present in the composition (or host cell) or otherwise available so that the pathway can potentially proceed. In other words, for example, if a figure depicts a process for producing a monatin composition, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP, wherein each reaction is facilitated by an appropriate enzyme, it is contemplated that practice of that pathway includes combining L-tryptophan with α-ketoglutarate and enzymes contemplated for facilitating the identified reactions, and under conditions suitable for each of the reactions to occur without also explicitly providing indole-3-pyruvate or MP. In such an instance L-tryptophan could react with α-ketoglutarate to produce indole-3-pyruvate. Depending upon the conditions and the provided enzyme, the indole-3-pyruvate produced from the L-tryptophan reaction can react to form MP, and then depending upon the conditions and the provided enzyme, the MP produced from the indole-3-pyruvate reaction can react to form monatin.

It should also be noted that practice of a method of the invention utilizing one or more of the pathways disclosed herein does not require the practitioner to explicitly provide the identified starting materials or enzymes, if such materials or enzymes are otherwise already present or available, or capable of being synthesized from a substance that is already present or available in the reaction milieu. In other words, it is contemplated that practice of any pathways that identify L-tryptophan as a starting material would include providing a compound that can produce L-tryptophan, under conditions suitable for L-tryptophan production to occur and combining that compound with enzymes capable of facilitating the series of reactions set forth under conditions that would be suitable for those reactions to occur. As another example, it is also contemplated that practicing the identified pathway includes providing a microorganism genetically engineered to produce monatin according to the described pathway, and providing appropriate conditions for the fermentation process to occur. For example, a microorganism, which naturally produces large amounts of L-tryptophan or D-tryptophan (see U.S. Pat. No. 5,728,555) be can be genetically engineered to produce or over-produce one or more of the enzymes used to facilitate (catalyze) reactions in the pathway to monatin, and appropriate conditions can be provided so that the microorganism would thereby produce monatin.

Turning now to FIG. 1, the flow chart shown schematically depicts a process in accordance with the invention for making a monatin composition including R,R monatin. As shown in FIG. 1, the overall pathway involves a reaction of tryptophan to form indole-3-pyruvate, a reaction of indole-3-pyruvate to produce MP, and a reaction of MP to produce monatin, including R,R monatin.

FIG. 1 further illustrates specific permutations of this overall pathway, designed to increase the production of the R,R form of monatin at the expense of the S,S, R,S and S,R forms of monatin. In particular, FIG. 1 illustrates the embodiment wherein: the aminotransferase enzyme utilized in the L-tryptophan reaction has greater activity and/or specificity for that reaction versus the reactions of MP and 4S monatin or the oxidase has greater activity and/or specificity for L-tryptophan than for 4R monatin; the enzyme which facilitates the reaction of indole-3-pyruvate is an R-specific aldolase; and, the enzyme which facilitates the reaction of MP is a broad specificity D-enzyme, preferably evolved to work more efficiently with the R isomer of MP.

FIG. 1 also illustrates particular permutations designed to make the production of R,R monatin more economical. For example, in FIG. 1 L-tryptophan—as opposed to D-tryptophan or combinations of L- and D-tryptophan—is identified as the starting material. While the choice of the specific form of tryptophan does not impact the chirality of the ultimate monatin compounds in the monatin composition (because the tryptophan reaction forms indole-3-pyruvate, which has no chirality), some may prefer utilizing L-tryptophan as a starting material at least because L-tryptophan is currently less expensive and more easily obtainable than D-tryptophan.

Focusing now on the first reaction shown in FIG. 1, when tryptophan is converted to indole-3-pyruvate any one or more of alpha-ketoglutarate, oxaloacetate, and/or pyruvate reacts with the tryptophan to form an amino acid (glutamate, aspartate, and alanine respectively) and indole-3-pyruvate. FIG. 1 depicts the embodiment wherein the tryptophan starting material is L-tryptophan, and the alpha-ketoglutarate, oxaloacetate, and/or pyruvate produce the L-isomer form of the amino acid (e.g. L-glutamate, L-aspartate, and/or L-alanine, respectively).

As shown in FIG. 1, an approach to enhancing the production of R,R monatin involves facilitating the reaction of L-tryptophan with an enzyme having greater specificity, greater activity, or both for tryptophan as opposed to MP or monatin, and facilitating the reaction of MP with a D-specific enzyme. As is disclosed in WO 03/091396 A2, certain enzymes can facilitate the reaction of tryptophan to produce indole-3-pyruvate, as well as the amination reaction of MP to produce monatin. Use of an L-aminotransferase in the amination step creates an S chiral center at the monatin C-4 position, whereas use of a D-enzyme creates a D chiral center at the monatin C-4 position. Thus, in the instance where an L-aminotransferase, which facilitates the tryptophan reaction, is also active in the MP reaction, R,S and S,S monatin can be formed, depending on the form of MP present. In addition, certain other enzymes—the L-amino acid oxidases—can not only facilitate the reaction of tryptophan to indole-3-pyruvate, but may have a side activity for the degradation of R,R monatin. According to some embodiments, this 4R side activity is minimized or eliminated. An oxidase side activity on 4S forms of monatin would decrease or minimize them from the final product and could be desirable depending on the final composition desired. Consequently, the greater the specificity and/or activity of the L-enzyme chosen for tryptophan versus the MP or monatin, the greater the amount of R,R and S,R produced versus S,S and R,S monatin.

Suitable enzymes for the tryptophan reaction, in accordance with the embodiment illustrated in FIG. 1, include: L-aminotransferases capable of facilitating a reaction of L-tryptophan to form indole-3-pyruvate, and which have greater specificity for that reaction over the reaction of R-MP to form 4S isomers of monatin; and, L-amino acid oxidases capable of facilitating a reaction of L-tryptophan to form indole-3-pyruvate, and which have greater specificity and/or activity for that reaction versus the reaction of 4R isomers of monatin to form MP, and functional equivalents of any of the foregoing. More specifically, non-limiting examples of suitable enzymes can be chosen from L-tryptophan aminotransferases (EC 2.6.1.27) and tyrosine (aromatic) aminotransferases (EC 2.6.1.5) and L-amino acid oxidases (EC 1.4.3.2), and mutants derived from enzymes having aspartate aminotransferase activity.

Example 6 identifies a specific enzyme, a mutant HEXaspC polypeptide which includes a Pro 9 to Tyr substitution and an Arg 122 to Gly substitution useful for facilitating the reactions of L-tryptophan and α-KG, oxaloacetate, pyruvate, or combinations thereof to form indole-3-pyruvate and L-glutamate, L-aspartate, and L-alanine, respectively. Another specific enzyme having “limited” activity is TatA, the L-tryptophan aminotransferase from *S. meliloti*. Other enzymes suitable for the tryptophan reaction in accordance with preferred embodiments of the pathway shown in FIG. 1 include those with the following characteristics: an enzyme that transaminates MP at 1/10 the rate or less than the rate of L-tryptophan as in Example 6 or an enzyme when used with a racemase, as in Example 9, that produces greater than 90% of the 4R isomers of monatin.

Examples of enzymes not having a high degree of specificity for the L-tryptophan to indole-3-pyruvate conversion compared to the MP to monatin conversion include: HEX-AspC (Example 6), *Leishmania major* broad specificity aminotransferase (WO 03/091396 A2), the Porcine aminotransferase (WO 03/091396 A2) and *Rhodobacter sphaeroides* TatA (Example 9). These enzymes may, however, be evolved, for example through mutagenesis to have limited activity for R-MP and/or R,R monatin versus tryptophan.

Focusing now on the second reaction identified in FIG. 1, the choice of enzyme for facilitating (or catalyzing) the reaction of indole-3-pyruvate to MP influences the relative amount of R,R monatin versus S,R monatin produced. In general, the greater the relative amount of R-MP versus S-MP produced, the greater the relative amount of R,R monatin versus S,R monatin produced (when a D-enzyme facilitates the reaction of NP to monatin). Enzymes useful in this regard include any enzymes that produce a higher R-MP:S-MP ratio than that produced by the reaction of indole-3-pyruvate and pyruvate when facilitated by any one of the *E. coli* KHG aldolase (Genbank Accession No. AAC74920.1), the *Bacillus* KHG aldolase (Genbank Accession No. CAB134127.1) or the *Comamonas testosteroni* ProA aldolase (SEQ ID NO:1 (nucleic acid sequence), SEQ ID NO:2 (amino acid sequence)). Thus, if it is desired to preferentially produce R-MP, one or more enzymes capable of producing greater amounts of R-MP relative to S-MP can be used. When a monatin composition having the R,R form of monatin as its only monatin component is desired, an enzyme that selectively produces R-MP as opposed to S-MP (an "R-specific enzyme") should be used. Examples of R-specific enzymes that may be used to selectively produce R-MP as opposed to S-MP are the aldolase of SEQ ID NO:22 and *Sinorhizobium meliloti* HMG aldolase, as shown in Example 3.

FIG. 1 identifies the particular embodiment wherein an R-specific aldolase facilitates the reaction of indole-3-pyruvate and pyruvate to form R-MP. Also contemplated, however, is the use of aldolases for the indole-3-pyruvate and pyruvate reaction which preferentially produce R-MP, as well as aldolases that produce a higher R-MP:S-MP ratio than is produced by any one of the *E. coli* KHG aldolase (Genbank Accession No. AAC74920.1), the *Bacillus* KHG aldolase (Genbank Accession No. CAB14127.1) or the *Comamonas testosteroni* ProA aldolase (SEQ ID NO:1 (nucleic acid sequence), SEQ ID NO:2 (amino acid sequence)). In addition, it is also contemplated that indole-3-pyruvate may react with a different C3 source (for example serine or cysteine) to form R-MP and consequently other enzymes (for example other lyases or synthases) may facilitate such a reaction. Other substrates that are readily converted to pyruvate (such as oxaloacetate) may also be used. Example 3 provides sources of aldolase enzymes that may preferentially or selectively produce R-MP or produce a higher R-MP:S-MP ratio than is produced by the reaction of indole-3-pyruvate and pyruvate when facilitated by any one of the *E. coli* KHG aldolase (Genbank Accession No. AAC74920.1), the *Bacillus* KHG aldolase (Genbank Accession No. CAB14127.1) or the *Comamonas testosteroni* ProA aldolase (SEQ ID NO:1 (nucleic acid sequence), SEQ ID NO:2 (amino acid sequence)), such as the aldolase of SEQ ID NO:22. Example 5 also provides screening methods for identifying such enzymes. It is also contemplated that enzymes, which preferentially or selectively produce R-MP or produce more R-MP than any one of the *E. coli* KHG aldolase (Genbank Accession No. AAC74920.1), the *Bacillus* KHG aldolase (Genbank Accession No. CAB14127.1) or the *Comamonas testosteroni* ProA aldolase (SEQ ID NO:1 (nucleic acid sequence), SEQ ID NO:2 (amino acid sequence)) may be evolved from aldolases known or found in nature. Any techniques known in the art for evolving enzymes, for example to improve a desired characteristic—such as to increase the activity of an enzyme for a substrate—as compared to the wild type enzyme can be used. Examples 4, 5, 6, 7, 9, 10, and 11 provide some techniques for evolving enzymes.

Focusing now on the last step of the pathway identified in FIG. 1, the reaction of R-MP to form R,R monatin is shown to be facilitated by a broad specificity D-aminotransferase, for example D-alanine aminotransferase (EC 2.6.1.21, also known as D-amino acid aminotransferase or D-aspartate aminotransferase) or a D-amino acid dehydrogenase. As discussed above, the conversion of MP to monatin is an amination reaction, which creates a chiral center at the monatin C-4 carbon. Where the R-chiral form is desired at the C-4 position, enzymes should be used which produce "R" chiral centers in amino acids. Non-limiting exemplary enzymes include: a D-alanine-aminotransferase derived from *Bacillus* (Examples 15-18), including the D-alanine-aminotransferase derived from *Bacillus halodurans* (Example 18) and a mutated branched chain aminotransferase that has modified stereospecificity (Example 7).

Another exemplary enzyme includes a hybrid D-aminotransferase. The hybrid D-aminotransferase can contain structural elements from two differing amino acid aminotransferases. The hybrid D-aminotransferase can then be further evolved (e.g. via mutagenesis or recombinant engineering) for improved performance in converting MP to monatin. An example of such a hybrid D-aminotransferase is shown in Example 19. The hybrid D-aminotransferase illustrated in Example 19 included elements from a D-aminotransferase from *B. spaericus* and a D-aminotransferase from *G. stearothermophilus*. R,R-monatin was produced utilizing this D-aminotransferase (Example 19).

Example 2 also illustrates the production of R,R monatin utilizing various D-aminotransferases.

According to some embodiments, the D-aminotransferase has greater specificity, greater activity, or both for the R-MP as a substrate than for indole-3-pyruvate. In certain other embodiments, the D-aminotransferase has limited activity for the indole-3-pyruvate as a substrate. Enzymes with such characteristics may be evolved or mutated from existing enzymes, for example as shown in Example 6.

Also, in some embodiments, the reaction of R-MP to form R,R monatin can be facilitated by a D-amino acid dehydrogenase. Example 20 illustrates the production of R,R monatin from R-MP utilizing a D-amino acid dehydrogenase (D-AADH-101 through 108, BioCatalytics). These D-amino acid dehydrogenases may be further evolved (e.g. via mutagenesis or recombinant engineering) for improved performance.

FIG. 2 depicts another strategy for targeting production of R,R monatin. Whereas in the embodiment of FIG. 1, the aldolase used in the reaction of indole-3-pyruvate to form R-MP influences the ratio of R,R:S,R formed, in the embodiment of FIG. 2, the D-enzyme that facilitates the conversion of MP to monatin influences the ratio of R,R:S,R formed. According to the embodiment of FIG. 2, a non-stereospecific enzyme may be used to facilitate the conversion of indole-3-pyruvate to MP, and consequently both S-MP and R-MP can be formed. To obtain a desired ratio of R,R monatin to S,R monatin, a D-enzyme is chosen (or evolved) with appropriate stereoselectivity for R-MP versus S-MP. Where a monatin composition having the R,R form of monatin as its only monatin component is desired, an enzyme that selectively facilitates the reaction of R-MP to monatin as opposed to S-MP to monatin would be preferred. For example, the *Bacillus halodurans* D-aminotransferase (Example 18) and the hybrid D-aminotransferase containing structural elements from both *Bacillus sphaericus* and *Geobacillus stearothermophilus* (Example 19) may be utilized as the enzyme that selectively facilitates the reaction of R-MP to monatin.

Figure 3:
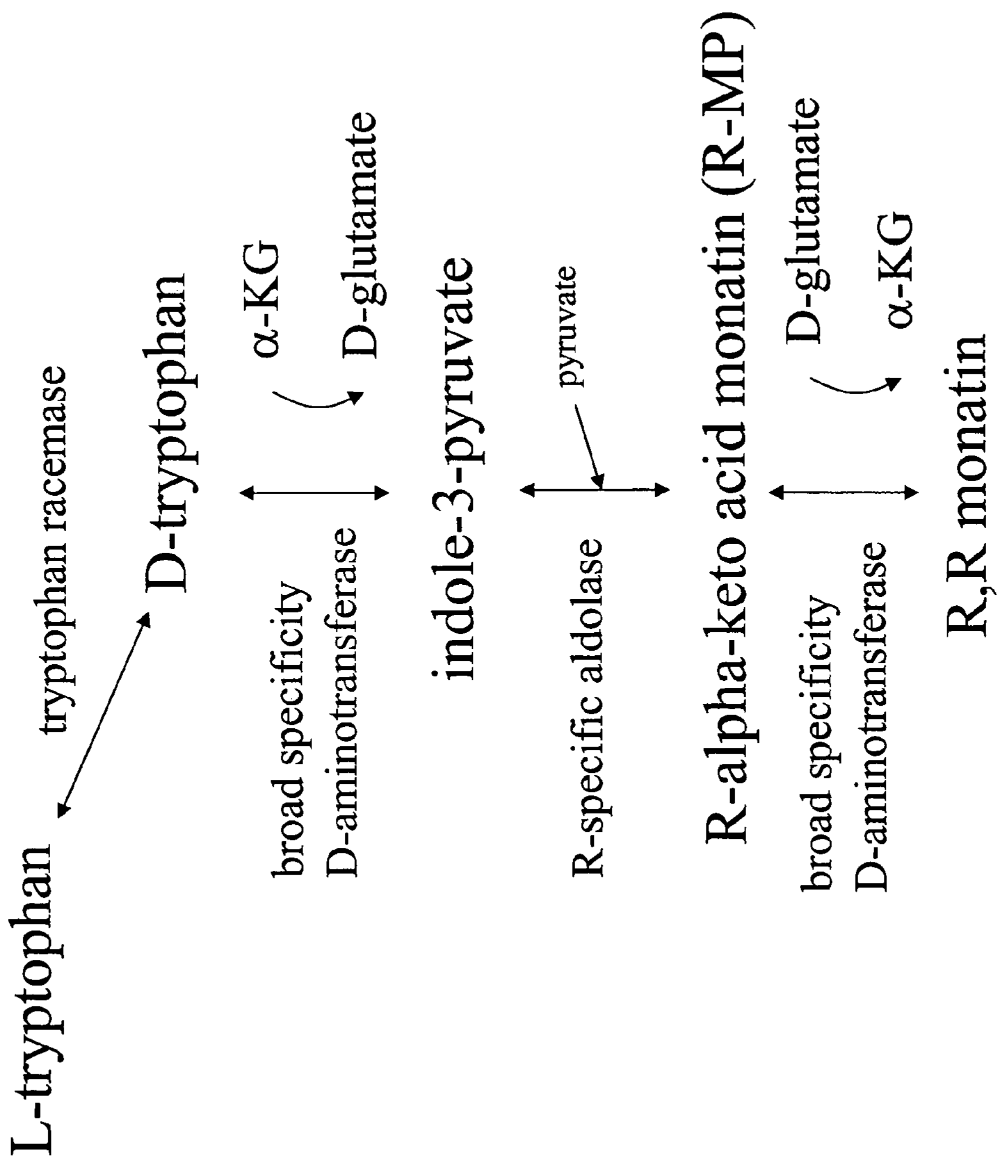
FIG. 3 is a flow chart that shows an example of yet another process for producing R,R monatin from L-tryptophan in accordance with the invention In this example, the process includes converting L-tryptophan to D-tryptophan using a tryptophan racemase and using a D-amino acid product in the reaction coupled to the reaction forming indole-3-pyruvate as a substrate in the reaction coupled to the reaction forming R,R monatin.

FIG. 3 illustrates another alternative pathway for production of compositions enriched in R,R monatin. The pathway of FIG. 3 is a modification of the pathway of FIG. 1. In the pathway shown in FIG. 3, indole-3-pyruvate is produced indirectly, rather than directly, from L-tryptophan. More specifically, L-tryptophan is converted to D-tryptophan, and D-tryptophan is then converted to indole-3-pyruvate. Example 4 illustrates the production of R,R monatin from L-tryptophan using a tryptophan racemase.

The conversion of L-tryptophan to D-tryptophan can be facilitated by a tryptophan racemase or functional equivalent thereof. Example 4 provides potential sources of tryptophan racemases and screening methods for identifying such enzymes. Example 4 describes examples of tryptophan racemases that are capable of converting L-tryptophan into D-tryptophan. These tryptophan racemases can be further evolved (e.g. via mutagenesis or recombinant engineering) for improved performance.

Non-limiting examples of tryptophan racemases include homologs or mutants of amino acid racemases (EC 5.1.1.-), for example serine racemase, in which the homologs or mutants are capable of converting L-tryptophan to D-tryptophan. Non-limiting examples of sources from which the amino acid racemase may be derived include microorganisms such as *Salmonella typhimurium, Escherichia coli, Bacillus subtilis, Bacillus sphaericus, Bacillus halodurans, Geobacillus stearothermophilus, Bacillus licheniformis, Pseudomonas aeruginosa, Vibrio cholerae, Schizosaccaroyces pombe, Bacillus cereus, Enterococcus gallinarum, Pediococcus pentosaceus, Bacillus pumilus, Lactobacillus fermenti, Lactobacillus brevis, Aquifex pyrophilus, Lactobacilli, Streptococcus, Anabaena* sp., *Pseudomonas striata, Lentinus edodes, Scapharca brouhtonii Desulfurococcus* sp., *Thermococcus* sp., and *Pseudomonas striata*. Additional non-limiting examples of sources from which the amino acid racemase may be derived include silkworm, rat brain, or mouse brain. These amino acid racemases may be evolved (e.g. via mutagenesis or recombinant engineering) for improved performance in converting L-tryptophan to D-tryptophan.

Non-limiting examples of potential sources from which suitable tryptophan racemases may be derived include: microorganisms such as *Pseudomonas*, for example *Pseudomonas chlororaphis* (*Pseudomonas aurereofaciens*) (ATCC15926), and *Burkholderia pyrrocina* (ATCC15958). Additional non-limiting examples of potential sources from which suitable tryptophan racemases may be derived include plants, for example tobacco plants, such as *Nicotiana tabacum*, wheat plants, such as *Triticum aestivum*, beets, tomatoes, and *Sclerochiton ilicifolius.*

The pathway shown in FIG. 3 has certain benefits, including that even when R,R monatin is the desired product, the same enzyme can be used for the reaction that produces indole-3-pyruvate as for the reaction that produces monatin as a product. That is, in the pathway illustrated in FIG. 1, an L-aminotransferase (or suitable L-enzyme) facilitates the reaction producing indole-3-pyruvate, but a D-aminotransferase facilitates the reaction producing monatin. By contrast in the pathway of FIG. 3, a certain D-aminotransferase that facilitates the reaction producing indole-3-pyruvate, can also facilitate the reaction producing monatin. Consequently, in pathways according to FIG. 3, broad specificity D-aminotransferases may be preferred when there is a desire to use the same enzyme for the reaction forming indole-3-pyruvate as for the reaction forming monatin. By contrast, in pathways according to FIGS. 1, 2, 4, 6, 7, and 8 production of monatin may be more efficient when a D-aminotransferase is chosen that has limited activity and/or specificity for indole-3-pyruvate as compared to R-MP.

Another benefit of the pathway schematically represented in FIG. 3 is that the amino acid product of the reaction coupled to the reaction producing indole-3-pyruvate can now be used as a substrate in the reaction coupled to the reaction producing monatin. That is, in the pathway illustrated in FIG. 1, L-tryptophan reacts to produce indole-3-pyruvate and at the same time oxaloacetate, alpha-ketoglutarate and/or pyruvate react to produce an L-amino acid. Because the reaction of R-MP to form monatin is coupled with a reaction utilizing a D-amino acid as a substrate, the L-amino acid of the reaction forming indole-3-pyruvate is not, under the conditions shown, recycled for use in the reaction coupled to the R-MP reaction. By contrast, in the pathway illustrated in FIG. 3, the reaction of D-tryptophan to form indole-3-pyruvate is coupled to a reaction forming a D-amino acid product, which D-amino acid can be recycled for use in the reaction coupled to the R-MP reaction. This allows one to use non-stoichiometric amounts of amino acceptor in step one and the amino donor for step 3 is produced in step 1.

Figure 4:
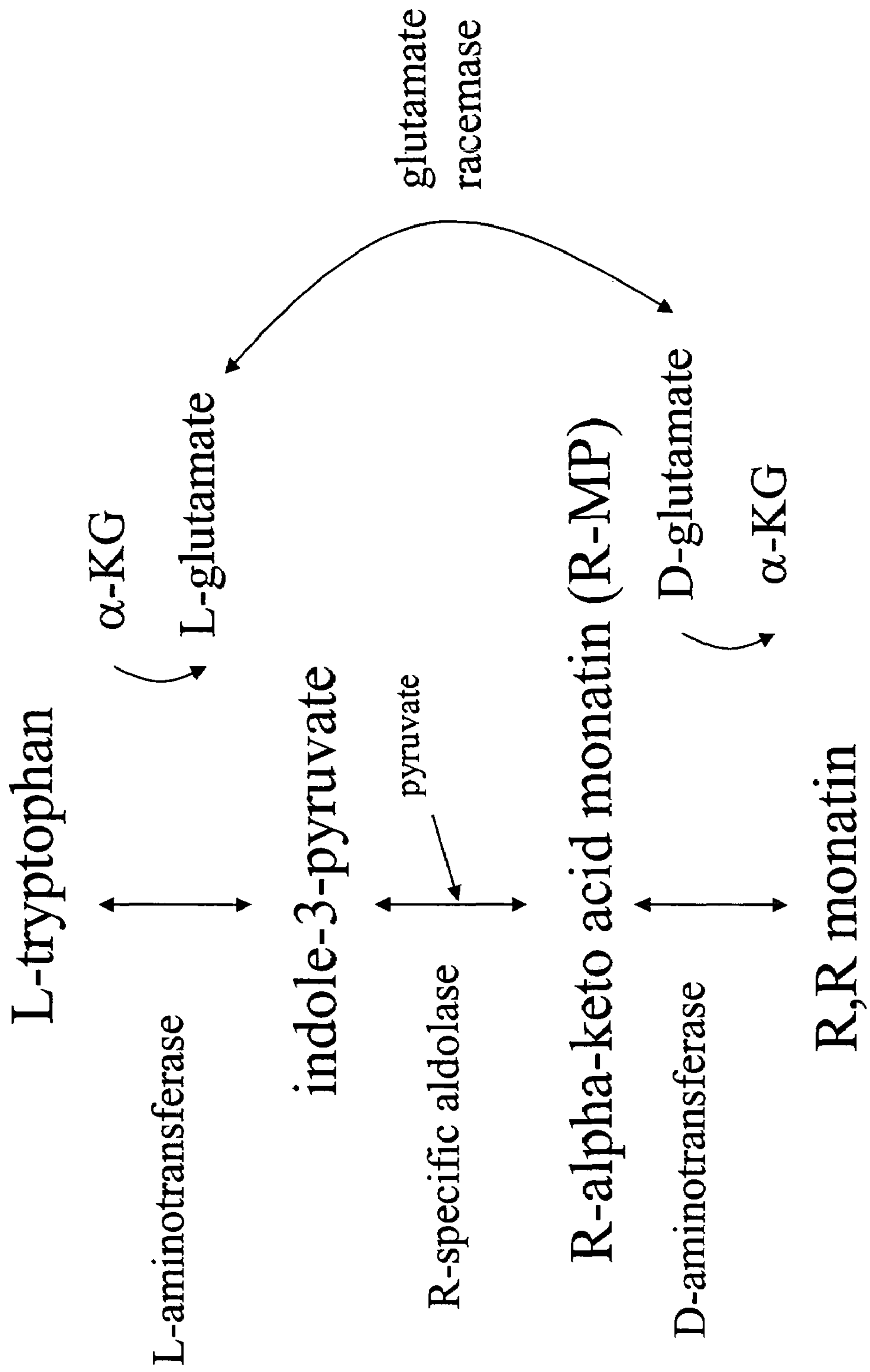
FIG. 4 is a flow chart that shows an example of yet another process for producing R,R monatin from L-tryptophan in accordance with the invention. In this example, the process includes converting the L-amino acid formed in the reaction coupled with the L-tryptophan reaction to a D-amino acid; this D-amino acid acts as an amino donor for the reaction in which R-MP is converted to R,R monatin.
Figure 5:
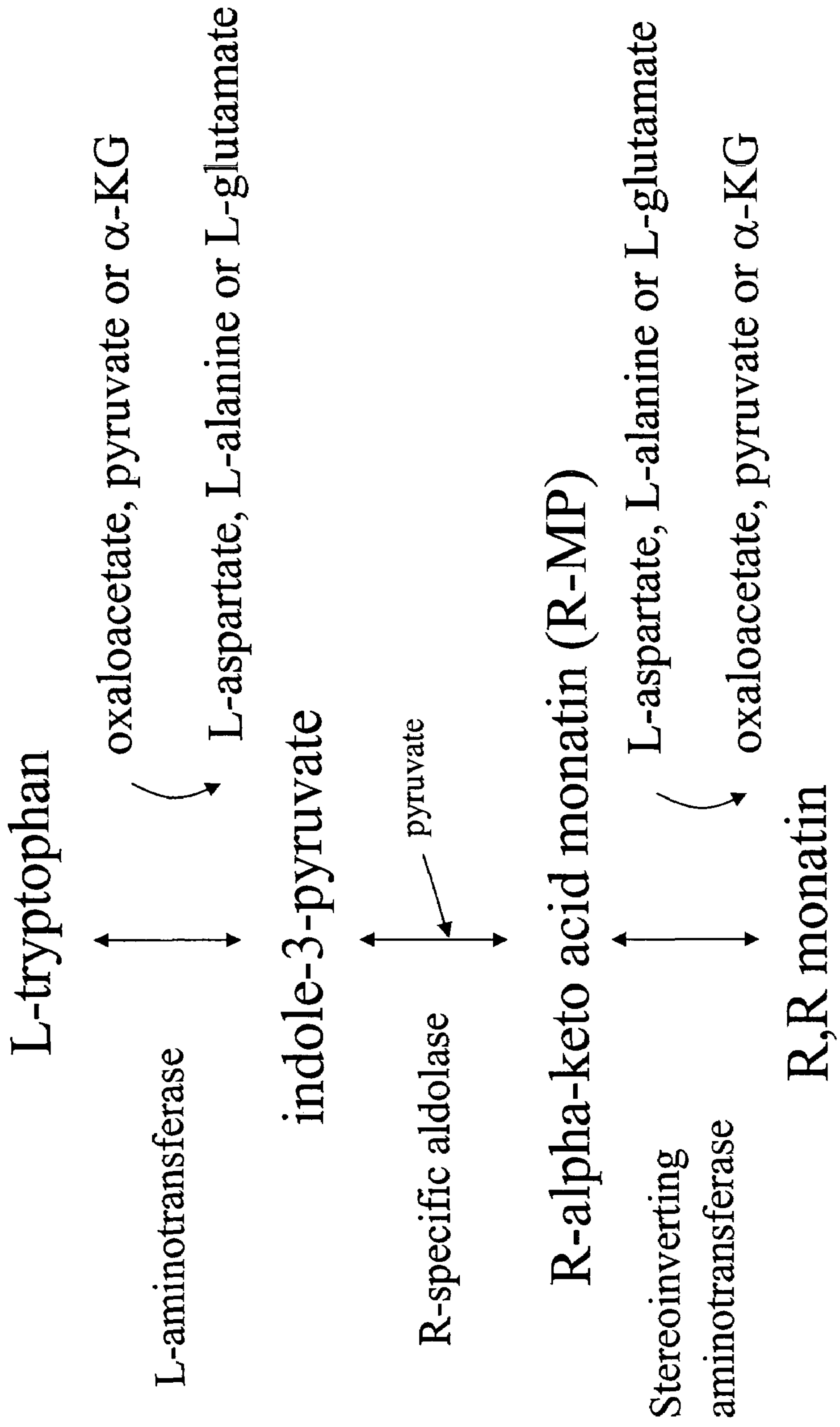
FIG. 5 is a flow chart that shows an example of yet another process for producing R,R monatin from L-tryptophan in accordance with the invention. In this example, the process includes enzymatically facilitating the conversion of R-MP to R,R monatin using a stereoinverting enzyme so that the L-amino acid formed by the reaction coupled to the L-tryptophan reaction can be used as a substrate for the reaction coupled to the R-MP to R,R monatin reaction.

FIGS. 4 and 5 illustrate additional modifications of the pathway shown in FIG. 1. These modifications are directed to recycling the amino acid product formed by the reaction coupled with the L-tryptophan transamination reaction with the amino acid reactant of the reaction coupled to the MP to monatin reaction.

Turning to FIG. 4, the recycling is accomplished by providing an enzyme that can facilitate the conversion of an L-amino acid to a D-amino acid and vice versa. More specifically, where, as is shown in FIG. 4, α-KG reacts to form L-glutamate when L-tryptophan reacts to form indole-3-pyruvate, a glutamate racemase (EC 5.1.1.3) or functional equivalent can be provided that can facilitate the conversion of L-glutamate to D-glutamate and vice versa. In such an instance, the L-glutamate formed as a product along with the production of indole-3-pyruvate is partially removed by virtue of its conversion to D-glutamate, and the D-glutamate formed from the conversion of L-glutamate is then available as a substrate for the reaction coupled with the MP to monatin reaction. Similarly, the α-KG formed in the reaction of D-glutamate is available as a substrate for the reaction coupled to the L-tryptophan to indole-3-pyruvate reaction.

Non-limited examples of potential sources from which a glutamate racemase may be derived include *Pediococcus pentosaceus, Bacillus pumilus, Lactobacillus fermenti, Lactobacillus brevis, E. coli, Aquifex pyrophilus*, and *Bacillus subtilis*. More specifically (also non-limiting), the glutamate racemase may be expressed from a nucleic acid such as *Pediococcus pentaosaceus* murI gene (Genbank Accession No. L22789), or *Lactobacillus brevis* glutamate racemase.

Where oxaloacetate reacts to form L-aspartate when L-tryptophan reacts to form indole-3-pyruvate, an aspartate racemase (EC 5.1.1.13) or functional equivalent can be provided to convert L-aspartate to D-aspartate. In such an instance, the L-aspartate that is formed in the same reaction that produces indole-3-pyruvate is partially removed by virtue of its conversion to D-aspartate, and the D-aspartate is then available to as a substrate for the reaction coupled to the MP to monatin reaction. Similarly, the oxaloacetate formed in the reaction of D-aspartate is available to act as a substrate for the reaction coupled to the L-tryptophan to indole-3-pyruvate reaction.

Non-limiting examples of suitable enzymes having aspartate racemase activity include ASPR-101 (BioCatalytics, Inc., 129 N. Hill Ave, Suite 103, Pasadena, Calif. 91106-1955) and homologs or mutants of an amino acid racemase (EC 5.1.1.-) which are capable of facilitating the conversion of L-aspartate to D-aspartate.

Non-limiting examples of potential sources from which aspartate racemases may be derived include: *Desulfurococcus, Thermococcus*, bivalve mollusk *Scapharca brouhtonii, Acinetobacter, Agrobacterium, Archaeoglobus, Bacillus, Bordetella, Bradyrhizobium, Brevibacterium, Burkholderia, Campylobacter, Candida, Caulobacter, Clostridium, Desulfitobacterium, Desulfotalea, Enterococcus, Erwinia, Escherichia, Ferroplasma, Helicobacter, Klebsiella, Lactobacillus, Mannheimia, Medicago, Mesorhizobium, Methanococcus, Methanosarcina, Oceanobacillus, Oenococcus, Pediococcus, Polaribacter, Pseudomonas, Pyrococcus, Ralsonia, Shigella, Sinorhizobium, Salmonella, Sphingomonas, Streptococcus, Thermoanaerobacter, Vibrio, Wolinella, Xanthomonas, Xanthobacter, Yersinia* and *Zymomonas*.

Where pyruvate reacts to form L-alanine when L-tryptophan reacts to form indole-3-pyruvate, an alanine racemase or functional equivalent can be provided to convert L-alanine to D-alanine. In such an instance, the L-alanine that is formed in the same reaction that produces indole-3-pyruvate is removed by virtue of its conversion to D-alanine, and the D-alanine formed from the conversion of L-alanine is then available to act as a substrate for the reaction coupled to the MP to monatin reaction. Similarly, the pyruvate formed in the reaction of D-alanine is available to act as a substrate for the reaction couple with the L-tryptophan to indole-3-pyruvate reaction.

Non-limiting examples of suitable alanine racemases include A8936 (Sigma, PO Box 14508, St. Louis, Mo., 63178) and the *Geobacillus stearothermophilus* alanine racemase as described in Example 4.

Non-limiting examples of potential sources from which the alanine racemase may be derived include: *Brucella abortus, Streptococcus faecalis Salmonella typhimurium, Escherichia coli, Bacillus subtilis, Pseudomonas aeruginosa, Vibrio cholerae, Schizosaccaroyces pombe, Bacillus cereus* and *Lentinus edodes*.

Examples 9 and 12 illustrate the use of the above racemases, their impact on increasing the ratio of the desired monatin product, and provide potential sources for the racemase enzymes.

Turning to FIG. 5, a stereoinverting aminotransferase is used to facilitate the reaction of R-MP to monatin. Although typically the R-MP (or S-MP) reaction to form R,R monatin (or S,R monatin) is coupled with the reaction of a D-amino acid, a stereoinverting aminotransferase may facilitate the coupled reactions of R-MP (or S-MP) to form R,R monatin (or S,R monatin) using an L-amino acid. In this way, the L-amino acid product of the L-tryptophan aminotransferase reaction may be used as a substrate for the transamination of MP to monatin, and the product (i.e. oxaloacetate, pyruvate, and/or α-KG) of the reaction coupled to the MP to monatin reaction can be used as a starting material for the reaction coupled to the L-tryptophan to indole-3-pyruvate reaction. Non-limiting examples of stereoinverting aminotransferases that may be used include mutants derived from D-phenylglycine aminotransferase (EC 2.6.1.72, also known as D-4-hydroxyphenylglycine aminotransferase), D-methionine aminotransferase (EC 2.6.1.41, also known as D-met-aminotransferase and D-methionine-pyruvate aminotransferase), and homologs thereof. Non-limiting examples of potential sources from which the mutants of D-phenylglycine aminotransferase may be derived include *Pseudomonas*, such as *Pseudomonas putida* LW-4 and *Pseudomonas stutzeri* ST-201. Non-limiting examples of potential sources from which the D-methionine aminotransferase may be derived include cauliflower and peanut.

Examples 10 and 11 together provide potential sources of stereoinverting enzymes, and methods of making such enzymes. The examples also provide screening methods for identifying such enzymes. It is also contemplated that such enzymes may be evolved from stereoinverting enzymes known or found in nature. As a non-limiting example, the stereoinverting aminotransferase can be a homolog or mutant of a D-amino acid aminotransferase or a homolog or mutant of an amino acid racemase (EC 5.1.1.-).

Figure 6:
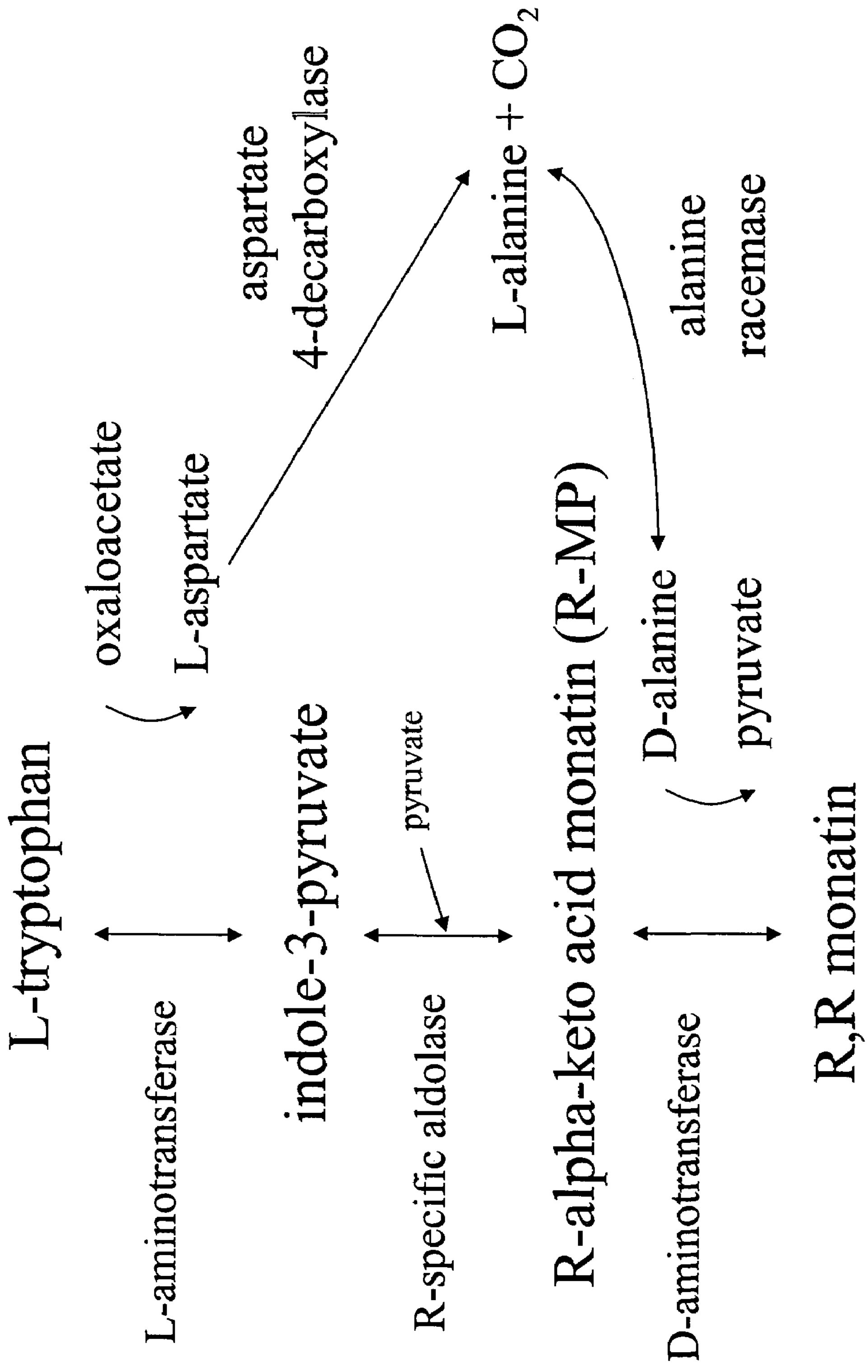
FIG. 6 is a flow chart that shows an example of yet another process for producing R,R monatin in accordance with the present invention. In this example, the process includes recycling the L-amino acid produced in the reaction forming indole-3-pyruvate with the D-amino acid used as a reactant with R-MP in the reaction forming R,R monatin through a series of conversion reactions.
Figure 7:
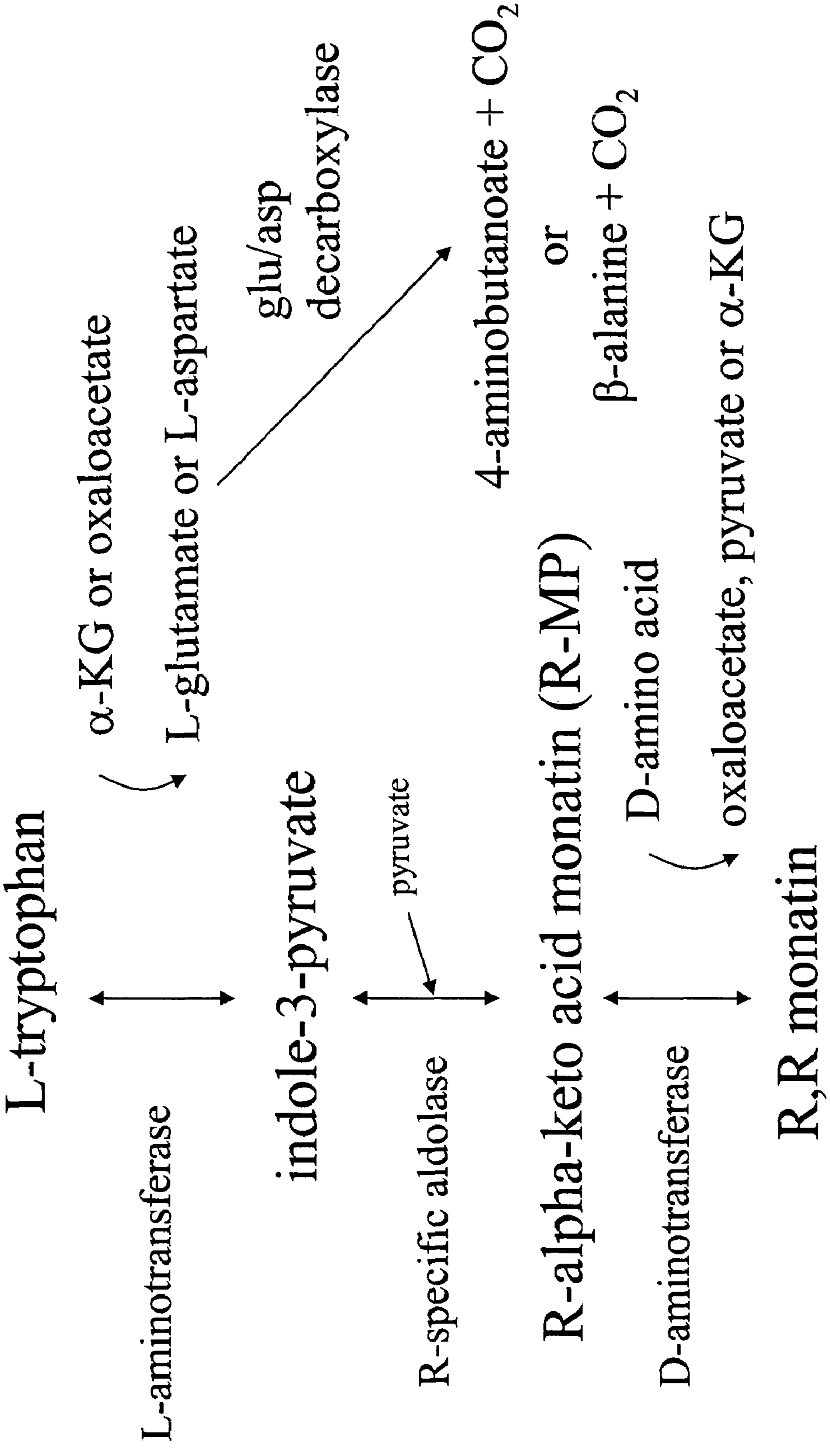
FIG. 7 is a flow chart that shows an example of yet another process for producing R,R monatin in accordance with the present invention. In this example, the process includes pushing the L-tryptophan reaction forward (i.e., driving the reaction toward the production of indole-3-pyruvate) by converting the L-amino acid byproduct of that reaction into another product. In this example, the L-amino acid L-aspartate byproduct is converted into L-alanine in an irreversible reaction using a decarboxylase.

FIGS. 6 and 7 also illustrate modifications to the pathway of FIG. 1. The pathways illustrated in FIGS. 6 and 7 provide methods to push equilibrium reactions forward (i.e., toward the direction of monatin production) by removing the byproduct of the tryptophan reaction with an irreversible reaction and in some cases providing substrate for the MP reaction.

Turning to FIG. 6, the pathway shown removes the L-amino acid product of the reaction coupled to the tryptophan reaction by converting it to a different L-amino acid and $CO_2$, and then provides a substrate for the reaction coupled to the MP reaction by converting the newly formed L-amino acid to a D-amino acid. Specifically, L-tryptophan is shown to react alongside oxaloacetate to form indole-3-pyruvate and L-aspartate. An aspartate 4-decarboxylase (EC 4.1.1.12) or functional equivalent is used to facilitate the conversion of L-aspartate to L-alanine and carbon dioxide, and an enzyme with alanine racemase activity is used to facilitate the conversion of L-alanine to D-alanine, which D-alanine can serve as an amino donor for the conversion of R-MP to monatin.

Turning to FIG. 7, the pathway shown illustrates additional methods for removing the L-amino acid product of the reaction coupled to the tryptophan reaction. Embodiments as presented in the figure produce a byproduct(s) that is unavailable to react in the reverse direction, for example due to volatility (e.g., carbon dioxide) or by spontaneous conversion to an unreactive endproduct. An example of such an approach includes embodiments in which α-KG reacts alongside L-tryptophan to produce L-glutamate, and, if desired, a glutamate decarboxylase (EC 4.1.1.15) or functional equivalent can be provided to facilitate the conversion of L-glutamate to 4-aminobutanoate (with carbon dioxide as a byproduct). Non-limiting examples of potential sources from which the L-glutamate decarboxylase can be derived include: *Clostridium perfringens, C. welchii*, or *E. coli*.

Another example of such an approach for driving the tryptophan reaction forward (in the direction of monatin production) includes reactions in which oxaloacetate is utilized as a co-substrate in the reaction that utilizes L-tryptophan and in which the oxaloacetate is converted to L-aspartate; if desired, an aspartate decarboxylase (EC 4.1.1.11) or functional equivalent can be provided to facilitate the conversion of L-aspartate to β-alanine (with carbon dioxide as a byproduct).

Figure 8:
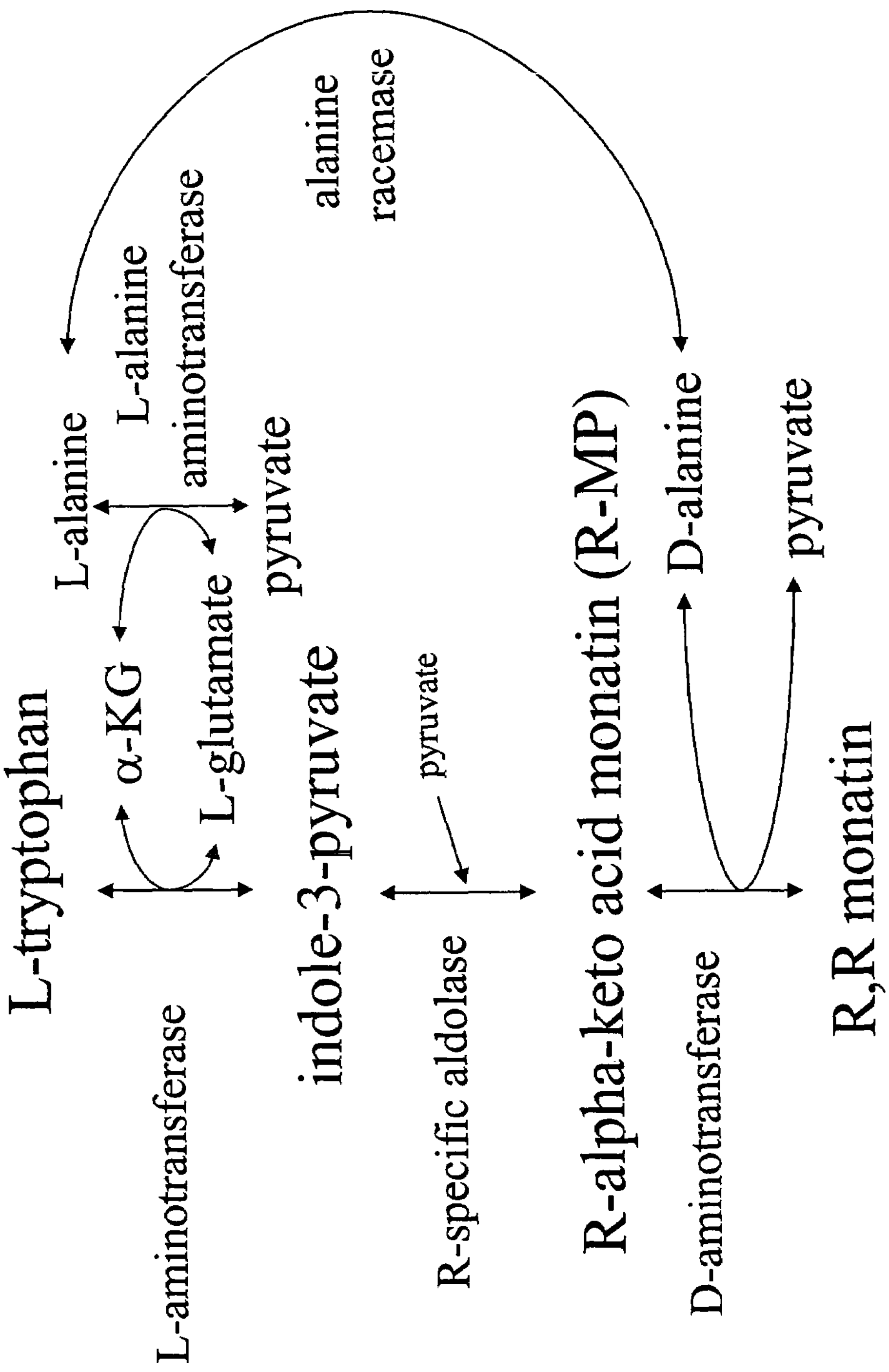
FIG. 8 is a flow chart that shows an example of yet another process for producing R,R monatin in accordance with the present invention. In this example, the process includes recycling the amino acid byproduct of the L-tryptophan reaction with the amino acid reactant of the R-MP reaction through a series of conversion reactions.

Turning to FIG. 8, the pathway shown illustrates yet additional methods for converting the L-amino acid product of the reaction coupled to the tryptophan reaction to a substrate for the reaction coupled to the MP reaction. Specifically, where α-KG is utilized in the same reaction as L-tryptophan, and in which the α-KG forms L-glutamate, an enzyme with L-alanine aminotransferase activity and pyruvate can be provided, wherein the L-alanine aminotransferase enzyme facilitates the reaction of pyruvate and L-glutamate to form L-alanine. An alanine racemase or functional equivalent can also be provided in order to facilitate the conversion of the L-alanine to D-alanine, which D-alanine can be used as a substrate along with MP to form monatin and pyruvate. See Example 12.

Implicitly described in the biosynthesis pathways above, and in the reactions described in the Examples below, are mixtures containing one or more compounds and/or enzymes required in the biosynthesis pathways for producing monatin, including R,R monatin, or monatin precursor, including R monatin precursor.

For production in vitro, any or all of the biosynthetic pathways described herein or individual steps in the pathways described herein can be conducted in in vitro solution or in vivo, in a host cell, in series or in parallel. When the method of the invention utilizes one or more reactions that are performed in vitro, the biosynthetic reaction that is performed in vitro can be performed by combining the desired ingredients for the reaction(s) by admixture in an aqueous reaction medium or solution. The reaction mixture so formed is maintained for a period of time sufficient for the desired product(s) to be synthesized.

Additionally, the activity of one or more enzymes can be enhanced through the continuous use of cofactors during purification of the one or more enzymes. For example, including pyridoxal-5'-phosphate when purifying *B. sphaericus* D-alanine aminotransferase results in increased activity (Example 14).

When one or more of the reactions in the pathways of the invention are to be performed in vitro, any or all of the enzymes utilized in the biosynthesis pathways described herein can optionally be immobilized onto a solid support. Examples of such solid supports include those that contains epoxy, aldehyde, chelators, or primary amine groups. Specific examples of suitable solid supports include, but are not limited to, Eupergit® C (Rohm and Haas Company, Philadelphia, Pa.) resin beads and SEPABEADS® EC-EP (Resindion). Example 21 illustrates the immobilization of the *B. sphaericus* D-alanine aminotransferase onto Eupergit® C resin beads. Example 22 illustrates the immobilization of the *Sinorhizobium meliloti* ProA aldolase onto Eupergit® C resin beads. Production of R,R monatin utilizing these immobilized enzymes is shown in Example 23.

The individual reactions shown in the biosynthetic pathways described herein can be facilitated (catalyzed) by a single enzyme or by a mixture of multiple enzymes acting concurrently.

The methods of the invention can be used to make a monatin composition that contains a desired percentage of R,R-monatin, or a minimum desired percentage of R,R-monatin. In addition to the reaction steps described above, a specific reaction step can be catalyzed by more than one enzyme, for example, a mixture of enzymes, so that the resulting composition or preparation contains a desired percentage of R,R-monatin, including, for example, a minimum desired percentage of R,R-monatin, or a maximum desired percentage of R,R-monatin. Alternatively, the monatin made by two separate engineered pathways according to the methods of the invention be combined to produce a composition or preparation containing such desired percentage of R,R-monatin.

When an enzyme of a designated class of enzymes is utilized as an example, it is expected that an enzyme with at least about 50%, 55%, 60%, 65%, 70%, 75%, 80%, 82%, 85%, 87%, 90%, 91%, 92%, 93%, 94%, 95%, 96%, 97%, 98%, and 99% homology could also be utilized in that reaction. For example, an R-specific aldolase with at least about 50%, 55%, 60%, 65%, 70%, 75%, 80%, 82%, 85%, 87%, 90%, 91%, 92%, 93%, 94%, 95%, 96%, 97%, 98%, and 99% homology to the aldolase of SEQ ID NO:22 could be utilized in any of the above described pathways to yield R,R monatin.

Additionally, when an enzyme of a designated class of enzymes is utilized as an example, it is expected that a fragment of that enzyme that has the same activity could also be utilized in that reaction. For example, a fragment of the aldolase of SEQ ID NO:22 that also functions as an aldolase could be utilized in any of the above described pathways to yield R,R monatin.

Monatin that is produced utilizing one or more of the polypeptides or biosynthetic pathways disclosed herein, is generally at least about 0.5-30% R,R-monatin, by weight of the total monatin produced. In other embodiments, the monatin produced utilizing one or more of the polypeptides or biosynthetic pathways disclosed herein, is greater than 30% R,R-monatin, by weight of the total monatin produced; for example, the R,R-monatin is 40%, 50%, 60%, 65%, 70%, 75%, 80%, 85%, 90%, 95% or 99% of the total monatin produced Alternatively, various amounts of two or more preparations of monatin can be combined so as to result in a preparation that is a desired percentage of R,R-monatin. For example, a monatin preparation that is 30% R,R-monatin can be combined with a monatin preparation that is 90% R,R-monatin; if equal amounts of 30% and 90% R,R-monatin preparations are combined, the resulting monatin preparation would be 60% R,R-monatin.

The monatin, or an intermediate (including monatin precursor), produced utilizing one or more of the polypeptides or biosynthetic pathways disclosed herein, may be purified from the components of the reaction. In one embodiment, the monatin or intermediate, such as monatin precursor, may be purified simply by removing the substance that is to be purified from the enzyme preparation in which it was synthesized.

In other embodiments, the intermediate, monatin precursor or monatin is purified from a preparation in which it was synthesized so that the resulting "purified" composition or preparation is at least about 5-60% monatin by weight of total organic compounds. In another embodiment, the monatin or intermediate, such as monatin precursor, may be purified to a degree of purity of at least about 70%, 80%, 90%, 95% or 99% by weight of total organic compounds.

The monatin, or the intermediate (including monatin precursor), produced utilizing one or more of the polypeptides or biosynthetic pathways disclosed herein, may be purified from the components of the reaction by any method known to a person of ordinary skill in the art. In one embodiment, the monatin or intermediate may be purified as described in Example 13. Optimally, the purified monatin or intermediate may be repeatedly recrystallized until the desired degree of purity is achieved.

EXAMPLES

Example 1

Detection of Monatin, Tryptophan, Alanine, and Glutamate

This example describes methods used to detect the presence of monatin, tryptophan and glutamate. It also describes a method for the separation and detection of the four stereoisomers of monatin.

LC/MS/MS Multiple Reaction Monitoring ("MRM") Analysis of Monatin and Tryptophan Analyses of mixtures for monatin and tryptophan derived from in vitro or in vivo biochemical reactions were performed using a Waters/Micromass liquid chromatography-tandem mass spectrometry (LC/MS/MS) instrument including a Waters 2795 liquid chromatograph with a Waters 996 Photo-Diode Array (PDA) absorbance monitor placed in series between the chromatograph and a Micromass Quattro Ultima triple quadrupole mass spectrometer. LC separations were made using an Xterra MS $C_8$ reversed-phase chromatography column, 2.1 mm×250 mm at 40° C. The LC mobile phase consisted of A) water containing 0.05% (v/v) trifluoroacetic acid and B) methanol containing 0.05% (v/v) trifluoroacetic acid.

The gradient elution was linear from 5% B to 35% B, 0-4 min, linear from 35% B to 60% B, 4-6.5 min, linear from 60% B to 90% B, 6.5-7 min, isocratic at 90% B 7-11 min, linear from 90% B to 95% B, 11-12 min, linear from 95% B to 5% B, 12-13 min, with a 2 min re-equilibration period between runs. The flow rate was 0.25 mL/min, and PDA absorbance was monitored from 200 nm to 400 nm. All parameters of the ESI-MS were optimized and selected based on generation of protonated molecular ions ($[M+H]^+$) of the analytes of interest, and production of characteristic fragment ions. The following instrumental parameters were used for LC/MS/MS Multiple Reaction Monitoring (MRM) analysis of monatin and tryptophan: Capillary: 3.5 kV; Cone: 40 V; Hex 1: 20 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5 V; Collision Energy: 8; Exit: 1V; Low mass resolution (Q2): 15; High mass resolution (Q2): 15; Ion energy (Q2): 3.5; Multiplier: 650. Five monatin-specific parent-to daughter MRM transitions are used to specifically detect monatin in in vitro and in vivo reactions. The transitions monitored are 293.1 to 158.3, 293.1 to 168.2, 293.1 to 211.2, 293.1 to 230.2, and 293.1 to 257.2. Tryptophan is monitored with the MRM transition 204.7 to 146.4. For internal standard quantification of monatin and tryptophan, four calibration standards containing four different ratios of each analyte to d5-tryptophan and d5-monatin, are analyzed. These data are subjected to a linear least squares analysis to form a calibration curve for monatin and tryptophan. To each sample is added a fixed amount of d5-tryptophan and d5-monatin (d5-monatin was synthesized from d5-tryptophan according to the methods from WO03/091396 A2), and the response ratios (monatin/d5-monatin; tryptophan/d5-tryptophan) used in conjunction with the calibration curves described above to calculate the amount of each analyte in the mixtures.

Accurate Mass Measurement of Monatin.

High resolution MS analysis was carried out using an Applied Biosystems-Perkin Elmer Q-Star hybrid quadrupole/time-of-flight mass spectrometer. The measured mass for protonated monatin used tryptophan as an internal mass calibration standard. The calculated mass of protonated monatin, based on the elemental composition $C_{14}H_{17}N_2O_5$ is 293.1137. Monatin produced using the biocatalytic process described in Examples 2 and 3 showed a measured mass of 293.1144. This is a mass measurement error of less than 2 parts per million (ppm"), providing conclusive evidence of the elemental composition of monatin produced enzymatically.

Chiral LC/MS/MS ("MRM") Measurement of Monatin

Determination of the stereoisomer distribution of monatin in in vitro and in vivo reactions was accomplished by derivitization with 1-fluoro-2-4-dinitrophenyl-5-L-alanine amide ("FDAA"), followed by reversed-phase LC/MS/MS MRM measurement.

Derivitization of Monatin with FDAA

To 50 μL of sample or standard was added 200 μL of a 1% solution of FDAA in acetone. Forty μL of 1.0 M sodium bicarbonate was added, and the mixture incubated for 1 h at 40° C. with occasional mixing. The sample was removed and cooled, and neutralized with 20 μL of 2.0 M HCl (more HCl may be required to effect neutralization of a buffered biological mixture). After degassing is complete, samples were ready for analysis by LC/MS/MS.

LC/MS/MS Multiple Reaction Monitoring for the Determination of the Stereoisomer Distribution of Monatin in In Vitro and In Vivo Reactions.

Analyses were performed using the LC/MS/MS instrumentation described above. LC separations capable of separating all four stereoisomers of monatin (specifically FDAA-monatin) were performed on a Phenomenex Luna 2.0×250 mm (3 μm) C18 reversed phase chromatography column at 40° C. The LC mobile phase consisted of A) water containing 0.05% (mass/volume) ammonium acetate and B) acetonitrile. The elution was isocratic at 13% B, 0-2 min, linear from 13% B to 30% B, 2-15 min, linear from 30% B to 80% B, 15-16 min, isocratic at 80% B 16-21 min, and linear from 80% B to 13% B, 21-22 min, with a 8 min re-equilibration period between runs. The flow rate was 0.23 mL/min, and PDA absorbance was monitored from 200 nm to 400 nm. All parameters of the ESI-MS were optimized and selected based on generation of deprotonated molecular ions ($[M-H]^-$) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1: 10 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5V; Collision Energy: 20; Exit: 1V; Low mass resolution (Q2): 12; High mass resolution (Q2): 12; Ion energy (Q2): 3.0; Multiplier: 650. Three FDAA-monatin-specific parent-to daughter transitions are used to specifically detect FDAA-monatin in in vitro and in vivo reactions. The transitions are 543.6 to 268.2, 543.6 to 499.2, and 543.6 to 525.2. Identification of FDAA-monatin stereoisomers is based on chromatographic retention time as compared to purified synthetic monatin stereoisomers, and mass spectral data.

Liquid Chromatography-Post Column Fluorescence Detection of Amino Acids Including Glutamate and Alanine Liquid chromatography with post-column fluorescence detection for the determination of glutamate in in vitro and in vivo reactions was performed on a Waters 2690 LC system or equivalent combined with a Waters 474 scanning fluorescence detector, and a Waters post-column reaction module. LC separations were performed on an Interaction-Sodium loaded ion exchange column at 60° C. Mobile phase A was Pickering Na 328 buffer (Pickering Laboratories, Inc.; Mountain View, Calif.). Mobile phase B was Pickering Na 740 buffer. The gradient elution was from 0% B to 100% B, 0-20 min, isocratic at 100% B, 20-36 min, and linear from 100% B to 0% B, 36-37 min, with at least an 8 min re-equilibration period between runs, depending on sample matrix. The flow rate for the mobile phase was 0.5 mL/min. The flow rate for the OPA post-column derivitization solution was 0.5 mL/min. The fluorescence detector settings were EX 338 nm and Em 425 nm. Norleucine was employed as an internal standard for the analysis. Identification of amino acids was based on chromatographic retention time data for purified standards.

Detection of L- and D-Amino Acids by LC/MS/MS

Samples containing a mixture of L- and D-amino acids such as tryptophan, glutamate, and aspartate from biochemical reaction experiments were first treated with formic acid to denature protein. The sample was then centrifuged and filtered through a 0.45 μm nylon syringe filter prior to LC/MS/MS analysis. Identification of L- and D-amino acids was based on retention time and mass selective detection. LC separation was accomplished by using Waters 2690 liquid chromatography system and an ASTEC 2.1 mm×250 mm Chirobiotic TAG chromatography column with column temperature set at 45° C. LC mobile phase A and B were 0.25% acetic acid and 0.25% acetic acid in methanol respectively. Isocratic elution of 60% mobile phase A and 40% B with flow rate of 0.25 ml/min. was set up for glutamate; whereas 30% mobile phase A and 70% B with flow rate of 0.3 ml/min was set up for aspartate and tryptophan.

The detection system for analysis of L- and D-amino acids included a Waters 996 Photo-Diode Array (PDA) detector and a Micromass Quattro Ultima triple quadrupole mass spectrometer. The PDA, scanning from 195 to 350 nm, was placed in series between the chromatography system and the mass spectrometer. Parameters for the Micromass Quattro Ultima triple quadrupole mass spectrometer operating in positive electrospray ionization mode (+ESI) were set as the following: Capillary: 3.0 kV; Cone: 20 V; Hex 1: 15 V; Aperture: 1 V; Hex 2: 0 V; Source temperature: 100° C.; Desolvation temperature: 350° C.; Desolvation gas: 530 L/h; Cone gas: 30 L/h; Low mass Q1 resolution: 12.5; High mass Q1 resolution: 12.5; Ion energy 1: 0.2; Entrance: −5; Collision: 8; Exit 1: 10; Low mass Q2 resolution: 12.5; High mass Q2 resolution: 12.5; Ion energy 2: 0.5; Multiplier: 650 V. MS/MS experiments with Multiple Reaction Monitoring (MRM) mode were set up to selectively monitor reaction transitions of 204.70 to 146.50, 147.8 to 84.2, 147.8 to 102.1, 134.00 to 74.30, and 134.00 to 88.2. Quantification of tryptophan, glutamate, and aspartate acids were based off signal responses of m/z=146.5, m/z=102.1, and m/z=88.2 respectively.

Production of Monatin and Monatin Precursor ("MP") for Standards and for Assays Production of Monatin A racemic mixture of R,R and S,S monatin was synthetically produced as described in U.S. Pat. No. 5,128,482.

The R,R and S,S monatin were separated by a derivatization and hydrolysis step. Briefly, the monatin racemic mixture was esterified, the free amino group was blocked with Cbz, a lactone was formed, and the S,S lactone was selectively hydrolyzed using an immobilized protease enzyme. The monatin can also be separated as described in Bassoli, A. et al., *Eur. J. Org. Chem.*, 8:1652-1658, (2005).

MP Production

R-MP was produced by the transamination of R,R monatin using AT-103 broad range D-aminotransferase (BioCatalytics) in 0.1 M potassium phosphate buffer, using sodium pyruvate as the amino acceptor. S-MP was produced by the transamination of S,S monatin using AT-102 L-aminotransferase (BioCatalytics) in 0.1 M potassium phosphate buffer, using sodium pyruvate as the amino acceptor. Both reactions were carried out at 30° C. and at a pH of approximately 8.0-8.3, for approximately 20 hours. Both compounds were purified using preparative scale HPLC with a Rohm and Haas (Philadelphia, Pa.) hydrophobic resin (XAD™ 1600), eluting in water. Samples containing greater than 90% purity monatin precursor were collected and freeze-dried.

Example 2

Production of Monatin from Indole-3-Pyruvate

AT-103 transaminase was part of a transaminase library purchased from BioCatalytics (Pasadena, Calif.) and the enzyme was tested for production of monatin in coupled reactions using the ProA aldolase from *C. testosteroni*. The aldolase was prepared as described in WO 03/091396 A2. AT-103 is a broad specificity D-transaminase (EC 2.6.1.21) from a *Bacillus* species that requires a D-amino acid (such as D-glutamate, D-aspartate, or D-alanine) as the amino acid donor. Enzymes and additional components/substrates were added directly to the reaction buffer provided in the kit, which contained 100 mM potassium phosphate buffer pH 7.5, 100 mM amino donor, and 0.1 mM pyridoxal-5'-phosphate ("PLP"). To one mL of reaction buffer were added: 4 mg indole-3-pyruvate, 20 mg pyruvate, approximately 50 μg ProA provided in a cellular extract, 1 μL 2 M $MgCl_2$, and 2 mg of aminotransferase enzyme. Reactions were performed in duplicate. The reactions were incubated overnight at 30° C. with gentle shaking (100 rpm). The samples were filtered and submitted for reversed-phase LC/MS/MS analysis as described in Example 1. The results indicated that approximately 370 μg/mL monatin were produced using AT-103 enzyme. The results were further analyzed to determine ratios of S,R/R,S versus R,R/S,S monatin, on the basis of the peak areas of the two stereoisomer pools that resolve during the chromatographic separation. Of the total monatin produced by AT-103, 69% was R,R/S,S monatin in comparison to the mixed isomers. This enzyme is homologous to the *Bacillus subtilis* DAT enzyme described in WO 03/091396 A2, which is known to have a broad specificity for D-amino acids. Chiral analysis was performed using the FDAA methodology described in Example 1, which verified that the D-aminotransferase was making predominantly R,R monatin, and some S,R monatin as expected. Further transamination experiments with S,S monatin or R,R monatin and α-ketoglutarate as substrates verified that the BioCatalytics enzyme was highly selective for the D-configuration at carbon 4, as expected. In these experiments, no glutamate was detected in the reaction with S,S monatin and α-ketoglutarate as substrates.

To decrease the amount of S,S monatin or R,S monatin produced as byproducts in coupled reactions with AT-103 (the broad range D-transaminase) and the ProA aldolase, the aldolase was purified using His-Bind cartridges, following manufacturer's protocols (Novagen, Madison, Wis.). The purified enzyme preferably should not contain wildtype L-aminotransferase activities that can be present in cellular extracts (such as the native *E. coli* AspC or TyrB activities). The His-Bind eluent was desalted to remove imidazole using PD-10 columns (G25 Sephadex, Amersham-Pharmacia) and was eluted in 50 mM Tris-Cl, pH 7. Experiments were carried out in duplicate in a volume of 1 mL and contained 100 mM Tris-Cl buffer, pH 7.8, 50 μg ProA aldolase, 4 mg indole-3-pyruvate, 1 or 2 mg D-aminotransferase, 200 mM sodium pyruvate, 2 mM $MgCl_2$, 3 mM potassium phosphate, 0.1 mM PLP, and 14.7 mg of D-glutamate. The tubes were incubated at 30° C. with gentle shaking. Two-hour time points were taken and frozen immediately at −20° C. The pH was adjusted at two hours from 5 to between 7-8 using NaOH, and the assays were incubated overnight. Samples were filtered and analyzed for monatin as described in Example 1. The two-hour samples did not have detectable amounts of monatin, probably due to the low pH. The overnight samples contained approximately 190 ng/mL monatin when 1 mg of D-aminotransferase was used, and approximately 84% was R,R monatin and 16% was S,R monatin. When 2 mg of D-aminotransferase were used, 540 ng/mL monatin was produced, approximately 71% was R,R monatin.

Similar experiments were conducted using Biocatalytics Aminotransferase buffer, which contained 100 mM potassium phosphate pH 7.5, 0.1 mM PLP, and 100 mM D-glutamate. Solid indole-3-pyruvate and D-aminotransferase were added as above. ProA aldolase (50 μg), $MgCl_2$, and 50 mM pyruvate were added from stock solutions. The assays were treated as above, although no pH adjustment was required in this case. A negative control was done with just the BioCatalytics supplied enzyme and buffer, which did not contain monatin. The experimental results are shown in Table 1.

TABLE 1

Production of Monatin from Indole-3-Pyruvate in Phosphate Buffer

| Mg D-Aminotransferase | Time (hours) | Total Monatin (ng/mL) | % R,R |
|---|---|---|---|
| 0 | 2 | 0 | n/a |
| 1 | 2 | 6780 | not determined |
| 2 | 2 | 13170 | 55% |
| 0 | 16 | 0 | n/a |
| 1 | 16 | 15000 | not determined |
| 2 | 16 | 28930 | 51% |

The production of monatin in phosphate buffer is clearly higher than that in Tris buffered systems.

To compare activities of the cloned *B. subtilis* DAT from WO 03/091396 A2 with the BioCatalytics enzyme (AT-103) additional assays were done. The *B. subtilis* dat gene was also subcloned into pET30a to remove the His-6 tag. Untagged and tagged enzyme were produced in BL21(DE3), as described in WO 03/091396 A2. Cellular extracts were made and total protein assays were done to estimate protein concentration as described previously. Duplicate one mL reactions were done which contained: 500 μg D-aminotransferase, 50 μg ProA aldolase, 100 mM potassium phosphate pH 7.5, 3 mM $MgCl_2$, 4 mg indole-3-pyruvate, 200 mM sodium pyruvate, 7.35 mg (50 mM) D-glutamate, and 0.1 mM PLP. Samples were incubated at 30° C. for 1 hour, 2 hours, and overnight, and were filtered for LC/MS/MS analysis. The samples contained only the S,R and R,R stereoisomers of monatin, as determined by the FDAA derivitization protocol described in Example 1. The results are summarized in Table 2 below. The % RR was determined by peak areas that were separated by reversed phase chromatography.

TABLE 2

Comparison of D-Aminotransferase Enzymes

| Enzyme | Time (Hours) | Monatin (ppb) | % RR Monatin |
|---|---|---|---|
| *B. sub* DAT-HIS | 1 | 512 | not determined |
| *B. sub* DAT untagged | 1 | 1056 | not determined |
| BioCatalytics AT-103 | 1 | 2353 | not determined |
| *B. sub* DAT-HIS | 2 | 894 | ~80-90% |
| *B. sub* DAT untagged | 2 | 1913 | ~80% |
| BioCatalytics AT-103 | 2 | 6887 | 92.5% |
| *B. sub* DAT-HIS | 16 | 3014 | 31 |
| *B. sub* DAT untagged | 16 | 5612 | 33 |
| BioCatalytics AT-103 | 16 | 16131 | 66 |

The removal of the HIS-6 tag appears to have improved the activity of the *B. subtilis* D-aminotransferase; however, the BioCatalytics D-aminotransferase homolog clearly had the highest activity. It also showed greater substrate preference for the R-monatin precursor. Increased incubation times appear to reduce the enantiomeric excess of R,R monatin that is produced.

Because the *Bacillus* D-aminotransferase enzymes have a preference for pyruvate as an amino acceptor, and D-alanine as an amino donor, it was expected that D-alanine could be utilized as the amino donor for conversion of MP to monatin with similar or better results. Duplicate one mL reactions were done which contained: 500 μg D-aminotransferase, 50 μg purified ProA aldolase, 100 mM potassium phosphate pH 7.5, 3 mM $MgCl_2$, 4 mg indole-3-pyruvate, 100 mM sodium pyruvate, 25 mM D-glutamate or D-alanine, and 0.1 mM PLP. Samples were incubated for 2 hours, and treated as above prior to analysis. When D-alanine was used as the amino donor, slightly higher levels of monatin were produced (23 versus 21 ppm) as expected. Additionally, it is expected that high concentrations of pyruvate may inhibit the transamination step, thus dosing in smaller amounts of pyruvate over time may improve the overall rate of monatin production. One can see from the above data that even though one-half of the pyruvate was used in this case compared to the above table, significantly more monatin was produced. Even though ProA aldolases in the literature were reported to produce primarily S-enantiomers of aldol condensation products, the ProA aldolase used in this study clearly makes a high percentage of R-MP and in coupled assays produces up to 92% R,R monatin. The high percentage of R,R monatin is not due to D-aminotransferase selectivity, as was shown in Example 19.

Example 3

Production of R,R Monatin from D-Tryptophan

The following were added per 1 mL of reaction mixture: approximately 60 μg *C. testosteroni* ProA aldolase (supplied in cellular extracts, as described in WO 03/091396 A2), 4 mM $MgCl_2$, 50 mM D-tryptophan, 0.5 mg BioCatalytics D-aminotransferase (AT-103), 100 mM sodium pyruvate, 100 mM potassium phosphate buffer pH 7.5 or 100 mM sodium acetate buffer pH 8, 0.05 mM PLP, 3 mM potassium phosphate (only to the acetate reactions), and 10 mM α-ketoglutarate. Experiments were run in duplicate, with negative controls in which no aldolase was added. Samples were incubated overnight (20 hours) at 30° C. with gentle shaking. The actual pH of the sodium acetate samples was approximately 5, while the final pH for the phosphate buffered samples was approximately 7. None of the aldolases appeared to have significant activity at pH 5; the sample containing ProA aldolase was slightly above the negative control but probably not above experimental error. In potassium phosphate, the ProA aldolase produced 73.4 ppm monatin with a ratio of R,R:S,R of 1.7:1 (~63% R,R from D-tryptophan).

Because the *Bacillus* D-aminotransferase enzymes have a preference for pyruvate as an amino acceptor, and D-alanine as an amino donor, it was expected that the addition of alpha-ketoglutarate is unnecessary when producing R,R or S,R monatin from D-tryptophan. The above experiment was repeated (in 100 mM potassium phosphate buffer) using purified ProA aldolase (50-60 μg), and an incubation time of 2.5 hours. Duplicate experiments were run, with and without alpha-ketoglutarate. When 10 mM alpha-ketoglutarate was added, 56.1 ppm monatin was formed using D-tryptophan as the substrate (79.5% R,R, 20.5% S,R). When alpha-ketoglutarate was omitted, 102.5 ppm monatin was formed (79% R,R, 21% S,R).

Comparison of Total Monatin Production and Isomeric Distribution for HMG Aldolases from *Sinorhizobium meliloti, C. testosteroni*, and the Aldolase of SEQ ID NO:22.

AT-103 transaminase (a broad specificity D-aminotransferase) was purchased from BioCatalytics (Pasadena, Calif.) and either this enzyme or the *B. sphaericus* recombinant enzyme produced in Example 18 was used in coupled reactions with HMG aldolases to produce monatin from D-tryptophan and pyruvate as described in U.S. Published Application No. 2005282260.

The HMG aldolases from *C. testosteroni* (ProA) and *S. meliloti* were prepared and purified as described in U.S. Publication No. 20040063175 and WO 03091396 A2. To produce test quantities of the aldolase of SEQ ID NO:22, a 50 mL culture was grown in Luria-Bertani ("LB") medium containing ampicillin (100 μg/mL), to an $OD_{600}$ of approximately 0.5. The strain containing the SEQ ID NO:21 construct was induced with 200 μg/L anhydrotetracycline. The cells were grown 5 hours post-induction, and cellular extracts were prepared according to manufacturer's protocols (Novagen, Bugbuster reagent). Benzonuclease and protease inhibitor were also added. The soluble proteins in the cellular extracts were separated on a BioRad Laboratories Experion Automated Electrophoresis Station and analyzed for concentration and percent expression using the Experion Software version 1.1.98.0. The aldolase of SEQ ID NO:22 was used as a crude (unpurified) enzyme for the reactions below.

The following were added per 1 mL of reaction mixture: approximately 50 μg aldolase, 4 mM $MgCl_2$, 50 mM D-tryptophan, 0.5 mg purified *B. sphaericus* D-aminotransferase, 200 mM sodium pyruvate, 100 mM potassium phosphate buffer pH 7.5, and 0.05 mM PLP. Experiments were run in duplicate, with negative controls in which no aldolase was added. Samples were incubated 1 hour and overnight (18 hours) at 30° C. with gentle shaking. Small amounts of monatin (<0.5 ppm) are produced without aldolase in overnight reactions, due to non-enzymatic reactions catalyzed by magnesium and phosphate. Those values were subtracted from the numbers shown below, and averaged results are shown. The only stereoisomers detected when producing monatin using these methods are R,R and S,R. The percent R,R is listed below, and was determined by reversed-phase LC peak area.

TABLE 3

Total Monatin Produced from D-Tryptophan and % R,R

| Enzyme (timepoint) | Total Monatin (ppm) | % R,R Monatin |
|---|---|---|
| *C. testosteroni* ProA (1 hour) | 16.63 | 86.45 |
| *C. testosteroni* ProA (18 hours) | 86.86 | 63.1 |
| *S. meliloti* HMG (1 hour) | 20.5 | 96.7 |
| *S. meliloti* HMG (18 hours) | 88.3 | 89.9 |
| SEQ ID NO: 22 (1 hour) | 14.70 | 100 |
| SEQ ID NO: 22 (18 hours) | 95.14 | 97.35 |

The 18 hour sample for the aldolase of SEQ ID NO:22 was also analyzed for stereoisomeric distribution by the FDAA derivatization method listed in Example 1, which yielded a result of 94.9% R,R and 5.1% S,R monatin. The aldolase of SEQ ID NO:22 has a higher enantiospecificity for production of R-MP as compared to *C. testosteroni* and *S. meliloti* HMG aldolases.

The same experiments were done, side by side, using L-tryptophan as the starting substrate and coupling the aldolases with HexAspC broad specificity L-aminotransferase produced and purified as described in U.S. Published Application No. 2005282260. These reactions should yield primarily S,S monatin and R,S monatin. The reactions were also supplemented with 10 mM alpha-ketoglutarate as the amino acceptor for L-tryptophan transamination. Again, duplicate results are averaged below for total monatin (subtracting background levels without aldolase present), and percent S,S monatin is shown based on reversed phase LC peak area. In some cases, because the aldolases are quite R-specific and produce little total monatin, the reversed phase estimates of stereoisomeric distribution are less accurate due to some tailing of the tryptophan peak that can co-elute with the S,S/R,R monatin peak. The trends are still informative in comparing R-specificity of the aldolases. Results from further analysis using the FDAA derivatization method are shown in parentheses for several samples, and are more accurate. Total monatin numbers above approximately 400 ppm are higher than the linear range of the scale of the standards used to quantitate the results, so are qualitative results. The *C. testosteroni* ProA aldolase typically produces 95-100% S,S monatin, as shown in U.S. Published Application No. 2005282260.

TABLE 4

Total Monatin Produced from L-Tryptophan and % S,S

| Enzyme (timepoint) | Total Monatin (ppm) | % S,S Monatin |
|---|---|---|
| *C. testosteroni* ProA (1 hour) | 440.35 | 92.5 |
| *C. testosteroni* ProA (18 hour) | 958.3 | 92.2 |
| *S. meliloti* HMG (1 hour) | 45.9 | 66.3 |
| *S. meliloti* HMG (18 hour) | 108.1 | 61.4 |
| SEQ ID NO: 22 (1 hour) | 17.85 | 55.1 (18.9) |
| SEQ ID NO: 22 (18 hour) | 135.5 | 27.3 (19.1) |

One can see that the R-specificity of the aldolase of SEQ ID NO:22 is quite high compared to the benchmark ProA enzyme. This R-specificity is also reflected in the low % S,S monatin produced, despite the high degree of specificity of the HexAspC aminotransferase for S-MP in these reactions. Again the *S. meliloti* HMG aldolase falls between the *C. testosteroni* ProA aldolase and the aldolase of SEQ ID NO:22 in terms of R-specificity, based on the levels of S,S monatin produced. The total monatin numbers, when comparing S,S monatin production versus R,R monatin production, are not indicative of the aldolase activity. The D-aminotransferase is less active than HexAspC for MP transamination reactions, particularly at the concentrations of MP that are present in these reactions.

For further comparison of the aldolase of SEQ ID NO:22 to the ProA enzyme from *C. testosteroni*, varying ratios of D-aminotransferase to aldolase were utilized in reactions starting with D-tryptophan (no duplicate samples for these experiments). The reactions were carried out as described above. For the reactions in which the aldolase concentration was kept constant, approximately 50 μg aldolase was used. For reactions in which the amount of D-aminotransferase was kept constant, 0.5 mg was used. For the 2 and 10 mg/mL concentration of D-aminotransferase, lyophilized enzyme was used. For the 2 highest D-aminotransferase concentrations, duplicates were run.

TABLE 5

Effect of D-Aminotransferase Concentration on R,R Monatin Production

| Aldolase | Concentration of D-Aminotransferase | Time | Total Monatin (approximate ppm) | % R,R Monatin |
|---|---|---|---|---|
| SEQ ID NO: 22 | 0.25 mg/mL | 1 hour | 2 | 100 |
| SEQ ID NO: 22 | 0.25 mg/mL | overnight | 141 | 97.1 |
| SEQ ID NO: 22 | 0.5 mg/mL | 1 hour | 8 | 100 |
| SEQ ID NO: 22 | 0.5 mg/mL | overnight | 273 | 96.5 |
| SEQ ID NO: 22 | 1 mg/mL | 1 hour | 34 | 100 |
| SEQ ID NO: 22 | 1 mg/mL | overnight | 638 | 96.5 |
| SEQ ID NO: 22 | 2 mg/mL | 1 hour | 979 | 100 |
| SEQ ID NO: 22 | 2 mg/mL | overnight | 1910 | 97.3 |
| SEQ ID NO: 22 | 10 mg/mL | 1 hour | 2930 | 99.1 |
| SEQ ID NO: 22 | 10 mg/mL | overnight | 2950 | 96.5 |
| *C. testosteroni* ProA | 0.25 mg/mL | 1 hour | 4 | 78.7 |
| *C. testosteroni* ProA | 0.25 mg/mL | overnight | 257 | 61.1 |
| *C. testosteroni* ProA | 0.5 mg/mL | 1 hour | 25 | 79.0 |
| *C. testosteroni* ProA | 0.5 mg/mL | overnight | 480 | 62.5 |
| *C. testosteroni* ProA | 1 mg/mL | 1 hour | 74 | 73.8 |
| *C. testosteroni* ProA | 1 mg/mL | overnight | 810 | 68.1 |
| *C. testosteroni* ProA | 2 mg/mL | 1 hour | 325 | 73.1 |
| *C. testosteroni* ProA | 2 mg/mL | overnight | 2220 | 71.9 |
| *C. testosteroni* ProA | 10 mg/mL | 1 hour | 2910 | 59.7 |
| *C. testosteroni* ProA | 10 mg/mL | overnight | 2450 | 67.5 |

For monatin levels above 400 ppm, the results are not in the linear range of the standard curve and are approximate values only. The maximum amount of R,R monatin produced, when diluted appropriately, was approximately 1100 ppm. FDAA stereoisomeric analysis was done for the aldolase of SEQ ID NO:22 with 10 mg/mL D-aminotransferase samples. At two hours, the sample contained 98.5% R,R monatin. At 17 hours, the sample contained 95.9% R,R monatin. The aldolase of SEQ ID NO:22 produced high percentages of R,R monatin, even after long incubation times and using large amounts of aminotransferase. If adequate D-aminotransferase is supplied, the aldolase of SEQ ID NO:22 produces as much total monatin as *C. testosteroni* ProA aldolase, indicating a similar specific activity.

TABLE 6

Effect of Aldolase Concentration on R,R Monatin Production

| Aldolase | Concentration of Aldolase | Time | Total Monatin (ppm) | % R,R Monatin |
|---|---|---|---|---|
| SEQ ID NO: 22 | 25 μg/mL | 1 hour | 7.0 | 100 |
| SEQ ID NO: 22 | 25 μg/mL | overnight | 275 | 97.4 |
| SEQ ID NO: 22 | 50 μg/mL | 1 hour | 9.0 | 97.3 |
| SEQ ID NO: 22 | 50 μg/mL | overnight | 334 | 95.7 |
| SEQ ID NO: 22 | 100 μg/mL | overnight | 297 | 93.3 |
| *C. testosteroni* ProA | 25 μg/mL | 1 hour | 16 | 78.2 |
| *C. testosteroni* ProA | 25 μg/mL | overnight | 491 | 73.2 |
| *C. testosteroni* ProA | 50 μg/mL | 1 hour | 18 | 64.1 |
| *C. testosteroni* ProA | 50 μg/mL | overnight | 437 | 63.0 |
| *C. testosteroni* ProA | 100 μg/mL | 1 hour | 26 | 62.5 |
| *C. testosteroni* ProA | 100 μg/mL | overnight | 513 | 61.5 |

When the aldolase concentration is varied, there is not much of an increase in total monatin. The percent R,R decreases with time and also with aldolase concentration, particularly when the D-aminotransferase is limiting.

To further examine the R-specificity of the aldolases tested, experiments were done starting with L-tryptophan and HexAspC aminotransferase, which was produced and purified as described in U.S. Published Application No. 2005282260. The HexAspC shows a strong selectivity for transamination of S-MP versus R-MP, thus percentages above 50% R,S monatin indicate a highly stereospecific aldolase. Ten mM alpha-ketoglutarate was supplied as an amino acceptor; however, at high concentrations, pyruvate is also utilized by the L-aminotransferase. In these reactions, typically only S,S and R,S monatin are produced within the limits of detection of the FDAA derivatization protocol.

TABLE 7

Effect of L-Aminotransferase Concentration on S,S Monatin Production

| Aldolase | Concentration of L-Aminotransferase | Time | Total Monatin (approximate ppm) | % S,S Monatin |
|---|---|---|---|---|
| SEQ ID NO: 22 | 0.25 mg/mL | 1 hour | 13 | 33.8 |
| SEQ ID NO: 22 | 0.25 mg/mL | overnight | 127 | 34.2 |
| SEQ ID NO: 22 | 0.5 mg/mL | 1 hour | 31 | 30.9 |
| SEQ ID NO: 22 | 0.5 mg/mL | overnight | 272 | 26.8 |
| SEQ ID NO: 22 | 1 mg/mL | 1 hour | 34 | 20.3 |
| SEQ ID NO: 22 | 1 mg/mL | overnight | 385 | 23.5 |
| *C. testosteroni* ProA | 0.25 mg/mL | 1 hour | 523 | 94.2 |
| *C. testosteroni* ProA | 0.25 mg/mL | overnight | 1817 | 93.7 |
| *C. testosteroni* ProA | 0.5 mg/mL | 1 hour | 602 | 91.8 |
| *C. testosteroni* ProA | 0.5 mg/mL | overnight | 2122 | 89.9 |
| *C. testosteroni* ProA | 1 mg/mL | 1 hour | 873 | 90.2 |
| *C. testosteroni* ProA | 1 mg/mL | overnight | 1237 | 82.6 |

TABLE 8

Effect of Aldolase Concentration on S,S Monatin Production

| Aldolase | Concentration of Aldolase | Time | Total Monatin (ppm) | % S,S Monatin |
|---|---|---|---|---|
| SEQ ID NO: 22 | 25 μg/mL | 1 hour | 11 | 25.1 |
| SEQ ID NO: 22 | 25 μg/mL | overnight | 112 | 20.0 |
| SEQ ID NO: 22 | 50 μg/mL | 1 hour | 18 | 31.8 |
| SEQ ID NO: 22 | 50 μg/mL | overnight | 160 | 27.0 |
| SEQ ID NO: 22 | 100 μg/mL | 1 hour | 33 | 33.2 |
| SEQ ID NO: 22 | 100 μg/mL | overnight | 238 | 41.4 |
| *C. testosteroni* ProA | 25 μg/mL | 1 hour | 305 | 86.4 |
| *C. testosteroni* ProA | 25 μg/mL | overnight | 1094 | 87.5 |

TABLE 8-continued

Effect of Aldolase Concentration on S,S Monatin Production

| Aldolase | Concentration of Aldolase | Time | Total Monatin (ppm) | % S,S Monatin |
|---|---|---|---|---|
| *C. testosteroni* ProA | 50 μg/mL | 1 hour | 575 | 90.9 |
| *C. testosteroni* ProA | 50 μg/mL | overnight | 1449 | 89.5 |
| *C. testosteroni* ProA | 100 μg/mL | 1 hour | 817 | 93.6 |
| *C. testosteroni* ProA | 100 μg/mL | overnight | 1360 | 89.7 |

For aldolases that are highly R-specific, such as SEQ ID NO:22, less total monatin is produced and increasing the amount of aldolase does increase total monatin (as well as % S,S). These aldolases produce less S-MP substrate, the preferred substrate for the L-aminotransferase used. For enzymes that are less R-specific, such as ProA, increasing aldolase does not significantly improve total monatin production or % S,S monatin. Increasing the amount of L-aminotransferase added decreases the percentage of S,S monatin produced.

The activity and specificity of the aldolase of SEQ ID NO:22 was further studied in two buffer systems—100 mM potassium phosphate, as above, and 100 mM 3-(N-morpholino)propanesulfonic acid ("MOPS") (with 3 mM potassium phosphate). The assays were performed as above, using 1 mg/ml AT-103 D-aminotransferase and 50 mM D-tryptophan. Experiments were run in duplicate for 4.5 hours. The aldolase of SEQ ID NO:22 produced 116 ppm monatin and 99.1% R,R monatin in potassium phosphate (FDAA derivatization method). In MOPS, the aldolase of SEQ ID NO:22 produced 75.5 ppm monatin, and 96.2% was R,R monatin. The background levels of monatin produced in MOPS, without the aldolase of SEQ ID NO:22, were significantly higher, and the percent R,R was lower with MOPS, even in the controls. It is possible that the D-aminotransferase selectivity and activity are affected by the presence of the MOPS.

Subcloning of SEQ ID NO:21

The aldolase gene of SEQ ID NO:21 was received from Diversa Corp. SEQ ID NO:21 was part of an environmental library which was screened by Diversa Corp. for aldolase genes. However, the aldolase gene of SEQ ID NO:21 may be reconstructed by any method known to a person of ordinary skill in the art. For example, the aldolase gene of SEQ ID NO:21 may be reconstructed utilizing assembly PCR methods, as described in Examples 10, 18 and 19.

The following primers were used to PCR amplify the aldolase gene (SEQ ID NO:21): 5'-gaggagctcgagtcagacgtatttcagtcctttttc-3' (SEQ ID NO:23) and 5'-agaagacatatgatttatcagccggggac-3' (SEQ ID NO:24). The resulting PCR product was digested with XhoI and NdeI to cut at the sites that had been engineered into the primers. The fragment was gel purified (QIAquick Gel extraction Kit (Qiagen, Velencia, Calif.)) and ligated (using T4 DNA ligase) with pET28b that had been digested with XhoI and NdeI and gel purified. The ligation was transformed into TOP10F' chemically competent cells. Colonies growing on the plates were screened for inserts and several isolates with inserts were submitted for DNA sequence analysis (Agencourt, Beverly, Mass.).

Purification of the Aldolase of SEQ ID NO:22

Confirmed aldolase clones were transformed into either BL21 (DE3) or BL21 (DE3) pLysS. Overnight cultures grown with the appropriate antibiotic were diluted into fresh media (typically 1:100) and grown to an $OD_{600}$ ~0.6 with aeration at 37° C. Cultures were then induced with 1 mM isopropyl thiogalacatoside ("IPTG") and shifted to 30° C. (with aeration) and incubation was continued overnight. Cells were harvested by centrifugation. The cell pellet was typically subjected to one freeze thaw cycle to assist with cell lysis. The cell pellet was lysed in BugBuster and Benzoase (Novagen, Madison, Wis.) (according to the manufacturer's protocol). Cell debris was removed by centrifugation. The crude protein extract was applied to a HisBind column (Novagen, Madison, Wis.) that had been prepared according to the manufacturer's protocol. The column was washed and protein was eluted according to the manufacturer's protocol. The purified protein was desalted with PD-10 columns (GE Healthcare, Piscataway, N.J.). The buffer used for the exchange was 50 mM potassium phosphate pH 7.5, 100 mM NaCl, 4 mM $MgCl_2$. Purified protein was concentrated with Amicon centrifugal concentrators (Millipore, Billerica, Mass.).

Example 4

(1) Tryptophan Racemase

R,R-monatin has been produced using D-aminotransferase and an aldolase when D-tryptophan was used as the starting material (Example 3). That notwithstanding, L-tryptophan may be a preferred starting material for several reasons. For example, L-tryptophan may be less expensive and more readily available than D-tryptophan. This disclosure describes several methods for obtaining an active tryptophan racemase. Yields of R,R monatin are improved by using an R-specific aldolase, i.e., an aldolase that preferentially or selectively produces R-MP. FIGS. 1 and 2 illustrate methods for producing stereoisomerically-enriched R,R monatin from L-tryptophan using a tryptophan racemase, a D-aminotransferase and an R-specific aldolase.

A selection for a tryptophan racemase was created by constructing a strain that requires an active racemase for growth. A tryptophan auxotroph needs a source of L-tryptophan when grown on minimal medium. Supplementing the medium with D-tryptophan is one way to select for a racemase that converts D-tryptophan to L-tryptophan. The tryptophan auxotrophs were tested for growth on minimal medium supplemented with D-tryptophan. The strains, CAG18455 and CAG18579 from the Coli Genetic Stock Center and NRRL12264 (also $lipA^-$, λDE3 lysogenized, and cured of its plasmid), did not grow when supplemented with D-tryptophan but grew when supplemented with L-tryptophan. *E. coli* may be used as a host organism but other host organisms also may used, such as yeast, other bacteria, or other eukaryotic organisms. A tryptophan auxotroph (specifically NRRL12264 (also $lipA^-$, λDE3 lysogenized and cured of its plasmid)) will grow on D-tryptophan when it has been transformed with a D-aminotransferase. This confirms the ability of *E. coli* to transport D-tryptophan into the cell.

Salcher and Lingens described the presence of a tryptophan racemase in *Pseudomonas aurereofaciens* (ATCC15926). Salcher, O., and Lingens, F., *J. Gen. Microbiol.* 121:465-471 (1980). Tryptophan racemase has also been described in several plants including tobacco, beets, tomato, and wheat and the enzyme appears to be induced by conditions of osmotic stress or drought. Tryptophan racemase may play a role in *Sclerochiton ilicifolius* in the native monatin production pathway. To isolate this racemase activity, an expression library is constructed from ATCC15926 (or another organism with tryptophan racemase activity) and the library is transformed into the tryptophan auxotroph. A strain is selected that will grow using D-tryptophan as the tryptophan source. A similar method is also used to screen many strains with known racemases to look for a racemase with activity on D-tryptophan. Examples of racemases that may have activity on D-tryptophan include alanine, serine, and glutamate racemases. Yoshimura T., and Esaki, N., "Amino Acid Racemases: Functions and Mechanisms," *Journal of Bioscience and Bioengineering* 96, 103-109, (2003).

Alanine racemase is PLP dependent and has been cloned from *Salmonella typhimurium* (dadB gene). Other sources of alanine racemases are *Escherichia coli, Bacillus subtilis, Pseudomonas aeruginosa, Vibrio cholerae, Schizosaccaroyces pombe*, and *Bacillus cereus*. A basidiomycetous mushroom, *Lentinus edodes*, also contains a broad activity alanine racemase.

Serine racemase is also PLP dependent and is found in Eukaryotes (e.g. silkworm, rat brain, mouse brain cDNA), as well as in bacteria (*Enterococcus gallinarum*).

Glutamate racemase is PLP-independent and has been cloned from *Pediococcus pentosaceus, Bacillus pumilus, Lactobacillus fermenti, Lactobacillus brevis, E. coli, Aquifex pyrophilus*, and *Bacillus subtilis*. Some glutamate racemases are very specific and, consequently, even structurally similar amino acids aspartate, asparagine, and glutamine may not be substrates for the enzyme.

Aspartate racemases also exist and are PLP independent. Aspartate racemases are found in *Lactobacilli, Streptococcus* strains, and some archaea such as *Desulfurococcus* and *Thermococcus* strains. The bivalve mollusk *Scapharca brouhtonii* also contains an aspartate racemase.

Other racemases found in the literature include amino acid racemase (EC 5.1.1.10) from *Anabaena* sp. and *Pseudomonas striata*, proline racemase, and multifunctional phenylalanine racemase. Related epimerases or racemases are also being tested. Potential racemases are tested to make sure they are not D-tryptophan aminotransferases. The screening of potential racemases is done by sequence analysis and/or an enzyme assay. This screening method for selection of a tryptophan racemase is also used for other bacteria or archaea for which tryptophan racemase has been described, as well as for eukaryotic cDNA libraries that have been constructed in such a manor as to allow expression.

Enzymes that pass the test as a tryptophan racemase are screened for activity on monatin as described in Example 8. Ideally, one obtains an enzyme that is very specific for tryptophan and has little or no racemase activity on monatin.

A tryptophan racemase also may be evolved and/or improved (via mutagenesis or recombinant engineering) from an existing racemase, transaminase, or epimerase. Additionally, because crystal structures for alanine aminotransferases (and other aminotransferases) are known, these may be used as a basis for rational, structure based mutagenesis. The process described above is used as an initial selection for tryptophan racemase activity and as a screen for improved activity.

(2) Tryptophan Racemase Libraries

Construction of Libraries:

*Burkholderia pyrrocina* (ATCC15958) and *Pseudomonas chlororaphis* (ATCC15926) were obtained from the American Type Culture Collection. They were grown as recommended by ATCC and genomic DNA was prepared according to the method described in Mekalanos, J. J., "Duplication and amplification of toxin genes in *Vibrio cholerae*," *Cell* 35:253-263, (1983). The genomic DNA was partially digested with the Sau3AI restriction enzyme. 1-3 Kbp fragments were gel purified using a Qiagen QIAquick Gel Extraction Kit (Valencia, Calif.). The purified DNA was ligated into pTrc99a (Amersham, Piscataway, N.J.) that had been digested with BamHI and purified as above. The ligation was done at room temperature with overnight incubation using a 3:1 molar ratio of insert to vector. The ligated library was transformed into TOP10F' chemically competent cells (Invitrogen, Carlsbad, Calif.) and plated on LB medium with 100 μg/ml ampicillin. After overnight incubation of the transformation plates, colonies were scraped off of the plates, washed with liquid LB medium and an appropriate size cell pellet was mini-prepped using a Qiagen QIAquick mini-prep kit (Valencia, Calif.). Approximately 30,000 colonies were pooled and mini-prepped.

The pooled plasmid was transformed into CAG18455 (trpC83::Tn10, rph-1) or CAG18579 (trpC::Tn10kan, rph-1). Both strains are tryptophan auxotrophs so they will not grow on M9 minimal medium (Difco) unless the medium is supplemented with tryptophan. The transformants were plated on M9 minimal medium supplemented with D-tryptophan. This selects for a strain that can convert D-tryptophan to L-tryptophan.

Prior to transformation of the library, the strains were tested for growth on minimal medium with L- or D-tryptophan. The strains were tested for growth on minimal medium supplemented with D-tryptophan and no growth was observed. Both strains grew on identical medium supplemented with L-tryptophan instead of D-tryptophan. Additionally, a derivative of NRRL12264 (the strain used had been cured of the tryptophan operon plasmid, lysogenized with λDE3, and deleted for lipA, in addition to the other chromosomally encoded mutations (serB, ΔtrpED, tnaA2, aroP)) was transformed with a D-specific aminotransferase from *Bacillus subtilis* (WO 03/091396). The NRRL12264 strain could not grow on minimal medium supplemented with D-tryptophan, but grew on identical medium supplemented with L-tryptophan instead of D-tryptophan. Expression of the D-aminotransferase was driven by the T7 promoter. The transformed strain was able to grow on M9 minimal medium supplemented with D-tryptophan.

The colonies that grow on the D-tryptophan medium are screened. The plasmid is isolated and retransformed into the parent strain (CAG18455 or CAG18579) to confirm that growth on D-tryptophan medium is dependent on the plasmid and not on a host mutation. The nucleotide sequence of the plasmids that complement the tryptophan auxotrophy are analyzed. Clones that are determined to contain a tryptophan racemase gene are further analyzed.

The tryptophan racemase from other tissue sources is isolated in a similar fashion. There are literature reports of tryptophan racemase activity in both tobacco tissue culture cells (*Nicotiana tabacum* L. var. Wisconsin 38) (Miura, G. A., and Mills, S. E., "The conversion of D-tryptophan to L-tryptophan in cell cultures of tobacco," *Plant Physiol.* 47:483-487, (1974)) and in crude protein extracts of wheat (*Triticum aestivum*) (Rekoslavskaya, N. I., et al., "Synthesis and physiological function of D-tryptophan during wheat germination," *Russian J. Plant Physiol.* 44:196-203, (1997)). A cDNA expression library is made from tissue, as described in the literature, and the expression library is used to transform a tryptophan auxotroph as described above.

It would be expected that if the same strains are used and the same growth conditions are reproduced as described in the literature, the enzyme with tryptophan racemase activity could be isolated or the mRNA could be isolated and a cDNA expression library could be prepared that would contain a coding sequence for an enzyme with tryptophan racemase activity. For instance, certain growth stages or certain medium components may be required to induce cellular production of an enzyme with tryptophan racemase activity.

(3) Tryptophan Racemase Assay

Clones that are identified as potentially having a tryptophan racemase are transformed into a strain of *E. coli* commonly used for expression of recombinant proteins, such as BL21. The cells are grown in LB broth to an optical density at 600 nm of 0.4-0.6. The promoter driving expression of the racemase is induced with IPTG (0.1 mM final concentration). After induction, the cells are allowed to express the protein for 1-3 hours at 37° C. (with aeration). The cells are harvested and lysed by French press, sonication, or by chemical means (such as BugBuster (Novagen)). The lysed cells are centrifuged to remove the cell debris. The clarified extract is used directly in assays.

Varying amounts of extract is added to a solution such that the final concentration is 50 mM potassium phosphate (pH 7.0) and 2 mM L-tryptophan. Pyridoxal-5'-phosphate is added at a final concentration of 10 μM. The samples are incubated and then analyzed by LC/MS. The presence of a D-tryptophan peak when only L-tryptophan is used as a substrate indicates a positive result. D-tryptophan concentration should increase with increasing time until equilibrium is reached, and the rate should also increase with protein concentration until the concentration of enzyme is high enough that it is no longer saturated with substrate. D-tryptophan may also be converted to L-tryptophan as above.

A complementing gene may code for a D-aminotransferase. This transamination reaction requires an alpha-keto acid such as α-ketoglutarate, oxaloacetate, or pyruvate as an amino acceptor. These compounds will likely be present in a cell extract, usually in small amounts. These compounds may be removed using a PD-10 desalting column and the assay may still be performed in a crude extract. Likewise, a complementing gene may also code for a D-amino acid oxidase or D-amino acid dehydrogenase. These enzymes also require cofactors and cosubstrates that can be removed by a PD-10 desalting column. The tryptophan racemase activity is purified using conventional column chromatography. Finally, the open reading frame identified as a potential tryptophan racemase is cloned into an expression vector with an affinity tag. The potential tryptophan racemase is then purified by affinity chromatography. In either case the purified protein is used in enzyme assays essentially as described above.

(4) Reverse Genetic Engineering of Tryptophan Racemase

The tryptophan racemase may be purified from either plant or microbial sources by conventional protein purification techniques, including ammonium sulfate fractionation and conventional column chromatography. Once the protein has been purified such that a spot can be isolated on a 2-D gel, peptide microsequencing techniques or conventional Edman type amino acid sequencing are utilized (on the internet, see "golgi.harvard.edu/microchem/" for descriptions of the protocols and equipment typically used for this type of work). In some cases, however, the genome sequence of the organism cannot be used as a source of the protein for the protein purification because such sequence has not been determined yet. In that situation, the first set of degenerate primers may be designed based on sequence available from the closest known relative of the protein source. Degenerate PCR and genome walking is then be performed according to established protocols to isolate the tryptophan racemase coding sequence.

(5) Cloning of Alanine Racemase from *Geobacillus stearothermophillus*

The alanine racemase (SEQ ID NO:41) from *Geobacillus stearothermophillus* was cloned. Genomic DNA from *G. stearothermophilus* (ATCC12980D) was purchased from ATCC (Manassas, Va.). The following primers were used to amplify the alanine racemase gene from *G. stearothermophilus:* 5'-atggacgagtttcaccgcga-3' (SEQ ID NO:25) and 5'-ttatgcatcgcttcatccgc-3' (SEQ ID NO:26). The PCR product was ligated to pCR-Blunt-TOPO using the Zero Blunt TOPO PCR cloning kit (Invitrogen, Carlsbad, Calif.). Correct clones were confirmed by sequencing (Agencourt, Beverly, Mass.). A correct clone was used as template in a subsequent PCR reaction.

The following primers were used to amplify the alanine racemase: 5'-ataataggatcctcatccgcggccaacggcg-3' (SEQ ID NO:27) and 5'-gggaaaggtaccgaggaataataaatggacgagtttcaccgcg-3' (SEQ ID NO:28). The PCR product was digested with the restriction enzymes KpnI and BamHI. These enzymes cut at sites that had been engineered into the primers. The digested PCR product was gel purified and ligated to pTrc99a that had been digested with KpnI and BamHI and subsequently gel purified. The ligation was transformed into TOP10F' chemically competent cells and plated on LB plated supplemented with 50 μg/ml kanamycin. Isolates were screened for inserts and several isolates with an insert were confirmed to have the correct sequence (SEQ ID NO:40) by sequence analysis (Agencourt, Beverly, Mass.).

The pTrc99a/alanine racemase construct was subjected to Site-Directed Mutagenesis ("SDM") using the Stratagene (La Jolla, Calif.) Quick-Change Multi Site-Directed Mutagenesis kit. The mutagenic primers were as follows:

```
                                          (SEQ ID NO:29)
5'-gccggacgacacgcacattnnkgcggtcgtgaaggcgaacgcc-3',

                                          (SEQ ID NO:30)
5'-gtgaaggcgaacgcctatggannkggggatgtgcaggtggcaag
g-3',

                                          (SEQ ID NO:31)
5'-cctcccgcctggcggttgccnnkttggatgaggcgctcgcttta
a-3'

                                          (SEQ ID NO:32)
5'-caaccaggcgaaaaggtgagcnnkggtgcgacgtacactgcgca
g-3',

                                          (SEQ ID NO:33)
5'-gatcgggacgattccgatcggcnnkgcggacggctggctccgcc
g-3',

                                          (SEQ ID NO:34)
5'-gccatttggaaacgatcaacnnkgaagtgccttgcacgatcag-3'
(n = any nucleotide and k = g or t).
```

Residues for mutagenesis were selected by analysis of the existing crystal structure of *G. stearothermophilus* alanine racemase. Large amino acid residues located between 5 and 10 Å from the active site were chosen.

All six primers were used in the SDM reaction as directed in the manufacturer's protocol. The SDM reaction was transformed into XL-10 Gold according to the manufacturer's protocol. The transformation reaction was plated on LB medium supplemented with 100 μg/ml ampicillin. LB broth was added to the plates and the colonies were scraped off the plates. The resuspended cells were allowed to grow at 37° C.

for several hours and the plasmids were mini-prepped using the QIAquick mini-prep kit. The resulting mutagenized library was then used to transform the tryptophan auxotroph CAG18455. The transformation was plated on M9 minimal medium that had been supplemented with glucose, trace elements, vitamins, 100 μg/ml ampicillin, 100 μM IPTG, and 3 mM D-tryptophan. After several days of incubation at 37° C., colonies grew. These colonies were streaked on LB (100 μg/ml ampicillin). The plasmids were isolated from these isolates and were retransformed into CAG18455. The retransformed cells were plated on LB containing 100 μg/ml ampicillin. After isolated colonies formed, they were streaked on M9 D-tryptophan medium as described above. The colonies all seemed to re-grow, indicating that the growth was because of the mutagenized version of the racemase. No growth of the control cells was observed.

Several of the isolates were assayed for in vitro activity. Cells were grown to an $OD_{600}$ approximately 0.6 and induced with 100 μM IPTG. Cells were incubated at 37° C. for an additional two hours and were harvested by centrifugation. Cell pellets were stored at −80° C. until use the next day. Cell pellets were thawed on ice. Cells were disrupted with BugBuster (primary amine free) cell lysis reagent and Benzoase (Novagen). Cell debris was removed by centrifugation (~10,000×g for 30 minutes at 4° C.). The supernatant was saved as the crude cell extract.

Assay buffer contained 50 mM potassium phosphate (pH 8.0), 10 μM pyridoxal phosphate, 0.01% β-mercaptoethanol, and 50 mM D- or L-tryptophan. 200 μL extract was added per mL of assay. Samples were frozen representing a time 0 timepoint, as well as, 30 minute and overnight timepoints. The samples were spun, filtered, and transferred to SRC for analysis.

TABLE 9

Results of Assay Starting from L-Tryptophan

| Time (Minutes) | L-Tryptophan (ppm) | D-Tryptophan (ppm) |
|---|---|---|
| 0 | 1240 | 3.6 |
| 30 | 1193 | 24.5 |
| overnight | 1192 | 583.2 |

TABLE 10

Results of Assay Starting from D-Tryptophan

| Time (minutes) | L-Tryptophan (ppm) | D-Tryptophan (ppm) |
|---|---|---|
| 0 | 0.5 | 7506 |
| 30 | 0.5 | 7519 |
| overnight | 14.9 | 7463 |

The DNA sequence of the racemase gene in this isolate was determined (SEQ ID NO:42) and the isolate was found to have three mutations. The mutations in the corresponding protein isolate are as follows: M35C, F66E, and Y354A (SEQ ID NO:43). An additional mutation (P197L) was found in this mutant. This is a spontaneous mutation and was not part of the site-directed mutagenesis.

The mutagenized racemase was cloned into pET30 for expression and purification. The following primers were used to PCR amplify the racemase gene from the pTrc99a construct: 5'-gggaaaggtaccgaggaataataaatggacgagtttcaccgcg-3 (SEQ ID NO:35) and 5'-gcggcgccatggacgagtttcaccgcg-3' (SEQ ID NO:36). The PCR product was digested with NcoI and BamHI, gel purified, and ligated to pET30 that had been digested with NcoI and BamHI and subsequently gel purified. The ligation was transformed into TOP10 chemically competent cells (Invitrogen, Carlsbad, Calif.). Isolates from the transformation were screened for inserts. Plasmids with an insert were submitted for sequencing (Agencourt, Beverly, Mass.). Isolates with the correct sequence were transformed into BL21 λDE3 or BL21 λDE3 pLysS for expression and purification. The new construct is designated pET30Trp racemase.

(6) Purification of Tryptophan Racemase

An overnight culture with the pET30Trp racemase construct was subcultured into fresh LB medium with the appropriate antibiotics (50 μg/ml kanamycin and 20 μg/ml chloramphenicol) and grown to an $OD_{600}$ ~0.6 (37° C. with aeration). Expression was induced with 100 μM IPTG and incubation was continued at 37° C. with aeration for 2 hours. The cells were harvested by centrifugation and stored at −80° C. until use. The cell pellet was thawed on ice and cells were lysed using BugBuster Primary Amine Free Cell Lysis Reagent and Benzoase Nuclease (Novagen, Madison, Wis.). Cell debris was removed by centrifugation and the supernatant was used as the crude protein extract. The crude protein extract was filtered using a 0.45 μm syringe filter and applied to a HisBind column (Novagen, Madison, Wis.) that had been pre-equilibrated according to the manufacturer's instructions. The column was washed and the protein was eluted as directed in the manufacturer's protocol. The purified protein was desalted with a PD-10 column (GE Healthcare, Piscataway, N.J.) using 50 mM potassium phosphate pH 8.0, 10 μM pyridoxal-5'-phosphate ("PLP") as the eluent. The desalted protein was concentrated using Amicon centrifugal concentrators (Millipore, Billerica, Mass.). Wild-type alanine racemase was purified as described above.

(7) Assay of Tryptophan Racemase

The purified racemase was tested in several assays. In one assay, the production of hydrogen peroxide by a D-amino acid oxidase was used as a detection system. D-tryptophan substrate for the oxidase was produced from L-tryptophan via the racemase enzyme isolated as described in this Example. The assay included 0, 1, 10, 25, 50, 100, 200 μg of enzyme per assay, 50 mM potassium phosphate pH 8.0, 10 μM PLP, 50 mM L-tryptophan. The assays were incubated 1 hour at 37° C. After incubation, 100 mg/ml D-amino acid oxidase (AOD-101 BioCatalytics, Pasadena, Calif.) and 0.5 mM FAD was added to the reaction mix. The generation of hydrogen peroxide was measured using the Amplex Red reagent kit (Molecular Probes, Eugene, Oreg.) and a Perkin Elmer HTS 7000 Plus BioAssay Reader Fluorometer (Wellesley, Mass.). The assay data is summarized in Tables 11 and 12 below:

TABLE 11

Standard Curve

| $H_2O_2$ Concentration (μM) | Fluorometer Reading |
|---|---|
| 0 | 485 |
| 1 | 8691 |
| 2 | 16958 |
| 3 | 24719 |
| 4 | 31692 |
| 5 | 38083 |

TABLE 12

| Protein Concentration (μg/assay) | Results of Assay<br>Wild-type Racemase (Fluorometer Reading) | Mutant (Trp) Racemase (Fluorometer Reading) |
|---|---|---|
| 0 | 5226 | 5192 |
| 1 | 4272 | 6215 |
| 10 | 4149 | 10543 |
| 25 | 4239 | 21177 |
| 50 | 3141 | 30465 |
| 100 | 3160 | 39068 |
| 200 | 2370 | 35163 |

The results of the assay indicate that the mutant racemase is required for production of hydrogen peroxide. The amount of hydrogen peroxide produced increased when the amount of the mutant racemase added was increased.

The activity of the racemase (wild-type and mutant) on alanine was analyzed. The reaction buffer contained: 100 mM potassium phosphate pH 8.0, 10 μM PLP, 50 mM L-alanine, 12 μg/mL wild-type racemase or 94 μg/ml mutant racemase. The reactions were stopped with 1 volume of 0.5 M formic acid and analyzed by LC/MS/MS using a Chirobiotic column as described in Example 1.

The assay data is summarized in Table 13 below.

TABLE 13

| Time (minutes) | Wild-type Racemase (ppm D-Alanine Produced) | Mutant Racemase (ppm D-Alanine Produced) |
|---|---|---|
| 0 | 65 | 87 |
| 5 | 334 | 2430 |
| 10 | 1161 | 3257 |
| 20 | 1670 | 4003 |
| 30 | 3075 | 4621 |
| 40 | 3177 | 4931 |
| 60 | 3986 | 5328 |

The mutated racemase appears to retain activity on the original substrate, alanine.

The activity of the mutated racemase was tested using one of L-tryptophan, D-tryptophan, L-alanine, and D-alanine as the substrate. The reaction buffer contained: 100 mM potassium phosphate pH 8.0, 10 μM PLP, 50 mM substrate, 94 μg/ml mutant racemase. The reactions were stopped with 1 volume of 0.5 M formic acid and analyzed as described in Example 1. The assays with alanine as the substrate were incubated at room temperature (~22° C.) and assays with tryptophan as the substrate were incubated at 37° C. The results are summarized in Table 14 below.

TABLE 14

| Time (minutes) | ppm D-trp Produced from L-trp | ppm L-trp Produced from D-trp | ppm D-ala Produced from L-ala | ppm L-ala Produced from D-ala |
|---|---|---|---|---|
| 0 | None detected | 0.8 | 420.5 | 565.9 |
| 5 | None detected | 1 | 1268 | 1874 |
| 10 | None detected | 1.4 | 1448 | 1968 |
| 20 | None detected | 2.2 | 1590 | 1505 |
| 30 | 0.3 | 2.8 | 1840 | 1923 |
| 40 | 3.1 | 2.8 | 1779 | 1960 |
| 60 | 9 | 3.7 | 1295 | 1070 |
| 1080 | 57.4 | 66.7 | 1611 | 2932 |

The racemase enzyme works in both directions and retains wild-type activity.

The mutant racemase was tested on several substrates. The enzyme used in the assay was purified as previously discussed. The assay conditions are as follows:

50 mM potassium phosphate pH 8.0, 10 μM PLP, 25 mM substrate, 40 μg/ml mutant racemase. The reactions were stopped with 1 volume of 2 M formic acid and analyzed as described in Example 1. The assays were incubated at 37° C. The results (in ppm D-isomer produced from the L-isomer) are summarized in Table 15 below (nd=none detected).

TABLE 15

| Time (Minutes) | Lys | Ala | Glu | Met | Tyr | Leu | Trp | Phe |
|---|---|---|---|---|---|---|---|---|
| 0 | 12 | 156 | 86 | 104 | nd | nd | nd | nd |
| 3 | 2310 | 2180 | 607 | 1200 | nd | 37 | nd | nd |
| 5 | 2450 | 1310 | 1110 | 1290 | nd | 80 | nd | 14 |
| 10 | 6630 | 2850 | 1950 | 2260 | 11 | 139 | nd | 14 |
| 20 | 9550 | 1970 | 4660 | 2090 | 30 | 280 | nd | 47 |
| 30 | 15500 | 2090 | 4860 | 1750 | 63 | 320 | nd | 22 |
| 60 | 10200 | 2540 | 4490 | 2150 | 136 | 710 | nd | 54 |
| 120 | 18000 | 2430 | 6340 | 1940 | 224 | 1050 | nd | 188 |
| 240 | 13200 | 1830 | 6560 | 1990 | 515 | 1170 | 15 | 490 |

It is likely that this racemase will racemize other amino acids in addition to the ones tested here.

Although the mutated racemase appears to have activity on a wide variety of amino acids, there does not appear to be any racemase activity on monatin. The enzyme used in the assay was purified as previously discussed. The assay conditions are as follows: 100 mM potassium phosphate pH 8.0, 10 μM PLP, 50 mM monatin, 1 mg/ml mutant racemase. The assays were incubated at 37° C. The assays were analyzed by FDAA derivitization as described in Example 1. The results of the assay are shown in Table 16 below.

TABLE 16

| Time (Hours) | S,S Monatin Starting Substrate | R,R Monatin Starting Substrate |
|---|---|---|
| 0 | 100% SS | 100% RR |
| 1 | 100% SS | 100% RR |
| 18 | 100% SS | 100% RR |

Even after 18 hours there was no apparent conversion of S,S monatin to S,R monatin or of R,R monatin to R,S monatin using the mutant racemase.

The ideal enzyme has activity on tryptophan, but little or no activity on other amino acids or amino acid like compounds, particularly monatin. If the enzyme has significant activity on monatin, the enzyme may be mutagenized to decrease the activity on monatin and/or glutamate, while keeping the tryptophan activity unchanged or at a level high enough for the enzyme to be useful in monatin production. Techniques that may be used for mutagenesis include, but are not limited to, error prone PCR, site-directed mutagenesis, modeling to identify site-directed mutagenesis targets (sites that may be involved in substrate binding), passage through mutagenic strains, and DNA shuffling.

(8) Tryptophan Racemase Monatin Production

The following were added per 1 mL of reaction mixture: approximately 50 μg aldolase of SEQ ID NO:22, 16 mg/mL purified tryptophan racemase, 4 mM $MgCl_2$, 50 mM L-tryptophan, 0.5 mg D-aminotransferase (purified from *Bacillus sphaericus* as described in Example 14), 100 mM sodium pyruvate, 100 mM potassium phosphate buffer pH 7.5, and 0.05 mM PLP. Because pyruvate is an acceptable amino acceptor for the broad specificity D-aminotransferase, α-ketoglutarate was not used. A control was included in which D-tryptophan was the starting substrate and no racemase was included. The samples were incubated 2 hours or overnight (20 hours) at 30° C. with gentle shaking. Samples were analyzed as described in Example 1. The results of the assay are shown below in Table 17 (nd=none detected).

TABLE 17

| Time (Hours) | Starting Substrate | ppm Total Monatin | RR/SS % RPLC | RS/SR % RPLC | % RR FDAA | % SR FDAA |
|---|---|---|---|---|---|---|
| 2 | L-trp | nd | 0 | 0 | | |
| 18 | L-trp | 7.4 | 100 | 0 | 96.5 | 3.5 |
| 2 | D-trp | 12 | 99.17 | 0.83 | | |
| 18 | D-trp | 170 | 98.65 | 1.35 | 97.5 | 2.5 |

Table 17 shows production of R,R monatin using a tryptophan racemase to convert the L-tryptophan substrate to D-tryptophan. The production of R,R monatin from D-tryptophan, without using the tryptophan racemase, was utilized as a control. The percent R,R monatin produced is nearly the same with either L- or D-tryptophan as the starting material. This result indicates the racemase does not have detectable activity in catalyzing the racemization of R,R monatin.

(9) Isolation of the Key Amino Acid Changes

Several revertants of the mutagenized alanine racemase were created. The revertants were made by site-directed mutagenesis using the QuikChange Multi Site-Directed Mutagenesis Kit (Stratagene, La Jolla, Calif.) as previously described using the following primers:

5'-gccatttggaaacgatcaactatgaagtgccttgcacgatcag-3' (SEQ ID NO:37)

5'-ctcccgcctggcggttgccttcttggatgaggcgctcgctttaag-3' (SEQ ID NO:38)

5'gccggacgacacgcacattatggcggtcgtgaaggcgaacgcc-3' (SEQ ID NO:39)

The primers were used individually, and in combination, in an attempt to make the six possible combinations of the three mutations in positions 35, 66, and 354 (numbering based on the ATCC 12980 derived amino acid sequence). Several combinations of the mutations were created and tested for tryptophan racemase activity. The assay conditions were as follows: 50 mM potassium phosphate pH 8.0, 10 μM PLP, 30 mM L-Tryptophan, 100 μg/ml enzyme. The assays were incubated at 37° C. for the specified timeperiod. The samples were analyzed as described in Example 1.

The results of the assays are summarized in Table 18 below (nd=none detected).

TABLE 18

| Time (Minutes) | MF1 | MF2 | MY1 | Mutated Racemase |
|---|---|---|---|---|
| 0 | nd | nd | nd | nd |
| 5 | nd | nd | nd | nd |
| 10 | nd | nd | nd | nd |
| 20 | nd | nd | nd | nd |
| 30 | nd | nd | nd | nd |
| 40 | nd | nd | nd | nd |
| 60 | 9.8 | nd | nd | 12.5 |
| 1080 | 54.8 | 90.8 | nd | 92.4 |

Mutation list:
MF1: N41S (spontaneous mutation), P197L, Y354A
MF2: F66E, P197L, Y354A
MY1: M35C, F66E, P197L
Mutagenized racemase: M35C, F66E, P197L, Y354A The results indicate that the Y354A mutation is required for activity on tryptophan. When this mutation was absent there was no detectable activity on tryptophan.

An alanine racemase may be further converted to a broader specificity racemase by random methods such as mutagenic PCR, passage through mutagenic strains, or other methods to those known in the art. A more focused evolution of the alanine racemase may be focused on active site residues, including Lys129, Met134, and the residues including and between Gly283 and Trp288 (numbering from *Geobacillus stearothermophilus*).

Example 5

Selection Method for Screening of Pyruvate Aldolases in Recombinant *E. coli*

Many of the processes described in Examples 4(5), 9 and 10(3), and shown in FIGS. 1-9, will work optimally with an aldolase that preferentially produces R-MP from indole-3-pyruvate and pyruvate. Therefore, methods are described to isolate and test clones containing nucleic acid encoding an aldolase that preferentially produces R-MP. Strains of *Escherichia coli* that require pyruvate supplementation when grown on M9 minimal medium with ribose as the carbon source have been described previously. Ponce, E., et al., "Cloning of the two pyruvate kinase isoenzymes structural genes from *Escherichia coli*: The relative roles of these enzymes in pyruvate biosynthesis," *J. Bacteriol.* 177:5719-5722, (1995). The relevant genotype of the strain is: ΔpykA ΔpykF. The double knockout was generated by the method of Datsenko and Wanner, *Proceed. Natl. Acad. Sci. USA* 97:6640-6645, (2000). These strains can form a basis for a pyruvate-generating aldolase screen and to screen for aldolases that are more active on a specific stereoisomer of monatin, a particular stereoisomer of monatin precursor, or an analog of monatin or monatin precursor. An analog of monatin precursor includes compounds that have been identified as substrates for ProA aldolases or KHG aldolases, such as 4-hydroxy-4-methyl-2-oxoglutarate, 4-carboxy-4-hydroxy-2-oxoadipate, 4-hydroxy-4-methyl-2-oxoadipate, or other carboxyl rich compounds that are converted to pyruvate in an aldol reaction. An example of an analog of monatin that can be used is 4-hydroxy-4-methyl glutamic acid, which can be easily transaminated to 4-hydroxy-4-methyl-2-oxoglutarate (a substrate of ProA) by native aminotransferases in a test cell.

Cloning

The following primers were used to generate the pykA knockout:

```
                                       (SEQ ID NO:3)
5'-ATGTCCAGAAGGCTTCGCAGAACAAAAATCGTTACCACGTTAGGTGT
AGGCTGGAGCTGCTTC-3'
and

                                       (SEQ ID NO:4)
5'-CTCTACCGTTAAAATACGCGTGGTATTAGTAGAACCCACGGTACCAT
ATGAATATCCTCCTTAG-3'.
```

The following primers were used to generate the pykF knockout:

```
                                       (SEQ ID NO:5)
5'-AGGACGTGAACAGATGCGGTGTTAGTAGTGCCGCTCGGTACCAGCAT
ATGAATATCCTCCTTAG-3'
and

                                       (SEQ ID NO:6)
5'-ATGAAAAAGACCAAAATTGTTTGCACCATCGGACCGAAAACCGGTGT
AGGCTGGAGCTGCTTC-3'.
```

A PCR reaction was performed with either pKD3 or pKD4 as template using standard protocols. The PCR product was electroporated into a strain of *E. coli* that expresses the lambda red homologous recombination system. The PCR product had homology to pykA or pykF and recombined into the chromosome at those sites. When the double crossover occurred, the resulting progeny carried a deleted pykA or pykF gene and an antibiotic resistance marker. The deleted genes with the antibiotic resistance markers were transduced into an *E. coli* strain (MG1655) using standard P1 transduction techniques.

Strain Analyses

The double knockout was tested for growth on minimal medium (M9 salts) (Difco) supplemented with Balch's vitamin solution, Balch's modified trace element solution (Balch, W. E., et al., "Methanogens: reevaluation of a unique biological group," *Microbiol. Rev.* 43:260-296, (1979)), and 0.4% D-ribose. No growth was seen for the double mutant unless 5 mM pyruvate was also included in the media. Wild-type MG1655 grew on the above media both in the presence and absence of pyruvate. The double knockout was tested for growth on the minimal medium described above supplemented with 0.4% glucose rather than ribose. Growth on this medium was similar to that seen with the wild-type strain. With this medium, pyruvate can be generated from glucose via the ptsI gene product (the enzyme of the phosphotransferase system that makes pyruvate from phosphoenolpyruvate and transfers the phosphate to glucose). The double knockout strain was also tested for growth using the medium as described above supplemented with 0.4% L-arabinose or 0.4% D-xylose rather than ribose. Pyruvate is not generated from growth on these 5-carbon containing (non-PTS) substrates. The double knockout did not grow under these conditions unless it was supplemented with 5 mM pyruvate, while the wild-type strain grew normally both in the presence and absence of pyruvate.

The proA aldolase gene from *Comamonas testosteroni* described in Example 2 of WO 03/091396 A2 (cloned in pET30 Xa/LIC) and the aspC/proA gene operon described in Example 3 of WO 03/091396 A2 (cloned in pET30 Xa/LIC and pET32) were subcloned into pBAD-TOPO using the pBAD TOPO TA expression kit (Invitrogen).

Expression of the gene(s), in these constructs, is regulated by the inducible araBAD promoter. In the presence of arabinose (for example 0.4%) and IPTG, the gene(s) are expressed. Unless supplemented with pyruvate or a source of pyruvate, the strain will not grow on minimal medium. The medium can be supplemented with monatin, monatin precursor, or an analog of monatin or monatin precursor. Typical ranges of substrate used in literature are 0.5-5 mM. The ProA aldolase can, for example, convert the monatin precursor into pyruvate and indole-3-pyruvate providing the strain a source of pyruvate and allowing growth on minimal medium with 0.4% arabinose. The construct expressing both the proA and the aspC genes can convert monatin into the monatin precursor and the monatin precursor into pyruvate and indole-3-pyruvate. Additionally, the aminotransferase can convert indole-3-pyruvate to L-tryptophan and complement a tryptophan auxotrophy. This system is used to screen for aldolases and to screen for aldolases that are more active on a specific stereoisomer of monatin, a specific stereoisomer of monatin precursor, or an analog of monatin or monatin precursor. For example, if directed evolution is performed on any of the aldolases disclosed in Example 2 of WO 03/091396 A2, a plate assay utilizing media containing either R or S monatin precursor is used to compare the enantiospecificity of the resulting mutant enzyme. If growth occurs on the plates containing R-monatin precursor and little or no growth occurs on the plate containing S-monatin precursor, the aldolase has a specificity for substrates containing the R-chirality at the reaction site.

M9 minimal medium plates were made containing 1× Balch's vitamin solution and Balch's modified trace element solution. Balch, W. E., et al., "Methanogens: reevaluation of a unique biological group." *Microbiol. Rev.* 43:260-296, (1979). Glucose or arabinose was included as the carbon source (0.4% w/v) and plates were supplemented with either 5 mM monatin (R,R; S,S racemic mixture) that had been dissolved in 20 mM potassium phosphate buffer (pH 8.0) or an equal volume of potassium phosphate buffer without monatin. Growth is summarized in Table 20 below.

TABLE 20

| | Glucose | Glucose monatin | Arabinose | Arabinose monatin |
|---|---|---|---|---|
| MG1655 | ++++ | ++++ | ++++ | ++++ |
| MG1655 ΔpykA ΔpykF | ++++ | ++++ | + | + |
| MG1655 ΔpykA ΔpykF + aspCproA/pBAD-TOPO | ++++ | ++++ | + | ++ |

It is expected that the screen could be optimized by controlling the levels of ProA and AspC, increasing uptake of monatin, using monatin precursor in the place of monatin (in this case the aminotransferase would not need to be present), or using a less hydrophobic analog of monatin such as those described above. Methods for increasing the uptake of monatin include addition of amino acid mixtures, addition of specific amino acids, and the use of detergents, antibiotics, antibiotic analogs, or enzymes that help to permeabilize the cell wall, and addition of a small amount of pyruvate to allow for growth in case the aldolase cannot provide enough pyruvate to support growth. Polymyxin B nonapeptide (Dixon and Chopra, *Antimicrobial Agents and Chemotherapy* 29:781-788 (1986)) and microcystin RR (Dixon, et al., *FEMS Microbiology Letters* 230:167-170 (2004)) have been described as agents that permeabilize the outer membrane of *E. coli.*

It is expected that other promoter systems/plasmids can be used in this screening system with equivalent results. Examples include T7 promoter systems, and IPTG inducible promoters such as tac and lac.

The aspC and the proA genes were cloned into the pTrc99a expression vector (Amersham, Piscataway, N.J.). The resulting vector was transformed into the tryptophan auxotrophs CAG18455 or CAG18579 (see Example 4 for strain descriptions). The transformants were plated on M9 minimal medium with 0.1 mM IPTG and 5 mM monatin. After 3 days at 37° C., the strains with the operon plasmids formed colonies, while the parent strains did not appear to grow. Additionally, the growth was dependent on the presence of IPTG indicating that expression of the operon was required for growth. In this complementation study, the aspC/proA operon formed MP from monatin and indole-3-pyruvate from MP. The indole-3-pyruvate could then be converted to L-tryptophan allowing the tryptophan auxotrophs to grow on M9 minimal medium.

Several potential organisms may have the R-specific aldolase and can be tested as described above. The presence of R,R-monatin has been detected in culture supernatants of *Corynebacterium glutamicum*. This suggests the presence of an enzyme that is capable of making the R-monatin precursor. Additionally, the presence of multiple isomers of monatin has been detected in cell free extracts of *Sinorhizobium meloti* using reversed phase chromatography, again indicating the possible presence of an aldolase or aminotransferase capable of making an R stereoisomer of monatin precursor.

*Pseudomonas straminea* (*Pseudomonas ochraceae* NGJI), *Sinorhizobium meliloti, Sphingomonas* sp. LB126, *Arthrobacter keyseri* 12B, *Yersinia pestis* strain CO92, *Bradyrhizobium japonicum* str. USDA 110, *Sphingomonas* (*Pseudomonas*) *paucimobilis, Yersinia pestis* KIM, *Ralstonia metallidurans* CH34, *Yersinia pseudotuberculosis* IP 32953, *Rhizobium leguminosarum* biovar viciae rhiz23g02-p1k__1009__341 (Sanger Institute), *Novosphingobium aromaticivorans* DSM 12444, *Pseudomonas putida* KT2440, *Magnetospirillum magnetotacticum* MS-1, *Rhodopseudomonas palustris* CGA009, *Xanthomonas campestris* ATCC-33913, *Xanthomonas axonopodis* citri 306, and *Streptomyces avermitilis* MA-4680 have homologs that have been discovered by BLAST analysis using proA (*Comamonas testosteroni*) as the template. See U.S. Application No. 20050282260 These organisms can be used as a source of DNA and tested in the screen mentioned above.

Organisms capable of growth on gallic acid, syringic acid, protocatechuate, phtalate, parahydroxybenzoate, and fluorene may have an aldolase that may make monatin and have potential for the screen mentioned above. The following organisms metabolize protocatechuate via the 4,5-dioxygenase pathway and may have an aldolase that may be of utility: *Bordetella bronchiseptica* RB50, *Bordetella parapertussis* 12822, *Klebsiella pneumoniae* MGH78578, *Magnetospirillum magnetotacticum* MS-1, *Rhodopseudomonas palustris* CGA009, *Sphingomonas aromaticivorans* F199, *Xanthomonas axonopodis* citri 306, *Xanthomonas campestris* ATCC 33913.

And the following organisms degrade protocatechuate via the 3,4 dioxygenase pathway and have an aldolase that may be of utility: *Acinetobacter calcoaceticus* ADP1, *Acinetobacter* species ATCC 33305, ADP1, *Agrobacterium tumefaciens* C58, *Azotobacter vinelandii* AvOP, *Bradyrhizobium japonicum* str. USDA 110, *Bradyrhizobium japonicum* tr. USDA 438, *Brucella abortus, Brucella melitensis* 16M, *Brucella melitensis* suis 1330, *Burkholderia cepacia* J2315, *Burkholderia fungorum* LB400, *Burkholderia pseudomallei* K96243, *Corynebacterium efficiens* YS-314, *Cornebacterium glutamicum* ATCC-13032, *Mesorhizobium loti* MAFF303099, *Mycobacterium avium* subsp. paratuberculosis str. k10, *Pseudomonas aeruginosa* PAO1, *Pseudomonas fluorescens* PF0-1, *Pseudomonas fluorescens* SBW25, *Pseudomonas putida* KT2440, *Pseudomonas syringae* pv. tomato str. DC3000, *Ralstonia solanacearum, Rhodococcus* sp. strain I24 (IG-15), *Sinorhizobium meliloti* 1021, *Streptomyces avermitilis* MA-4680, *Streptomyces coelicolor* A3 (2), *Xanthomonas axonopodis* citri 306, *Xanthomonas campestris* ATCC-33913.

Example 6

Site Directed Mutagenesis of HEXAspC

Experimental Overview

A hexamutant of *E. coli* AspC (HEXaspC) was found to have better activity as compared to AspC for the production of S,S monatin, as described in Example 6 of WO 03/091396 A2. HEX (accession number:/AHFA gi:127190) contains the following mutations from AspC (*E. coli* numbering): V35L, K37Y, T431, N64L, T104S, and N285S. Based on structural analysis and literature reports (Rothman, S., and Kirsch, J., *J. Mol. Biol.* 327:593-608, (2003); Rothman, S., et al., *Protein Science* 13:763-772, (2004)), 5 more mutants were created that were expected to increase the kinetic activity toward substrates utilized in the monatin production pathway: L-tryptophan, S-MP, or both. Two of the mutants increased transamination rates for both tryptophan and S,S monatin. Two of the mutants showed an increased stereoselectivity for the formation of S,S monatin while one was less stereoselective. Based on this, it is expected that a broad specificity D-aminotransferase from *Bacillus* sp. with similar mutations would be useful as the D-aminotransferase in the R,R monatin pathways shown in FIG. 3, and described in Example 4(4). One of the mutants (HEXaspCP9T/R122G) had increased activity for L-tryptophan transamination, but activity in S,S monatin production or S,S monatin transamination was decreased significantly. Thus, it is expected that this enzyme is useful in the first step of the R,R monatin production pathways shown in FIGS. 1, 2, 4, 5, 6, 7, and 8 and described in Examples 9 and 10(3) In general, an aminotransferase that has activity similar to that of AspC on L-tryptophan, and limited activity on R-MP and S-MP, would be useful for the processes depicted in FIGS. 1, 2, 4, 5, 6, 7, and 8.

Methods and Materials

The HEX gene cloned in pUC19 was provided by Professor J. F. Kirsch (Department of Molecular and Cell Biology, University of California, Berkeley, Berkeley, Calif. 94720-3206) and used as the template for the cloning of the gene into pET23a. See Onuffer, J. J., and Kirsch, J. F., "Redesign of the substrate specificity of *Escherichia coli* aspartate aminotransferase to that of *Escherichia coli* tyrosine aminotransferase by homology modeling and site-directed mutagenesis," *Protein Science* 4:1750-1757 (1995). See also NCBI accession number 1AHF_A GI:1127190 (HEX amino acid sequence). The following primers were designed for cloning the HEX gene into the pET23a vector (Novagen, Madison, Wis.):

HEXaspC Primers:

```
                                        (SEQ ID NO:7)
N term: 5'-GCGGAACATATGTTTGAGAACATTACCGCC-3';

                                        (SEQ ID NO:8)
C term: 5'-ATAACCGGATCCTTACAGCACTGCCACAATCG-3'.
```

The following PCR protocol was used for gene amplification: In a 100 μL reaction, 50 ng DNA template, 1.0 μM of each primer, 0.2 mM each dNTP, 1 U Pfu Turbo Polymerase (Stratagene; LaJolla, Calif.), and 1× Cloned Pfu buffer were added. The thermocycler program utilized a hot start of 94° C. for 5 minutes; followed by 25 cycles of a denaturing step at 94° C. (30 sec), an annealing step at 55° C. (1 min), an extension step at 72° C. (2 min), and finally a finishing step at 72° C. (7 min). The purified PCR product was digested with BamHI and NdeI (New England Biolabs) restriction enzymes. The PCR product was ligated into pET23a that was also digested with NdeI and BamHI, using the Roche Rapid DNA Ligation kit. The desalted ligations were electroporated into *E. coli* DH10B cells using a Bio-Rad Gene Pulser II system, according to manufacturer's protocols. Miniprep DNA was prepared using a Qiagen Spin Miniprep kit and was used as a template for mutagenesis reactions. The plasmid was transformed into *E. coli* BL21 (DE3) cells according to the manufacturer's protocols (Novagen).

The tryptophan residue at position 130 is thought to be important for stacking interactions with the pyridoxyl ring, but also appears to be a source of steric hindrance with the S-monatin precursor ("S-MP") substrate, based on protein modeling observations. Therefore, an amino acid with a smaller hydrophobic side chain (phenylalanine) was used to replace the tryptophan. The rest of the mutations were based on kinetics data in literature, although new combinations of desirable mutations were created. All mutations to HEXaspC, with the exception of W130F, were made using the Stratagene Multi-Change kit by following the manufacturer's instructions. The W130F mutation was made using the Stratagene QuikChange kit according to the manufacturer's instructions with the only exception being that the extension temperature for the PCR reaction was decreased to 66° C. The primers for the multi-change kit were designed using the QuikChange multi-kit primer design tool on <www.stratagene.com>, except for the W130F single mutation primers.

The primer sequences are listed in Table 21 below:

Liquid cultures (5 mL) of Novagen Overnight Express™ Autoinduction System 2 (Catalog # 71366-3; solutions 1-6) were inoculated from fresh plates or frozen glycerol stocks of the following strains:

*E. coli* BL21(DE3)::HEXaspCpET23a

*E. coli* BL21(DE3)::HEXaspCW130FpET23a

*E. coli* BL21(DE3)::HEXaspCT156ApET23a

*E. coli* BL21(DE3)::HEXaspCP9T/T156ApET23a

*E. coli* BL21(DE3)::HEXaspCP9T/R122GpET23a

*E. coli* BL21(DE3)::HEXaspCR122G/T156ApET23a

The cultures were incubated at 37° C. at 230 rpm for 6-8 h. The $OD_{600}$ of each culture was determined and the volume of culture necessary to obtain an $OD_{600}$ of 0.03-0.05 in 25 mL was calculated. The calculated volumes of each liquid culture were transferred to flasks containing 25 mL of the same medium. The Overnight Express™ Autoinduction System 2 is a complete, chemically defined medium for high-level expression with IPTG-inducible expression systems that uses lactose as the inducing agent and does not require monitoring of cell growth. The Overnight Express cultures were incubated at 30° C. with shaking at 230 rpm for 18 h. The cells were harvested by centrifugation and washed once with cold 50 mM MOPS, pH 7.0. The cells were then lysed using Bugbuster™ (primary amine free) Extraction Reagent (Novagen Catalog #70923-3) containing 1 μL/mL benzonase nuclease (Novagen Catalog #70746-3), 5 μL/mL Protease Inhibitor Cocktail Set II (Novagen Catalog #539132) and 0.33 μL/10 mL r-Lysozyme (Novagen Catalog #71110-3) following the Novagen recommended protocol. After incubation at 25° C. for 15 min with gentle shaking, the cell debris from each suspension was pelleted by centrifugation at 21,000 g for 15 min at 4° C. The supernatant was carefully decanted and analyzed as the cell free extract. Inclusion body fractions were isolated by suspending the cell debris fractions in 30% Bugbuster™ (primary amine free) Extraction Reagent, centrifuging at 21,000×g for 10 min; suspending the centrifuged pellets in 10% Bugbuster™ (primary amine free) Extraction Reagent, centrifuging again to isolate the washed pellets.

The cell free extracts and inclusion body fractions were analyzed for protein expression by SDS-PAGE on 4-15% gradient gels (Bio-Rad # 161-1104). For the cell extract samples, twenty micrograms of soluble protein were loaded in each gel lane (premixed with 1× protein loading buffer and heated at 95° C. for 5 min). The inclusion body fractions were dissolved in 1× protein loading buffer (0.2 mL), heated for 10

TABLE 21

| Primer | Sequence (5' to 3') | |
|---|---|---|
| aspCW130F_backward | CGCTCTTATGGTTCGGTTTGCTTGGGTTGCTCACCC | (SEQ ID NO:9) |
| aspCW130F_forward | GGGTGAGCAACCCAAGCTTTCCGAACCATAAGAGCG | (SEQ ID NO:10) |
| R122G-1[a] | CAAAAAATACCAGCGTTAAGGGAGTGTGGGTGAGCAACC | (SEQ ID NO:11) |
| P9T_4[a] | CATTACCGCCGCTACTGCCGACCCGATTC | (SEQ ID NO:12) |
| 168V-1[a] | CACCAAAAATTACCTCGGCGTAGACGGCATCCCTGAATT | (SEQ ID NO:13) |
| T156A[a] | TGATGCGGAAAATCACGCTCTTGACTTCGATGCAC | (SEQ ID NO:14) |

[a]Denotes a primer that was modified by 5' phosphorylation

Expression of HEXaspC Mutant Genes and Analysis of Enzyme Activity min at 95° C. and 5 μL of each solution was loaded per gel lane. The amount of each HEX mutant in comparison to the total soluble protein loaded into each lane was calculated by band intensity analysis using Labworks BioImaging 1D-gel tool (UVP, Inc. Upland, Calif.), and is reported in Table 22 below:

TABLE 22

| Sample | HEXaspC Protein/ Total Soluble Protein |
|---|---|
| *E. coli* BL21(DE3)::HEXaspCP9T/ T156ApET23a CFE | 0.310 |
| *E. coli* BL21(DE3)::HEXaspCP9T/ R122ApET23a CFE | 0.145 |
| *E. coli* BL21(DE3)::HEXaspCpET23a CFE | 0.172 |
| *E. coli* BL21(DE3)::HEXaspCR122A/ T156ApET23a CFE | 0.174 |
| *E. coli* BL21(DE3)::HEXaspCW130FpET23a CFE | 0.114 |
| *E. coli* BL21(DE3)::HEXaspCT156ApET23a CFE | 0.120 |

Analysis of the gels showed that the HEXaspCR122A/T156A mutant was the only protein that was found in substantial quantities as inclusion bodies. The HEXaspCP9T/T156A protein gave the highest level of expression, approximately 90% better than HEXaspC protein. In contrast, the W130F, T156A and P9T/R122G proteins were expressed in lower concentrations than HEXaspC.

The activity of the HEXaspC mutant proteins for the production of S,S-monatin was measured using the following reaction conditions: Each 1 mL reaction contained 50 mM TAPS, pH 8.2, 4 mM $MgCl_2$, 3 mM sodium phosphate, pH 8.0, 200 mM sodium pyruvate (pH adjusted to 8), 5 mM α-ketoglutarate (pH adjusted to 8), 50 mM tryptophan, 0.05 mM pyridoxal 3-phosphate, 50 μg/mL ProA aldolase (added as a cell free extract) and varying concentrations (approximately 50 and 500 μg/mL) of aminotransferase (added as a cell free extract). Deaerated water was used to prepare the stock solutions and to adjust the volume of the reaction mixtures to 1.0 mL. The pyridoxal phosphate was added just prior to the addition of the enzymes. The reaction tubes were incubated at 30° C. with gentle shaking for 4 h. Samples (0.01 mL) were withdrawn at 1, 2, and 4 h after the addition of the enzymes, filtered, and analyzed by LC/MS/MS, as described in Example 1. Monatin production was normalized based on the amount of aminotransferase present in the reactions.

Under the conditions of these assays, the HEXaspC and the HEXaspCT156A produced the most total monatin per mg of aminotransferase while the P9T/R122G protein produced the least, followed by HEXaspCW130F. The HEXaspCW130F and P9T/R122G enzymes showed the greatest stereoselectivity for S-MP (greater than 98% S,S-monatin), even when high enzyme concentrations were used (greater than 300 μg/mL). The percentage of S,S-monatin product decreased to less than 90% in the enzymatic reactions containing the P9T/T156A enzyme at high concentration. The other mutants showed a product stereoselectivity very similar to the original HEXaspC mutant (approximately 95% S,S-monatin). Analysis of the product of the reaction containing the HEXaspC enzyme using the FDAA derivitazation reagent described in Example 1 showed that the second stereoisomer formed is R,S-monatin.

Assaying of Tryptophan and Monatin Aminotransferase Activity

The mutants were tested for transamination activity using S,S monatin and L-tryptophan as substrates. The aminotransferase activity was measured by following the formation of the co-product of the reaction, glutamate, by HPLC with OPA-post-column derivitization as described in Example 1. The reaction mixture contained, in 1.0 mL, 100 mM HEPPS buffer, pH 8.0, 20 mM alpha-ketoglutarate, 0.08 mM pyridoxal phosphate, 25 mM tryptophan or S,S monatin, and enzyme (supplied as 2.5 mg of in cellular extracts protein). All components except the enzyme were mixed together. The enzyme was added to start the reaction and the reaction solution was incubated at 30° C. (gentle shaking) for 90 min. Reactions were done in duplicate, with negative controls in which no enzyme was added. The reaction was stopped by the addition of 10% formic acid (final concentration), the mixture was centrifuged at 21,000 rpm, and the supernatant was carefully removed and filtered. The data were corrected for background levels of glutamate and for the dilution from the addition of acid to precipitate the proteins, then normalized by amount of mutant aminotransferase added. When tryptophan was utilized as a substrate, HEXaspC produced 13.0 mM glutamate per mg of aminotransferase per hour. The relative activity, expressed as a percentage, of the mutants is as follows: HEXaspCW130F (156%), HEXaspCT156A (151%), HEXaspCP9T/T156A (63.7%), HEXaspCP9T/R122G (116%), and HEXaspCR122G/T156A (107%). When S,S monatin was utilized as a substrate, HEXaspC produced 7.43 mM glutamate per mg of aminotransferase per hour. The relative activity, expressed as a percentage, of the mutants is as follows: HEXaspCW130F (113%), HEXaspCT156A (87.7%), HEXaspCP9T/T156A (67.3%), HEXaspCP9T/R122G (11.2%), and HEXaspCR122G/T156A (114%).

The HEXaspCP9T/R122G mutant had increased activity for tryptophan to indole-3-pyruvate conversion, but decreased activity for S,S monatin transamination. The ratio of tryptophan to monatin activity was 18.2 in comparison to 1.75 for HEXaspC, making it a desirable candidate for production of R,R monatin using pathways that require an L-aminotransferase, such as those described in Examples 9 and 10(2). As such, the HEXaspCP9T/R122G is an example of an aminotransferase with limited activity on S,S monatin, as well as, MP.

Most of the mutations improved L-tryptophan activity, but only two mutants increase activity toward both L-tryptophan and S,S monatin (HEXaspCW130F and HEXaspCR122G/T156A). Because 25 mM of substrate was used in these assays, the enzymes were most likely saturated and the activity is a reflection of the $k_{cat}$ of the enzymes. However, under the conditions in which the assays for S,S monatin production were performed, described above, it is unlikely that the concentration of S-MP is sufficient to saturate the enzyme, thus there is no overall increase in S,S monatin production because the increase in $k_{cat}$ is offset by an increase in $K_m$. It has been reported, for similar substrates, that some of the mutations made increase the $k_{cat}$ but also increase the apparent $K_m$ for the amino acid substrate. If increasing concentrations of substrates were used, it is expected that these two mutants would provide a benefit in production rates of S,S monatin in comparison to HEXaspC. The HEXaspCT156A mutation appears to have increased tryptophan transamination rates without having a significant effect on MP transamination rate under the conditions above for S,S monatin production.

By comparison of the structures of HEXaspC and one of the *Bacillus* sp. D-aminotransferase enzymes (see, for example, Sugio, S, et al., *Biochemistry* 34:9661-9669, (1995)), the W130F, R122G, T156A, and HEX mutations of AspC could be mapped to corresponding residues in the D-aminotransferase structure. It is expected that similar mutations in the broad specificity D-aminotransferase would improve the overall production of R,R monatin, as described in Example 3. For example, the functionality provided by tryptophan 130 in AspC is replaced in *Bacillus* D-aminotransferases by hydrogen bonding between the side chains of serines 179-181 and glutamate 166 (YM-1 numbering scheme). To lessen steric hindrance, the glutamate could be mutated to an aspartate residue. Some D-aminotransferases have a threonine residue at position 179, which would increase steric hindrance and should be avoided. The *B. sphaericus* enzyme has an alanine in place of serine at position 181, which may also reduce steric hindrance.

Additional information from studies of aspartate aminotransferase can be applied to the D-aminotransferase as well. While the AspC enzyme has an arginine in the active site that interacts with the side chain of dicarboxylate substrates, the D-aminotransferase has a loop from Ser240 to Ser243. The side chains of Ser240, Thr242, and Ser243 face the same direction and form a pocket with the hydroxyl group of Ser180 which provides a surface for both nonpolar and polar substrates can interact. Ser180 is involved in PLP binding; however, to improve the activity of a D-aminotransferase with R-MP, one can modify the Ser240, Thr242, or Ser243 residues to accept larger substrates or to favor negatively charged substrates. For instance, Thr242 can be mutated to Ser to reduce the side chain length. One of the residues can be mutated to lysine or arginine, such as Ser243. The residues (YM-1 numbering) Val30-Val36 are located in a beta strand across the active site of the D-aminotransferase, and are also important for activity. Tyr31, Val33, Glu32, and Lys35 are thought to face the active site. Tyr31, Glu32, and Val33 are invariant in all the *Bacillus* homologs. Ro, et al., *FEBS Lett* 398:141-145, (1996)) mutagenized Val33 to Ala and found a slightly increased catalytic efficiency for alpha-ketoglutarate transamination and a significantly improved catalytic efficiency for bulkier substrates (less steric hindrance). In some homologs Lys35 is replaced with Arg, but if steric hindrance is a concern the Lys residue may be preferable. Valines 34 and 36 are also preferable over conservative substitutions such as isoleucine, again due to less steric hindrance for large molecules such as MP. Because the novel D-aminotransferase ("4978") described in Examples 15 and 16 had higher activity than the *B. sphaericus* enzyme and the hybrid DAT described in Example 19 it is the obvious choice for further mutagenesis reactions. The ideas above, based upon crystal structure analysis of YM-1 D-aminotransferase, can be applied to the D-aminotransferase from ATCC strain 4978. The numbering above is one amino acid less than the corresponding amino acid in the 4978 protein sequence.

Example 7

Use of Branched Chain Aminotransferases ("BCAT") in the Production of Monatin AT-102 and AT-104 are branched chain L-transaminases (EC 2.6.1.42) that were purchased from BioCatalytics (Pasadena, Calif.). The enzymes were tested for transamination activity using S,S and R,R monatin substrates that were produced chemically. Reactions were performed in a total volume of 0.5 mL, and run in duplicate. The assays contained 50 mM Tris pH 7.8, 0.08 mM PLP, 10 mM α-ketoglutarate ("α-KG"), 5 mM monatin, and 1 mg/mL aminotransferase enzyme. Negative controls did not contain exogenous aminotransferase enzyme. The samples were incubated for 2 hours at 30° C. at 100 rpm shaking. The samples were filtered and LC/MS/MS analysis, as described in Example 1, was run to ascertain glutamate levels. Glutamate levels should correlate stoichiometrically with MP production. When R,R was used as the reaction substrate, very low levels of glutamate were present in the negative controls. AT-104 produced slightly more glutamate than the negative controls, indicating a low level of activity with the R,R monatin substrate (a D-amino acid). Both of the branched chain L-aminotransferases showed activity on S,S monatin. AT-102 produced 102 μg/mL glutamate and AT-104 produced 64 μg/mL glutamate. For comparison, a broad specificity aminotransferase (AT-101, also from BioCatalytics) produced 75 μg/mL under these conditions. The high activity with a branched chain aminotransferase is somewhat unexpected because monatin has more structural similarities to dicarboxylic amino acids and aromatic amino acids that normally serve as substrates for the broad specificity or aspartate aminotransferases. However, due to the glutamatic acid backbone of monatin, many of the aminotransferases that can utilize glutamate as an amino donor may also have activity on monatin.

Monatin Production from Indole-3-Pyruvate Using BCAT

AT-102 and AT-104 were tested for production of monatin in coupled reactions using the ProA aldolase from *C. testosteroni* (produced as described in WO 03091396 A2). Enzymes and additional components/substrates were added directly to the reaction buffer provided in the kit, which contained 100 mM potassium phosphate buffer pH 7.5, 100 mM L-glutamate, and 0.1 mM PLP. To one mL of reaction buffer were added: 4 mg indole-3-pyruvate, 20 mg pyruvate, approximately 50 μg ProA provided in a cellular extract, 1 μL 2 M $MgCl_2$, and 2 mg of aminotransferase enzyme to be tested. All reactions were performed in duplicate, and a negative control reaction was done with no additional aminotransferase added. A positive control (AT-101) was utilized for comparison; this enzyme is a broad specificity L-aminotransferase. Background production of monatin is due to native *E. coli* aminotransferases present in the cellular extract of the recombinant ProA enzyme. The reactions were incubated overnight at 30° C. with gentle shaking (100 rpm). The samples were filtered and submitted for reverse phase LC/MS/MS analysis as described in Example 1. The results are presented in Table 23 below.

TABLE 23

| Enzyme | μg/mL Monatin Produced |
|---|---|
| AT-101 | 173.05 |
| AT-102 | 122.05 |
| AT-104 | 133.05 |
| negative | 73.25 |

AT-102 and AT-104 aminotransferases clearly produced more monatin than the negative control and were about 50-60% as active as the positive control.

The branched chain aminotransferase enzyme from *E. coli* has been well studied and crystal structures have been analyzed in detail. Okada, K., et al., (1997) *J. Biochem* (*Tokyo*) 121:637-641, (1997). The enzyme has a similar overall fold and significant sequence homology to *Bacillus* D-aminotransferase enzymes such as those mentioned in Examples 2, 3, and 6. In addition, the BCAT enzymes and the D-aminotransferases from *Bacillus* are the only two types of PLP-dependent aminotransferases to show stereospecificity for re face addition of hydrogen to PLP. Yoshimura, T., et al., *J. Am.*

*Chem. Soc.* 115:3897-3900, (1993). BCAT is thought to be the only enzyme in which the alpha-amino acid substrate is bound with its carboxyl group on the same side as the phosphate group, allowing the enzyme to have a similar fold and mechanism to the D-aminotransferases while still retaining specificity for L-amino acids. Peisach, D., et al., *Biochemistry* 37:4958-4967, (1998). It is thought that the L-specificity of BCAT comes from the fact that the polar amino acid side chains of the D-aminotransferase that position the alpha-carboxyl group of the substrate are replaced by nonpolar residues in BCAT. It is expected that if all, or some, of these residues are mutated to the corresponding amino acids of the *Bacillus* D-aminotransferase, one could convert the BCAT into a D-specific aminotransferase. The following mutations can be made to the *E. coli* BCAT (numbering based on accession number gi:14719463): Phe37 to Tyr, Val110 to His, Met108 to Arg. Other polar amino acid substitutions could be made at these sites as well, to tailor the enzyme active site to accept large dicarboxylic acid substrates as described in Example 6. Tyr165 may need to be converted to Leu as well, to mirror the PLP interaction of the D-aminotransferase; Tyr96 (to Phe), Arg41, and Arg98 may also need to be mutated to prevent binding of the alpha carboxyl group in the incorrect orientation in the BCAT enzyme. Trp127 can also be mutated to Tyr to decrease the likelihood of the hydrophobic side chains binding in a pro-S configuration; Tyr32 and Tyr130 may interact with L-glutamate in the active site of BCAT and can be mutated to negatively charged amino acids to minimize this interaction. Goto, M., et al., *Biochemistry* 42:3725-3733, (2003); Okada, K., *Biochemistry* 40:7453-7463, (2001).

Because both the D-aminotransferase enzymes and the branched-chain aminotransferase have activity in production of monatin, it is expected that the BCAT can be converted to a D-aminotransferase with activity in R,R monatin production, while providing another possible D-aminotransferase enzyme to be utilized in the reaction schemes described in many of the Examples. Based on the above results, it is possible that the AT-104 enzyme already shows some activity toward D-amino configurations of monatin.

*Bacillus* Branched-Chain Aminotransferase Cloning and Mutagenesis

*Bacillus licheniformis* contains a putative branched-chain aminotransferase that is more closely related to D-aminotransferases than the *E. coli* branched chain aminotransferase is. It was assayed for D-transamination activity, and mutagenized based on predicted active site residues mentioned above for the *E. coli* BCAT.

Strain

*B. licheniformis* (ATCC number 14580) was grown on Nutrient Agar at 30° C. overnight. Groups of colonies were placed in 100 μL of sterile water and heated for 10 minutes at 95° C., to disrupt the cells. Three μL was used in subsequent Polymerase Chain Reaction (PCR) amplifications.

Polymerase Chain Reaction Protocol

Primers were designed for the *B. licheniformis* gene (915 bp) for cloning into pET 28b and pET 30a vectors (Novagen, Madison, Wis.) and pTRC99a (GE Healthcare Life Sciences), using the NcoI and SalI sites. The pET30 construct contains an N-terminal His-tag and S-tag, whereas the pET 28 construct is untagged.

*B. licheniformis* bcat Primers:

```
                                        (SEQ ID NO:44)
N term  5'-GGTTAAGGCCATGGGGGACCAGAAAGACCA-3';
and
                                        (SEQ ID NO:45)
C term: 5'-GGCCTTCCGTCGACTCAGCTGACACTTAAGCT-3'
```

The coding region was amplified using the following PCR protocol. In a 50 μL reaction, 3 μL template, 1 μM of each primer, 0.4 mM each dNTP, 3.5 U Expand High Fidelity Polymerase, and 1× Expand™ buffer (Roche, Indianapolis, Ind.) with Mg were used. The thermocycler program used included a hot start at 96° C. for 5 minutes, followed by 30 repetitions of the following steps: 94° C. for 30 seconds, 50° C. for 1 minute 45 seconds, and 72° C. for 2 minutes 15 seconds. After 30 cycles, the sample was maintained at 72° C. for 7 minutes and then stored at 4° C. Clean PCR products of the correct size were obtained (approximately 900 bp).

Cloning

The PCR product was purified and digested with SalI and NcoI in SalI buffer (New England Biolabs, Ipswich, Mass.). The digested vectors (pET28, pET30, and pTRC99a) and the insert were purified using the Qiagen QIAquick Gel Extraction Kit. The ligations were done using the Roche Rapid DNA Ligation Kit (Roche) and purified. The ligations were transformed into *Escherichia coli* DH10B using a 0.2 cm cuvette and a Bio-Rad Gene Pulser II system, as described in the Bio-Rad electroporation manual. The cells were allowed to recover in 900 μL SOC medium for 30 minutes at 37° C. at 225 rpm. The cells were plated on LB-agar plates containing kanamycin (25 μg/mL). The plasmid DNA was purified using the Qiagen spin miniprep kit and screened for the correct inserts by restriction digest with SalI and NcoI. The sequences of plasmids that appeared to have the correct insert were verified by dideoxy chain termination DNA sequencing at Agencourt BioScience Corporation (Beverly, Mass.). Sequencing verified the coding sequence found in NCBI accession number CP000002 GI 56160984 2851268 . . . 2850354, which produces a protein with amino acid sequence as listed in accession number AAU24468 GI:52004526.

Gene Expression and Assays

Plasmid DNA (pET vectors) was transformed into *E. coli* expression host BL21(DE3) (Novagen, Madison, Wis.) for constructs in pET vectors. The cultures were grown and the plasmids were isolated using Qiagen miniprep kit, and analyzed by restriction digest to confirm identity. Induction was typically performed in LB medium containing kanamycin (50 μg/mL). The cells were grown to an $OD_{600}$ of 0.4-0.8 at 37° C. and induced with 0.1 mM IPTG (isopropyl thiogalacatoside) and sampled at 3-4 hours post induction. Cell extracts were prepared according to the protocol accompanying the Novagen BugBuster™ reagent (with benzonase nuclease and Roche complete protease inhibitor cocktail added). High levels of soluble protein were obtained at the predicted molecular weight, as judged by SDS-PAGE. The soluble proteins in the cellular extracts were separated by SDS-PAGE.

Cell extracts were analyzed for D-aminotransferase activity by following production of alanine from pyruvate (or glutamate from alpha-ketoglutarate) and D-tryptophan using the following protocol. Duplicate one mL reactions were typically carried out in 100 mM potassium phosphate buffer (pH 7.5), 50 μM pyridoxal phosphate, 25 mM sodium pyruvate, and 50 mM D-tryptophan. The reactions were initiated by the addition of cell free extracts or purified enzyme and were incubated 15 minutes overnight at 30° C., with mild shaking. Approximately the same level of D-aminotransferase was added (typically around 0.5 mg) in each assay for comparative purposes, and AT-103 (BioCatalytics) was often used as a benchmark enzyme. Formic acid was added to a final concentration of two percent to stop the reaction, and the precipitated protein was removed by centrifugation. Control reactions without added protein were also performed. Zero time points were also used as negative controls. Alanine and glutamate were detected using OPA derivatization as described in Example 1. The branched-chain aminotransferase had low levels of D-aminotransferase activity in comparison to the AT-103 and *B. sphaericus* enzymes.

The branched chain aminotransferase was also tested for the ability to produce monatin from D-tryptophan (as in Example 3), but did not appear to have activity under the conditions tested.

The pTRC99a construct was transformed into electrocompetent *E. coli* CAG18455 cells, which are auxotrophic for tryptophan production. Cells were grown in M9 minimal medium with Balch's vitamins with 100 mg/L L-tryptophan, 0.4% glucose, and calcium chloride. Cells were not able to grow without L-tryptophan. Induction was tested at 10, 100 and 1000 μM IPTG, at an OD600 of 0.4 for 4.5 hours. Bands at the correct MW were visible on SDS-PAGE. The plasmid was mutagenized using the QuikChange® Multi Site-Directed Mutagenesis Kit (Stratagene). The primers in Table 24 below were designed as described by the manufacturer.

TABLE 24

| Amino Acid Mutation (*E. coli* Numbering) | Nucleotide Mutation (*B. lich* Numbering) | Primer Sequence |
|---|---|---|
| Y32F | tac 96-->ttc | ATCACGGATTTTTATTCGGGGACGGCGTG (SEQ ID NO:46) |
| Y32D | tac 96-->gac | ATCACGGATTTTTAGACGGGGACGGCGTG (SEQ ID NO:47) |
| F37Y | ttt 111-->tat | GGACGGCGTGTATGAAGGGATCAGGG (SEQ ID NO:48) |
| R41K | agg 123-->aag | TGTTTGAAGGGATCAAGGTATACGACGGCAAC (SEQ ID NO:49) |
| F37Y + R41K | | GACGGCGTGTATGAAGGGATCAAGGTATACGACG (SEQ ID NO:50) |
| Y96F | tac 276-->ttc | GCTGAAAGACGCTTTCATCCGCTTGGTCG (SEQ ID NO:51) |
| Y96H | tac 276-->cac | GCTGAAAGACGCTCACATCCGCTTGGTC (SEQ ID NO:52) |
| R98Y | cgc 282-->tac | CTGAAAGACGCTTACATCTACTTGGTCGTTTCAAGAGG (SEQ ID NO:53) |
| Y96F + R98Y | | GGCTGAAAGACGCTTTCATCTACTTGGTCGTTTCAAGAGG (SEQ ID NO:54) |
| Y96H + R9SY | | GCTGAAAGACGCTCACATCTACTTGGTCGTTTCAAGAGG (SEQ ID NO:55) |
| L108R | ctc 312-->cgc | GCAGGTGACCGCGGACTCGATCCAAAC (SEQ ID NO: 56) |
| L110H | ctc 318-->cac | GCAGGTGACCTCGGACACGATCCAAAC (SEQ ID NO:57) |
| L108R + L110H | | GCAGGTGACCGCGGACACGATCCAAACAATTG (SEQ ID NO:58) |
| L127Y | ttg 369-->tac | GTCATCATAATTGTCGAACCATACGCAATATTCCCGAAAC (SEQ ID NO:59) |
| L127K | ttg 369-->aag | GTCATCATAATTGTCGAACCAAAGGCAATATTCCCGAAAC (SEQ ID NO:60) |
| I130E | ata 375-->gaa | GTCATCATAATTGTCGAACCATTGGCAGAATTCCCGAAAC (SEQ ID NO:61) |
| L127Y + I130E | | CGAGTGTCATCATAATTGTCGAACCATACGCAGAATTCCCGAAAC (SEQ ID NO:62) |

TABLE 24-continued

| Amino Acid Mutation (*E. coli* Numbering) | Nucleotide Mutation (*B. lich* Numbering) | Primer Sequence |
|---|---|---|
| LI27K + I130E | | CCGAGTGTCATCATAATTGTCGAACCAAAGGCAGAATTCCCGAAAC (SEQ ID NO:63) |
| Y165L | tac 477-->ttg | AATCGCTGAACTTGTTAAACAATATTCTTGTCCGGATCGAGG (SEQ ID NO:64) |

Amino acid mutations were based on the *E. coli* BCAT crystal structure and the numbering in the above table is for the *E. coli* protein. The numbering for the DNA mutations is based on the *B. licheniformis* bcat gene.

The primers were diluted to 0.1 mg/mL and approximately 100 ng of each oligonucleotide primer was typically used in a 50 μL mutagenesis reaction, proportionately higher concentrations were used for larger primers. For oligonucleotide primers that were essentially competing for annealing to the same template region, sometimes a sum of 100 ng was used for the whole pool of primers in that region. Two hundred nanograms of template (*B. lich* bcat in pTRC99a) were used in the reaction, with 5 μL of 10× QuikChange buffer, 2 μL dNTPs, and 2 μL of the enzyme blend. The amplification products were treated with DpnI restriction endonuclease (Stratagene) (2 μL) for 2 hours at 37° C., and transferred to a thick wall 1.5 mL tube for ethanol precipitation. The resuspended (concentrated) reaction mix was transformed (2.5 μL) into XL10-Gold Ultracomp cells included in the QuikChange kit. Several colonies were miniprepped and sequenced to ensure that mutations were random and to estimate the level of mutagenesis achieved. Colonies were resuspended from the plate and bulk minipreps were done. The miniprep DNA was then transformed into the tryptophan auxotroph strain, and plated on minimal medium (with IPTG) described above or using minimal medium containing D-tryptophan as the sole nitrogen source. A second and third round of mutagenesis was done on the bulk minipreps using primers that did not appear to incorporate well in the previous rounds. At each stage, colonies that grew quickly on the minimal medium (larger colonies) were retained for further analysis. The mutants shown in Table 25 below were isolated from the selection plates. In some cases these same mutants appeared on the selection medium more than one time.

TABLE 25

| Clone | Mutations |
|---|---|
| 4 | F37Y, Y96F |
| 6 | Y96F |
| 28 | F37Y, Y165L |
| 32 | Y96F, L127K |
| 5-1 | F37Y, Y96F, R98Y, L108R, L110H, L127Y |
| 5-2 | F37Y, R41K, Y96F, R98Y, L108R, L110H, L127Y |

The mutant constructs were induced to make recombinant protein in LB media, and cell extracts were prepared as above. The soluble proteins in the cellular extracts were separated on a BioRad Laboratories Experion Automated Electrophoresis Station and analyzed for concentration and percent expression using the Experion Software version 1.1.98.0. Very low levels of soluble recombinant protein were observed; thus quantitation of the band of interest was not possible. Assays were done to test D-tryptophan transamination as above using 50-250 μL of cellular extracts. Clones 4, 6, 28, and 32 were assayed using both alpha-ketoglutarate and pyruvate as the amino acceptor, and incubated for 2 hours and overnight at 30° C. The background levels of alanine/glutamate present from the cellular extracts was subtracted. For the assays with 5-1 and 5-2, the protein concentrations estimated by the Experion software for the BCATs were 275.1 ng/μl for the wildtype enzyme, 409.3 ng/μl for BCAT 5-1, and 148.2 ng/μl for BCAT 5-2. The results of the assays are shown in Tables 26-28 below.

TABLE 26

| BCAT | Glutamate (mM) 2 Hours | Glutamate (mM) Overnight |
|---|---|---|
| wildtype (100 μL) | 0.0912 | 0.2304 |
| wildtype (250 μL) | 0.251 | 0.521 |
| 4 (100 μL) | 0.0642 | 0.1202 |
| 4 (250 μL) | 0.154 | 0.295 |
| 6 (100 μL) | 0.053 | 0.112 |
| 6 (250 μL) | 0.141 | 0.289 |
| 28 (100 μL) | 0.0586 | 0.1402 |
| 28 (250 μL) | 0.155 | 0.367 |
| 32 (100 μL) | 0.0616 | 0.1236 |
| 32 (250 μL) | 0.167 | 0.339 |

TABLE 27

| BCAT | Alanine (mM) 2 Hours | Alanine (mM) Overnight |
|---|---|---|
| wildtype (250 μL) | 0.199 | 0.438 |
| 4 (250 μL) | 0.093 | 0.249 |
| 6 (250 μL) | 0.097 | 0.249 |
| 28 (250 μL) | 0.117 | 0.325 |
| 32 (250 μL) | 0.102 | 0.285 |

TABLE 29

| BCAT | Glutamate (mM) 1 Hour | Glutamate (mM) Overnight |
|---|---|---|
| wildtype (50 μL) | 0.018 | 0.075 |
| wildtype (100 μL) | 0.037 | 0.152 |
| 5-1 (50 μL) | 0.005 | 0.017 |
| 5-1 (100 μL) | 0.01 | 0.045 |
| 5-2 (50 μL) | 0.001 | 0.011 |
| 5-2 (100 μL) | 0.003 | 0.031 |

It is evident that like most L-aminotransferases, the enzymes have a preference for alpha-ketoglutarate compared to pyruvate for the amino acceptor. All the mutants did have D-aminotransferase activity, as did the wildtype parent. It is not clear whether the wildtype enzyme had more or less D-aminotransferase activity, because exact quantitation of the BCAT protein from cellular extracts was not possible. However, it is expected that the mutant enzymes have less L-aminotransferase activity than the wildtype; thus the ratio of D- to L-transamination rate is being improved. Continued mutagenesis could provide an alternative enzyme in pathways to monatin.

Example 8

Cloning, Expression, and Testing of Glutamate and Aspartate Racemases

This example describes methods used to clone and test amino acid racemase enzymes, which can be used to interconvert between L-glutamate and D-glutamate (or L- and D-aspartate or L- and D-alanine). Glutamate, aspartate, or alanine racemases are useful in a biosynthetic pathway to produce R,R monatin when a step in that pathway produces an L-amino acid (e.g., L-glutamate, L-aspartate, or L-alanine) and another step in the pathway consumes a D-amino acid (e.g., D-glutamate, D-aspartate, or D-alanine). FIG. 4 illustrates a biosynthetic pathway for producing R,R monatin from L-tryptophan using an L-tryptophan-specific aminotransferase, an R-specific aldolase, a D-aminotransferase and a glutamate (or aspartate or alanine) racemase.

Genes were cloned into the pET28 and pET30 vectors to generate both non-tagged proteins and fusion proteins with cleavable N-terminal $HIS_6$-Tag/T7-Tags. The resulting proteins were purified using immobilized metal affinity chromatography.

Experimental Overview

Genes encoding glutamate racemases (EC 5.1.1.3) from *Lactobacillus brevis* (Genbank Accession No. D29627, nucleic acid sequence), and *Pediococcus pentosaceus* (murI gene) (Genbank Accession No. L22789) were cloned and expressed in *E. coli*. The extracts were tested for activity in conversion of L-glutamate to D-glutamate and D-glutamate to L-glutamate. BioCatalytics aspartate racemase enzyme (EC 5.1.1.13) was also tested for interconversion between L- and D-aspartate.

Isolation of Genomic DNA for Cloning

*L. brevis* genomic DNA (ATCC 8287D) was obtained from the American Type Culture Collection. *P. pentosaceus* (ATCC 25745) was grown at 37° C. in lactobacilli MRS broth and 2 ml was used for genomic DNA isolation using the method of Mekalanos, J. J., "Duplication and amplification of toxin genes in *Vibrio cholerae*," *Cell* 35:253-263, (1983).

Polymerase Chain Reaction Protocol

Primers were designed with 5' restriction sites and overhangs for cloning into the pET 28 and pET30 vectors (Novagen, Madison, Wis.).

*L. brevis* Glutamate Racemase Primers:

```
                                         (SEQ ID NO:15)
N term: 5'-GCGGCGCCATGGAAAATGATCCGATTGGTCTAATG-3',
and

                                         (SEQ ID NO:16)
C term: 5'-GCGGCGGTCGACGCAATTACAATTGTGTTTGTC-3'.
```

*P. pentosaceus* Glutamate Racemase Primers:

```
                                         (SEQ ID NO:17)
N term:   5'-GCGGCGCCATGGATGTATGTATAATTTTATTTAG-3',
and

                                         (SEQ ID NO:18)
C term:   5'-GCGGCGGTCGACAAATTTCATTATTCATTCTAATT
          T-3'.
```

The gene derived from *L. brevis* was amplified using the following PCR protocol. In a 50 μL reaction, 0.150 μg template, 1.6 μM of each primer, 0.4 mM each dNTP, 2.8 U Expand High Fidelity™ Polymerase (Roche, Indianapolis, Ind.), 0.5 U Pfu polymerase (Stratagene, La Jolla, Calif.) and 1× Expand™ buffer with Mg were used. The thermocycler program used included a hot start at 96° C. for 3 minutes, 8 repetitions of the following steps: 94° C. for 30 seconds, 52° C. for 45 seconds, and 72° C. for 2 minutes, followed by 22 repetitions of the following steps: 94° C. for 30 seconds, 60° C. for 45 seconds, and 72° C. for 2 minutes. After the 22 repetitions, the sample was maintained at 72° C. for 7 minutes and then stored at 4° C. This PCR protocol produced a product of ~830 bp, as judged by comparison to DNA size markers.

The gene derived from *P. pentosaceus* was amplified using the following PCR protocol. In a 50 μL reaction, 0.15 μg template, 1.6 μM of each primer, 0.4 mM each dNTP, 2.8 U Expand High Fidelity™ Polymerase, 0.5 U Pfu polymerase and 1× Expand™ buffer with Mg were used. The thermocycler program used included a hot start at 96° C. for 3 minutes, followed by 8 repetitions of the following steps: 94° C. for 30 seconds, 37° C. for 45 seconds, and 72° C. for 2 minutes, followed by 8 repetitions of the following steps: 94° C. for 30 seconds, 45° C. for 45 seconds, and 72° C. for 2 minutes, followed by 14 repetitions of the following steps: 94° C. for 30 seconds, 55° C. for 45 seconds, and 72° C. for 2 minutes. After the 14 repetitions, the sample was maintained at 72° C. for 7 minutes and then stored at 4° C. This PCR protocol produced a product of ~840 bp, as judged by comparison to DNA size markers.

Cloning

The PCR products were gel purified from 0.8% TAE-agarose gels using the Qiagen gel extraction kit (Valencia, Calif.). The PCR products were quantified using a SmartSpec 3000™ spectrophotometer. The products were digested with restriction enzymes NcoI and SalI following the manufacturer's recommended protocols (New England Biolabs, Beverly, Mass.) and gel purified from 0.8% TAE-agarose gels using the Qiagen gel extraction kit. Vectors pET28 and pET30 were prepared by digestion with restriction enzymes NcoI and SalI, followed by treatment with shrimp alkaline phosphatase and purification from 0.8% TAE-agarose gels using the Qiagen gel extraction kit.

The digested vectors and inserts were ligated using the Rapid™ DNA Ligation Kit (Roche, Indianapolis, Ind.). Approximately 50 ng of treated insert, 100 ng of treated vector (3 to 1 molar ratio of insert to vector), 5 U of T4 DNA ligase (included with the Rapid™ DNA Ligation Kit, and 1× ligation buffer were incubated for 5 minutes at room temperature. The ligation reactions were purified using the High Pure PCR Product Purification Kit (Roche) and were used to transform *E. coli* DH10B electrocompetent cells (Invitrogen, Carlsbad, Calif.). Ten μL of each ligation reaction was added to 40 μL of DH10B cells and were transformed by electroporation using the BioRad Gene Pulser II under the following conditions: 2.5 kV, 25° F., 200 ohm in a 0.2 cm cuvette. The cells were allowed to recover in 1 mL of room temperature SOC for 1 hour at 37° C. with shaking at 225 rpm. The cells were plated on LB plates containing kanamycin (50 μg/mL).

Plasmid DNA was purified from the resulting transformants using the Qiagen spin miniprep kit and screened for the correct inserts by restriction digest with NcoI and Sail. The sequences of plasmids appearing to have the correct insert were verified by dideoxy chain termination DNA sequencing.

Gene Expression and Assays

Plasmid DNA, verified by sequence analysis, was subcloned into *E. coli* expression host BL21(DE3) (Novagen, Madison, Wis.). The cultures were grown and the plasmids were isolated using Qiagen miniprep kit, and analyzed by restriction digest to confirm identity.

Induction in BL21(DE3) was initially performed with *L. brevis* and *P. pentosaceus* glutamate racemases in both pET28 (untagged) and pET 30 (histidine-tagged) vectors. A time course study was performed with cultures grown in 250 mL LB containing kanamycin (50 mg/L) to an $OD_{600}$ of 0.5-0.6 and induced with 100 mM IPTG (isopropyl thiogalacatoside) and sampled at 0 and 3 hours post induction. Cells from 600 μL (0 hour) and 275 μL (3 hour) were resuspended in 40 μL sodium dodecyl sulfate buffer containing 2-mercaptoethanol, and heated at 95° C. for 10 minutes, and cooled. Aliquots of these total cellular protein samples were analyzed by SDS-PAGE using a 4-15% gradient gel.

Cell extracts were also prepared from the 3 hour cultures by suspending cell pellets from 5 mL of culture in 0.625 mL Novagen BugBuster™ reagent containing 0.625 μL benzonase nuclease and 3 μL protease inhibitor cocktail set #3 (Calbiochem-Novabiochem Corp., San Diego, Calif.) at room temperature for 20 minutes with gentle shaking, and centrifuging at 16,000×g to remove cell debris. The supernatants (cell extracts) were loaded onto 4-15% gradient gels for analysis of the cellular soluble proteins.

The 3-hour samples from cloned *L. brevis* glutamate racemase and *P. pentosaceus* glutamate racemase showed both total and soluble protein that corresponded to the correct size (approximately 31 kDa). The *L. brevis* pET30 (histidine-tagged) gene product was over-expressed at a higher level than, and was also more soluble (>20% of soluble protein) than, the *L. brevis* pET 28 (untagged) gene product, as well as the *P. pentosaceus* gene products in both vectors. The *P. pentosaceus* gene product showed equal overexpression and solubility in the pET28 and pET30 vectors, which was significantly less than that observed for the *L. brevis* pET30 gene product.

Cells from the induced cultures (250 mL) were centrifuged and washed once with 0.85% NaCl. Cell pellets were resuspended in 5 mL/g wet cell weight of BugBuster™ (Novagen) reagent containing 5 μL/mL protease inhibitor cocktail set #3 (Calbiochem-Novabiochem Corp., San Diego, Calif.) and 1 μL/mL benzonase nuclease. Samples were incubated at room temperature for 20 minutes on an orbital shaker. Insoluble cell debris was removed by centrifugation at 16,000×g for 20 minutes at 4° C.

Cell extracts were assayed for glutamate racemase activity using the following protocol. 400-μL reactions were carried out in 10 mM potassium phosphate (pH 8.0), 0.2 mM dithiothreitol ("DTT"), and 10 mM L-glutamate or D-glutamate. The reactions were initiated by the addition of 20-100 μL of cell free extracts and were incubated at room temperature. Sample aliquots were taken over a time course of 1 minute, 5 minutes, 10 minutes, 20 minutes and 1 hour (zero minute samples served as control reactions). 2 M formic acid (25 μL) was added to each 40-μL sample aliquot to stop the reaction and the precipitated protein was removed by centrifugation. Supernatants were removed and frozen at −80° C. until they were analyzed by LC/MS/MS.

Assay results from cell extracts from pET30 induction with 100 mM IPTG (3 hours) demonstrate that *L. brevis* (Genbank Accession No. BAA06106.1 GI:468450) and *P. pentosaceus* (Genbank Accession No. AAA16761.1 GI:349029) enzymes have significant levels of racemase activity on both glutamate isomers. The *P. pentosaceus* racemase (20 μL of cellular extracts) reached equilibrium between L- and D-glutamate in 10-20 minutes starting with either substrate. The *L. brevis* enzyme (20 μL of cellular extracts) also reached equilibrium in approximately 20 minutes.

A partially purified aspartate racemase enzyme (catalog # ASPR-101) purchased from BioCatalytics, Inc. (Pasadena, Calif.) was assayed for activity on L-aspartate and D-aspartate using a protocol similar to the one above. The commercial enzyme showed racemase activity on both isomers. Using 0.5-1 mg of enzyme, equilibrium was achieved in 20-60 minutes.

All three racemases (*L. brevis* glutamate racemase, *P. pentosaceus* glutamate racemase and BioCatalytics aspartate racemase were also assayed for activity on S,S monatin using the following protocol. 400-μL reactions were carried out in 10 mM potassium phosphate (pH 8.0), 0.2 mM DTT, and 10 mM S,S monatin. The reactions were initiated by the addition of cell free extracts (*L. brevis* and *P. pentosaceus*) or purified enzyme (BioCatalytics aspartate racemase) and were incubated at room temperature. Sample aliquots were taken over a time course of 1 minute, 5 minutes, 10 minutes, 20 minutes and 1 hour (zero minute samples served as control reactions as well as samples without enzyme). 2 M formic acid (25 μL) was added to each 40-μL sample aliquot to stop the reaction and the precipitated protein was removed by centrifugation. Supernatants were removed and frozen at −80° C. until they were analyzed by LC/MS/MS (Example 1). No decrease in S,S monatin concentration was noted over time, nor was there any increase in S,R monatin (present initially as <5% contaminating byproduct, even in the no enzyme control). Therefore, none of the racemases assayed showed activity towards monatin.

Example 9

Production of R,R Monatin from L-Tryptophan Using Alanine, Glutamate, or Aspartate Racemases This example describes methods of producing stereoisomerically-enriched R,R monatin from L-tryptophan using an L-tryptophan (L-tyrosine, or aromatic) aminotransferase, ProA aldolase, alanine, glutamate or aspartate racemase, and a broad specificity D-amino acid aminotransferase. FIG. 5 is a diagram that illustrates the pathway. This approach to production of stereoisomerically enriched R,R monatin requires an enzyme for step 1 that has low activity in the production of monatin from monatin precursor (MP). Based upon earlier results, we used the *Sinorhizobium meliloti* and *Rhodobacter sphaeroides* tatA gene products described in Example 1 from WO 03/091396 A2.

Materials and Methods

Glutamate racemases from *L. brevis* and *P. pentosaceus* were produced in *E. coli* as described in Example 8. In some cases the $His_6$-tagged version of these enzymes were purified using His-Bind 900 cartridges according to manufacturer's protocols (Novagen, Madison, Wis.) and were desalted to remove imidazole using PD-10 columns (G25 Sephadex, Amersham-Pharmacia). The enzymes were eluted in 25 mM potassium phosphate pH 8.0. Aspartate racemase (ASPR-101) and D-aminotransferase (AT-103) were purchased from BioCatalytics, Inc., alanine racemase was purchased from Sigma (St. Louis, Mo.) (catalog number A8936). *S. meliloti* and *R. sphaeroides* tyrosine (aromatic) aminotransferases were prepared as described in Example 1 from WO 03/091396 A2. *Comamonas testosteroni* ProA aldolase was prepared as described in Example 4 from WO 03/091396 A2. Total protein assays were done utilizing the Bio-Rad Protein Assay according to manufacturer's protocols (Hercules, Calif.).

Reduction in Amount of S,S Monatin Produced Using Racemases

Reaction mixtures (1 mL volume, run in duplicate) contained 100 mM potassium phosphate buffer (pH 8), 2 mM $MgCl_2$, 0.05 mM pyridoxal 5'-phosphate ("PLP"), 200 mM sodium pyruvate, 5 mM sodium α-ketoglutarate or oxaloacetate, approximately 280 μg/mL *S. meliloti* TatA supplied in a cellular extract, 1 mg/mL BioCatalytics D-aminotransferase (AT-103), 100 μL/mL of glutamate racemase cellular extract or 1 mg/mL aspartate racemase, and approximately 100 μg/mL of ProA aldolase provided as a cellular extract. Solid tryptophan was added at a concentration of 10.2 mg/ml. Negative controls did not contain racemase. Samples were incubated at 30° C. (shaking at 250 rpm) for 1 hour, 2 hours, or overnight. Samples were centrifuged to remove precipitate, syringe filtered, and stored at −80° C. prior to analysis for monatin using the LC/MS/MS method described in Example 1.

Most of the samples contained >95% S,S monatin, due to the amounts of native L-aminotransferase present in the cellular extracts. However, the samples that contained racemase had a reduced amount of total monatin as a result of the racemase enzymes making L-glutamate less available for transamination of MP. Without racemase, 1545-2355 ppm monatin (predominantly S,S) was produced during the time-course. With the racemases present, only 340-879 ppm (*L. brevis* enzyme), 444-531 ppm (*P. pentosaceus* enzyme), and 506-1460 ppm monatin (aspartate racemase) were produced. These data indicate that the racemases are active in the reaction conditions required to produce monatin. To minimize formation of S,S monatin from cellular extract enzymes, such as aspartate aminotransferases, further experiments were done with purified enzymes and a higher ratio of D-aminotransferase to L-aminotransferase enzymes.

Conversion of L-Tryptophan to 4-R Containing Isomers of Monatin

The above experiments were repeated using approximately 54 μg of purified L-aminotransferase (either *S. meliloti* or *R. sphaeroides* TatA), 1 mg aspartate aminotransferase (BioCatalytics), 1 mg D-aminotransferase, 5 mM oxaloacetate as the amino acceptor, and 75 μg purified aldolase. The reactions were run in duplicate with a 2-hour sampling time and an overnight incubation time. Negative controls were done with *S. meliloti* L-aminotransferase, but with no racemase. In addition to quantification of R,R/S,S and S,R/R,S monatin peak quantification based on reversed phase chromatography, the percentage of each stereoisomer was determined using the FDAA derivitization technique described in Example 1. The results are shown in Table 29 below.

TABLE 29

| L-Aminotransferase | Incubation Time | Total Monatin (ppm) | % S,S | % R,R | % R,S | % S,R |
|---|---|---|---|---|---|---|
| *S. meliloti* TatA | 2 h | 17.1 | 10.2 | 58.1 | 0.8 | 31.0 |
| *S. meliloti* TatA | 2 h | 15.8 | 13.3 | 55.3 | 1.0 | 30.4 |
| *S. meliloti* TatA | overnight | 77.7 | 25.8 | 40.0 | 1.3 | 32.9 |
| *S. meliloti* TatA | overnight | 67.9 | 29.4 | 37.3 | 1.5 | 31.8 |
| *R. sphaeroides* TatA | 2 h | 241.2 | 96.3 | 2.3 | 0.8 | 0.6 |
| *R. sphaeroides* TatA | 2 h | 223.2 | 95.7 | 2.7 | 1.0 | 0.6 |
| *R. sphaeroides* TatA | overnight | 600.4 | 96.6 | 1.8 | 0.5 | 1.1 |
| *R. sphaeroides* TatA | overnight | 618.5 | 96.1 | 2.1 | 0.5 | 1.3 |
| no racemase control | 2 h | 7.1 | 92.0 | 1.4 | 6.6 | 0.0 |
| no racemase control | 2 h | 5.7 | 94.0 | 1.2 | 4.8 | 0.0 |
| no racemase control | overnight | 44.6 | 93.5 | 1.3 | 4.7 | 0.5 |
| no racemase control | overnight | 37.5 | 95.4 | 0.9 | 3.7 | 0.0 |

Clearly, the presence of the racemase increased the total amount of monatin produced when *S. meliloti* TatA was used as the enzyme for L-tryptophan transamination. Monatin levels increased from an average of 6.4 to 16.5 ppm in the two-hour assay, and from 41-73 ppm in the overnight assay. Additionally, the percent of R,R formed increased from about 1% up to as much as 58% by utilizing the racemase enzyme. The S,R stereoisomer of monatin, another potent sweetener, was the other major component, increasing from nearly 0 in the negative controls to 31%. The *R. sphaeroides* TatA clearly had more activity on S-MP than the *S. meliloti* L-transaminase, demonstrating the importance of having an enzyme that has a high substrate specificity for L-tryptophan as compared to MP when 4-R isomers of monatin are the desired products. With about 10% of the total monatin being 4S at the two-hour timepoint, the *S. meliloti* TatA could be considered as having limited activity on MP.

The experiments were repeated with the purified *S. meliloti* TatA (54 μg) and the *L. brevis* glutamate racemase. When purified glutamate racemase was used, approximately 64 μg was used per 1 mL reaction. Cellular extracts containing the glutamate racemase were also tested and 1.4 mg of soluble protein was used. A no racemase negative control was utilized again and all samples were run in duplicate. The results are shown in Table 30 below.

TABLE 30

| Glutamate racemase | Incubation Time | Total Monatin (ppm) | % S,S | % R,R | % R,S | % S,R |
|---|---|---|---|---|---|---|
| *L. brevis* (purified) | 2 h | 3.3 | 49.1 | 34.2 | 3.7 | 13.0 |
| *L. brevis* (purified) | 2 h | 3.6 | 47.9 | 35.2 | 3.5 | 13.4 |
| *L. brevis* (purified) | overnight | 29.3 | 58.9 | 24.7 | 3.2 | 13.2 |
| *L. brevis* (purified) | overnight | 40.2 | 55.1 | 25.0 | 4.7 | 15.3 |
| *L. brevis* (cell extract) | 2 h | 10.5 | 45.8 | 35.9 | 1.1 | 17.2 |
| *L. brevis* (cell extract) | 2 h | 10.5 | 47.4 | 33.9 | 1.1 | 17.6 |
| *L. brevis* (cell extract) | overnight | 79.4 | 70.3 | 17.9 | 1.3 | 10.5 |
| *L. brevis* (cell extract) | overnight | 80.1 | 69.1 | 19.1 | 1.1 | 10.7 |
| none | 2 h | 2.7 | 84.1 | 7.1 | 6.3 | 2.4 |
| none | 2 h | 3.2 | 84.9 | 6.0 | 6.8 | 2.2 |
| none | overnight | 36.5 | 92.3 | 2.3 | 4.2 | 1.2 |
| none | overnight | 30.5 | 92.7 | 2.0 | 4.1 | 1.3 |

Again, it is clear that the addition of the racemase increases the total monatin produced from L-tryptophan, as well as increases the relative amounts of 4R-containing isomers of monatin as compared to S,S monatin. The use of purified aldolase, racemase, and L-aminotransferase greatly improves the ability to control the desired stereoisomer formation. The ratio of L to D aminotransferase is also a way to manipulate stereochemistry of the final product.

When comparing results shown in Tables 1 and 2 in Example 2, to results with reaction conditions similar to the conditions above, one can see that approximately 7-29 ppm of monatin were formed from indole-3-pyruvate and the percentages of R,R monatin formed were approximately 51-90%. Using the aspartate racemase increased the total amount of monatin produced to 16-78 ppm monatin, with % R,R of approximately 40-58%. Additionally, a more stable and less expensive raw material (L-tryptophan) was utilized. In Example 3, approximately 73 ppm monatin was produced from D-tryptophan at a ratio of R,R:S,R of approximately 1.7:1. The total amount of 4R isomers was >80% of the total monatin. Because both R,R-monatin and R,S-monatin are potent sweeteners (>1000 times sweeter than sucrose), the ability to enrich for these isomers, without the need for expensive D-amino acid substrates, is critical.

It is expected that the availability of a non-specific or R-specific aldolase would increase the reaction rate as well as increasing the percentage of R,R monatin formed. See Example 5. Although the ProA aldolase from *C. testosteroni* used in these assays is reported to predominantly favor substrates in the S-configuration for fission reactions, this Pro A aldolase clearly does produce R-MP. Thus, aldolases that more preferentially produce MP in the R-configuration can help generate even greater percentages of R,R monatin. Additionally, it is expected that finding an L-tryptophan aminotransferase with even lower activity for monatin production would also decrease the amount of S,S and R,S monatin formed. Lastly, improvements can be made to the D-aminotransferase enzyme, or alternative D-aminotransferase enzymes can be used, that would have increased substrate specificity for R-MP versus S-MP. This would also increase formation of the R,R product, if so desired.

The aspartate racemase experiments were repeated to compare the activity of R-selective aldolase of SEQ ID NO:22 with the activity of the ProA aldolase from *C. testosteroni*. Approximately 50 μg of purified L-aminotransferase (*S. meliloti* TatA), 1 mg aspartate racemase (BioCatalytics), 1 mg D-aminotransferase (AT-103, BioCatalytics), 5 mM oxaloacetate as the amino acceptor, and 50 μg of the appropriate purified aldolase. The reactions were run in duplicate and incubated overnight at 30° C. The percentage of each stereoisomer was determined using the FDAA derivitization technique described in Example 1. The results are shown below in Table 31.

TABLE 31

| Aldolase | Total Monatin (ppm) | % S,S | % R,R | % R,S | % S,R |
|---|---|---|---|---|---|
| SEQ ID NO: 22 | 211 | | 72.7 | | 27.3 |
| *C. testosteroni* | 422 | 30.2 | 38.5 | | 31.3 |

The *C. testosteroni* ProA distribution of isomers is consistent with the earlier experiments above, whereas when the R-selective aldolase of SEQ ID NO:22 is used, the percent R,R is much higher, undetectable amounts of S,S are formed, and the amount of S,R monatin is lower.

As described in Examples 2 and 3, D-alanine can serve as the amino donor for transamination of MP to monatin. Many L-aminotransferases have the ability to utilize pyruvate as an amino acceptor to some extent and produce L-alanine. Because the above-mentioned reactions use high concentrations of pyruvate, it is likely that some of the pyruvate is converted to L-alanine. For example, during transamination of L-tryptophan, the HexAspC enzyme described in Example 6 has been found to convert 10-18% of pyruvate (50-200 mM initial concentrations) to L-alanine in 2 hours if alpha-ketoglutarate is absent. The enzyme showed a 10-fold preference for alpha-ketoglutarate when both amino acceptors were present at high (>50 mM) concentrations. AspC (described in WO 03/091396 A2) also produced some L-alanine from pyruvate. Therefore, it was expected that one can omit the addition of alpha-ketoglutarate or oxaloacetate in the above reactions and utilize an alanine racemase (EC 5.1.1.1) in place of glutamate or aspartate racemase.

Alanine racemase enzymes were first identified in *Brucella abortus* and *Streptococcus faecalis*. Marr, A G., and Wilson, P. W., *Arch. Biochem. Biophys.*, 49:424-433, (1954); Wood, W. A., and Gunsalus, I. C., *J. Biol. Chem.* 190:403-416, (1951). The dadB gene in *Salmonella typhimurium* was identified as the source of alanine racemase activity and several hundred homologs can be found in genomics databases. Other known sources of alanine racemase activity are *Escherichia coli, Bacillus subtilis, Pseudomonas aeruginosa, Vibrio cholerae, Schizosaccaroyces pombe*, and *Bacillus cereus*. A basidiomycetous mushroom, *Lentinus edodes*, also contains a broad activity alanine racemase. A thermostable homolog from *Bacillus stearothermophilus* is available for purchase from Sigma-Aldrich (catalog # A8936) and has been immobilized for commercial applications. Inagaki, K., *Biochemistry* 25: 3268 (1986).

Monatin Production with Alanine Racemase

Monatin production was tested using ProA aldolase from *C. testosteroni*. Approximately 50 μg of purified L-aminotransferase (*S. meliloti* TatA), 1 mg D-aminotransferase (AT-103, BioCatalytics), pyruvate as the amino acceptor, 50 μg purified aldolase, and 70 μg alanine racemase purchased from Sigma (St. Louis, Mo.) (catalog number A8936). The reactions were run in duplicate and incubated overnight. The percentage of each stereoisomer was determined using the FDAA derivitization technique described in Example 1. Controls with no racemase were included. The results are shown in Table 32 below.

TABLE 32

| Conditions | Total Monatin | % SS | % RS | % RR | % SR |
|---|---|---|---|---|---|
| Ala racemase (1 hour) | 4 | 66 | 21 | 12 | 1 |
| No ala racemase (1 hour) | 2.7 | 69 | 26 | 5 | 0 |
| Ala racemase (24 hours) | 82.9 | 90 | 5 | 4 | 2 |
| No ala racemase (24 hours) | 170.3 | 89 | 5 | 4 | 2 |

There was three-fold more R,R monatin in the one hour timepoint when alanine racemase was present compared to the sample with no alanine racemase. This result shows that it is possible to produce R,R monatin using alanine racemase. The percentage of R,R monatin produced could be improved using an aldolase that selectively produces R-monatin precursor, an L-aminotransferase that does not work or has limited activity on R-monatin precursor and a D-aminotransferase that does not work or has limited activity on indole-3-pyruvate.

Example 10

D-Phenylglycine Aminotransferase (D-4-Hydroxyphenylglycine Aminotransferase)

As shown in FIG. 3, a stereoinverting aminotransferase is useful in a biosynthetic pathway for the production of monatin. For example, a D-phenylglycine aminotransferase or mutant thereof could produce R,R monatin from R-MP with L-glutamate as the amino donor.

(1) PCR Synthesis of *P. stutzeri* 4 D-Hydroxyphenylglycine Aminotransferase from Oligonucleotide Primers This example describes methods that were used to synthesize 4 D-hydroxyphenylglycine aminotransferase, a stereoinverting enzyme that can be used to convert R monatin precursor to R,R monatin using L-glutamate as the amino donor.

Primer Design

The published sequence (Genbank Accession No. AY319935, nucleic acid sequence; Genbank Accession No. AAQ8290, protein sequence) for *Pseudomonas stutzeri* 4 D-hydroxyphenylglycine aminotransferase (4 D-HPG AT) was used as a template for PCR primer design. Alternatively, the 4-D-hydroxyphenylglycine aminotransferase from *Pseudomonas putida*, (CAD42450 (protein), AX467211 (nucleotide)) is used as a sequence template. A total of 34 forward primers and 35 reverse primers were designed; forward and reverse primers were 40-mers sharing 20 overlapping base pairs. In addition, 2 outer primers were designed with 5' restriction sites and overhangs for cloning into the pET 28 and pET30 vectors (Novagen, Madison, Wis.).

*P. stutzeri* 4 D-HPG AT Outer Primers:

```
N term (with NdeI Site):
                                        (SEQ ID NO:19)
5'-GGCCGGCATATGTCGATCCTTAACGACTACAAACGT-3',
and

C term (with XhoI site):
                                        (SEQ ID NO:20)
5'-GGAAGGCTCGAGTCATGATTGGTTTCCAGACAAATT-3'.
```

Polymerase Chain Reaction Protocol

The gene sequence from *P. stutzeri* was amplified using the following protocols. The primary 100 μL PCR reaction included 0.05 μM of each of the internal 69 primers, 0.4 mM each dNTP, 10 U rTth Polymerase XL (Roche, Indianapolis, Ind.), 0.625 U Pfu polymerase (Stratagene, La Jolla, Calif.), 1×XL buffer and 1 mM $Mg(OAc)_2$. The thermocycler program used included a hot start at 94° C. for 3 minutes, 15 repetitions of the following steps: 94° C. for 30 seconds, 42° C. for 30 seconds, and 68° C. for 15 seconds, followed by 10 repetitions of the following steps: 94° C. for 30 seconds, 52° C. for 30 seconds, and 68° C. for 30 seconds, followed by 10 repetitions of the following steps: 94° C. for 30 seconds, 60° C. for 30 seconds, and 68° C. for 1 minute and 15 seconds. After the final 10 cycles, the sample was maintained at 68° C. for 7 minutes and then stored at 4° C. This PCR protocol produced a smear of product at ~0.5 kb on a 0.8% TAE-agarose gel.

The secondary PCR reaction was set up using the primary PCR reaction as template. The secondary 100 μL PCR reaction included 2.5 μL of the primary PCR reaction, 0.5 μM of each of the 2 outer primers (with NdeI and XhoI restriction sites), 0.4 mM each dNTP, 10 U rTth Polymerase XL, 0.625 U Pfu polymerase, 1×XL buffer and 1 mM $Mg(OAc)_2$. The thermocycler program used included a hot start at 94° C. for 3 minutes, 10 repetitions of the following steps: 94° C. for 30 seconds, 52° C. for 30 seconds, and 68° C. for 1 minute 30 seconds, followed by 15 repetitions of the following steps: 94° C. for 30 seconds, 60° C. for 30 seconds, and 68° C. for 1 minute 30 seconds. After the 15 repetitions, the sample was maintained at 68° C. for 7 minutes and then stored at 4° C. This PCR protocol produced a distinctive product band at ~1.4 kb on a 0.8% TAE-agarose gel.

The PCR product was gel purified from 0.8% TAE-agarose gel using the Qiagen gel extraction kit (Valencia, Calif.). The product was TOPO cloned and transformed into TOP 10 cells according to manufacturer's protocol (Invitrogen, Carlsbad, Calif.). Plasmid DNA was purified from the resulting transformants using the Qiagen spin miniprep kit and screened for the correct inserts by restriction digest with NdeI and XhoI. The sequences of plasmids appearing to have the correct insert were verified by dideoxy chain termination DNA sequencing with universal M13 forward and M13 Reverse primers. Of the 10 clones sequenced, all had at least one mutation from the desired sequence. The best clone had a single base-pair mutation that resulted in an amino acid change. The sequence of this clone was corrected using the QuickChange Mutagenesis protocol according to manufacturer recommendations (Stratagene, La Jolla, Calif.).

The corrected TOPO clone was digested with restriction enzymes NdeI and XhoI following the manufacturer's recommended protocols (New England Biolabs, Beverly, Mass.) and gel purified from 0.8% TAE-agarose gels using the Qiagen gel extraction kit. Vectors pET 28 and pET 30 were prepared by digestion with restriction enzymes NdeI and XhoI, followed by treatment with shrimp alkaline phosphatase and purification from 0.8% TAE-agarose gels using the Qiagen gel extraction kit.

The digested vectors and insert were ligated using the NEB Quick Ligation Kit (Beverly, Mass.). Approximately 50 ng of treated insert, 100 ng of treated vector (3 to 1 molar ratio of insert to vector), 5 U of T4 DNA ligase, and 1× ligation buffer were incubated for 5 minutes at room temperature. The ligation mixture was transformed into TOP10F' chemically competent cells (Invitrogen). The cells were allowed to recover in 0.25 mL of room temperature SOC for 1 hour at 37° C. with shaking at 225 rpm. The cells were plated on LB plates containing kanamycin (50 μg/mL). The plasmid DNA was purified from the resulting transformants using the Qiagen spin miniprep kit and screened for the correct inserts by restriction digest with NdeI and XhoI.

Gene Expression and Assays

Plasmid DNA was transformed into *E. coli* expression host BL21(DE3) (Novagen, Madison, Wis.). The cultures were grown and the plasmids were isolated using Qiagen miniprep kit and analyzed by restriction digest to confirm identity.

Induction in BL21(DE3) was performed with *P. stutzeri* D-4-hydroxyphenylglycine aminotransferase in both pET 28 (histidine-tagged) and pET 30 (untagged) vectors. A time course study was performed with cultures grown in 250 mL LB containing kanamycin (50 mg/L) to an $OD_{600}$ of 0.5-0.6, induced with 100 mM isopropyl thiogalacatoside ("IPTG") and sampled at 0 and 3 hours post induction. An appropriate volume of cells from 0 hours and 3 hours was resuspended in 40 μL sodium dodecyl sulfate buffer containing 2-mercaptoethanol, heated at 95° C. for 10 min, and cooled. Aliquots of these total cellular protein samples was analyzed by SDS-PAGE using a 4-15% gradient gel.

The cell extracts were also prepared from the 3 hour cultures by suspending cell pellets from 5 mL of culture in 0.625 mL Novagen BugBuster™ reagent containing 0.625 μL benzonase nuclease and 3 μL protease inhibitor cocktail set #3 (Calbiochem-Novabiochem Corp., San Diego, Calif.) at room temperature for 20 minutes with gentle shaking and centrifuging at 16,000×g to remove cell debris. The supernatants (cell extracts) were loaded onto 4-15% gradient gels for analysis of the cellular soluble proteins. When noted, the protein was purified using His-Bind 900 cartridges according to manufacturer's protocols (Novagen, Madison, Wis.) and were desalted to remove imidazole using PD-10 columns (G25 Sephadex, Amersham-Pharmacia).

(2) Isolation of Organisms with D-Phenylglycine Aminotransferase ("DPGAT")

Organisms of the genus *Pseudomonas* and like genera, with a stereoinverting D-phenylglycine aminotransferase (also called D-4-hydroxyphenylglycine aminotransferase) are isolated in the following manner. Soil samples are incubated on petri plates with the following medium: (per liter) 15 g agar, 3.4 g $KH_2PO_4$, 3.55 g $Na_2HPO_4$, 0.2 g $MgSO_4.7H_2O$, 8 mg $CaCl_2.2H_2O$, 10 mg yeast extract, 1 ml 1000× trace elements solution (Balch, W. E., et al., "Methanogens: reevaluation of a unique biological group," *Microbiol. Rev.* 43:260-296, (1979)), and 1 g D-phenylglycine (D-4-hydroxyphenylglycine).

Isolates are tested by PCR for the presence of a stereoinverting aminotransferase primers are designed from known D-phenylglycine aminotransferases) or are further enriched for the presence of a stereoinverting aminotransferase as follows: isolates from the plates could be grown in liquid medium as above, without the agar, at 30° C. with shaking to an $OD_{600}$ of about 1.0. The cells are harvested by centrifugation and washed twice with 0.85% NaCl. A 10 mg (wet weight) sample is suspended in 1 ml potassium phosphate buffer (pH 7.0) and 5 mM D-phenylglycine or D-4-hydroxyphenylglycine. Neutralized 15 mM (aminooxy)acetic acid is added to duplicate samples prepared as described above. Consumption of D-phenylglycine (or D-4-hydroxyglycine) is measured by HPLC.

Isolates capable of degrading D-phenlyglycine (or D-4-hydroxyphenylglycine), but do so at a slower rate in the presence of (aminooxy)acetic acid, are selected for further analysis. Isolates are tested, by PCR, for the presence of a stereoinverting aminotransferase (primers are designed from known D-phenylglycine aminotransferases).

The presence of the stereoinverting aminotransferase is confirmed by growing a culture in a liquid medium as described above, harvesting the cells and making a cell-free crude extract ("CFE") and testing for D-phenylglycine aminotransferase or D-4-hydroxyphenylglycine aminotransferase enzyme activity. CFE is added to a reaction mixture with the following final concentrations: 0.1 M 3-(cyclohexylamino)-1-propanesulfonic acid ("CAPS") (pH 9.5), 60 mM L-glutamate (sodium salt), 5 mM benzoylformate or 4-hydroxybenzoate and 50 μM PLP.

The reverse reaction is measured by adding CFE to a reaction mixture with the following concentrations: 50 mM potassium phosphate (pH 7.0), 60 mM D-phenylglycine or D-4-hydroxyphenylglycine, 5 mM α-ketoglutarate, and 50 μM PLP. The assays are incubated at 35° C. and aliquots are taken at time points and stopped by boiling for 2 minutes. The product will be quantitated by the HLPC method of Gil-Av, E., et al., "Resolution of underivatized amino acids by reversed phase chromatography," *J. Am. Chem. Soc.,* 102: 5115-5117, (1980), or by the methods described in Example 1 directed to the measurement of glutamate formation.

As an alternative to PCR based methods, the stereoinverting D-phenylglycine aminotransferase is purified from the isolated bacteria by conventional protein purification techniques, including ammonium sulfate fractionation, and conventional column chromatography. Once the protein has been purified to a reasonable degree, peptide microsequencing techniques or conventional Edman type amino acid sequencing are utilized (see http://golgi.harvard.edu/microchem/ for descriptions of the protocols and equipment used for this type of work). Degenerate primers are designed based on the sequence available from the closest known relative of the protein source. Degenerate PCR and genome walking is then performed according to established protocols to isolate the stereoinverting D-phenylglycine aminotransferase coding sequence.

(3) DPGAT Monatin Production

D-hydroxyphenylglycine aminotransferases, as described in (1) and (2) above, are used in crude cell free protein extracts, or purified as described in (1) above. *S. meliloti* and *R. sphaeroides* tyrosine (aromatic) aminotransferases are prepared as described in Example 1 from WO 03/091396 A2. *Comamonas testosteroni* ProA aldolase is prepared as described in Example 4 from WO 03/091396 A2. Total protein assays are done utilizing the Bio-Rad Protein Assay according to manufacturer's protocols (Hercules, Calif.).

Reaction mixtures (1 mL volume, run in duplicate) contain 100 mM potassium phosphate buffer (pH 8), 2 mM $MgCl_2$, 0.05 mM pyridoxal 5'-phosphate ("PLP"), 200 mM sodium pyruvate, 5 mM sodium α-ketoglutarate, approximately 280 μg/mL *S. meliloti* TatA supplied in a cellular extract, 100 μL/mL of D-hydroxyphenylglycine aminotransferase cellular extract or 1 mg/mL purified D-hydroxyphenylglycine aminotransferase, and approximately 100 μg/mL of ProA aldolase provided as a cellular extract. Solid tryptophan is added at a concentration of 10.2 mg/ml. Negative controls are set up without D-hydroxyphenylglycine aminotransferase. The samples are incubated at 30° C. with gentle shaking for ~1 hour or overnight. The samples are centrifuged to remove precipitate, syringe filtered, and stored at −80° C. prior to analysis for monatin using the LC/MS/MS method described in Example 1.

D-hydroxyphenylglycine aminotransferases with improved activity for monatin production are made using mutagenesis techniques known to those in the art, including: mutagenic PCR, passage through mutagenic strains, site-directed mutagenesis, error-prone PCR, or by methods such as DNA shuffling or other directed evolution technologies. The improved D-hydroxyphenylglycine aminotransferases are selected by growth on minimal medium with R,R-monatin as the source of nitrogen. Initially, the selection is based on growth, but as improved aminotransferases are selected, the screen is growth rate based. That is, cells with mutated versions of the gene are grown and the gene is expressed in minimal medium with R,R-monatin as the nitrogen source. The growth rates of the cells with the mutated versions of the gene are compared to the unmutated version. Those cells with a faster growth rate are selected and the aminotransferase is analyzed further. The D-hydroxyphenylglycine aminotransferase may be further mutagenized until the desired activity is obtained.

(4) DPGAT Assay

The un-His-tagged version of the DPGAT was expressed as described in (1) above and extracts were used in assays.

Assays were set up and included 100 mM potassium phosphate pH 7.0, 60 mM D-phenylglycine, 5 mM α-ketoglutarate, and 50 μM pyridoxal-5'-phosphate. The assays were started by adding 100 μL of extract, prepared as described above in this example, per ml of assay volume. Samples were taken at several timepoints (0, 1, 2, 5, 10, 30, 60, and 120 minutes) and were stopped with an equal volume of 2 M formic acid. A sample was also taken after overnight incubation (~1200 minutes). The samples were analyzed for glutamate production by the OPA method described in Example 1. The results are summarized in Table 33 below.

TABLE 33

| Condition | Time (Minutes) | μmole/mL L-Glutamate |
|---|---|---|
| No substrate | 0 | 0.033 |
| | 1 | 0.033 |
| | 2 | 0.033 |
| | 5 | 0.035 |
| | 10 | 0.034 |
| | 30 | 0.036 |
| | 60 | 0.044 |
| | 120 | 0.038 |
| | ~1200 | 0.058 |
| D-phenylglycine | 0 | 0.055 |
| | 1 | 0.112 |
| | 2 | 0.169 |
| | 5 | 0.315 |
| | 10 | 0.387 |
| | 30 | 0.892 |
| | 60 | 1.304 |
| | 120 | 1.514 |
| | ~1200 | 1.056 |

The enzyme clearly has some activity on the D-phenylglycine. The enzyme activity was also tested on R,R monatin. The assay was set up as described above and R,R monatin was included at a concentration of 60 mM. The results are indicated below in Table 34.

TABLE 34

| Condition | Time (Minutes) | μmole/mL L-Glutamate |
|---|---|---|
| R,R monatin | 0 | 0.041 |
| | 1 | 0.040 |
| | 2 | 0.041 |
| | 5 | 0.041 |
| | 10 | 0.041 |
| | 30 | 0.042 |
| | 60 | 0.041 |
| | 120 | 0.040 |
| | ~1200 | 0.045 |

There did not appear to be any detectable activity on R,R monatin. However, it is expected that the random or SDM methods described in this part (3) of this Example could be utilized to improve the transamination activity on R,R monatin or R-MP. For instance, the crystallization and preliminary analysis of the *P. stutzeri* enzyme has been done. Kongsaeree, P., et al., *Acta Cryst. D*59:953-954, (2003). Once the structure is published, docking experiments can be done using software such as Accelrys, to determine where steric hindrances or ionic repulsion may be prohibiting the R,R monatin from binding to the D-hydroxyphenylglycine substrate binding site. D-hydroxyphenylglycine is a somewhat large amino acid, as is R,R monatin. Both compounds have hydrophobic regions and hydroxyl groups. Modifications can be done to the binding pocket, as described in Example 6, to make the enzyme more amenable to dicarboxylic acid substrates. For instance, a residue near the second carboxyl group may be modified to a base such as arginine. Additionally, The *P. putida* gene described in part (1) and the additional genes that may be isolated as described in (2) can be used as templates for gene shuffling. Additionally, the *P. stutzeri* gene assembled in this Example can be mutagenized using oligonucleotide shuffling or other random mutagenesis methods, and screened as described in (3) above.

Example 11

Discovery of a D-Methionine Aminotransferase Gene

Background

D-methionine-pyruvate aminotransferase (EC 2.6.1.41) is thought to be another example, although rare, of a stereoinverting transaminase. This enzyme catalyzes the reversible conversion of D-methionine and pyruvate to L-alanine and 4-methylthio-2-oxobutanoate. Oxaloacetate, phenylpyruvate, 2-oxobutyrate, 2-oxovalerate, 2-oxoheptanoate, glyoxylate, and oxoglutarate can also serve as amino acceptors.

Transamination of D or L methionine is thought to be part of a pathway to ethylene production in higher plants (cauliflower, tomato, apple, pea stem, banana, peanut), as well as in soil microorganisms (*Escherichia coli, Pseudomonas pisi, Pseudomonas aeruginosa, Bacillus mycoides, Acinetobacter calcoaceticus, Aeromonas hydrophila* B12E, *Rhizobium trifolii* N2P7, *Penicillium digitatum, Saccharomyces cerevisiae, Corynebacterium* D7F). Billington, D. C., et al., *Biochem J.* 182:827-836, (1978). In bacteria, L-methionine is typically used as the substrate in the ethylene production studies and broad specificity enzymes such as TyrB or AspC from *E. coli* are thought to be responsible for the transamination. However, Primrose, S. B., *J. Gen. Microbiol.* 95:159-65, (1976) and Primrose, S. B., *J. Gen. Microbiol.* 98:519-528, (1977) showed that *E. coli* strain SPA 0 (University of Warwick culture collection) produced nearly as much ethylene from D-methionine as from L-methionine in batch cultures. Because no broad specificity D-aminotransferase has been identified in *E. coli*, one possible explanation could be that the *E. coli* D-amino acid dehydrogenase (encoded by the dada gene) converts the D-methionine to 4-methylthio-2-oxobutanoate. It is also possible that there is a methionine racemase in *E. coli*; however, no such enzyme has been described in the literature.

In contrast to *E. coli*, in cauliflower florets (mitochondrial extract preparations) and germinating peanut seeds production of ethylene was higher when D-methionine and pyruvate were supplied to the enzyme extract as compared to L-methionine and pyruvate. Mapson, L. W., et al., *Biochem J.* 115:653-661, (1969); Durham, J. I., et al., *Phytochemistry* 12:2123-2126, (1973). Therefore, the possibility of a combination of methionine racemase and an L-aminotransferase is not supported by the data. Dehydrogenase activity was ruled out by dialysis of cellular extracts of cauliflower; no NAD was present in the assay mixtures. Oxidase activity was ruled out as no consumption of oxygen was noted and there was no requirement for FAD. The D-methionine aminotransferase from peanut tissues was purified, shown to be dependent on PLP, and shown to be independent of L-methionine aminotransferase activity. There is a possibility that these D-methionine-pyruvate aminotransferases actually produce D-alanine as a byproduct (similar to the *Bacillus* enzymes described in Examples 2 and 3) and that the cells contain alanine racemase to recycle the D-alanine back to L-alanine (or an analogous amino donor). In either case, discovery of the broad specificity D-aminotransferase from higher plants is advantageous for development of processes that produce R,R monatin or S,R monatin.

Experimental Overview

D-methionine aminotransferase is partially purified from cauliflower florets and germinating peanut embryos using standard chromatography protocols and a Pharmacia AKTA Explorer system. The protein sequences of homologous proteins are determined by LC/MS/MS fingerprinting techniques and database searching performed by Harvard Microchemistry facility. The coding regions of the plant genes are cloned from a cDNA library using standard PCR protocols or by synthesis of the gene as described in Example 10(1).

Alternatively, cDNA expression libraries are constructed (Stratagene, La Jolla, Calif.) from cauliflower tissue or peanut seeds grown in the presence of D-methionine (and producing ethylene). The libraries are transformed into *E. coli* methionine auxotrophs from the *E. coli* Genetic Stock Center (Yale) such as strains RC519 or AB1931. Plasmids of strains capable of growth on minimal media containing D-methionine contain the coding region of interest (see Example 4(1), an analogous screening technique).

Once the coding regions of interest are obtained and are expressed in a standard *E. coli* laboratory strain, the resulting gene products can be used in assays to produce R,R monatin, as described in Example 10(3), in place of the D-hydroxyphenylglycine aminotransferase, with the exception of the pH being 7.5 (the optimal pH for the aminotransferase). If the D-methionine aminotransferase has a strict requirement for D-amino acid donor substrates, the enzyme can be used to make R,R monatin as described in Example 2 and 3. The gene can be mutagenized and screened for increased activity as described in Example 10(3).

Methods

Isolation from Cauliflower

Four hundred grams of freshly picked cauliflower florets are extracted with 400 mL of a 4° C. sucrose/buffer solution (0.4 M sucrose and 0.1 M sodium phosphate buffer pH 7.4) by alternating soaking and mixing using a blender. Cell debris is removed by filtration with cheesecloth and the resulting solution is centrifuged at 40,000×g for 30 minutes at 4° C. The solid material (containing mitochondrial organelles) is resuspended in 20 mL 10 mM sodium phosphate buffer pH 7.4 and enzymes are extracted with 200 mL cold (−30° C.) acetone. The suspension is recentrifuged and the precipitate is dried using a Savant Speed Vac. The solid material is dissolved in 10 mM sodium phosphate buffer pH 7.4 and residual acetone is removed using a PD-10 column.

Aminotransferase activity is assayed by incubation of the enzyme preparation with 5 mM D-methionine, 1 mM pyruvate, 0.05 mM PLP and 2 mM EDTA in 0.1 M sodium phosphate buffer pH 7.4. Assays are performed at 25° C. for 16 hours. The 4-methylthio-2-oxobutanoate is measured by formation of the 2,4-dinitrophenylhydrazone derivative, using LC/MS (m/z of 328) and similar methodology described in Example 1. A 0.4% (w/v) solution of 2,4-dinitrophenylhydrazine in 2M sulfuric acid is prepared and a half volume is added to the assay mixture after incubation. The mixture is mixed with gentle shaking at 30° C. for 30 minutes and the precipitate is collected by centrifugation and analyzed by LC/MS. Protein fractions separated by standard chromatographic techniques are assayed for activity in a similar manner, but the co-product alanine is measured by the OPA post-column derivitization technique described in Example 1.

Isolation from Peanut (*Arachia hypogea* L. cv. Starr)

The D-methionine aminotransferase enzyme from germinating peanut embryo homogenate (minus the cotyledons) is purified according to the method of Durham, J. I., et al., *Phytochemistry* 12:2123-2126, (1973). Reducing agents are used during the preparation of crude extracts to stabilize the enzymes and the cell debris is removed by centrifugation at 33,000×g. A 35-50% ammonium sulfate fraction is further purified by incubation at low temperature and by removal of the proteins in the precipitate. The supernatant is further fractionated using acetone. The active pools are then further purified by gel filtration chromatography (Sephadex 200 G.E. Healthcare, Piscataway, N.J.).

As protein fractions become enriched with the transaminase protein, 2D-gel electrophoresis is utilized to separate the enzyme of interest for microsequencing. After elucidation of homologous coding regions in plant sequences deposited at NCBI, the D-aminotransferase protein is produced recombinantly in *Escherichia coli* using standard molecular biology techniques. It is expected that the cellular extracts from cauliflower florets or peanut seeds or recombinantly produced homologous enzymes can be used in production of R,R monatin as described in Example 10(3) (if a stereoinverting transaminase) or Examples 2 and 3 (if a broad specificity D-aminotransferase).

Example 12

L-Alanine Aminotransferase/Alanine Racemase/D-Alanine Aminotransferase

FIG. 8 illustrates the biosynthetic pathway for producing stereoisomerically-enriched R,R monatin from L-tryptophan using L-amino acid aminotransferases (such as L-aromatic aminotransferases, L-alanine-aminotransferases and/or L-tryptophan-aminotransferases), an R-specific aldolase, an alanine racemase and a D-alanine aminotransferase.

A tryptophan-specific aminotransferase is described in Example 6. Alternatively, *S. meliloti* and *R. sphaeroides* tyrosine (aromatic) aminotransferases are prepared as described in Example 1 from WO 03/091396 A2. *Comamonas testosteroni* ProA aldolase is prepared as described in Example 4 from WO 03/091396 A2. Total protein assays are done utilizing the Bio-Rad Protein Assay according to manufacturer's protocols (Hercules, Calif.). Alanine racemase is purchased from Sigma (St. Louis, Mo.) (catalog number A8936). D-alanine aminotransferase is purchased from BioCatalytics (Pasadena, Calif.) (catalog number AT-103).

L-alanine aminotransferases are widely distributed in eukaryotes, bacteria, and archaea. The following organisms have been identified (based on sequence homology) as containing an L-alanine aminotransferase (EC 2.6.1.2): *Arabidopsis thaliana, Ashbya gossypii, Azotobacter vinelandii, Bifidobacterium longum, Caenorhabditis elegans, Candida albicans, Candida glabrata, Chlamydomonas reinhardtii, Cryptococcus neoformans, Debaryomyces hansenii, Homo sapiens, Hordeum vulgare, Kluyveromyces lactis, Magnaporthe grisea, Medicago truncatula, Mus musculus, Neurospora crassa, Oryza sativa, Phanerochaete chrysosporium, Pinus taeda, Pseudomonas putida, Pyrococcus abyssi, Pyrococcus furiosus, Pyrococcus horikoshii, Rattus norvegicus, Saccharomyces cerevisiae, Schizosaccharomyces pombe, Takifugu rubripes, Trypanosoma cruzi, Vibrio cholerae, Vibrio parahaemolyticus, Vibrio vulnificus, Yarrowia lipolytica*, and *Zea mays*. Additionally, many aminotransferases have low-level alanine aminotransferase activity and given high levels of L-glutamate and pyruvate can convert it to L-alanine and α-ketoglutarate. An enzyme with low activity is improved with standard mutagenesis techniques, such as error-prone PCR and passage through mutagenic strains, or by directed evolution techniques. The gene for an L-alanine aminotransferase is cloned using publicly available sequences to design primers and using standard techniques to amplify, clone, express and purify the gene/enzyme.

The reaction mixtures (1 mL volume, run in duplicate) contain 100 mM potassium phosphate buffer (pH 8), 2 mM $MgCl_2$, 0.05 mM pyridoxal 5'-phosphate ("PLP"), 200 mM sodium pyruvate, 5 mM sodium α-ketoglutarate, approximately 280 μg/mL *S. meliloti* TatA supplied in a cellular extract (or other L-tryptophan specific aminotransferase) (as in Example 4 section (5), 100 μg of an L-alanine aminotransferase, 100 μL/mL of alanine racemase cellular extract or 1 mg/mL purified alanine racemase (Sigma), approximately 280 μg/mL of a broad specificity D-alanine aminotransferase supplied in a cellular extract (Examples 15 and 18 have examples of D-aminotransferases that could work for this reaction) and approximately 100 μg/mL of ProA aldolase provided as a cellular extract. Solid tryptophan is added at a concentration of 10.2 mg/ml. Negative controls are set up without alanine racemase. The samples are incubated at 30° C. with gentle shaking for ~1 hour or overnight. The samples are centrifuged to remove precipitate, syringe filtered, and stored at −80° C. prior to analysis for monatin using the LC/MS/MS method described in Example 1.

Example 13

Purification of R,R-Monatin from an Enzymatic Reaction Mixture

The product, R,R-monatin, was purified from the following reaction mixture. In 0.33 liter, 50 mM ammonium bicarbonate, pH 8.2, 4 mM $MgCl_2$, 0.05 mM pyridoxal phosphate ("PLP"), 200 mM sodium pyruvate, and 50 mM D-tryptophan were mixed at room temperature in a 500 mL glass bottle until the tryptophan dissolved. The liquid was flushed with nitrogen for several minutes and then 3.0 mg/mL Biocatalytics, Inc. (Pasadena, Calif.) Broad range D-transaminase (catalog # AT-103) and 0.1 mg/mL purified aldolase of SEQ ID NO:22 were added. The reaction mixture was stirred gently at room temperature. The aldolase was purified as described in Example 3. Additional aliquots of 50 mM D-tryptophan were added as a solid 15 hours and 22 hours after the mixture was initially prepared. The head space was flushed with nitrogen after each addition. All of the added tryptophan did not dissolve, but the concentration was maintained at about 50 mM. After 40 hours, the remaining solid tryptophan was filtered off. Analysis of the reaction mixture by post column fluorescence detection liquid chromatography (see Example 1) showed that the concentration of tryptophan in the solution was 49 mM and the concentration of monatin was 3.9 mM.

The product monatin was purified utilizing two ion exchange chromatography steps. The filtered reaction solution was first applied to a column of BioRad AG50W-X8 resin (140 mL; binding capacity of 1.7 meq/mL). The column was washed with 2×150 mL $H_2O$ and then eluted with 1 M $NH_4OH$ (1×450 mL, followed by 3×150 mL). The $NH_4OH$ fractions were combined, neutralized with HCl and filtered successively through Whatman (Maidstone, England) glass microfibre filters and Gelman Sciences (Ann Arbor, Mich.) 0.45 μm filters. The clarified solution was then ultrafiltered using an Amicon (Millipore; Billerica, Mass.) ultrafiltration stirred cell (Model 8200) with a YM100 (MWCO 100 kDa). The filtrate from the ultrafiltration was evaporated to approximately 160 mL using a roto-evaporator with a tepid water bath. The liquid was again clarified by filtering through glass microfibre filters.

The resulting solution was applied to a 1 L Fast Flow DEAE Sepharose (Amersham Biosciences) column previously converted to the bicarbonate form by washing with 0.5 L 1 M NaOH, $H_2O$, and 1.0 M ammonium bicarbonate, pH 8.3, followed by an additional washing using $H_2O$. The solution was loaded at <2 mL/min and the column was washed with water at 3-4 mL/min until the absorbance at 280 nm was <1. The R,R-monatin was eluted with 50 mM ammonium bicarbonate, pH 8.3 (2.5 L). This fraction was evaporated using a roto-evaporator with a tepid water bath. The resulting syrup was incubated at 4° C. for several days until crystals formed. The crystals were collected, washed with cold 100% ethanol and dried in a vacuum dessicator (0.38 g).

Analysis of the solid product for isomeric purity using FDAA derivitization, followed by LC/MS/MS multiple reaction monitoring, (see Example 1) showed that the sample was 96.3% R,R monatin and 3.7% S,R-monatin.

The sample was also analyzed for purity with respect to other organic compounds using the total monatin method (see Example 1). The UV absorbance was scanned from 200-500 nm using a Photodiode Array detector. Based upon the integrated peak areas, monatin accounted for 96.1% of the area (including both R,R and S,R peaks).

Analysis of the sample by post column fluorescence detection liquid chromatography showed that the amino acid composition of the sample was 98.8% monatin with trace amounts of tryptophan (1.2%) and alanine (0.02%).

Elemental analysis was performed at Midwest Microlab, LLC (Indianapolis, Ind.). This analysis indicated that the sample contained 1% non-combustible (inorganic) material by weight, and ammonium and bicarbonate residuals.

Example 14

Improvement of D-Aminotransferase Activity Retention During Purification

Standard Procedure for the Purification of *B. sphaericus* $HIS_6$-D-Alanine Aminotransferase Starting from a fresh culture plate (LB agar with 50 μg/mL kanamycin) of BL21(DE3)::*B. sphaericus* dat pET30a (Example 18), the cells were grown in 5 mL of Luria-Bertani broth ("LB") with 50 μg/ml kanamycin, at 37° C. and 225 rpm for 3-5 hours. Subsequently, the culture was transferred at 0.25% (v/v) into flasks containing Novagen Overnight Express System II solutions 1-6 (EMD Bioscience, Madison, Wis.) plus 50 μg/mL kanamycin. The cells were grown at 37° C. and 225 rpm overnight (16-18 hours). When the $OD_{600}$ was approximately 8.0, the cells were harvested by centrifugation in a Beckman (Fullerton, Calif.) J25II centrifuge with a JS-16.25 rotor at 10,000 rpm for 10 minutes. The cell pellet was washed once with cold 50 mM EPPS buffer (pH 8.2), and the cells were centrifuged again. The washed cell pellet was harvested and used immediately or frozen at −80° C. until needed for purification.

To prepare cell-free extract containing the *B. sphaericus* $HIS_6$-D-alanine aminotransferase ($HIS_6$-BsphDAT) protein, the cells were suspended in 3-4 volumes of 50 mM EPPS, pH 8.2 and then disrupted using a Microfluidics (Newton, Mass.) homogenizer (3 passes at 20,000 psi), maintaining the temperature of the suspension below 15° C. All subsequent purification steps were carried out at 4° C. The cell extract was centrifuged for 15 minutes at 15,000×g to remove the cell debris. The supernatant was decanted and used immediately or frozen at −80° C. An aliquot of the cell free extract was applied either to Novagen HIS-Bind columns (catalog # 70971-4) or to a column of GE Healthcare (Piscataway, N.J.) Chelating Sepharose™ Fast Flow resin (nickel(II) form) (at a ratio of 1.2-1.5 v/v) that had been previously equilibrated with 50 mM EPPS, pH 8.2, containing 200 mM sodium chloride. After loading the sample, the column was washed/eluted successively with 3-5 volumes of the equilibration buffer, 3-5 volumes of the equilibration buffer containing 25 mM imidazole, 3-5 volumes of the equilibration buffer containing 100 mM imidazole and 3-5 volumes of the equilibration buffer containing 500 mM imidazole. The $HIS_6$-BsphDAT protein eluted in the last wash. The 500 mM imidazole wash was concentrated 2-10× with Amicon (Billerica, Mass.) Centricon-70 or Ultra-15 centrifugal filter devices (MWCO 10 kDa). The imidazole and sodium chloride were removed by passage through disposable GE Healthcare PD10 desalting columns previously equilibrated with 50 mM EPPS, pH 8.2, containing 50 μM PLP.

The protein concentration of the desalted solution was determined using the Pierce BCA assay kit (Rockford, Ill.). The purity of each fraction and the level of expression in the cell free extract fraction were determined using a Bio-Rad (Hercules, Calif.) Experion Pro260 microcapillary chip system or by SDS-PAGE with 4-15% gradient gels. Typically, this procedure produces more than 300 mg of enzyme (from 600 mL of Overnight Express II culture) that is ~90% pure as judged by the Experion software. Aliquots (1-5 mL) of the purified enzyme were stored at −80° C. until use.

Improved Procedure

Cell-free extract was prepared as described above. $His_6$-BsphDAT protein was similarly purified with the following changes: all buffers used for cell disruption and protein purification contained 100 mM potassium phosphate, pH 7.8, with 50 μM PLP. The protein was purified exclusively with GE Healthcare Chelating Sepharose™ Fast Flow resin (nickel(II) form).

Activity Assay

The formation of indole-3-pyruvate and alanine from tryptophan and pyruvate was assayed using the enzyme prepared by both purification procedures. The reaction mixtures contained 100 mM potassium phosphate, pH 7.8, 0.05 mM pyridoxal phosphate, 100 mM sodium pyruvate, 40 mM D-tryptophan, and 0.03-0.1 mg/mL of purified enzyme. The tryptophan was added as a solid. All components except the enzyme were mixed together and incubated at 30° C. until the tryptophan dissolved. The enzyme was then added and the reaction solution was incubated at room temperature. At predetermined time points, the reactions were sampled and the samples immediately stored on ice and diluted for alanine analysis by the post-column fluorescence detection liquid chromatography method described in Example 1. Table 34 below lists the specific activity of the enzyme preparations as the concentration of alanine formed per mg of enzyme per minute.

TABLE 34

Effect of Improved Purification Procedure on Enzyme Activity

| Enzyme Preparation | Specific Activity (μmole Alanine(mg)$^{-1}$(min)$^{-1}$) |
|---|---|
| $HIS_6$-BsphDAT purified without 50 μM PLP | 2.9 |
| $HIS_6$-BsphDAT purified with 50 μM PLP | 14.2 |

The results shown in Table 34 indicate that the use of pyridoxal phosphate during the purification process resulted in an enhanced activity.

Example 15

Cloning of Two Novel *Bacillus* D-Amino Acid Aminotransferases

Several *Bacillus* D-amino acid aminotransferases (EC 2.6.1.21, also known as D-alanine aminotransferase or D-aspartate aminotransferase) were produced recombinantly for use in coupled assays for production of R,R monatin, as described in Example 18. These enzymes are homologous to D-aminotransferases described previously for production of monatin (U.S. Publication No. 20040063175 and U.S. Publication No. 2005282260). An approach used for the selection of strains that could be candidates containing novel D-amino acid aminotransferases ("DAATs") was to review the list of *B. sphaericus* strains deposited in ATCC and analyze some that were previously deposited under different species names. The following organisms were ordered from the ATCC: ATCC 4978—*Bacillus sphaericus* originally deposited as *Bacillus rotans* and ATCC 7063—*Bacillus sphaericus* originally deposited as *Bacillus serositidis* and ATCC 21538—*Bacillus sphaericus* originally deposited as *Bacillus circulans*. Known DAAT protein sequences from *Bacillus sphaericus, Bacillus halodurans, Geobacillus stearothermophilus, Bacillus cereus, Bacillus subtilis*, and *Bacillus licheniformis* were aligned to obtain sequence regions that were conserved in the various DAAT proteins. Primers were designed in the regions of protein sequence conservation and used for polymerase chain reactions ("PCR") amplification of DAAT gene sequences from the ATCC strains mentioned above.

Five PCR primers were designed based on conserved regions in alignment of published *Bacillus* DAAT sequences (see alignment in FIG. 9).

Polymerase Chain Reaction Protocol

Primers were designed as mentioned above based on conserved regions in an alignment of DAATs. Oligonucleotide Primer Sequences are indicated below: 5' GAAGACCGTGGTTATCAATTT 3' (SEQ ID NO:65) (forward primer), 5' GATGGTATTTACGAAGTAATC 3' (SEQ ID NO:66) (forward primer), 5' AGATTTAATATCACAACGTAAC 3' (SEQ ID NO:67) (reverse primer), 5' GCCAAGTAAAATTTAAGATTTA 3' (SEQ ID NO:68) (reverse primer), 5' ATTTGCTGGGTGCGTATAAAG 3' (SEQ ID NO:69) (reverse primer). Expected sizes of PCR fragments based on primer combinations alignment with known DAATs: SEQ ID NO:65 and SEQ ID NO:67—approx. 380 bp, SEQ ID NO:65 and SEQ ID NO:68—approx. 395 bp, SEQ ID NO:65 and SEQ ID NO:69—approx. 534 bp, SEQ ID NO:66 and SEQ ID NO:67—approx. 336 bp, SEQ ID NO:66 and SEQ ID NO:68—approx. 346 bp, SEQ ID NO:66 and SEQ ID NO:69—approx. 510 bp.

Combinations of the above primers were used for colony PCR from the following ATCC strains: ATCC 4978—*Bacil-*

*lus sphaericus*, originally deposited as *Bacillus rotans*; ATCC 7063—*Bacillus sphaericus*, originally deposited as *Bacillus serositidis*; and ATCC 21538—*Bacillus sphaericus*, originally deposited as *Bacillus circulans.*

The three above mentioned strains were grown on nutrient agar at 30° C. A single colony was scraped from plates and resuspended in 25 μL sterile distilled water. The cells were lysed at 96° C. for 10 minutes. PCR was carried out as follows: per 50 μL reaction, 5 μL lysed cells, 0.8 μL of each primer, 2 μL dNTPs, 0.8 μL Expand High Fidelity Polymerase (Roche, Indianapolis, Ind.) and 1× Expand™ buffer were added. A 3 minute hot start was done at 94° C., followed by 15 cycles of 94° C. for 30 seconds, 40° C. for 45 seconds, and 72° C. for 2 minutes. Fifteen more cycles were done with an increased annealing temperature of 45° C. Lastly, a chain extension step was done for seven minutes at 72° C. Several primer combinations gave expected PCR product sizes for the above strains. PCR products were cloned using the Zero Blunt TOPO® cloning kit as per manufacturers' protocols (Invitrogen) and sequenced by dideoxy chain termination DNA sequencing at Agencourt BioScience Corporation (Beverly, Mass.). Sequences at both the DNA and amino acid level were aligned with the *B. sphaericus* DAAT sequence. Valid DAAT/DAT sequences were obtained from all three strains, ATCC 4978, ATCC 7063 and ATCC 21538. Two specific strains, ATCC 4978 and ATCC 7063 gave PCR products which when translated yielded protein sequences with distinct amino acid residue changes when compared to the *B. sphaericus* D-aminotransferase sequence.

Genome walking was carried out to obtain the complete gene sequences for the ATCC 4978 and ATCC 7063 strains. Strain ATCC 4978 was grown up in nutrient broth at 30° C. Strain ATCC 7063 was grown up on nutrient agar. Genomic DNA was prepared from each strain using the Gentra Kit (Gentra Systems, Minneapolis, Minn.) as per manufacturer's protocols. Four libraries were constructed for each strain as per manufacturer's protocols (BD GenomeWalker™ Universal Kit, Clontech, www.Clontech.com). Gene-specific primers were designed as per GenomeWalker™ manufacturer's protocols based on sequences obtained using conserved primer combinations (see above), allowing for a few hundred homologous base pair overlap with original product. These gene-specific primers were subsequently used with GenomeWalker™ adaptor primers for PCR of upstream and downstream sequences to complete DAT ORFS.

The gene-specific oligonucleotide primer sequences are indicated below:

```
4978 DAT GSP1 Upstrm
                                        (SEQ ID NO:70)
5' GACATGCTCCTCCGCTGTAAATAATTCACC 3'

4978 DAT GSP1 Dwnstr
                                        (SEQ ID NO:71)
5' CCCTGGTGATGAAGTGAAGCCAGTATTAAC 3'

4978 DAT GSP2 Upstrm
                                        (SEQ ID NO:72)
5' ATCGCCAAATTGATAACCACGGTCTTC 3'

4978 DAT GSP2 Dwnstr
                                        (SEQ ID NO:73)
5' ACGTCCCGTAGCAAACTTTGAAAAAGGTGT 3'

7063 DAT GSP1 Upstrm
                                        (SEQ ID NO:74)
5' TGCATAGAATCGGTCGATATGTTCAGTAGC 3'
```

-continued

```
7063 DAT GSP1 Dwnstr
                                        (SEQ ID NO:75)
5' GCGGAGAAACGATTACAGAAGGTTCTTCAA 3'

7063 DAT GSP2 Upstrm
                                        (SEQ ID NO:76)
5' GTCACCAAATTGATAACCACGGTCTTC 3'

7063 DAT GSP2 Dwnstr
                                        (SEQ ID NO:77)
5' GGTGTACTTTATACGCACCCAGCAAAT 3'
```

Adaptor Oligonucleotide Primer Sequences:

```
AP1 5' GTAATACGACTCACTATAGGGC 3'    (SEQ ID NO:78)

AP2 5' ACTATAGGGCACGCGTGGT 3'       (SEQ ID NO:79)
```

Primary GenomeWalker™ PCRs were carried out as follows: per 50 μL reaction, 2.5 μL of DNA library, 2 μL of each primer (AP1 (SEQ ID NO:78) and the appropriate GSP1), 1.5 μL dNTPs, 1×XL PCR buffer, 1 mM magnesium acetate, and 1 μL $RT^{TH}$ polymerase (Roche, Indianapolis, Ind.) were added. A 3 minute hot start was done at 94° C., followed by 10 cycles of 94° C. for 30 seconds, 55° C. for 30 seconds, and 68° C. for 1 minute. Twenty more cycles were done with a decreased annealing temperature of 48° C. Lastly, a chain extension step was done for seven minutes at 68° C. Secondary Genome Walker™ PCRs were carried out as follows: per 50 μL reaction, 1.0 μL (of a 1:50 dilution) of the primary PCR reaction, 2 μL of each primer (AP2 (SEQ ID NO:79) and the appropriate GSP2), 1.5 μL dNTPs, 1×XL PCR buffer, 1 mM magnesium acetate, and 1 μL $RT^{TH}$ polymerase were added. A 3 minute hot start was done at 94° C., followed by 10 cycles of 94° C. for 30 seconds, 55° C. for 30 seconds, and 68° C. for 1 minute. Fifteen more cycles were done with a decreased annealing temperature of 48° C. Lastly, a chain extension step was done for seven minutes at 68° C.

Several libraries gave PCR products ranging in size from ~200 bp to ~1.5 Kb. PCR products were TOPO cloned (as above) and sequenced by dideoxy chain termination DNA sequencing at Agencourt BioScience Corporation (Beverly, Mass.); these new sequences were aligned with initial sequences obtained using conserved primer combinations and start and stop codons were identified. In this way the DAAT complete ORFs were obtained. New primer pairs were designed (with restriction sites for cloning) based on the specific complete DAAT sequences to PCR the entire DAAT gene from ATCC strains 4978 and 7063 individually.

Oligonucleotide Primer Sequences are Indicated Below:

```
ATCC4978DAATNde1F
                                        (SEQ ID NO:80)
5' GGCCTTGGCATATGAGTTATAGCTTATGGAATGACC 3'

ATCC4978DAATBamH1R
                                        (SEQ ID NO:81)
5' GGCCTTAAGGATCCTTATGCGCGAATACCTTTTGGG 3'

ATCC7063DAATNde1F
                                        (SEQ ID NO:82)
5' GGCCTTGGCATATGAGCTACACTTTATGGAATGA 3'

ATCC7063DAATBamH1R2a
                                        (SEQ ID NO:83)
5' GGCCAAGGATCCGCTACCCACTAATCATTAGA 3'
```

The coding regions of the ATCC 4978 and ATCC 7063 DAAT genes were amplified using the following PCR protocol. In a 50 μL reaction, 3 μL genomic DNA, 0.8 μL of each primer, 2 μL dNTPs, 0.8 μL Expand High Fidelity Polymerase (Roche, Indianapolis, Ind.), 1× Expand™ buffer with Mg, and 0.2 μL Pfu polymerase (Stratagene, La Jolla, Calif.) were added. The thermocycler program used included a hot start at 94° C. for 3 minutes, followed by 8 repetitions of the following steps: 94° C. for 30 seconds, 50° C. for 30 seconds, and 72° C. for 90 seconds. Twenty-two subsequent cycles were done with an annealing temperature of 58° C. Lastly, a chain extension step was done for seven minutes at 72° C. Clean PCR products of the correct size (approximately 850 bp) were obtained for both strains.

The PCR products for ATCC 4978 and ATCC 7063 DAAT genes were purified using the Qiagen QIAquick PCR purification kit (Valencia, Calif.), and digested with NdeI and BamHI in BamHI buffer (New England Biolabs, Ipswich, Mass.). NdeI and BamHI digested vectors (pET28 and pET30) and insert were purified using the Qiagen QIAquick Gel Extraction Kit. The ligations were done using the Roche Rapid DNA Ligation Kit (Roche) and purified using the QIAquick PCR purification kit. The ligations were transformed into *Escherichia coli* DH10B using a 0.2 cm cuvette and a Bio-Rad Gene Pulser II system as described in the Bio-Rad electroporation manual. The cells were allowed to recover in 900 μL SOC medium for 30 minutes at 37° C. at 225 rpm. The cells were plated on LB-agar plates containing kanamycin (50 μg/mL). The plasmid DNA was purified using the Qiagen spin miniprep kit and screened for the correct inserts by PCR and restriction digestion with NdeI and BamHI. The sequences of plasmids that appeared to have the correct insert were verified by dideoxy chain termination DNA sequencing at Agencourt BioScience Corporation (Beverly, Mass.). Sequence analyses verified the coding sequence for DAAT genes from ATCC 4978 and ATCC 7063, which produced the DNA sequences of SEQ ID NO:84 (ATCC 4978 DAAT DNA sequence) and SEQ ID NO:85 (ATCC 7063 DAAT DNA sequence) and the amino acid sequence of SEQ ID NO:86 (ATCC 4978 DAAT amino acid sequence) and SEQ ID NO:87 (ATCC 7063 DAAT amino acid sequence).

The alignments of the two novel DAATs from ATCC 4978 and ATCC 7063 with the *B. sphaericus* DAAT (cloned in Example 18) shown in FIG. 10.

We obtained novel D-aminotransferases from strains ATCC 4978 and ATCC 7063 with protein sequences that have distinct amino acid residue changes when compared to the *B. sphaericus* D-aminotransferase. The DAATs from ATCC 4978 and ATCC 7063 have only 72% and 67% identity with the DAAT from *B. sphaericus* (ATCC 10208). While both of these strains are currently listed as *B. sphaericus* in the ATCC, they were deposited as *B. rotans* and *B. serositidis*. Based on the sequence alignments and the highlighted differences between these two novel DAATs and the DAAT from *B. sphaericus*, a number of candidate residues are identified that can be evaluated for their role (individually or in combination) in increasing DAAT activity for R,R monatin biosynthesis, in these, as well as other DAAT sequences.

Example 16

Gene Expression and Assays for ATCC 4978 and ATCC 7063 DAAT Proteins

The novel DAATs from ATCC 4987 and ATCC 7063, as described in Example 15, (in pET vectors) were transformed into the *E. coli* expression host BL21(DE3) (Novagen, Madison, Wis.). The cultures were grown using the protocols described above and the plasmids were isolated using Qiagen miniprep kit and analyzed by restriction digestion, as described above, to confirm plasmid identity.

Induction of the DAAT gene was typically performed in LB medium containing kanamycin (50 μg/mL). The cells were grown to an $OD_{600}$ of 0.4-0.8 at 37° C., induced with 0.1 mM IPTG (isopropyl thiogalacatoside) and sampled at 3-4 hours post induction. Cell extracts were prepared according to the protocol accompanying the Novagen BugBuster™ reagent (with benzonase nuclease and Roche complete protease inhibitor cocktail added). Soluble proteins were obtained at the predicted molecular weight, as judged by SDS-PAGE, for both ATCC 4978 and ATCC 7063 gene products in pET vectors. Higher levels of soluble protein were observed using constructs without His tags (pET 30). Soluble proteins in the cellular extracts were separated on a BioRad Laboratories Experion Automated Electrophoresis Station (Hercules, Calif.) and analyzed for concentration and percent expression using the Experion Software version 1.1.98.0.

Protein extracts from cells with untagged (pET30) constructs were analyzed for D-aminotransferase activity by following production of alanine from pyruvate and D-tryptophan (or R,R monatin) using the following protocol. Duplicate 500 μL reactions were, unless specified below, carried out in 100 mM potassium phosphate buffer (pH 7.5), 80 μM pyridoxal phosphate, 25 mM sodium pyruvate, and 50 mM D-tryptophan or R,R monatin. The reactions were initiated by the addition of cell free extracts (4978 or 7063) or purified enzyme (*B. sphaericus*) and were incubated 15 minutes-2 hours at 30° C., with mild shaking. Approximately the same level of total protein was added (1.0 mg), unless specified below, in each assay for comparative purposes. Purified *B. sphaericus* (ATCC number 10208) aminotransferase was used as a benchmark enzyme. Formic acid was added to a final concentration of two percent to stop the reaction and the precipitated protein was removed by centrifugation. Control reactions without added protein were also performed. Alanine was detected using OPA derivatization as described in Example 1. The averaged results of the duplicate reactions are shown in Tables 35 and 36 below.

TABLE 35

Transamination Activity of ATCC 4978 and ATCC 7063 D-Aminotransferases (15 min)

| D-aminotransferase | Alanine (mM) D-Tryptophan as Substrate | Alanine (mM) R,R Monatin as Substrate |
|---|---|---|
| ATCC 4978 | 7.78 | 0.32 |
| ATCC 7063 | 0.28 | 0.025 |
| *B. sphaericus* (untagged) | 11.93 | 3.57 |

TABLE 36

Transamination Activity of ATCC 4978 and ATCC 7063 D-Aminotransferases (2 Hours)

| D-aminotransferase | Alanine (mM) D-Tryptophan as Substrate | Alanine (mM) R,R Monatin as Substrate |
|---|---|---|
| ATCC 4978 | 16.46 | 2.33 |
| ATCC 7063 | 2.51 | 0.21 |
| *B. sphaericus* (untagged) | 13.73 | 12.23 |

Thus, we demonstrated that the D-amino acid aminotransferases from ATCC 4978 and ATCC 7063 indeed possessed D-aminotransferase activity and have the capability to make R,R monatin. The activity of the ATCC 4978 DAAT was higher than that observed for the ATCC 7063 DAAT. Quantitative comparison between 4978 and *B. sphaericus* could not be made since 4978 was unpurified.

Example 17

Production of R,R Monatin Using the DAAT from ATCC 4978

The aminotransferase from ATCC 4978 was also tested for ability to produce monatin from D-tryptophan (as in Example 3). The following were added per 1 mL of reaction mixture: approximately 50 μg aldolase (*C. testosteroni* ProA aldolase or the aldolase of SEQ ID NO:22, purified), 4 mM $MgCl_2$, 50 mM D-tryptophan (supplied as solid), 1.0 mg D-aminotransferase, 100 mM sodium pyruvate, 100 mM potassium phosphate buffer pH 7.5, and 0.05 mM PLP. Experiments were run in duplicate, with negative controls in which no aminotransferase was added. Samples were incubated for various lengths of time at 30° C. with gentle shaking. The only stereoisomers detected when producing monatin using these methods are R,R and S,R. The total monatin and percent R,R monatin were detected as described in Example 1 are listed in Tables 37-39 below. The results shown in each of Tables 37-39 is the average value from duplicate reactions.

TABLE 37

Comparison of *B. sphaericus* and ATCC 4978 D-Aminotransferases for Production of Monatin using Approximately 50 μg *C. testosteroni* ProA

| D-Aminotransferase | Total Monatin (mg per g DAT protein) 15 Minutes | Total Monatin (mg per g DAT protein) 30 Minutes | Total Monatin (mg per g DAT protein) 1 Hour | Total Monatin (mg per g DAT protein) 2 Hours |
|---|---|---|---|---|
| ATCC 4978 | 419.3 | 598 | 1017 | 1348 |
| *B. sphaericus* (tagged) | 46.5 | 128 | 232 | 241 |

TABLE 38

Comparison of *B. sphaericus* and ATCC 4978 D-Aminotransferases for Production of Monatin using Approximately 50 μg *C. testosteroni* ProA

| D-Aminotransferase | % R,R Monatin 15 Minutes | % R,R Monatin 30 Minutes | % R,R Monatin 1 Hour | % R,R Monatin 2 Hours |
|---|---|---|---|---|
| ATCC 4978 | 48.9 | 38.4 | 34.4 | 33.25 |
| *B. sphaericus* (tagged) | 72.3 | 63.4 | 56.1 | 53.5 |

TABLE 39

Comparison of *B. sphaericus* and ATCC 4978 D-Aminotransferases for Production of Monatin using Approximately 50 μg of the Aldolase of SEQ ID NO: 22

| D-Aminotransferase | Total Monatin (mg per g DAT Protein) 2 Hours | % R,R Monatin 2 Hours |
|---|---|---|
| ATCC 4978 | 501 | 92.1 |
| *B. sphaericus* (tagged) | 201 | 95.6 |

Thus, we demonstrated that the D-amino acid aminotransferase from ATCC 4978 has the capability to make R,R monatin. The activity of the ATCC 4978 DAAT, when comparing total monatin production in terms of mg monatin per gram protein, was higher than that observed for the *B. sphaericus* DAAT. The use of an R-specific aldolase of SEQ ID NO:22 clearly made an improvement in percentage of R,R monatin formed in comparison to the amount of total monatin produced.

Example 18

Cloning of Published *Bacillus* D-Amino Acid Aminotransferases

Several *Bacillus* D-amino acid aminotransferases (EC 2.6.1.21, also known as D-alanine aminotransferase or D-aspartate aminotransferase) were produced recombinantly for use in coupled assays for production of R,R monatin. These enzymes are homologous to D-aminotransferases described previously for production of monatin (U.S. Publication No. 20040063175 and U.S. Publication No. 2005282260).

Strains

*B. sphaericus* (ATCC number 10208) and *B. licheniformis* (ATCC 10716) were grown on Nutrient Agar at 30° C. overnight. Groups of colonies were placed in 100 μL of sterile water and heated for 5 minutes at 95° C., to disrupt the cells. Three μL was used in subsequent Polymerase Chain Reaction ("PCR") amplifications. Genomic DNA was ordered for *B. halodurans* (ATCC number BAA-125D) and resuspended in water to a concentration of 100 ng/μL. *Bacillus cereus* genomic DNA (ATCC numbers 1-987D and 14579D) was ordered for cloning as well.

Polymerase Chain Reaction Protocol

Primers were designed for the *B. sphaericus* dat gene for cloning into pET 28b and pET 30a vectors (Novagen, Madison, Wis.), using the NcoI and BamHI sites. The pET30 construct contains an N-terminal His-tag and S-tag, whereas the pET 28 construct is untagged.

*Bacillus sphaericus* dat Primers:

```
                                        (SEQ ID NO:88)
N term: 5'-GATATACCATGGCATACTCATTATGGAATG-3'
and
                                        (SEQ ID NO:89)
C term: 5'-GTTATCGGATCCTTAGGCATTAATTGAAATTG-3'.
```

The *B. licheniformis* primers and *B. halodurans* primers were designed for cloning into pET 28b and pET 30a vectors using NdeI and BamHI sites. The pET30 constructs were untagged in this case, whereas the pET 28 constructs contain a small N-terminal his-tag.

*B. licheniformis* dat Primers:

```
                                    (SEQ ID NO:90)
N term 5'-GGCCGGTTCATATGAAAGTTCTTTTTAACGGC
and

                                    (SEQ ID NO:91)
C term: 5'-CCTTCCGGATCCTTAAACCGTTTTGGCTGTCT-3'
```

*B. halodurans* Primers:

```
                                    (SEQ ID NO:92)
N term 5'-GATATACATATGGATTATTGCCTTTACCAA-3'
and

                                    (SEQ ID NO:93)
C term: 5'-GAATCCGGATCCTCACTGCTTCATCGCTGTTTG-3'
```

Primers were designed for the *B. cereus* coding sequences. One set of primers yielded the sequence listed in NCBI as accession AE016877 gi:29899096 5138634 . . . 5139506 (873 bp). One set of primers yielded a product with an additional 12 bp upstream, similar to the *B. thuringiensis* predicted dat NCBI accession number AE017355 gi: 49328240 4965653 . . . 4966537 (885 bp). Both sets of primers were designed with NdeI for the N-terminal region and BamHI restriction site for the C-terminal region. The primers were designed for cloning into pBAD-TOPO TA cloning.

*B. cereus* Primers:

```
                                    (SEQ ID NO:94)
N term 5'-TAAGAGGAATAACATATGGCATACGAAAGATTT-3'
and

                                    (SEQ ID NO:95)
C-term 5'-GAATTCGGATCCTTAAGAAGATGACATATTGG-3'
(shorter PCR product)

                                    (SEQ ID NO:96)
N term 5'-TAAGAGGAATAACATATGGGATCGAAATTGGCA-3'
(longer PCR product)
```

The coding regions of the *B. sphaericus*, *B. halodurans*, and *B. licheniformis* dat genes were amplified using the following PCR protocol. In a 50 μL reaction, 3 μL template (2 μL for genomic DNA), 1.6 μM of each primer, 0.25 mM each dNTP, 3.5 U Expand High Fidelity Polymerase (Roche, Indianapolis, Ind.), and 1× Expand™ buffer with Mg were used. The thermocycler program used included a hot start at 94° C. for 3 minutes, followed by 8 repetitions of the following steps: 94° C. for 30 seconds, 52° C. for 30 seconds, and 72° C. for 2 minutes. Twenty-two subsequent cycles were done with an annealing temperature of 58° C. After 30 cycles the sample was maintained at 72° C. for 7 minutes and then stored at 4° C. Clean PCR products of the correct size were obtained (approximately 850 bp for the dat gene).

*Geobacillus stearothermophilus* dat (accession number J04460 gi:142541), which codes for protein accession number AAA22252 (gi:142542) was constructed using assembly PCR techniques. The source of this gene/protein is often described as *Bacillus* sp., thermostable *Bacillus* species, or *Bacillus* YM-1. The assembly process is as follows: 43 oligonucleotides (40 mers) were ordered from IDT based on the gene sequence above and its complementary DNA sequence, with 20 basepair overlaps between the sense and antisense strands. The primers were diluted to 250 μM in water and 5 μL of each primer was mixed together in a microfuge tube. PCR was carried out as follows: per 100 μL reaction, 1.5 μL of the primer pool, 4 μL dNTPs, 1×XL PCR buffer, 1 mM magnesium acetate, 2 μL rTth polymerase (Roche, Indianapolis, Ind.), and 0.25 μL Pfu polymerase (Stratagene, La Jolla, Calif.) were added. A 3 minute hot start was done at 94° C., followed by 15 cycles of 94° C. for 30 seconds, 40° C. for 30 seconds, and 68° C. for 15 seconds. Ten more cycles were done with an increased annealing temperature of 44° C. and an extension time of 30 seconds (at 68° C.). Ten more cycles were performed at an annealing temperature of 48° C. and an extension time of 75 seconds. Lastly, a chain extension step was done for seven minutes at 68° C. A secondary PCR was done using the following primers, designed for cloning with NdeI (N-term) and BamHI (C-term):

```
                                    (SEQ ID NO:97)
N-term-5'-GGCCTTGGCATATGGGATACACTTTATGGAATGACC-3'
and

                                    (SEQ ID NO:98)
C-term-5'-TTGGAACCGGATCCTTATATATGAAGCGGTTTTGG-3'
```

The PCR contained per 100 μL, 2.5 μL of the primary reaction, 0.4 μL of each primer, 3 μL dNTPs, 1×XL PCR buffer, 1 mM magnesium acetate, 2 μL rTth polymerase, and 0.25 μL Pfu polymerase. A 3 minute hot start was done at 94° C., followed by 10 cycles of 94° C. for 30 seconds, 42° C. for 30 seconds, and 68° C. for 90 seconds. Fifteen more cycles were done with an increased annealing temperature of 48° C., and lastly a chain extension step was done for seven minutes at 68° C. A third PCR reaction was done using template from the second PCR, and using the same conditions as the second PCR reaction. A product of approximately 900 bp was visible on an agarose gel.

Cloning

The PCR product for *B. sphaericus* DAT was purified using the Qiagen QIAquick PCR purification kit (Valencia, Calif.) and digested with BamHI and NcoI in BamHI buffer (New England Biolabs, Ipswich, Mass.). The digested vectors (pET28 and pET30) and insert were purified using the Qiagen QIAquick Gel Extraction Kit. The ligations were done using the Roche Rapid DNA Ligation Kit (Roche) and purified using the QIAquick PCR purification kit. The ligations were transformed into *Escherichia coli* DH10B using a 0.2 cm cuvette and a Bio-Rad Gene Pulser II system as described in the Bio-Rad electroporation manual. The cells were allowed to recover in 900 μL SOC medium for 30 minutes at 37° C. at 225 rpm. The cells were plated on LB-agar plates containing kanamycin (25 μg/mL). The plasmid DNA was purified using the Qiagen spin miniprep kit and screened for the correct inserts by restriction digest with BamHI and NcoI. The sequences of plasmids that appeared to have the correct insert were verified by dideoxy chain termination DNA sequencing at Agencourt BioScience Corporation (Beverly, Mass.). Sequencing verified the coding sequence found in NCBI accession number AF081278 Region: 134.985 (gi: 3513754), which produces a protein with amino acid sequence as listed in accession number AAC33964 (gi: 3513755).

The PCR products for *B. licheniformis* DAT (~850 bp) and *G. stearothermophilus* were gel purified and cloned using the Zero Blunt TOPO® cloning kit as per manufacturers' protocols (Invitrogen). The plasmids were transformed into TOP10 chemically competent cells for initial screening. The plasmid DNA was screened by restriction digest and the sequences were verified to match the coding sequence found in NCBI. For *B. licheniformis*, the sequence matched accession number U26947 region 247 . . . 1098 (gi:857560), which produces a protein with an amino acid sequence as listed in accession number P54692 (gi:1706292), with the exception of one silent mutation at position 429 from A to G. For *G. stearothermophilus*, the sequence matched the accession number listed above. The coding regions were subcloned by restriction digest (NdeI/BamHI), ligated into the pET vectors, and transformed into electrocompetent DH10B cells for amplification.

The PCR product for *B. halodurans* DAT was gel purified and digested with NdeI and BamHI and ligated into pET 28 and pET 30 vectors as above. Amplification of the vector was done in DH10B cells. The miniprep DNA was screened by PCR and the sequence was verified. The gene sequence can be found in accession number NC_002570 (gi:57596592) 2934903 . . . 2935754 coding for a protein with amino acid sequence listed in accession number NP_243677 (gi: 15615374).

The *B. cereus* coding sequences were amplified using a typical PCR protocol and cloned according to manufacturer's protocols (Invitrogen).

Gene Expression and Assays

Plasmid DNA was subcloned into *E. coli* expression host BL21(DE3) (Novagen, Madison, Wis.) for constructs in pET vectors. The cultures were grown and the plasmids were isolated using Qiagen miniprep kit, and analyzed by restriction digest to confirm identity. Induction was typically performed in LB medium containing kanamycin (50 μg/mL). The cells were grown to an $OD_{600}$ of 0.4-0.8 at 37° C., induced with 0.1 mM IPTG (isopropyl thiogalacatoside) and sampled at 3-4 hours post induction. The cell extracts were prepared according to the protocol accompanying the Novagen BugBuster™ reagent (with benzonase nuclease and Roche complete protease inhibitor cocktail added). High levels of soluble protein were obtained at the predicted molecular weight, as judged by SDS-PAGE, for both *B. halodurans* gene products, both *B. sphaericus* gene products, both *G. stearothermophilus* gene products, and the untagged *B. licheniformis* gene product. For reactions in which purified protein was used, the His-tagged gene products were purified using His-Bind cartridges following manufacturer's protocols (Novagen, Madison, Wis.). The eluent fractions were desalted on PD-10 (Amersham Biosciences, Piscataway, N.J.) columns and eluted in 25-100 mM potassium phosphate buffer, pH 7.5. Total protein assays were done using the Pierce BCA kit, and percent expression was estimated from SDS-PAGE. Alternatively, the soluble proteins in the cellular extracts were separated on a BioRad Laboratories Experion Automated Electrophoresis Station and analyzed for concentration and percent expression using the Experion Software version 1.1.98.0. The pBAD-TOPO constructs containing the *B. cereus* genes were expressed as recommended by Invitrogen, but the levels of expression of the DAATs was such that the recombinant protein could not be distinguished from the other proteins during SDS-PAGE analysis.

The cell extracts were analyzed for D-aminotransferase activity by following production of alanine from pyruvate and D-tryptophan (or R,R monatin) using the following protocol. Duplicate one mL reactions were typically carried out in 100 mM potassium phosphate buffer (pH 7.5), 50 μM pyridoxal phosphate, 25 mM sodium pyruvate, and 50 mM D-tryptophan or R,R monatin. The reactions were initiated by the addition of cell free extracts or purified enzyme and were incubated 15 minutes-overnight at 30° C., with mild shaking. Approximately the same level of D-aminotransferase was added (typically around 0.5 mg) in each assay for comparative purposes. AT-103 (BioCatalytics) was used as a positive control (or benchmark). Formic acid was added to a final concentration of two percent to stop the reaction and the precipitated protein was removed by centrifugation. Control reactions, without added protein, were also performed. Zero time points were also used as negative controls. Alanine was detected using OPA derivatization as described in Example 1.

The aminotransferases were also tested for their ability to produce monatin from D-tryptophan (as in Example 3). The following were added per 1 mL of reaction mixture: approximately 50-100 μg aldolase (typically *C. testosteroni* ProA aldolase, purified), 4 mM $MgCl_2$, 50 mM D-tryptophan (supplied as solid), 0.5-2 mg D-aminotransferase, 200 mM sodium pyruvate, 100 mM potassium phosphate buffer pH 7.5, and 0.05 mM PLP. Experiments were run in duplicate, with negative controls in which no aminotransferase was added. The samples were incubated 1 hour, 2 hours, and overnight (17-20 hours) at 30° C. with gentle shaking. The only stereoisomers detected when producing monatin using these methods are R,R and S,R. The percent R,R is listed below, and was determined by reversed-phase LC peak area. The results of the transamination activity of *B. sphaericus, B. licheniformis*, and *B. halodurans* D-aminotransferases after 1 hour is shown in Table 40 below. The data was normalized to 0.5 mg of the D-aminotransferase per mL.

TABLE 40

Transamination Activity of *B. sphaericus*, *B. licheniformis*, and *B. halodurans* D-Aminotransferases

| D-Aminotransferase | Alanine (mM) D-Tryptophan as Substrate | Alanine (mM) R,R Monatin as Substrate |
|---|---|---|
| *B. halodurans* (tagged) | 15.5 | 1.3 |
| *B. halodurans* (untagged) | 17.5 | 1.4 |
| *B. licheniformis* (untagged) | 28.4 | 0.21 |
| *B. sphaericus* (untagged) | 29.0 | 22.5 |
| *B. sphaericus* (tagged) | 17.1 | 12.0 |

The production of monatin using *B. sphaericus, B. licheniformis*, and *B. halodurans* D-aminotransferases is shown in Table 41 below. Each reaction contained approximately 90 μg *C. testosteroni* Pro A. The data for the total monatin produced was normalized to the use of 0.5 mg of the D-aminotransferase.

TABLE 41

Comparison of *B. sphaericus*, *B. licheniformis*, and *B. halodurans* D-Aminotransferases for Production of Monatin

| D-Aminotransferase | Total Monatin (ppm) 3 Hours | Total Monatin (ppm) Overnight | % R,R 3 Hours | % R,R Overnight |
|---|---|---|---|---|
| *B. halodurans* (tagged) | 3.2 | 13.7 | 100 | 99.3 |
| *B. halodurans* (untagged) | 4 | 15.5 | 100 | 99.3 |
| *B. licheniformis* (untagged) | 0.6 | 8.1 | 100 | 29.3 |
| *B. sphaericus* (untagged) | 279.6 | 577.6 | 61.55 | 65.7 |
| *B. sphaericus* (tagged) | 111.2 | 246 | 61.0 | 63.1 |

The *B. sphaericus* D-aminotransferase (untagged) had the highest activity for production of monatin from D-tryptophan, but the *B. halodurans* enzyme had much higher selectivity for R-MP versus S-MP than the other enzymes, resulting in higher stereopurity of R,R monatin. The *B. cereus* cell extracts did not have detectable amounts of activity under the conditions tested, although the genes may not have been expressed in the hosts chosen.

The *G. stearothermophilus* DAT (untagged, which expressed better) was assayed as above and compared to the purified *B. sphaericus* DAT and AT-103 (BioCatalytics). The results are shown in Tables 42 and 43 below. The transamination activity of *G. stearothermophilus*, AT-103, and *B. sphaericus* D-aminotransferase was tested using 0.5 mg of D-aminotransferase per mL (Table 42).

TABLE 42

Transamination Activity of *G. stearothermophilus*, AT-103, and *B. sphaericus* (Purified) D-Aminotransferases

| D-Aminotransferase | Alanine (mM)-15 Minutes D-Tryptophan as Substrate | Alanine (mM)-15 Minutes R,R Monatin as Substrate | Alanine (mM)-2 Hours D-Tryptophan as Substrate | Alanine (mM)-2 Hours R,R Monatin as Substrate |
|---|---|---|---|---|
| AT-103 | 8.91 | 1.21 | 9.47 | 6.13 |
| *B. sphaericus* (tagged) | 8.91 | 1.65 | 9.53 | 7.17 |
| *G. stearothermophilus* (untagged) | 2.05 | 0.053 | 8.10 | 0.78 |

TABLE 43

Comparison of *G. stearothermophilus*, AT-103, and *B. sphaericus* (purified) for Total Monatin Production

| D-Aminotransferase | Total Monatin (ppm) 2 Hours | Total Monatin (ppm) Overnight | % R,R 2 Hours | % R,R Overnight |
|---|---|---|---|---|
| AT-103 | 450 | 645 | 65.5 | 60.6 |
| *B. sphaericus* (tagged) | 110 | 175 | 64 | 54 |
| *G. stearothermophilus* (untagged) | nd | 10 | n/a | 27 |

The native *G. stearothermophilus* enzyme is clearly less active for monatin transamination than the AT-103 and *B. sphaericus* enzymes.

Example 19

Creation of a Hybrid D-Aminotransferase

Several *Bacillus* D-amino acid aminotransferases were described in Examples 18 and 15. Although the *G. stearothermophilus* enzyme had low transamination activity on monatin, causing less total monatin to be produced from D-tryptophan, it still had structural elements of interest and it is a thermostable enzyme. Therefore, a hybrid protein was created between the higher activity enzyme (*B. sphaericus*) and the *Geobacillus* enzyme.

Assembly of Hybrid DAT Coding Sequence

The target protein sequence that was designed is SEQ ID NO:99. SEQ ID NO:100, the coding sequence corresponding to SEQ ID NO:99, was designed based on *E. coli* codon usage.

The hybrid DAT was constructed using assembly PCR techniques. The assembly process is as follows: 43 oligonucleotides (40 mers) were ordered from IDT based on the gene sequence above and its complementary DNA sequence, with 20 basepair overlaps between the sense and antisense strands. The primers were diluted to 250 μM in water and 5 μL of each primer was mixed together in a microfuge tube. PCR was carried out as follows: per 100 μL reaction, 1.5 μL of the primer pool, 4 μL dNTPs, 1×XL PCR buffer, 1 mM magnesium acetate, 2 μL rTth polymerase (Roche, Indianapolis, Ind.), and 0.25 μL Pfu polymerase (Stratagene, La Jolla, Calif.) were added. A 3 minute hot start was done at 94° C., followed by 15 cycles of 94° C. for 30 seconds, 40° C. for 15 seconds, and 68° C. for 30 seconds. Ten more cycles were done with an increased annealing temperature of 44° C. and an increased annealing time of 30 seconds. Ten more cycles were performed at an annealing temperature of 48° C. and an extension time of 75 seconds. Lastly, a chain extension step was done for seven minutes at 68° C. A secondary PCR was done using the following primers, designed for cloning with NdeI (N-term) and BamHI (C-term):

```
                                    (SEQ ID NO:101)
N-term-5'-GGCCTTGGCATATGGGATACACTTTATGGAATGACCA-3'
and

                                    (SEQ ID NO:102)
C-term-5'-TTGGAACCGGATCCTTAGCTGTTAAGGCTCAGTGGAA-
3'
```

The PCR contained per 100 μL, 2.5 μL of the primary reaction, 3 μL dNTPs, 1×XL PCR buffer, 1 mM magnesium acetate, 2 μL rTth, and 0.25 μL Pfu polymerase. A 3 minute hot start was done at 94° C., followed by 10 cycles of 94° C. for 30 seconds, 42° C. for 30 seconds, and 68° C. for 75 seconds. Fifteen more cycles were done with an increased annealing temperature of 48° C., and lastly a chain extension step was done for seven minutes at 68° C. A product of approximately 850 bp was visible on an agarose gel.

Cloning

The PCR product was gel purified using the Qiagen QIAquick Gel Extraction Kit (Valencia, Calif.), and cloned using the Zero Blunt TOPO® cloning kit as per manufacturers' protocols (Invitrogen). The plasmids were transformed into TOP10 chemically competent cells for initial screening by PCR. The plasmid DNA was screened by restriction digest and the DNA sequence was verified.

The plasmid minipreps were digested with BamHI and NdeI (New England Biolabs, Ipswich, Mass.). The digested vectors (pET28 and pET30) and insert were ligated using the Roche Rapid DNA Ligation Kit (Roche) and purified using the Roche High-Pure PCR Product Purification Kit. The ligations were transformed into *Escherichia coli* DH10B using a 0.2 cm cuvette and a Bio-Rad Gene Pulser II system as described in the Bio-Rad electroporation manual. The cells were allowed to recover in 900 μL SOC medium for 30 minutes at 37° C. at 225 rpm. The cells were plated on LB-agar plates containing kanamycin (25 μg/mL). The plasmid DNA was purified using the Qiagen spin miniprep kit and screened for the correct inserts by restriction digest with BamHI and NdeI.

Gene Expression and Assays

Plasmid DNA was transformed into *E. coli* expression host BL21(DE3) according to manufacturers' protocols (Novagen, Madison, Wis.). The cultures were grown and the plasmids were isolated using Qiagen miniprep kit and analyzed by PCR to confirm identity. The induction was performed in LB medium containing kanamycin (50 μg/mL). The cells were grown to an $OD_{600}$ of 0.5 at 37° C., induced with 0.1 mM IPTG (isopropyl thiogalacatoside) and sampled at 3 hours post induction. The cell extracts were prepared according to the protocol accompanying the Novagen BugBuster™ reagent (with benzonase nuclease and Roche complete protease inhibitor cocktail added). High levels of total protein were obtained at the predicted molecular weight, as judged by SDS-PAGE, for both gene products. However, the soluble levels of protein were lower. The untagged version of the gene product expressed better and was assayed as a cellular extract. The soluble proteins in the cellular extracts were separated on a BioRad Laboratories Experion Automated Electrophoresis Station and analyzed for concentration and percent expression using the Experion Software version 1.1.98.0, to normalize the amount of D-aminotransferase used in comparative assays.

The cell extracts were analyzed for D-aminotransferase activity by following production of alanine from pyruvate and D-tryptophan (or R,R monatin) using the following protocol. Duplicate one mL reactions were carried out in 100 mM potassium phosphate buffer (pH 7.5), 50 μM pyridoxal phosphate, 25 mM sodium pyruvate, and 50 mM D-tryptophan or R,R monatin (unless otherwise noted). The reactions were initiated by the addition of cell free extracts or purified enzyme and were incubated 15 minutes-overnight at 30° C., with mild shaking. Approximately the same level of D-aminotransferase was added (0.5 mg) in each assay for comparative purposes (unless otherwise noted). AT-103 (BioCatalytics) or *B. sphaericus* D-aminotransferase (Example 18) was used as a benchmark enzyme. Formic acid was added to a final concentration of two percent to stop the reaction and the precipitated protein was removed by centrifugation. Control reactions without added protein were also performed. Zero time points were also used as negative controls. Alanine was detected using OPA post-column derivatization as described in Example 1. The results of the reactions using 0.5 mg D-aminotransferase per 1 mL reaction volume are shown in Table 44 below.

TABLE 44

Transamination Activity of *B. sphaericus* (purified), *G. stearothermophilus*, and Hybrid D-Aminotransferases

| D-Aminotransferase | Alanine (mM)-15 Minutes D-Tryptophan as Substrate | Alanine (mM)-15 Minutes R,R Monatin as Substrate | Alanine (mM)-2 Hours D-Tryptophan as Substrate | Alanine (mM)-2 Hours R,R Monatin as Substrate |
|---|---|---|---|---|
| Hybrid DAT (untagged) | 13.5 | 0.084 | 14.2 | 0.54 |
| *B. sphaericus* (tagged) | 13.6 | 4.60 | 13.9 | 10.6 |
| *G. stearothermophilus* (untagged) | 6.6 | 0.18 | 13.5 | 2.2 |

The aminotransferases were also tested for their ability to produce monatin from D-tryptophan (as in Example 3). The following were added per 1 mL of reaction mixture: approximately 50-100 μg purified *C. testosteroni* ProA aldolase, 4 mM $MgCl_2$, 50 mM D-tryptophan (supplied as solid), 0.5-2 mg D-aminotransferase, 200 mM sodium pyruvate, 100 mM potassium phosphate buffer pH 7.5, and 0.05 mM PLP. Experiments were run in duplicate, with negative controls in which no aminotransferase was added. The samples were incubated 1 hour, 2 hours, and overnight (17-20 hours) at 30° C. with gentle shaking. The only stereoisomers detected when producing monatin using these methods were R,R and S,R. The percent R,R is listed in Table 45 below, and was determined by reversed-phase LC peak area. At low monatin concentrations, the percent R,R is not as accurate as judged by RPLC peak area. Therefore, some of the samples were further analyzed by the FDAA derivatization method described in Example 1. The numbers from those results are shown in the table in parentheses.

TABLE 45

Comparison of *G. stearothermophilus*, Hybrid DAT, and *B. sphaericus* (purified) for Total Monatin Production

| D-Aminotransferase | Total Monatin (ppm) 2 Hours | Total Monatin (ppm) Overnight | % R,R 2 Hours | % R,R Overnight |
|---|---|---|---|---|
| Hybrid DAT (untagged) | 9.5 | 42.5 | 84.1 (79.8) | 81.1 (69.6) |
| *B. sphaericus* (tagged) | 68.5 | 182.5 | 62.7 (53.8) | 55.1 (53.5) |
| *G. stearothermophilus* (untagged) | 4.5 | 15.0 | 34.1 (20.7) | 32.1 (21.7) |

The Hybrid DAT makes more monatin than the *G. stearothermophilus* enzyme, although the monatin transamination rate of the Hybrid DAT is lower. It is possible that under the conditions for monatin production (where there are low MP concentrations), the Hybrid performs better possibly due to a lower $K_m$. Also, the Hybrid DAT makes a higher percentage of R,R than either of the parent enzymes. This enzyme appears to have a higher enantioselectivity for R-MP than the parent enzymes. The same assays were done (4 hour incubation time) using the *Sinorhizobium* aldolase described in Example 3 with the Hybrid DAT. The Hybrid DAT produced similar amounts of monatin as above, but using the alternative aldolase, produced 95% R,R (according to FDAA derivatization), as opposed to 80% with the *C. testosteroni* ProA aldolase.

The hybrid DAT was also tested for transamination activity of R-MP versus S-MP (produced as described in Example 1). Two hour and overnight assays were conducted at 30° C. using 10 mM R-MP or S-MP, 50 mM D-alanine, 100 mM potassium phosphate pH 7.5, 0.5 mg/mL D-aminotransferase, and 50 μM PLP. Experiments were run in duplicate and the background levels of monatin from the MP samples was subtracted. The ratios of monatin produced from each substrate are reported for both D-aminotransferases in Table 46 below. Similar trends were observed when pyruvate (produced) ratios were plotted. It is clear that the Hybrid DAT is more selective for R-MP than the AT-103 D-aminotransferase, which does not appear to be selective.

TABLE 46

Comparison of Hybrid DAT and AT-103 for S-MP and R-MP Transamination

| D-Aminotransferase | R-Activity/S-Activity 2 Hours | R-Activity/S-Activity Overnight |
|---|---|---|
| Hybrid DAT (untagged) | 8.6 | 2.2 |
| AT-103 | 0.68 | 1.68 |

In an effort to further improve the Hybrid DAT activity, site directed mutagenesis was done. Primers were designed as suggested in the QuikChange Multi Site-Directed Mutagenesis Kit (Stratagene). Two different mutants were created: Hybrid DAT 2 and Hybrid DAT 3. The Hybrid DAT 2 includes a mutation at amino acid position 153 from alanine to arginine and a deletion of serine 181. The alanine to arginine mutation was designed to help coordinate the second carboxyl group in the monatin precursor substrate, as has been shown to be present in the AspC L-aminotransferase. The serine deletion was an attempt to remove some steric hindrance such that the larger monatin precursor molecule can get to the active site more easily. The Hybrid DAT 3 contains a deletion of serines 180-182, replaced by one arginine. Two additional mutants were created, having only the 153 ala to arg mutation or the serine deletion, respectively. All three of the mutants that contained deletions did not make soluble protein, although they overexpressed at very high concentrations. Clearly it is important structurally not to remove amino acids in this region. The ala153arg mutant did not produce monatin under the conditions tested (as above). There is a fair amount of steric hindrance near the 153 position which would make it more difficult to fit the monatin precursor substrate in without the deletions in the 180-182 region. It is expected that mutating the serines to smaller amino acids, such as glycine or alanine, would improve activity toward monatin precursor, particularly when combined with the ala153arg mutation.

Example 20

Use of Commercially Available D-Amino Acid Dehydrogenase Enzymes

D-amino acid dehydrogenases were part of a library purchased from BioCatalytics (Pasadena, Calif.).

Interconversion Between MP and Monatin

The amination of MP to form monatin can be catalyzed by aminotransferases or by dehydrogenases that require a reducing cofactor such as NADH or NADPH. These reactions are reversible and can be measured in either direction. The directionality when using a dehydrogenase enzyme can be largely controlled by the concentration of ammonium salts.

Conversion of Monatin to MP (Monatin Precursor) Using Commercially Available Dehydrogenases The oxidative deamination of monatin was monitored by following the increase in absorbance at 340 nm as $NAD^+$ was converted to the more chromophoric NADH.

The assay mixture contained 100 mM sodium bicarbonate, pH 9, 10 mM $NAD^+$, 20 mg/mL of D-amino acid dehydrogenase (D-AADH-101 through 108, BioCatalytics), and 50 mM R,R monatin (monopotassium salt) in 0.2 mL. The assay was performed, in duplicate, in a UV-transparent microtiter plate, with incubation at 30° C. Endpoint absorbances were measured using a Molecular Devices SpectraMax Plus platereader. Negative controls were carried out without the addition of enzyme. The change in absorbance for overnight reactions was as follows: no enzyme control, 0.05; D-AADH-101, 0.865; D-AADH-102, 1.075; D-AADH-103, 0.94; D-AADH-104, 0.335; D-AADH-105, 0.78; D-AADH-106, 0.745; D-AADH-107, 0.925; and D-AADH-108, 1.06.

Production of Monatin from MP Using Dehydrogenases

R-MP used as a substrate for this assay was produced by the transamination of R,R monatin using AT-103 broad range D-aminotransferase (BioCatalytics) in potassium phosphate buffer, using pyruvate as the amino acceptor. S-MP was produced by the transamination of S,S monatin using AT-102 L-aminotransferase (BioCatalytics) in potassium phosphate buffer, using 2-oxoglutarate as the amino acceptor. Both compounds were purified using preparative scale HPLC.

The assay mixture contained 200 mM ammonium formate, 50 mM potassium phosphate pH 7.5, 5 mM NADH, 20 mg/mL D-amino acid dehydrogenase (D-AADH-101 through 108, BioCatalytics), and 10 mM MP (potassium salt) in 0.25 mL. To half of the assays, 2 mg/mL formate dehydrogenase ("FDH") was added (FDH-101, BioCatalytics, 4.8 U/mg). The samples were incubated for 16 hours at 30° C. The samples were analyzed for monatin using LC/MS/MS and the isomeric distribution was determined using the FDAA method described in Example 1. The background levels of the no D-amino acid dehydrogenase control were subtracted to account for the monatin contamination present in the MP.

For production of R,R monatin from R-MP, the enzyme activity was as follows: D-AADH-103>D-AADH-101>D-AADH-107>D-AADH 106>D-AADH-108>D-AADH-105. The amount of monatin generated from D-AADH 102 was quite low and D-AADH-104 did not appear to produce monatin from R-MP. Approximately 43 ppm of R,R monatin was produced by D-AADH-103 during the reaction in the absence of formate dehydrogenase. The addition of FDH improved the production of monatin for all the enzymes that had activity. The improvements ranged from 2.4 fold higher monatin to 10.1 fold higher monatin (D-AADH-103). D-AADH-103 produced approximately 434 ppm R,R monatin.

When S-MP was used as the reaction substrate and production of S,R monatin was followed, the enzyme activity was as follows: D-AADH-106>D-AADH-107>D-AADH-105>D-AADH-101>D-AADH-102>D-AADH-103>D-AADH-108. D-AADH-104 did not appear to produce S,R monatin in the assays. Approximately 15 ppm S,R monatin was generated by D-AADH-106, 26 ppm when FDH enzyme was also used.

Production of Monatin from Indole-3-Pyruvate

Production of monatin from indole-3-pyruvate and pyruvate, using BioCatalytics amino acid dehydrogenase enzymes coupled with the aldolase of SEQ ID NO:22, was assayed under the following conditions: 1 mg/mL dehydrogenase enzyme, 10 mM NADH, 500 μg/mL aldolase (purified), 50 mM potassium phosphate buffer pH 7.5, 4 mM $MgCl_2$, 20 mg/mL indole-3-pyruvate, 200 mM ammonium formate, and 200 mM pyruvate were incubated at 30° C. at 100 rpm for 20 hours. Negative controls contained no amino acid dehydrogenase enzyme. The experiments were performed in duplicate. None of the dehydrogenases appeared to produce quantifiable amounts of monatin from indole pyruvate and pyruvate (as measured by LC/MS/MS as described in Example 1) in comparison to the negative controls. However, large amounts of alanine and tryptophan were produced. It is expected that increasing the ratio of aldolase to dehydrogenase would improve monatin production. It is also expected that directed evolution approaches can be used to improve the ratio of reductive amination activity on MP versus pyruvate and indole-3-pyruvate.

Example 21

Immobilization of *B. sphaericus* D-Alanine Aminotransferase

The *Bacillus sphaericus* D-alanine aminotransferase was purified as the $HIS_6$-tagged protein as described in Example 14.

The enzyme was immobilized onto Eupergit® C resin beads according to the procedure of Mateo, C, et al., *Biotechnology Progress* 18:629-634, (2002). The purified enzyme (4 mL at 6.0 mg/mL) was dialyzed in 0.4 L of 0.5 M potassium phosphate, pH 7.8 using a Pierce Slide-A-Lyzer Dialysis Cassette (7K MWCO; catalog # 66370; Rockford, Ill.) for 1 hour at ambient temperature. The buffer was changed and the dialysis was continued for 1 hour. Pyridoxal phosphate ("PLP") was added to a final concentration of 0.05 mM and the resulting solution was mixed with 0.2 g of Eupergit® C resin purchased from Sigma-Aldrich (Fluka catalog #46115; St. Louis, Mo.). The enzyme-resin suspension was incubated at ambient temperature with gentle mixing overnight. The resin beads were separated from the enzyme solution by centrifugation at 4000×g for 5 minutes. The supernatant was removed and the resin was washed with 3×3 mL of 100 mM potassium phosphate, pH 7.8 containing 0.05 mM PLP. The mixture was centrifuged at 3000×g for 5 minutes between washes. The amount of protein bound to the resin was determined by measuring the amount of protein in each supernatant and subtracting the sum from the original amount of protein to be immobilized. The protein concentrations were measured using a Pierce BCA™ Protein Assay Kit with bovine serum albumin as the standard (catalog #23225; Rockford, Ill.). The washed immobilized-enzyme beads were finally suspended in 4 mL of 100 mM potassium phosphate, pH 7.8 containing 0.05 mM PLP. The unreacted epoxy groups of the immobilized-enzyme beads were blocked by incubation with 1.9 M alanine at ambient temperature with gentle mixing. After 24 hours, the beads were washed, as described above, to remove the excess alanine and finally resuspended in 100 mM potassium phosphate, pH 7.8 containing 0.05 mM PLP. The final concentration of immobilized enzyme was 118 mg protein per g resin bead.

Example 22

Immobilization of *S. meliloti* ProA Aldolase

The *Sinorhizobium meliloti* HMG aldolase ("proA") was purified as the $HIS_6$-tagged protein using a procedure similar to the one described in Example 14 for the $HIS_6$-tagged *B. sphaericus* D-alanine aminotransferase.

Starting from a fresh culture plate (LB agar with 50 μg/mL kanamycin) of BL21(DE3)::*S. meliloti* proA pET30(Xa/LIC), cells were grown in 5 ml of Luria-Bertani broth ("LB") with 50 μg/ml kanamycin, at 37° C. and 225 rpm overnight. Subsequently, the culture was transferred at 0.5-0.6% (v/v) into flasks containing 800 mL of LB broth with 50 μg/ml kanamycin. The cells were grown at 37° C. and 225 rpm until the $OD_{600}$ reached 0.6-0.7. The gene expression was induced by the addition of 0.2 mM IPTG. The cultures were further incubated at 30° C. for 4 hours at 225 rpm and then harvested by centrifugation in a Beckman (Fullerton, Calif.) J25II centrifuge with a JS-16.25 rotor at 10,000 rpm for 10 minutes. The cell pellet was washed once with cold 50 mM EPPS buffer, pH 8.2, and the cells were centrifuged again. The washed cell pellet was harvested and used immediately. To prepare cell-free extract containing the *S. meliloti* $HIS_6$-proA aldolase ($HIS_6$-SmelproA) protein, the cells were suspended in 3-4 volumes of 50 mM EPPS, pH 8.2, containing 100 mM NaCl, and then disrupted using a Microfluidics (Newton, Mass.) homogenizer (3 passes at 20,000 psi), maintaining the temperature of the suspension below 15° C. All subsequent purification steps were carried out at 4° C. The cell extract was centrifuged for 15 minutes at 15,000×g to remove the cell debris. Aliquots of the cell free extract, each containing between 15 and 20 mg of soluble protein, were applied to Novagen HIS-Bind columns (catalog # 70971-4) that had been previously equilibrated with the Novagen Bind buffer. The columns were washed with 2×10 mL of the Novagen Bind buffer and 1×10 mL of the Novagen Wash buffer diluted 1:1 with the Bind buffer. The $HIS_6$-SmelproA was eluted with 5 mL of the Novagen Elute buffer from each column. The elution fractions from each column were combined and concentrated 2× with Amicon (Billerica, Mass.) Ultra-15 centrifugal filter devices (MWCO 10 kDa). The buffer was exchanged by passage through disposable GE Healthcare PD10 desalting columns (catalog #17-0851-01) previously equilibrated with 50 mM EPPS, pH 8.2, containing 100 mM NaCl.

The protein concentration of the desalted solution was determined using the Pierce BCA™ Protein Assay Kit (catalog #23225; Rockford, Ill.). The purity of each fraction and the level of expression in the cell free extract fraction were determined by SDS-PAGE with a Bio-Rad Protean II minigel system (Hercules, Calif.) and 4-15% gradient gels. Typically, this procedure produced about 60-70 mg of enzyme from 3200 mL of LB culture with a purity of ~90%. Aliquots (1-5 mL) of the purified enzyme were stored at −80 C until use.

The enzyme was immobilized onto Eupergit® C resin beads according to the procedure of Mateo, C., et al., (2002) *Biotechnology Progress* 18:629-634, (2002) and as described in Example 21 for the *B. sphaericus* D-alanine aminotransferase, except that 4 mM magnesium chloride was present in the buffer during immobilization instead of 0.05 mM PLP. After blocking with glycine, the washed immobilized enzyme was suspended in 100 mM potassium phosphate, pH 7.8 containing 4 mM magnesium chloride. The final concentration of *S. meliloti* proA aldolase was 52 mg protein per gram resin bead.

Example 23

Production of R,R-Monatin Using Immobilized Enzymes

The *B. sphaericus* $HIS_6$-tagged D-alanine aminotransferase and the *R. meliloti* $HIS_6$-tagged proA aldolase were purified and immobilized as described in Examples 21 and 22.

Solutions of 50 mM sodium pyruvate, 40 mM D-tryptophan, 4 mM $MgCl_2$, and 50 μM PLP in 100 mM potassium phosphate, pH 7.8 were prepared in 15-mL polypropylene tubes with screw caps. To each of these solutions was added both of the immobilized enzymes to a final volume of 4 mL. The resulting suspensions were incubated at room temperature with gentle mixing for up to 24 hours. The progress of each reactions was followed by HPLC and/or LC-MS analyses, measuring D-tryptophan, D-alanine, R,R-monatin, and pyruvic acid. The isomeric purity of the product monatin was determined using chiral LC/MS/MS. All analytical methods are described in Example 1. Typical results from experiments using immobilized enzymes are shown in Table 47 below. Analysis of the isomeric purity of the monatin formed during the reaction showed that the product of the enzymatic reactions was between 74 and 80% R,R.

TABLE 47

Production of R,R-Monatin Using Immobilized Enzymes

| proA Aldolase Concentration (μg/mL) | D-Alanine Aminotransferase Concentration (μg/mL) | Monatin Concentration (mM) (4 Hour Timepoint) | Tryptophan Concentration (mM) (4 Hour Timepoint) | Alanine Concentration (mM) (4 Hour Timepoint) |
|---|---|---|---|---|
| 50 | 500 | 0.06 | 17.75 | 20.51 |
| 50 | 1000 | 0.29 | 15.03 | 24.71 |
| 100 | 1000 | 0.33 | 15.17 | 24.73 |
| 100 | 2000 | 0.54 | 14.40 | 29.45 |

SEQUENCE LISTING

```
<160> NUMBER OF SEQ ID NOS: 102

<210> SEQ ID NO 1
<211> LENGTH: 684
<212> TYPE: DNA
<213> ORGANISM: Comamonas testosteroni

<400> SEQUENCE: 1

atgtacgaac tgggagttgt ctaccgcaat atccagcgcg ccgaccgcgc tgctgctgac      60

ggcctggccg ccctgggctc cgccaccgtg cacgaggcca tgggccgcgt cggtctgctc     120

aagccctata tgcgccccat ctatgccggc aagcaggtct cgggcaccgc cgtcacggtg     180

ctgctgcagc ccggcgacaa ctggatgatg catgtggctg ccgagcagat tcagcccggc     240

gacatcgtgg tcgcagccgt caccgcagag tgcaccgacg gctacttcgg cgatctgctg     300

gccaccagct tccaggcgcg cggcgcacgt gcgctgatca tcgatgccgg cgtgcgcgac     360

gtgaagacgc tgcaggagat ggactttccg gtctggagca aggccatctc ttccaagggc     420

acgatcaagg ccaccctggg ctcggtcaac atccccatcg tctgcgccgg catgctggtc     480

acgcccggtg acgtgatcgt ggccgacgac gacggcgtgg tctgcgtgcc cgccgcgcgt     540

gccgtggaag tgctggccgc cgcccagaag cgtgaaagct tcgaaggcga aaagcgcgcc     600

aagctggcct cgggcatcct cggcctggat atgtacaaga tgcgcgagcc cctggaaaag     660

gccggcctga aatatattga ctaa                                            684

<210> SEQ ID NO 2
<211> LENGTH: 227
<212> TYPE: PRT
<213> ORGANISM: Comamonas testosteroni

<400> SEQUENCE: 2
```

-continued

Met Tyr Glu Leu Gly Val Val Tyr Arg Asn Ile Gln Arg Ala Asp Arg
1 5 10 15

Ala Ala Ala Asp Gly Leu Ala Ala Leu Gly Ser Ala Thr Val His Glu
20 25 30

Ala Met Gly Arg Val Gly Leu Leu Lys Pro Tyr Met Arg Pro Ile Tyr
35 40 45

Ala Gly Lys Gln Val Ser Gly Thr Ala Val Thr Val Leu Leu Gln Pro
50 55 60

Gly Asp Asn Trp Met Met His Val Ala Ala Glu Gln Ile Gln Pro Gly
65 70 75 80

Asp Ile Val Val Ala Ala Val Thr Ala Glu Cys Thr Asp Gly Tyr Phe
85 90 95

Gly Asp Leu Leu Ala Thr Ser Phe Gln Ala Arg Gly Ala Arg Ala Leu
100 105 110

Ile Ile Asp Ala Gly Val Arg Asp Val Lys Thr Leu Gln Glu Met Asp
115 120 125

Phe Pro Val Trp Ser Lys Ala Ile Ser Ser Lys Gly Thr Ile Lys Ala
130 135 140

Thr Leu Gly Ser Val Asn Ile Pro Ile Val Cys Ala Gly Met Leu Val
145 150 155 160

Thr Pro Gly Asp Val Ile Val Ala Asp Asp Asp Gly Val Val Cys Val
165 170 175

Pro Ala Ala Arg Ala Val Glu Val Leu Ala Ala Ala Gln Lys Arg Glu
180 185 190

Ser Phe Glu Gly Glu Lys Arg Ala Lys Leu Ala Ser Gly Ile Leu Gly
195 200 205

Leu Asp Met Tyr Lys Met Arg Glu Pro Leu Glu Lys Ala Gly Leu Lys
210 215 220

Tyr Ile Asp
225

<210> SEQ ID NO 3
<211> LENGTH: 63
<212> TYPE: DNA
<213> ORGANISM: Artificial sequence
<220> FEATURE:
<223> OTHER INFORMATION: pykA Knockout Primer 1

<400> SEQUENCE: 3
atgtccagaa ggcttcgcag aacaaaaatc gttaccacgt taggtgtagg ctggagctgc 60
ttc 63

<210> SEQ ID NO 4
<211> LENGTH: 64
<212> TYPE: DNA
<213> ORGANISM: Artificial sequence
<220> FEATURE:
<223> OTHER INFORMATION: pykA Knockout Primer 2

<400> SEQUENCE: 4
ctctaccgtt aaaatacgcg tggtattagt agaacccacg gtaccatatg aatatcctcc 60
ttag 64

<210> SEQ ID NO 5
<211> LENGTH: 64
<212> TYPE: DNA
<213> ORGANISM: Artificial sequence -continued
<220> FEATURE:
<223> OTHER INFORMATION: pykF Knockout Primer 1

<400> SEQUENCE: 5
aggacgtgaa cagatgcggt gttagtagtg ccgctcggta ccagcatatg aatatcctcc 60
ttag 64

<210> SEQ ID NO 6
<211> LENGTH: 63
<212> TYPE: DNA
<213> ORGANISM: Artificial sequence
<220> FEATURE:
<223> OTHER INFORMATION: pykF Knockout Primer 2

<400> SEQUENCE: 6
atgaaaaaga ccaaaattgt ttgcaccatc ggaccgaaaa ccggtgtagg ctggagctgc 60
ttc 63

<210> SEQ ID NO 7
<211> LENGTH: 30
<212> TYPE: DNA
<213> ORGANISM: Artificial sequence
<220> FEATURE:
<223> OTHER INFORMATION: HEXaspC Primer 1

<400> SEQUENCE: 7
gcggaacata tgtttgagaa cattaccgcc 30

<210> SEQ ID NO 8
<211> LENGTH: 32
<212> TYPE: DNA
<213> ORGANISM: Artificial sequence
<220> FEATURE:
<223> OTHER INFORMATION: HEXaspC Primer 2

<400> SEQUENCE: 8
ataaccggat ccttacagca ctgccacaat cg 32

<210> SEQ ID NO 9
<211> LENGTH: 36
<212> TYPE: DNA
<213> ORGANISM: Artificial sequence
<220> FEATURE:
<223> OTHER INFORMATION: aspCW130F Backward Primer

<400> SEQUENCE: 9
cgctcttatg gttcggtttg cttgggttgc tcaccc 36

<210> SEQ ID NO 10
<211> LENGTH: 36
<212> TYPE: DNA
<213> ORGANISM: Artificial sequence
<220> FEATURE:
<223> OTHER INFORMATION: aspCW130F Forward Primer

<400> SEQUENCE: 10
gggtgagcaa cccaagcttt ccgaaccata agagcg 36

<210> SEQ ID NO 11
<211> LENGTH: 39
<212> TYPE: DNA
<213> ORGANISM: Artificial sequence
<220> FEATURE:
<223> OTHER INFORMATION: R122G-1 Primer -continued

<400> SEQUENCE: 11
caaaaaatac cagcgttaag ggagtgtggg tgagcaacc 39

<210> SEQ ID NO 12
<211> LENGTH: 29
<212> TYPE: DNA
<213> ORGANISM: Artificial sequence
<220> FEATURE:
<223> OTHER INFORMATION: P9T_4 Primer

<400> SEQUENCE: 12
cattaccgcc gctactgccg acccgattc 29

<210> SEQ ID NO 13
<211> LENGTH: 39
<212> TYPE: DNA
<213> ORGANISM: Artificial sequence
<220> FEATURE:
<223> OTHER INFORMATION: I68V-1 Primer

<400> SEQUENCE: 13
caccaaaaat tacctcggcg tagacggcat ccctgaatt 39

<210> SEQ ID NO 14
<211> LENGTH: 35
<212> TYPE: DNA
<213> ORGANISM: Artificial sequence
<220> FEATURE:
<223> OTHER INFORMATION: T156A Primer

<400> SEQUENCE: 14
tgatgcggaa aatcacgctc ttgacttcga tgcac 35

<210> SEQ ID NO 15
<211> LENGTH: 35
<212> TYPE: DNA
<213> ORGANISM: Artificial sequence
<220> FEATURE:
<223> OTHER INFORMATION: L. brevis Glutamate Racemase Primer 1

<400> SEQUENCE: 15
gcggcgccat ggaaaatgat ccgattggtc taatg 35

<210> SEQ ID NO 16
<211> LENGTH: 33
<212> TYPE: DNA
<213> ORGANISM: Artificial sequence
<220> FEATURE:
<223> OTHER INFORMATION: L. brevis Glutamate Racemase Primer 2

<400> SEQUENCE: 16
gcggcggtcg acgcaattac aattgtgttt gtc 33

<210> SEQ ID NO 17
<211> LENGTH: 34
<212> TYPE: DNA
<213> ORGANISM: Artificial sequence
<220> FEATURE:
<223> OTHER INFORMATION: P. pentosaceus Glutamate Racemase Primer 1

<400> SEQUENCE: 17
gcggcgccat ggatgtatgt ataattttat ttag 34

<210> SEQ ID NO 18
<211> LENGTH: 36

-continued

```
<212> TYPE: DNA
<213> ORGANISM: Artificial sequence
<220> FEATURE:
<223> OTHER INFORMATION: P. pentosaceus Glutamate Racemase Primer 2

<400> SEQUENCE: 18

gcggcggtcg acaaatttca ttattcattc taattt                              36


<210> SEQ ID NO 19
<211> LENGTH: 36
<212> TYPE: DNA
<213> ORGANISM: Artificial sequence
<220> FEATURE:
<223> OTHER INFORMATION: P. stutzeri 4 D-HPG AT Outer Primer 1

<400> SEQUENCE: 19

ggccggcata tgtcgatcct taacgactac aaacgt                              36


<210> SEQ ID NO 20
<211> LENGTH: 36
<212> TYPE: DNA
<213> ORGANISM: Artificial sequence
<220> FEATURE:
<223> OTHER INFORMATION: P. stutzeri 4 D-HPG AT Outer Primer 2

<400> SEQUENCE: 20

ggaaggctcg agtcatgatt ggtttccaga caaatt                              36


<210> SEQ ID NO 21
<211> LENGTH: 693
<212> TYPE: DNA
<213> ORGANISM: Aldolase (Bacillus subtilis)

<400> SEQUENCE: 21

atgatttatc agccggggac aacaggcatc gtcgtgcagg atattgcacg cgctgatcaa     60

gccattatcg atggcctagc agaatgtggt gtggcgacgg tgcatgaggc acaggggcgc    120

aagggcctgt tggcggatta tatgacgccg atttactcgg gcgcgcgcat cgctggatct    180

gcggtgacca ttctggcacc gccgtgtgac aattggatga tccatgtggc ggtagaacag    240

ttgcaaaagg gcgatgtgtt gctgctgggc acgatcacac cgtccaatgc tggctatttc    300

ggtgacttgc tggccacgtc agccatggcg cacggttgtc gcggattgat cattgatggc    360

ggtgtgcgcg atgtgcaaga gctgacggat atgggctttc cggtttggtc caaggccgta    420

catgcccaag gcacaatcaa agaaacgctg ggatcggtca acgtgccagt tgtctgcggc    480

caagagttgg taaaccccgg tgatattgtg gtggccgacg atgacggggt gtgcgttgtg    540

cgccgcgaag aagctgctga tgtgctggct aaggcgcggg cgcgcgagag caatgaagcg    600

gccaagcgcg cgcgttttga ggccggtgag ctggggctgg atatctatga catgcgcgcg    660

cggctggccg aaaaaggact gaaatacgtc tga                                 693


<210> SEQ ID NO 22
<211> LENGTH: 230
<212> TYPE: PRT
<213> ORGANISM: Aldolase (Bacillus subtilis)

<400> SEQUENCE: 22

Met Ile Tyr Gln Pro Gly Thr Thr Gly Ile Val Val Gln Asp Ile Ala
1               5                   10                  15

Arg Ala Asp Gln Ala Ile Ile Asp Gly Leu Ala Glu Cys Gly Val Ala
            20                  25                  30
```

-continued

```
Thr Val His Glu Ala Gln Gly Arg Lys Gly Leu Leu Ala Asp Tyr Met
        35                  40                  45

Thr Pro Ile Tyr Ser Gly Ala Arg Ile Ala Gly Ser Ala Val Thr Ile
    50                  55                  60

Leu Ala Pro Pro Cys Asp Asn Trp Met Ile His Val Ala Val Glu Gln
65                  70                  75                  80

Leu Gln Lys Gly Asp Val Leu Leu Leu Gly Thr Ile Thr Pro Ser Asn
                85                  90                  95

Ala Gly Tyr Phe Gly Asp Leu Leu Ala Thr Ser Ala Met Ala His Gly
            100                 105                 110

Cys Arg Gly Leu Ile Ile Asp Gly Gly Val Arg Asp Val Gln Glu Leu
        115                 120                 125

Thr Asp Met Gly Phe Pro Val Trp Ser Lys Ala Val His Ala Gln Gly
    130                 135                 140

Thr Ile Lys Glu Thr Leu Gly Ser Val Asn Val Pro Val Val Cys Gly
145                 150                 155                 160

Gln Glu Leu Val Asn Pro Gly Asp Ile Val Val Ala Asp Asp Asp Gly
                165                 170                 175

Val Cys Val Val Arg Arg Glu Glu Ala Ala Asp Val Leu Ala Lys Ala
            180                 185                 190

Arg Ala Arg Glu Ser Asn Glu Ala Ala Lys Arg Ala Arg Phe Glu Ala
        195                 200                 205

Gly Glu Leu Gly Leu Asp Ile Tyr Asp Met Arg Ala Arg Leu Ala Glu
    210                 215                 220

Lys Gly Leu Lys Tyr Val
225                 230


<210> SEQ ID NO 23
<211> LENGTH: 36
<212> TYPE: DNA
<213> ORGANISM: Artificial sequence
<220> FEATURE:
<223> OTHER INFORMATION: Aldolase Primer

<400> SEQUENCE: 23

gaggagctcg agtcagacgt atttcagtcc tttttc                                36


<210> SEQ ID NO 24
<211> LENGTH: 29
<212> TYPE: DNA
<213> ORGANISM: Artificial sequence
<220> FEATURE:
<223> OTHER INFORMATION: Aldolase Primer

<400> SEQUENCE: 24

agaagacata tgatttatca gccggggac                                        29


<210> SEQ ID NO 25
<211> LENGTH: 20
<212> TYPE: DNA
<213> ORGANISM: Artificial sequence
<220> FEATURE:
<223> OTHER INFORMATION: Alanine Racemase Primer

<400> SEQUENCE: 25

atggacgagt ttcaccgcga                                                  20


<210> SEQ ID NO 26
<211> LENGTH: 20
<212> TYPE: DNA
```

-continued

<213> ORGANISM: Artificial sequence
<220> FEATURE:
<223> OTHER INFORMATION: Alanine Racemase Primer

<400> SEQUENCE: 26
ttatgcatcg cttcatccgc 20

<210> SEQ ID NO 27
<211> LENGTH: 31
<212> TYPE: DNA
<213> ORGANISM: Artificial sequence
<220> FEATURE:
<223> OTHER INFORMATION: Alanine Racemase Primer

<400> SEQUENCE: 27
ataataggat cctcatccgc ggccaacggc g 31

<210> SEQ ID NO 28
<211> LENGTH: 43
<212> TYPE: DNA
<213> ORGANISM: Artificial sequence
<220> FEATURE:
<223> OTHER INFORMATION: Alanine Racemase Primer

<400> SEQUENCE: 28
gggaaaggta ccgaggaata ataaatggac gagtttcacc gcg 43

<210> SEQ ID NO 29
<211> LENGTH: 43
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t

<400> SEQUENCE: 29
gccggacgac acgcacattn nkgcggtcgt gaaggcgaac gcc 43

<210> SEQ ID NO 30
<211> LENGTH: 45
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 30
gtgaaggcga acgcctatgg annkggggat gtgcaggtgg caagg 45

<210> SEQ ID NO 31
<211> LENGTH: 45

-continued

<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (23)..(23)
<223> OTHER INFORMATION: k is g or t

<400> SEQUENCE: 31
cctcccgcct ggcggttgcc nnkttggatg aggcgctcgc tttaa 45

<210> SEQ ID NO 32
<211> LENGTH: 45
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 32
caaccaggcg aaaaggtgag cnnkggtgcg acgtacactg cgcag 45

<210> SEQ ID NO 33
<211> LENGTH: 45
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: k is g or t

<400> SEQUENCE: 33
gatcgggacg attccgatcg gcnnkgcgga cggctggctc cgccg 45

<210> SEQ ID NO 34
<211> LENGTH: 43
<212> TYPE: DNA
<213> ORGANISM: Artificial sequence
<220> FEATURE:
<223> OTHER INFORMATION: Mutagenic Primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (23)..(23)
<223> OTHER INFORMATION: k is g or t

<400> SEQUENCE: 34
gccatttgga aacgatcaac nnkgaagtgc cttgcacgat cag 43

<210> SEQ ID NO 35

-continued

<211> LENGTH: 43
<212> TYPE: DNA
<213> ORGANISM: Artificial sequence
<220> FEATURE:
<223> OTHER INFORMATION: Racemase Primer

<400> SEQUENCE: 35
gggaaaggta ccgaggaata ataaatggac gagtttcacc gcg 43

<210> SEQ ID NO 36
<211> LENGTH: 27
<212> TYPE: DNA
<213> ORGANISM: Artificial sequence
<220> FEATURE:
<223> OTHER INFORMATION: Racemase Primer

<400> SEQUENCE: 36
gcggcgccat ggacgagttt caccgcg 27

<210> SEQ ID NO 37
<211> LENGTH: 43
<212> TYPE: DNA
<213> ORGANISM: Artificial sequence
<220> FEATURE:
<223> OTHER INFORMATION: Alanine Racemase Primer

<400> SEQUENCE: 37
gccatttgga aacgatcaac tatgaagtgc cttgcacgat cag 43

<210> SEQ ID NO 38
<211> LENGTH: 45
<212> TYPE: DNA
<213> ORGANISM: Artificial sequence
<220> FEATURE:
<223> OTHER INFORMATION: Alanine Racemase Primer

<400> SEQUENCE: 38
ctcccgcctg gcggttgcct tcttggatga ggcgctcgct ttaag 45

<210> SEQ ID NO 39
<211> LENGTH: 43
<212> TYPE: DNA
<213> ORGANISM: Artificial sequence
<220> FEATURE:
<223> OTHER INFORMATION: Alanine Racemase Primer

<400> SEQUENCE: 39
gccggacgac acgcacatta tggcggtcgt gaaggcgaac gcc 43

<210> SEQ ID NO 40
<211> LENGTH: 1152
<212> TYPE: DNA
<213> ORGANISM: Alanine Racemase (Geobacillus stearothermophilus)

<400> SEQUENCE: 40
atggacgagt ttcaccgcga tacgtgggcg gaagtggatt tggacgccat ttacgacaat 60
gtggagaatt tgcgccgttt gctgccggac gacacgcaca ttatggcggt cgtgaaggcg 120
aacgcctatg gacatgggga tgtgcaggtg gcaaggacag cgctcgaagc gggggcctcc 180
cgcctggcgg ttgccttttt ggatgaggcg ctcgctttaa gggaaaaagg aatcgaagcg 240
ccgattctag ttctcggggc ttcccgtcca gctgatgcgg cgctggccgc ccagcagcgc 300
attgccctga ccgtgttccg ctccgactgg ttggaagaag cgtccgccct ttacagcggc 360
ccttttccta ttcatttcca tttgaaaatg gacaccggca tgggacggct tggagtgaaa 420

-continued

```
gacgaggaag agacgaaacg aatcgtagcg ctgattgagc gccatccgca ttttgtgctt    480

gaaggggtgt acacgcattt tgcgactgcg gatgaggtga acaccgatta tttttcctat    540

cagtataccc gttttttgca catgctcgaa tggctgccgt cgcgcccgcc gctcgtccat    600

tgcgccaaca gcgcagcgtc gctccgtttc cctgaccgga cgttcaatat ggtccgcttc    660

ggcattgcca tgtatgggct tgccccgtcg cccggcatca agccgctgct gccgtatcca    720

ttaaaagaag cattttcgct ccatagccgc ctcgtacacg tcaaaaaact gcaaccaggc    780

gaaaaggtga gctatggtgc gacgtacact gcgcagacgg aggagtggat cgggacgatt    840

ccgatcggct atgcggacgg ctggctccgc cgcctgcagc actttcatgt ccttgttgac    900

ggacaaaagg cgccgattgt cggccgcatt tgcatggacc agtgcatgat ccgcctgcct    960

ggtccgctgc cggtcggcac gaaggtgaca ctgattggtc gccaagggga cgaggtaatt   1020

tccattgatg atgtcgctcg ccatttggaa acgatcaact acgaagtgcc ttgcacgatc   1080

agttatcgag tgccccgtat ttttttccgc cataagcgta taatggaagt gagaaacgcc   1140

gttggccgcg ga                                                       1152
```

<210> SEQ ID NO 41
<211> LENGTH: 384
<212> TYPE: PRT
<213> ORGANISM: Alanine Racemase (Geobacillus stearothermophilus)

<400> SEQUENCE: 41

```
Met Asp Glu Phe His Arg Asp Thr Trp Ala Glu Val Asp Leu Asp Ala
1               5                   10                  15

Ile Tyr Asp Asn Val Glu Asn Leu Arg Arg Leu Leu Pro Asp Asp Thr
            20                  25                  30

His Ile Met Ala Val Val Lys Ala Asn Ala Tyr Gly His Gly Asp Val
        35                  40                  45

Gln Val Ala Arg Thr Ala Leu Glu Ala Gly Ala Ser Arg Leu Ala Val
    50                  55                  60

Ala Phe Leu Asp Glu Ala Leu Ala Leu Arg Glu Lys Gly Ile Glu Ala
65                  70                  75                  80

Pro Ile Leu Val Leu Gly Ala Ser Arg Pro Ala Asp Ala Ala Leu Ala
                85                  90                  95

Ala Gln Gln Arg Ile Ala Leu Thr Val Phe Arg Ser Asp Trp Leu Glu
            100                 105                 110

Glu Ala Ser Ala Leu Tyr Ser Gly Pro Phe Pro Ile His Phe His Leu
        115                 120                 125

Lys Met Asp Thr Gly Met Gly Arg Leu Gly Val Lys Asp Glu Glu Glu
    130                 135                 140

Thr Lys Arg Ile Val Ala Leu Ile Glu Arg His Pro His Phe Val Leu
145                 150                 155                 160

Glu Gly Val Tyr Thr His Phe Ala Thr Ala Asp Glu Val Asn Thr Asp
                165                 170                 175

Tyr Phe Ser Tyr Gln Tyr Thr Arg Phe Leu His Met Leu Glu Trp Leu
            180                 185                 190

Pro Ser Arg Pro Pro Leu Val His Cys Ala Asn Ser Ala Ala Ser Leu
        195                 200                 205

Arg Phe Pro Asp Arg Thr Phe Asn Met Val Arg Phe Gly Ile Ala Met
    210                 215                 220

Tyr Gly Leu Ala Pro Ser Pro Gly Ile Lys Pro Leu Leu Pro Tyr Pro
225                 230                 235                 240
```

-continued

```
Leu Lys Glu Ala Phe Ser Leu His Ser Arg Leu Val His Val Lys Lys
                245                 250                 255

Leu Gln Pro Gly Glu Lys Val Ser Tyr Gly Ala Thr Tyr Thr Ala Gln
            260                 265                 270

Thr Glu Glu Trp Ile Gly Thr Ile Pro Ile Gly Tyr Ala Asp Gly Trp
        275                 280                 285

Leu Arg Arg Leu Gln His Phe His Val Leu Val Asp Gly Gln Lys Ala
    290                 295                 300

Pro Ile Val Gly Arg Ile Cys Met Asp Gln Cys Met Ile Arg Leu Pro
305                 310                 315                 320

Gly Pro Leu Pro Val Gly Thr Lys Val Thr Leu Ile Gly Arg Gln Gly
                325                 330                 335

Asp Glu Val Ile Ser Ile Asp Asp Val Ala Arg His Leu Glu Thr Ile
            340                 345                 350

Asn Tyr Glu Val Pro Cys Thr Ile Ser Tyr Arg Val Pro Arg Ile Phe
        355                 360                 365

Phe Arg His Lys Arg Ile Met Glu Val Arg Asn Ala Val Gly Arg Gly
    370                 375                 380


<210> SEQ ID NO 42
<211> LENGTH: 1152
<212> TYPE: DNA
<213> ORGANISM: Artificial sequence
<220> FEATURE:
<223> OTHER INFORMATION: Mutagenized Ala Racemase

<400> SEQUENCE: 42

atggacgagt ttcaccgcga tacgtgggcg gaagtggatt tggacgccat ttacgacaat     60

gtggagaatt tgcgccgttt gctgccggac gacacgcaca tttgtgcggt cgtgaaggcg    120

aacgcctatg gacatgggga tgtgcaggtg gcaaggacag cgctcgaagc gggggcctcc    180

cgcctggcgg ttgccgagtt ggatgaggcg ctcgctttaa gggaaaaagg aatcgaagcg    240

ccgattctag ttctcggggc ttcccgtcca gctgatgcgg cgctggccgc ccagcagcgc    300

attgccctga ccgtgttccg ctccgactgg ttggaagaag cgtccgccct ttacagcggc    360

ccttttccta ttcatttcca tttgaaaatg gacaccggca tgggacggct tggagtgaaa    420

gacgaggaag agacgaaacg aatcgtagcg ctgattgagc gccatccgca ttttgtgctt    480

gaaggggtgt acacgcattt tgcgactgcg gatgaggtga acaccgatta tttttcctat    540

cagtataccc gtttttgca catgctcgaa tggctgccgt cgcgcccgct gctcgtccat    600

tgcgccaaca gcgcagcgtc gctccgtttc cctgaccgga cgttcaatat ggtccgcttc    660

ggcattgcca tgtatgggct tgccccgtcg cccggcatca agccgctgct gccgtatcca    720

ttaaaagaag cattttcgct ccatagccgc ctcgtacacg tcaaaaaact gcaaccaggc    780

gaaaaggtga gctatggtgc gacgtacact gcgcagacgg aggagtggat cgggacgatt    840

ccgatcggct atgcggacgg ctggctccgc cgcctgcagc actttcatgt ccttgttgac    900

ggacaaaagg cgccgattgt cggccgcatt tgcatggacc agtgcatgat ccgcctgcct    960

ggtccgctgc cggtcggcac gaaggtgaca ctgattggtc gccaagggga cgaggtaatt   1020

tccattgatg atgtcgctcg ccatttggaa acgatcaacg cggaagtgcc ttgcacgatc   1080

agttatcgag tgccccgtat ttttttccgc cataagcgta taatggaagt gagaaacgcc   1140

gttggccgcg ga                                                       1152
```

-continued

```
<210> SEQ ID NO 43
<211> LENGTH: 384
<212> TYPE: PRT
<213> ORGANISM: Artificial sequence
<220> FEATURE:
<223> OTHER INFORMATION: Mutagenized Ala Racemase

<400> SEQUENCE: 43

Met Asp Glu Phe His Arg Asp Thr Trp Ala Glu Val Asp Leu Asp Ala
1               5                   10                  15

Ile Tyr Asp Asn Val Glu Asn Leu Arg Arg Leu Leu Pro Asp Asp Thr
            20                  25                  30

His Ile Cys Ala Val Val Lys Ala Asn Ala Tyr Gly His Gly Asp Val
        35                  40                  45

Gln Val Ala Arg Thr Ala Leu Glu Ala Gly Ala Ser Arg Leu Ala Val
    50                  55                  60

Ala Glu Leu Asp Glu Ala Leu Ala Leu Arg Glu Lys Gly Ile Glu Ala
65                  70                  75                  80

Pro Ile Leu Val Leu Gly Ala Ser Arg Pro Ala Asp Ala Ala Leu Ala
                85                  90                  95

Ala Gln Gln Arg Ile Ala Leu Thr Val Phe Arg Ser Asp Trp Leu Glu
            100                 105                 110

Glu Ala Ser Ala Leu Tyr Ser Gly Pro Phe Pro Ile His Phe His Leu
        115                 120                 125

Lys Met Asp Thr Gly Met Gly Arg Leu Gly Val Lys Asp Glu Glu Glu
    130                 135                 140

Thr Lys Arg Ile Val Ala Leu Ile Glu Arg His Pro His Phe Val Leu
145                 150                 155                 160

Glu Gly Val Tyr Thr His Phe Ala Thr Ala Asp Glu Val Asn Thr Asp
                165                 170                 175

Tyr Phe Ser Tyr Gln Tyr Thr Arg Phe Leu His Met Leu Glu Trp Leu
            180                 185                 190

Pro Ser Arg Pro Leu Leu Val His Cys Ala Asn Ser Ala Ala Ser Leu
        195                 200                 205

Arg Phe Pro Asp Arg Thr Phe Asn Met Val Arg Phe Gly Ile Ala Met
    210                 215                 220

Tyr Gly Leu Ala Pro Ser Pro Gly Ile Lys Pro Leu Leu Pro Tyr Pro
225                 230                 235                 240

Leu Lys Glu Ala Phe Ser Leu His Ser Arg Leu Val His Val Lys Lys
                245                 250                 255

Leu Gln Pro Gly Glu Lys Val Ser Tyr Gly Ala Thr Tyr Thr Ala Gln
            260                 265                 270

Thr Glu Glu Trp Ile Gly Thr Ile Pro Ile Gly Tyr Ala Asp Gly Trp
        275                 280                 285

Leu Arg Arg Leu Gln His Phe His Val Leu Val Asp Gly Gln Lys Ala
    290                 295                 300

Pro Ile Val Gly Arg Ile Cys Met Asp Gln Cys Met Ile Arg Leu Pro
305                 310                 315                 320

Gly Pro Leu Pro Val Gly Thr Lys Val Thr Leu Ile Gly Arg Gln Gly
                325                 330                 335

Asp Glu Val Ile Ser Ile Asp Asp Val Ala Arg His Leu Glu Thr Ile
            340                 345                 350

Asn Ala Glu Val Pro Cys Thr Ile Ser Tyr Arg Val Pro Arg Ile Phe
        355                 360                 365

Phe Arg His Lys Arg Ile Met Glu Val Arg Asn Ala Val Gly Arg Gly
```

-continued 370 375 380

<210> SEQ ID NO 44
<211> LENGTH: 30
<212> TYPE: DNA
<213> ORGANISM: Artificial sequence
<220> FEATURE:
<223> OTHER INFORMATION: B. licheniformis BCAT Primer

<400> SEQUENCE: 44
ggttaaggcc atgggggacc agaaagacca 30

<210> SEQ ID NO 45
<211> LENGTH: 32
<212> TYPE: DNA
<213> ORGANISM: Artificial sequence
<220> FEATURE:
<223> OTHER INFORMATION: B. licheniformis BCAT Primer

<400> SEQUENCE: 45
ggccttccgt cgactcagct gacacttaag ct 32

<210> SEQ ID NO 46
<211> LENGTH: 29
<212> TYPE: DNA
<213> ORGANISM: Artificial sequence
<220> FEATURE:
<223> OTHER INFORMATION: Mutagenic Primer

<400> SEQUENCE: 46
atcacggatt tttattcggg gacggcgtg 29

<210> SEQ ID NO 47
<211> LENGTH: 29
<212> TYPE: DNA
<213> ORGANISM: Artificial sequence
<220> FEATURE:
<223> OTHER INFORMATION: Mutagenic Primer

<400> SEQUENCE: 47
atcacggatt tttagacggg gacggcgtg 29

<210> SEQ ID NO 48
<211> LENGTH: 26
<212> TYPE: DNA
<213> ORGANISM: Artificial sequence
<220> FEATURE:
<223> OTHER INFORMATION: Mutagenic Primer

<400> SEQUENCE: 48
ggacggcgtg tatgaaggga tcaggg 26

<210> SEQ ID NO 49
<211> LENGTH: 32
<212> TYPE: DNA
<213> ORGANISM: Artificial sequence
<220> FEATURE:
<223> OTHER INFORMATION: Mutagenic Primer

<400> SEQUENCE: 49
tgtttgaagg gatcaaggta tacgacggca ac 32

<210> SEQ ID NO 50
<211> LENGTH: 34
<212> TYPE: DNA

-continued

```
<213> ORGANISM: Artificial sequence
<220> FEATURE:
<223> OTHER INFORMATION: Mutagenic Primer

<400> SEQUENCE: 50

gacggcgtgt atgaagggat caaggtatac gacg                              34


<210> SEQ ID NO 51
<211> LENGTH: 29
<212> TYPE: DNA
<213> ORGANISM: Artificial sequence
<220> FEATURE:
<223> OTHER INFORMATION: Mutagenic Primer

<400> SEQUENCE: 51

gctgaaagac gctttcatcc gcttggtcg                                    29


<210> SEQ ID NO 52
<211> LENGTH: 28
<212> TYPE: DNA
<213> ORGANISM: Artificial sequence
<220> FEATURE:
<223> OTHER INFORMATION: Mutagenic Primer

<400> SEQUENCE: 52

gctgaaagac gctcacatcc gcttggtc                                     28


<210> SEQ ID NO 53
<211> LENGTH: 38
<212> TYPE: DNA
<213> ORGANISM: Artificial sequence
<220> FEATURE:
<223> OTHER INFORMATION: Mutagenic Primer

<400> SEQUENCE: 53

ctgaaagacg cttacatcta cttggtcgtt tcaagagg                          38


<210> SEQ ID NO 54
<211> LENGTH: 40
<212> TYPE: DNA
<213> ORGANISM: Artificial sequence
<220> FEATURE:
<223> OTHER INFORMATION: Mutagenic Primer

<400> SEQUENCE: 54

ggctgaaaga cgctttcatc tacttggtcg tttcaagagg                        40


<210> SEQ ID NO 55
<211> LENGTH: 39
<212> TYPE: DNA
<213> ORGANISM: Artificial sequence
<220> FEATURE:
<223> OTHER INFORMATION: Mutagenic Primer

<400> SEQUENCE: 55

gctgaaagac gctcacatct acttggtcgt ttcaagagg                         39


<210> SEQ ID NO 56
<211> LENGTH: 27
<212> TYPE: DNA
<213> ORGANISM: Artificial sequence
<220> FEATURE:
<223> OTHER INFORMATION: Mutagenic Primer

<400> SEQUENCE: 56

gcaggtgacc gcggactcga tccaaac                                      27
```

-continued

<210> SEQ ID NO 57
<211> LENGTH: 27
<212> TYPE: DNA
<213> ORGANISM: Artificial sequence
<220> FEATURE:
<223> OTHER INFORMATION: Mutagenic Primer

<400> SEQUENCE: 57
gcaggtgacc tcggacacga tccaaac 27

<210> SEQ ID NO 58
<211> LENGTH: 32
<212> TYPE: DNA
<213> ORGANISM: Artificial sequence
<220> FEATURE:
<223> OTHER INFORMATION: Mutagenic Primer

<400> SEQUENCE: 58
gcaggtgacc gcggacacga tccaaacaat tg 32

<210> SEQ ID NO 59
<211> LENGTH: 40
<212> TYPE: DNA
<213> ORGANISM: Artificial sequence
<220> FEATURE:
<223> OTHER INFORMATION: Mutagenic Primer

<400> SEQUENCE: 59
gtcatcataa ttgtcgaacc atacgcaata ttcccgaaac 40

<210> SEQ ID NO 60
<211> LENGTH: 40
<212> TYPE: DNA
<213> ORGANISM: Artificial sequence
<220> FEATURE:
<223> OTHER INFORMATION: Mutagenic Primer

<400> SEQUENCE: 60
gtcatcataa ttgtcgaacc aaaggcaata ttcccgaaac 40

<210> SEQ ID NO 61
<211> LENGTH: 40
<212> TYPE: DNA
<213> ORGANISM: Artificial sequence
<220> FEATURE:
<223> OTHER INFORMATION: Mutagenic Primer

<400> SEQUENCE: 61
gtcatcataa ttgtcgaacc attggcagaa ttcccgaaac 40

<210> SEQ ID NO 62
<211> LENGTH: 45
<212> TYPE: DNA
<213> ORGANISM: Artificial sequence
<220> FEATURE:
<223> OTHER INFORMATION: Mutagenic Primer

<400> SEQUENCE: 62
cgagtgtcat cataattgtc gaaccatacg cagaattccc gaaac 45

<210> SEQ ID NO 63
<211> LENGTH: 46
<212> TYPE: DNA
<213> ORGANISM: Artificial sequence
<220> FEATURE:

<223> OTHER INFORMATION: Mutagenic Primer

<400> SEQUENCE: 63
ccgagtgtca tcataattgt cgaaccaaag gcagaattcc cgaaac 46

<210> SEQ ID NO 64
<211> LENGTH: 42
<212> TYPE: DNA
<213> ORGANISM: Artificial sequence
<220> FEATURE:
<223> OTHER INFORMATION: Mutagenic Primer

<400> SEQUENCE: 64
aatcgctgaa cttgttaaac aatattcttg tccggatcga gg 42

<210> SEQ ID NO 65
<211> LENGTH: 21
<212> TYPE: DNA
<213> ORGANISM: Artificial sequence
<220> FEATURE:
<223> OTHER INFORMATION: Oligo Primer

<400> SEQUENCE: 65
gaagaccgtg gttatcaatt t 21

<210> SEQ ID NO 66
<211> LENGTH: 21
<212> TYPE: DNA
<213> ORGANISM: Artificial sequence
<220> FEATURE:
<223> OTHER INFORMATION: Oligo Primer

<400> SEQUENCE: 66
gatggtattt acgaagtaat c 21

<210> SEQ ID NO 67
<211> LENGTH: 22
<212> TYPE: DNA
<213> ORGANISM: Artificial sequence
<220> FEATURE:
<223> OTHER INFORMATION: Oligo Primer

<400> SEQUENCE: 67
agatttaata tcacaacgta ac 22

<210> SEQ ID NO 68
<211> LENGTH: 22
<212> TYPE: DNA
<213> ORGANISM: Artificial sequence
<220> FEATURE:
<223> OTHER INFORMATION: Oligo Primer

<400> SEQUENCE: 68
gccaagtaaa atttaagatt ta 22

<210> SEQ ID NO 69
<211> LENGTH: 21
<212> TYPE: DNA
<213> ORGANISM: Artificial sequence
<220> FEATURE:
<223> OTHER INFORMATION: Oligo Primer

<400> SEQUENCE: 69
atttgctggg tgcgtataaa g 21

-continued

<210> SEQ ID NO 70
<211> LENGTH: 30
<212> TYPE: DNA
<213> ORGANISM: Artificial sequence
<220> FEATURE:
<223> OTHER INFORMATION: 4978 DAT GSP1 Upstrm Primer

<400> SEQUENCE: 70
gacatgctcc tccgctgtaa ataattcacc 30

<210> SEQ ID NO 71
<211> LENGTH: 30
<212> TYPE: DNA
<213> ORGANISM: Artificial sequence
<220> FEATURE:
<223> OTHER INFORMATION: 4978 DAT GSP1 Dwnstr Primer

<400> SEQUENCE: 71
ccctggtgat gaagtgaagc cagtattaac 30

<210> SEQ ID NO 72
<211> LENGTH: 27
<212> TYPE: DNA
<213> ORGANISM: Artificial sequence
<220> FEATURE:
<223> OTHER INFORMATION: 4978 DAT GSP2 Upstrm Primer

<400> SEQUENCE: 72
atcgccaaat tgataaccac ggtcttc 27

<210> SEQ ID NO 73
<211> LENGTH: 30
<212> TYPE: DNA
<213> ORGANISM: Artificial sequence
<220> FEATURE:
<223> OTHER INFORMATION: 4978 DAT GSP2 Dwnstr Primer

<400> SEQUENCE: 73
acgtcccgta gcaaactttg aaaaaggtgt 30

<210> SEQ ID NO 74
<211> LENGTH: 30
<212> TYPE: DNA
<213> ORGANISM: Artificial sequence
<220> FEATURE:
<223> OTHER INFORMATION: 7063 DAT GSP1 Upstrm Primer

<400> SEQUENCE: 74
tgcatagaat cggtcgatat gttcagtagc 30

<210> SEQ ID NO 75
<211> LENGTH: 30
<212> TYPE: DNA
<213> ORGANISM: Artificial sequence
<220> FEATURE:
<223> OTHER INFORMATION: 7063 DAT GSP1 Dwnstr Primer

<400> SEQUENCE: 75
gcggagaaac gattacagaa ggttcttcaa 30

<210> SEQ ID NO 76
<211> LENGTH: 27
<212> TYPE: DNA
<213> ORGANISM: Artificial sequence
<220> FEATURE:
<223> OTHER INFORMATION: 7063 DAT GSP2 Upstrm Primer -continued

<400> SEQUENCE: 76
gtcaccaaat tgataaccac ggtcttc 27

<210> SEQ ID NO 77
<211> LENGTH: 27
<212> TYPE: DNA
<213> ORGANISM: Artificial sequence
<220> FEATURE:
<223> OTHER INFORMATION: 7063 DAT GSP2 Dwnstr Primer

<400> SEQUENCE: 77
ggtgtacttt atacgcaccc agcaaat 27

<210> SEQ ID NO 78
<211> LENGTH: 22
<212> TYPE: DNA
<213> ORGANISM: Artificial sequence
<220> FEATURE:
<223> OTHER INFORMATION: Adaptor Oligo Primer 1

<400> SEQUENCE: 78
gtaatacgac tcactatagg gc 22

<210> SEQ ID NO 79
<211> LENGTH: 19
<212> TYPE: DNA
<213> ORGANISM: Artificial sequence
<220> FEATURE:
<223> OTHER INFORMATION: Adaptor Oligo Primer 2

<400> SEQUENCE: 79
actatagggc acgcgtggt 19

<210> SEQ ID NO 80
<211> LENGTH: 36
<212> TYPE: DNA
<213> ORGANISM: Artificial sequence
<220> FEATURE:
<223> OTHER INFORMATION: ATCC4978DAATNdelF Oligo Primer

<400> SEQUENCE: 80
ggccttggca tatgagttat agcttatgga atgacc 36

<210> SEQ ID NO 81
<211> LENGTH: 36
<212> TYPE: DNA
<213> ORGANISM: Artificial sequence
<220> FEATURE:
<223> OTHER INFORMATION: ATCC4978DAATBamH1R Oligo Primer

<400> SEQUENCE: 81
ggccttaagg atccttatgc gcgaatacct tttggg 36

<210> SEQ ID NO 82
<211> LENGTH: 34
<212> TYPE: DNA
<213> ORGANISM: Artificial sequence
<220> FEATURE:
<223> OTHER INFORMATION: ATCC7063DAATNdelF Oligo Primer

<400> SEQUENCE: 82
ggccttggca tatgagctac actttatgga atga 34

<210> SEQ ID NO 83
<211> LENGTH: 32

-continued

<212> TYPE: DNA
<213> ORGANISM: Artificial sequence
<220> FEATURE:
<223> OTHER INFORMATION: ATCC7063DAATBamH1R2a Oligo Primer

<400> SEQUENCE: 83
ggccaaggat ccgctaccca ctaatcatta ga 32

<210> SEQ ID NO 84
<211> LENGTH: 852
<212> TYPE: DNA
<213> ORGANISM: Bacillus rotans

<400> SEQUENCE: 84
atgagttata gcttatggaa tgaccaaatt gtgaatgatg aagaagtagt agttgataag 60
gaggaccgtg gctatcaatt tggcgatggt gtttatgaag ttgtaaaagt atataacggt 120
gaattattta cagcggagga gcatgtcgat cgtttttacg cgagtgctga aaaaattcgc 180
gttacgatcc cttatacaaa agacaaattg catcaattat tgcatcagtt agttgaaatg 240
aataaagttc aaacaggaca tatttatttc caaattacgc gtggtgcagg ccctcgtaat 300
catattttcc ctggtgatga agtgaagcca gtattaacag gtaataccaa ggaaaatcca 360
cgtcccgtag caaactttga aaaaggtgtg aaagcaacat ttgtagaaga cattcgttgg 420
ttacgctgtg acattaaatc attaaattta cttggtgcgg tacttgctaa acaagaagca 480
catgaaaaag gatgctatga agcggtttta catcgtgatg aaatcgtaac agaaggctct 540
tcttcaaata tttatggaat taaagatggc gtattataca cacatccagc gaataacttc 600
atcttaaatg gtattacacg tcaagtaatc attaaatgtg ctgctgaaat tggcttacca 660
gtgaaggaag aagcaatgac aaaaactcag cttcttgcaa tggatgaagt gattgtttca 720
tcaacgactt cagaagtaac gccaattatc gacatagatg gaacagtaat tggtgcgggt 780
aaaccgggtg actggacacg taaattacaa gcacaatttg atacgaaaat cccaaaaggt 840
attcgcgcat aa 852

<210> SEQ ID NO 85
<211> LENGTH: 870
<212> TYPE: DNA
<213> ORGANISM: Bacillus serositidis

<400> SEQUENCE: 85
atgagctaca ctttatggaa tgacaaaatt gtggatgata accaagtatt cattaataaa 60
gaagacagag gctatcaatt tggtgacggc gtttatgaag ttataaaagt atatgatggg 120
gaaatgttta ctgctactga acatatcgac cgattctatg caagtgcaga gaagattaaa 180
ttgactgtac cctatacaaa gcataaactg catcaattac tgcatgaatt agtggaagca 240
aacgagctga aaactggaaa cttatacttt cagataacac gcggtgcgtc tccgcgtaat 300
catctatttc caggagacga tgtacttccg gtattaacgg gaaatgtaaa agaagcacca 360
cgctccatcg aaaatgcgca aaaaggtgta aaagccacat ttgcagaaga tattcgctgg 420
ctgcgctgcg atattaaatc gctaaatctt ttaggggctg ttttagcgaa acaagaggca 480
catgaaaagg gctgctacga agcaatttta catcgcggag aaacgattac agaaggttct 540
tcaacaaacg ttttcggtat aaaaaatggt gtactctata cacatccagc tgataatttc 600
atcttaagcg gcattacacg cggtgttgtt ttggcatgtg cgaacgaaat tggacttcct 660
gtaaaacaag aagcatttac aaaagacaaa gcactgcaaa tggacgaaat gttcgtatcc 720

-continued

```
tctactactt ctgaaataac accagttatc gatcttgatg gagtggccat taatggtgga    780

gaaattggcg aatggacgcg caagctgcaa aagcaatttg caacgaagct tccgggaagc    840

ccagcatata atttaacaga atataaatag                                      870


<210> SEQ ID NO 86
<211> LENGTH: 283
<212> TYPE: PRT
<213> ORGANISM: Bacillus rotans

<400> SEQUENCE: 86

Met Ser Tyr Ser Leu Trp Asn Asp Gln Ile Val Asn Asp Glu Glu Val
1               5                   10                  15

Val Val Asp Lys Glu Asp Arg Gly Tyr Gln Phe Gly Asp Gly Val Tyr
            20                  25                  30

Glu Val Val Lys Val Tyr Asn Gly Glu Leu Phe Thr Ala Glu Glu His
        35                  40                  45

Val Asp Arg Phe Tyr Ala Ser Ala Glu Lys Ile Arg Val Thr Ile Pro
    50                  55                  60

Tyr Thr Lys Asp Lys Leu His Gln Leu Leu His Gln Leu Val Glu Met
65                  70                  75                  80

Asn Lys Val Gln Thr Gly His Ile Tyr Phe Gln Ile Thr Arg Gly Ala
                85                  90                  95

Gly Pro Arg Asn His Ile Phe Pro Gly Asp Glu Val Lys Pro Val Leu
            100                 105                 110

Thr Gly Asn Thr Lys Glu Asn Pro Arg Pro Val Ala Asn Phe Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Val Leu His Arg Asp Glu Ile Val
                165                 170                 175

Thr Glu Gly Ser Ser Ser Asn Ile Tyr Gly Ile Lys Asp Gly Val Leu
            180                 185                 190

Tyr Thr His Pro Ala Asn Asn Phe Ile Leu Asn Gly Ile Thr Arg Gln
        195                 200                 205

Val Ile Ile Lys Cys Ala Ala Glu Ile Gly Leu Pro Val Lys Glu Glu
    210                 215                 220

Ala Met Thr Lys Thr Gln Leu Leu Ala Met Asp Glu Val Ile Val Ser
225                 230                 235                 240

Ser Thr Thr Ser Glu Val Thr Pro Ile Ile Asp Ile Asp Gly Thr Val
                245                 250                 255

Ile Gly Ala Gly Lys Pro Gly Asp Trp Thr Arg Lys Leu Gln Ala Gln
            260                 265                 270

Phe Asp Thr Lys Ile Pro Lys Gly Ile Arg Ala
        275                 280


<210> SEQ ID NO 87
<211> LENGTH: 289
<212> TYPE: PRT
<213> ORGANISM: Bacillus serositidis

<400> SEQUENCE: 87

Met Ser Tyr Thr Leu Trp Asn Asp Lys Ile Val Asp Asp Asn Gln Val
1               5                   10                  15
```

-continued

```
Phe Ile Asn Lys Glu Asp Arg Gly Tyr Gln Phe Gly Asp Gly Val Tyr
            20                  25                  30

Glu Val Ile Lys Val Tyr Asp Gly Glu Met Phe Thr Ala Thr Glu His
        35                  40                  45

Ile Asp Arg Phe Tyr Ala Ser Ala Glu Lys Ile Lys Leu Thr Val Pro
    50                  55                  60

Tyr Thr Lys His Lys Leu His Gln Leu Leu His Glu Leu Val Glu Ala
65                  70                  75                  80

Asn Glu Leu Lys Thr Gly Asn Leu Tyr Phe Gln Ile Thr Arg Gly Ala
                85                  90                  95

Ser Pro Arg Asn His Leu Phe Pro Gly Asp Asp Val Leu Pro Val Leu
            100                 105                 110

Thr Gly Asn Val Lys Glu Ala Pro Arg Ser Ile Glu Asn Ala Gln Lys
        115                 120                 125

Gly Val Lys Ala Thr Phe Ala Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Ile Leu His Arg Gly Glu Thr Ile
                165                 170                 175

Thr Glu Gly Ser Ser Thr Asn Val Phe Gly Ile Lys Asn Gly Val Leu
            180                 185                 190

Tyr Thr His Pro Ala Asp Asn Phe Ile Leu Ser Gly Ile Thr Arg Gly
        195                 200                 205

Val Val Leu Ala Cys Ala Asn Glu Ile Gly Leu Pro Val Lys Gln Glu
    210                 215                 220

Ala Phe Thr Lys Asp Lys Ala Leu Gln Met Asp Glu Met Phe Val Ser
225                 230                 235                 240

Ser Thr Thr Ser Glu Ile Thr Pro Val Ile Asp Leu Asp Gly Val Ala
                245                 250                 255

Ile Asn Gly Gly Glu Ile Gly Glu Trp Thr Arg Lys Leu Gln Lys Gln
            260                 265                 270

Phe Ala Thr Lys Leu Pro Gly Ser Pro Ala Tyr Asn Leu Thr Glu Tyr
        275                 280                 285

Lys
```

```
<210> SEQ ID NO 88
<211> LENGTH: 29
<212> TYPE: DNA
<213> ORGANISM: Artificial sequence
<220> FEATURE:
<223> OTHER INFORMATION: B. sphaericus DAT Primer 1

<400> SEQUENCE: 88

gatataccat ggatactcat tatggaatg                                        29


<210> SEQ ID NO 89
<211> LENGTH: 32
<212> TYPE: DNA
<213> ORGANISM: Artificial sequence
<220> FEATURE:
<223> OTHER INFORMATION: B. sphaericus DAT Primer 2

<400> SEQUENCE: 89

gttatcggat ccttaggcat taattgaaat tg                                    32


<210> SEQ ID NO 90
```

-continued

<211> LENGTH: 32
<212> TYPE: DNA
<213> ORGANISM: Artificial sequence
<220> FEATURE:
<223> OTHER INFORMATION: B. licheniformis DAT Primer 1

<400> SEQUENCE: 90
ggccggttca tatgaaagtt ctttttaacg gc 32

<210> SEQ ID NO 91
<211> LENGTH: 32
<212> TYPE: DNA
<213> ORGANISM: Artificial sequence
<220> FEATURE:
<223> OTHER INFORMATION: B. licheniformis DAT Primer 2

<400> SEQUENCE: 91
ccttccggat ccttaaaccg ttttggctgt ct 32

<210> SEQ ID NO 92
<211> LENGTH: 30
<212> TYPE: DNA
<213> ORGANISM: Artificial sequence
<220> FEATURE:
<223> OTHER INFORMATION: B. halodurans Primer 1

<400> SEQUENCE: 92
gatatacata tggattattg cctttaccaa 30

<210> SEQ ID NO 93
<211> LENGTH: 33
<212> TYPE: DNA
<213> ORGANISM: Artificial sequence
<220> FEATURE:
<223> OTHER INFORMATION: B. halodurans Primer 2

<400> SEQUENCE: 93
gaatccggat cctcactgct tcatcgctgt ttg 33

<210> SEQ ID NO 94
<211> LENGTH: 33
<212> TYPE: DNA
<213> ORGANISM: Artificial sequence
<220> FEATURE:
<223> OTHER INFORMATION: B. cereus Primer 1

<400> SEQUENCE: 94
taagaggaat aacatatggc atacgaaaga ttt 33

<210> SEQ ID NO 95
<211> LENGTH: 32
<212> TYPE: DNA
<213> ORGANISM: Artificial sequence
<220> FEATURE:
<223> OTHER INFORMATION: B. cereus Primer 2

<400> SEQUENCE: 95
gaattcggat ccttaagaag atgacatatt gg 32

<210> SEQ ID NO 96
<211> LENGTH: 33
<212> TYPE: DNA
<213> ORGANISM: Artificial sequence
<220> FEATURE:
<223> OTHER INFORMATION: B. cereus Primer 3

<400> SEQUENCE: 96

-continued

```
taagaggaat aacatatggg atcgaaattg gca                              33


<210> SEQ ID NO 97
<211> LENGTH: 36
<212> TYPE: DNA
<213> ORGANISM: Artificial sequence
<220> FEATURE:
<223> OTHER INFORMATION: NdeI Primer

<400> SEQUENCE: 97

ggccttggca tatgggatac actttatgga atgacc                           36


<210> SEQ ID NO 98
<211> LENGTH: 35
<212> TYPE: DNA
<213> ORGANISM: Artificial sequence
<220> FEATURE:
<223> OTHER INFORMATION: BamHI Primer

<400> SEQUENCE: 98

ttggaaccgg atccttatat atgaagcggt tttgg                            35


<210> SEQ ID NO 99
<211> LENGTH: 283
<212> TYPE: PRT
<213> ORGANISM: Artificial sequence
<220> FEATURE:
<223> OTHER INFORMATION: Hybrid DAT

<400> SEQUENCE: 99

Met Gly Tyr Thr Leu Trp Asn Asp Gln Ile Val Glu Asp Gly Ser Val
1               5                   10                  15

Ser Ile Ser Pro Glu Asp Arg Gly Tyr Gln Phe Gly Asp Gly Val Tyr
            20                  25                  30

Glu Val Val Lys Val Tyr Asn Gly Asn Met Phe Thr Val Asn Glu His
        35                  40                  45

Ile Asp Arg Leu Tyr Ala Ser Ala Glu Lys Ile Arg Ile Val Ile Pro
    50                  55                  60

Tyr Thr Lys Asp Val Phe His Lys Leu Leu His Glu Leu Val Glu Lys
65                  70                  75                  80

Asn Asn Leu Asn Thr Gly His Ile Tyr Phe Gln Val Thr Arg Gly Thr
                85                  90                  95

Ser Ser Arg Ala His Val Phe Pro Glu Ala Thr Val Pro Ala Val Ile
            100                 105                 110

Thr Gly Asn Val Lys Ser Gly Glu Arg Ala Leu Glu Asn Leu Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Val
                165                 170                 175

Thr Glu Cys Ser Ser Ser Asn Val Phe Gly Ile Lys Asp Gly Lys Leu
            180                 185                 190

Tyr Thr His Pro Ala Asn Asn Leu Ile Leu Asn Gly Ile Thr Arg Gln
        195                 200                 205

Val Val Ile Lys Cys Ala Glu Glu Ile Asn Ile Pro Val Val Glu Glu
    210                 215                 220
```

-continued

```
Pro Phe Thr Lys Gly Glu Ile Leu Thr Met Asp Glu Leu Phe Val Thr
225                 230                 235                 240

Ser Val Thr Ser Glu Ile Thr Pro Val Ile Glu Ile Asp Gly Asn Gln
                245                 250                 255

Ile Gly Ala Gly Val Pro Gly Glu Trp Thr Arg Lys Leu Gln Lys Ala
            260                 265                 270

Phe Glu Ala Lys Ile Pro Leu Ser Leu Asn Ser
        275                 280


<210> SEQ ID NO 100
<211> LENGTH: 852
<212> TYPE: DNA
<213> ORGANISM: Artificial sequence
<220> FEATURE:
<223> OTHER INFORMATION: Hybrid DAT

<400> SEQUENCE: 100

atgggataca ctttatggaa tgaccaaatc gtggaagatg gtagcgtcag tattagcccg     60

gaagatcgcg gttatcaatt cggtgatggc gtatatgaag ttgtgaaagt atataacggt    120

aacatgttta ctgtaaatga acatattgac cgcttatatg catcagctga aaaaatccgt    180

attgttattc catatacaaa ggatgtgttt cataagttgc tgcatgaatt agtggaaaaa    240

aataacttaa acactgggca tatttatttt caagttactc gcggaacttc gagtcgtgcg    300

catgttttcc ctgaggccac tgtaccagcg gtaatcaccg gtaacgtgaa aagcggcgag    360

cgtgcgttag aaaatcttga aaaaggtgta aaagctacct ttgtggaaga tatccgttgg    420

ttacgctgtg atattaaatc tttgaacttg cttggtgcag tattagcaaa acaagaagct    480

agcgaaaaag gctgctatga agcgattctg catcgaggcg acatcgtaac agaatgctct    540

tcttcaaatg tatttggaat caaagatggt aagttgtata cccatcctgc aaacaatctg    600

attttaaatg gaatcactcg ccaggttgtc attaaatgtg cagaggaaat taatatccct    660

gtagtggaag agccatttac aaaaggcgaa atcttgacga tggatgaatt atttgtaaca    720

agtgttactt ctgaaattac gccggttatt gaaatcgatg gtaatcagat tggtgcagga    780

gtgccaggag aatggactcg taaattacaa aaagcttttg aagccaaaat tccactgagc    840

cttaacagct aa                                                        852


<210> SEQ ID NO 101
<211> LENGTH: 37
<212> TYPE: DNA
<213> ORGANISM: Artificial sequence
<220> FEATURE:
<223> OTHER INFORMATION: NdeI Primer

<400> SEQUENCE: 101

ggccttggca tatgggatac actttatgga atgacca                              37


<210> SEQ ID NO 102
<211> LENGTH: 37
<212> TYPE: DNA
<213> ORGANISM: Artificial sequence
<220> FEATURE:
<223> OTHER INFORMATION: BamHI Primer

<400> SEQUENCE: 102

ttggaaccgg atccttagct gttaaggctc agtggaa                              37
```

What is claimed is:

1. A method for producing monatin, or a salt thereof, comprising reacting D-tryptophan and one or more D-aminotransferases chosen from a *Bacillus halodurans* D-aminotransferase, a hybrid D-aminotransferase having the sequence of SEQ ID NO:99, a *Geobacillus stearothermophilus* D-aminotransferase, a *Bacillus lichenformis* D-aminotransferase, a D-aminotransferase from a *Bacillus sphaericus* deposited with American Type Culture Collection (ATCC) and designated ATCC 4978, and a D-aminotransferase from a *Bacillus sphaericus* deposited with ATCC and designated ATCC 7063, wherein D-tryptophan is converted to indole-3-pyruvate, indole-3-pyruvate is converted to 2-hydroxy-2-(indoly-3-ylmethyl)-4-keto glutaric acid (MP), and MP is converted to monatin.

2. The method of claim 1, wherein at least about 75% of monatin produced is R,R monatin.

3. A method for producing monatin, or a salt thereof, comprising reacting monatin precursor (MP) and one or more D-aminotransferases chosen from a *Bacillus halodurans* D-aminotransferase, a hybrid D-aminotransferase having the sequence of SEQ ID NO:99, a Geo *bacillus stearothermophilus* D-aminotransferase, a *Bacillus lichenformis* D-aminotransferase, a D-aminotranferase from a *Bacillus sphaericus* deposited with ATCC and designated ATCC 4978, a D-aminotransferase from a *Bacillus sphaericus* deposited with ATCC and designated ATCC 7063, and a *Bacillus lichenformis* branched chain aminotransferase having D-aminotransferase activity, wherein and MP is converted to monatin.

* * * * *

UNITED STATES PATENT AND TRADEMARK OFFICE

CERTIFICATE OF CORRECTION

PATENT NO. : 7,582,455 B2
APPLICATION NO. : 11/411229
DATED : September 1, 2009
INVENTOR(S) : Brazeau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 319 days.

Signed and Sealed this

Fourteenth Day of September, 2010

David J. Kappos
*Director of the United States Patent and Trademark Office*

UNITED STATES PATENT AND TRADEMARK OFFICE

CERTIFICATE OF CORRECTION

PATENT NO. : 7,582,455 B2
APPLICATION NO. : 11/411229
DATED : September 1, 2009
INVENTOR(S) : Brian J. Brazeau et al.

It is certified that error appears in the above-identified patent and that said Letters Patent is hereby corrected as shown below:

In column 13, line 17, delete "NP" and insert -- MP --, therefor.

In column 13, line 22, delete "CAB134127.1" and insert -- CAB14127.1 --, therefor.

In column 55-56, in TABLE 24, line 23, after "Y96H +" delete "R9SY" and insert -- R98Y --, therefor.

In column 97-98, in SEQUENCE LISTING, line 1, delete "102" and insert -- 108 --, therefor.

In column 127-128, in SEQUENCE LISTING, line 17, delete "Oligo Primer" and insert -- Oligonucleotide --, therefor.

In column 127-128, in SEQUENCE LISTING, line 25, delete "Oligo Primer" and insert -- Oligonucleotide --, therefor.

In column 127-128, in SEQUENCE LISTING, line 33, delete "Oligo Primer" and insert -- Oligonucleotide --, therefor.

In column 127-128, in SEQUENCE LISTING, line 41, delete "Oligo Primer" and insert -- Oligonucleotide --, therefor.

In column 127-128, in SEQUENCE LISTING, line 49, delete "Oligo Primer" and insert -- Oligonucleotide --, therefor.

In column 129-130, in SEQUENCE LISTING, line 6, delete "4978 DAT GSP1 Upstrm Primer" and insert -- Oligonucleotide (4978 DAT GSP1 Upstrm Primer) --, therefor.

In column 129-130, in SEQUENCE LISTING, line 14, delete "4978 DAT GSP1 Dwnstr Primer" and insert -- Oligonucleotide (4978 DAT GSP1 Dwnstr Primer) --, therefor.

Signed and Sealed this
Third Day of July, 2012

David J. Kappos

David J. Kappos
*Director of the United States Patent and Trademark Office*

In column 129-130, in SEQUENCE LISTING, line 22, delete “4978 DAT GSP2 Upstrm Primer” and insert -- Oligonucleotide (4978 DAT GSP2 Upstrm Primer) --, therefor.

In column 129-130, in SEQUENCE LISTING, line 30, delete “4978 DAT GSP2 Dwnstr Primer” and insert -- Oligonucleotide (4978 DAT GSP2 Dwnstr Primer) --, therefor.

In column 129-130, in SEQUENCE LISTING, line 38, delete “7063 DAT GSP1 Upstrm Primer” and insert -- Oligonucleotide (7063 DAT GSP1 Upstrm Primer) --, therefor.

In column 129-130, in SEQUENCE LISTING, line 46, delete “7063 DAT GSP1 Dwnstr Primer” and insert -- Oligonucleotide (7063 DAT GSP1 Dwnstr Primer) --, therefor.

In column 129-130, in SEQUENCE LISTING, line 54, delete “7063 DAT GSP2 Upstrm Primer” and insert -- Oligonucleotide (7063 DAT GSP2 Upstrm Primer) --, therefor.

In column 131-132, in SEQUENCE LISTING, line 8, delete “7063 DAT GSP2 Dwnstr Primer” and insert -- Oligonucleotide (7063 DAT GSP2 Dwnstr Primer) --, therefor.

In column 131-132, in SEQUENCE LISTING, line 16, delete “Adaptor Oligo Primer 1” and insert -- Oligonucleotide (Adaptor Primer 1) --, therefor.

In column 131-132, in SEQUENCE LISTING, line 24, delete “Adaptor Oligo Primer 2” and insert -- Oligonucleotide (Adaptor Primer 2) --, therefor.

In column 131-132, in SEQUENCE LISTING, line 32, delete “ATCC4978DAATNde1F Oligo Primer” and insert -- Oligonucleotide (ATCC4978DAATNde1F Primer) --, therefor.

In column 131-132, in SEQUENCE LISTING, line 40, delete “ATCC4978DAATBamH1R Oligo Primer” and insert -- Oligonucleotide (ATCC4978DAATBamH1R Primer) --, therefor.

In column 131-132, in SEQUENCE LISTING, line 48, delete “ATCC7063 DAATNde1F Oligo Primer” and insert -- Oligonucleotide (ATCC7063DAATNde1F Primer) --, therefor.

In column 133-134, in SEQUENCE LISTING, line 4, delete “ATCC7063DAATBamH1R2a Oligo Primer” and insert -- Oligonucleotide (ATCC7063DAATBamH1R2a Primer) --, therefor.

In column 137-138, in SEQUENCE LISTING, line 41, delete “B. sphaericus DAT Primer 1” and insert -- Oligonucleotide (B. sphaericus DAT Primer 1) --, therefor.

In column 137-138, in SEQUENCE LISTING, line 49, delete “B. sphaericus DAT Primer 2” and insert -- Oligonucleotide (B. sphaericus DAT Primer 2) --, therefor.

In column 139-140, in SEQUENCE LISTING, line 5, delete "B. licheniformis DAT Primer 1" and insert -- Oligonucleotide (B. licheniformis DAT Primer 1) --, therefor.

In column 139-140, in SEQUENCE LISTING, line 13, delete "B. licheniformis DAT Primer 2" and insert -- Oligonucleotide (B. licheniformis DAT Primer 2) --, therefor.

In column 139-140, in SEQUENCE LISTING, line 21, delete "B. halodurans Primer 1" and insert -- Oligonucleotide (B. halodurans Primer 1) --, therefor.

In column 139-140, in SEQUENCE LISTING, line 29, delete "B. halodurans Primer 2" and insert -- Oligonucleotide (B. halodurans Primer 2) --, therefor.

In column 139-140, in SEQUENCE LISTING, line 37, delete "B. cereus Primer 1" and insert -- Oligonucleotide (B. cereus Primer 1) --, therefor.

In column 139-140, in SEQUENCE LISTING, line 45, delete "B. cereus Primer 2" and insert -- Oligonucleotide (B. cereus Primer 2) --, therefor.

In column 139-140, in SEQUENCE LISTING, line 53, delete "B. cereus Primer 3" and insert -- Oligonucleotide (B. cereus Primer 3) --, therefor.

In column 141-142, in SEQUENCE LISTING, line 7, delete "NdeI Primer" and insert -- Oligonucleotide (NdeI Primer) --, therefor.

In column 141-142, in SEQUENCE LISTING, line 15, delete "BamHI Primer" and insert -- Oligonucleotide (BamHI Primer) --, therefor.

In column 143-144, in SEQUENCE LISTING, line 36, delete "NdeI Primer" and insert -- Oligonucleotide (NdeI Primer) --, therefor.

In column 143-144, in SEQUENCE LISTING, line 44, delete "BamHI Primer" and insert -- Oligonucleotide (BamHI Primer) --, therefor.

In column 143-144, in SEQUENCE LISTING, below line 46, insert

<210> 103
<211> 283
<212> PRT
<213> Bacillus sphaericus

<400> 103
Met Ala Tyr Ser Leu Trp Asn Asp Gln Ile Val Glu Glu Gly Ser Ile
1 5 10 15

Thr Ile Ser Pro Glu Asp Arg Gly Tyr Gln Phe Gly Asp Gly Ile Tyr
20 25 30

Glu Val Ile Lys Val Tyr Asn Gly His Met Phe Thr Ala Gln Glu His
35 40 45

Ile Asp Arg Phe Tyr Ala Ser Ala Glu Lys Ile Arg Leu Val Ile Pro
50 55 60

Tyr Thr Lys Asp Val Leu His Lys Leu Leu His Asp Leu Ile Glu Lys
65 70 75 80

Asn Asn Leu Asn Thr Gly His Val Tyr Phe Gln Ile Thr Arg Gly Thr
85 90 95

Thr Ser Arg Asn His Ile Phe Pro Asp Ala Ser Val Pro Ala Val Leu
100 105 110

Thr Gly Asn Val Lys Thr Gly Glu Arg Ser Ile Glu Asn Phe Glu Lys
115 120 125

Gly Val Lys Ala Thr Leu Val Glu Asp Val Arg Trp Leu Arg Cys Asp
130 135 140

Ile Lys Ser Leu Asn Leu Leu Gly Ala Val Leu Ala Lys Gln Glu Ala
145 150 155 160

Ser Glu Lys Gly Cys Tyr Glu Ala Ile Leu His Arg Gly Asp Ile Ile
165 170 175

Thr Glu Cys Ser Ser Ala Asn Val Tyr Gly Ile Lys Asp Gly Lys Leu
180 185 190

Tyr Thr His Pro Ala Asn Asn Tyr Ile Leu Asn Gly Ile Thr Arg Gln
195 200 205

--

Val Ile Leu Lys Cys Ala Ala Glu Ile Asn Leu Pro Val Ile Glu Glu
210 215 220

Pro Met Thr Lys Gly Asp Leu Leu Thr Met Asp Glu Ile Ile Val Ser
225 230 235 240

Ser Val Ser Ser Glu Val Thr Pro Val Ile Asp Val Asp Gly Gln Gln
245 250 255

Ile Gly Ala Gly Val Pro Gly Glu Trp Thr Arg Lys Leu Gln Lys Ala
260 265 270

Phe Glu Ala Lys Leu Pro Ile Ser Ile Asn Ala
275 280

<210> 104
<211> 283
<212> PRT
<213> Bacillus halodurans

<400> 104
Met Asp Tyr Cys Leu Tyr Gln Asp Gln Leu Val Pro Arg Glu Gln Leu
1 5 10 15

Lys Ile Asp Pro Glu Asp Arg Gly Tyr His Phe Gly Asp Gly Ile Tyr
20 25 30

Glu Val Val His Val Tyr His Gly Lys Ala Phe Ala Leu Ser Asp His
35 40 45

Leu Thr Arg Phe Lys Glu Ser Ala Glu Lys Leu Asp Leu Pro Met Leu
50 55 60

Tyr Ser Thr Asp Lys Leu Gly Glu Leu Val Gln Gln Leu Ile Glu Lys
65 70 75 80

Asn Lys Leu Glu His Gly Met Val Tyr Phe Gln Met Thr Arg Gly Ile
85 90 95

Ser Pro Arg Asn His Leu Tyr Thr Arg Asn Glu Thr Pro Val Leu Thr
100 105 110

Gly Phe Ser Lys Pro Leu Pro Asp Glu Lys Arg Glu Ser Val Arg Leu
115 120 125

Tyr Leu Thr Asp Asp Ile Arg Trp Leu Arg Cys Asp Ile Lys Thr Ile
130 135 140

Asn Leu Leu Gly Asn Val Leu Ala Lys Arg Glu Ala Thr Asp His Gln
145 150 155 160

Cys Asp Glu Ala Leu Leu His Arg Asp Gly Thr Val Thr Glu Gly Ser
165 170 175

Ser Ser Asn Val Phe Leu Ile Lys Asn Glu Thr Leu Tyr Thr His Pro
180 185 190

Ala Thr Asn Leu Ile Leu Asn Gly Ile Thr Arg Gln Ile Thr Ile Arg
195 200 205

Leu Ala Lys Ala Lys Gly Tyr Thr Val Val Glu Glu Pro Phe Pro Lys
210 215 220

Glu Val Ile Lys Asp Ala Asp Glu Ala Phe Ile Thr Ser Thr Ile His
225 230 235 240

Glu Ile Thr Pro Val Thr Glu Val Ile Gly Asp Glu Thr Ala His Phe
245 250 255

Pro Val Gly Pro Val Thr Lys Met Leu Gln Gln Ala Phe Ala Glu Glu
260 265 270

Ile Ala Lys His Ser Gln Thr Ala Met Lys Gln
275 280

<210> 105
<211> 283
<212> PRT
<213> G. stearothermophilus

<400> 105

Met Gly Tyr Thr Leu Trp Asn Asp Gln Ile Val Lys Asp Glu Glu Val
1 5 10 15

Lys Ile Asp Lys Glu Asp Arg Gly Tyr Gln Phe Gly Asp Gly Val Tyr
20 25 30

Glu Val Val Lys Val Tyr Asn Gly Glu Met Phe Thr Val Asn Glu His
35 40 45

Ile Asp Arg Leu Tyr Ala Ser Ala Glu Lys Ile Arg Ile Thr Ile Pro
50 55 60

Tyr Thr Lys Asp Lys Phe His Gln Leu Leu His Glu Leu Val Glu Lys
65 70 75 80

Asn Glu Leu Asn Thr Gly His Ile Tyr Phe Gln Val Thr Phe Gly Thr
85 90 95

Ser Pro Arg Ala His Gln Phe Pro Glu Asn Thr Val Lys Pro Val Ile
100 105 110

Ile Gly Tyr Thr Lys Glu Asn Pro Arg Pro Leu Glu Asn Leu Glu Lys
115 120 125

Gly Val Lys Ala Thr Phe Val Glu Asp Ile Arg Trp Leu Arg Cys Asp
130 135 140

Ile Lys Ser Leu Asn Leu Leu Gly Ala Val Leu Ala Lys Gln Glu Ala
145 150 155 160

His Glu Lys Gly Cys Tyr Glu Ala Ile Leu His Arg Asn Asn Thr Val
165 170 175

Thr Glu Gly Ser Ser Ser Asn Val Phe Gly Ile Lys Asp Gly Ile Leu
180 185 190

Tyr Thr His Pro Ala Asn Asn Met Ile Leu Lys Gly Ile Thr Arg Asp
195 200 205

Val Val Ile Ala Cys Ala Asn Glu Ile Asn Met Pro Val Lys Glu Ile
210 215 220

Pro Phe Thr Thr His Glu Ala Leu Lys Met Asp Glu Leu Phe Val Thr
225 230 235 240

Ser Thr Thr Ser Glu Ile Thr Pro Val Ile Glu Ile Asp Gly Lys Leu
245 250 255

Ile Arg Asp Gly Lys Val Gly Glu Trp Thr Arg Lys Leu Gln Lys Gln
260 265 270

Phe Glu Thr Lys Ile Pro Lys Pro Leu His Ile
275 280

<210> 106
<211> 290
<212> PRT
<213> Bacillus cereus

<400> 106

Leu Ala Tyr Glu Lys Phe Val Leu Trp Asn Asp Glu Val Ile Asp Thr
1 5 10 15

```
Thr Lys Gln Gln Thr Tyr Ile Glu Leu Glu Glu Arg Gly Ser Gln Phe
            20                  25                  30

Gly Asp Gly Val Tyr Glu Val Ile Arg Leu Tyr Lys Gly Asn Phe His
        35                  40                  45

Leu Leu Asp Pro His Ile Thr Arg Leu Tyr Arg Ser Met Glu Glu Val
    50                  55                  60

Glu Leu Ser Leu Pro Phe Ser Lys Ala Glu Leu Ile Thr Leu Leu Tyr
65                  70                  75                  80

Lys Leu Ile Glu Arg Asn His Phe His Glu Asp Gly Thr Ile Tyr Leu
                85                  90                  95

Gln Val Ser Arg Gly Val Gln Ala Arg Thr His Val Phe Ser Tyr Asp
            100                 105                 110

Thr Pro Pro Thr Ile Tyr Ala Tyr Ile Thr Lys Lys Glu Arg Pro Ala
        115                 120                 125

Leu Trp Ile Glu Tyr Gly Ile Arg Ala Ile Ser Glu Pro Asp Thr Arg
    130                 135                 140

Trp Leu Arg Cys Asp Ile Lys Ser Leu Asn Leu Leu Pro Asn Val Leu
145                 150                 155                 160

Ala Ala Thr Lys Ala Glu Arg Lys Gly Cys Lys Glu Ala Leu Leu Val
                165                 170                 175

Arg Asn Gly Ile Val Thr Glu Gly Ser His Ser Asn Phe Phe Leu Ile
            180                 185                 190

Lys Asn Gly Thr Leu Tyr Thr His Pro Ala Asn His Leu Ile Leu Asn
        195                 200                 205

Gly Ile Ile Arg Gln Tyr Val Leu Ser Leu Ala Asn Thr Leu His Ile
    210                 215                 220

Pro Val Gln Glu Glu Leu Phe Ser Val Arg Asp Val Tyr Gln Ala Asp
225                 230                 235                 240

Glu Cys Phe Phe Thr Gly Thr Thr Ile Glu Ile Leu Pro Met Thr His
                245                 250                 255

Leu Asp Gly Thr Ala Ile Gln Asp Gly Gln Val Gly Ala Ile Thr Lys

            260                 265                 270

Lys Leu Gln Lys Ser Phe Asn Lys Ile Leu Leu Gln Ser Asn Met Ser
        275                 280                 285

Ser Ser
    290

<210>  107
<211>  282
<212>  PRT
<213>  Bacillus subtilis

<400>  107

Met Lys Val Leu Val Asn Gly Arg Leu Ile Gly Arg Ser Glu Ala Ser
1               5                   10                  15

Ile Asp Leu Glu Asp Arg Gly Tyr Gln Phe Gly Asp Gly Ile Tyr Glu
            20                  25                  30

Val Ile Arg Val Tyr Lys Gly Val Leu Phe Gly Leu Arg Glu His Ala
        35                  40                  45

Glu Arg Phe Phe Arg Ser Ala Ala Glu Ile Gly Ile Ser Leu Pro Phe
    50                  55                  60

Ser Ile Glu Asp Leu Glu Trp Asp Leu Gln Lys Leu Val Gln Glu Asn
65                  70                  75                  80

Ala Val Ser Glu Gly Ala Val Tyr Ile Gln Thr Thr Arg Gly Val Ala
                85                  90                  95

Pro Arg Lys His Gln Tyr Glu Ala Gly Leu Glu Pro Gln Thr Thr Ala
            100                 105                 110

Tyr Thr Phe Thr Val Lys Lys Pro Glu Gln Glu Gln Ala Tyr Gly Val
        115                 120                 125

Ala Ala Ile Thr Asp Glu Asp Leu Arg Trp Leu Arg Cys Asp Ile Lys
    130                 135                 140

Ser Leu Asn Leu Leu Tyr Asn Val Met Thr Lys Gln Arg Ala Tyr Glu
145                 150                 155                 160

Ala Gly Ala Phe Glu Ala Ile Leu Leu Arg Asp Gly Val Val Thr Glu
                165                 170                 175

Gly Thr Ser Ser Asn Val Tyr Ala Val Ile Asn Gly Thr Val Arg Thr
```

180 185 190

His Pro Ala Asn Arg Leu Ile Leu Asn Gly Ile Thr Arg Met Asp Ile
195 200 205

Leu Gly Leu Ile Glu Lys Asp Gly Ile Lys Leu Asp Glu Thr Pro Val
210 215 220

Ser Glu Glu Glu Leu Lys Gln Ala Glu Glu Ile Phe Ile Ser Ser Thr
225 230 235 240

Thr Ala Glu Ile Ile Pro Val Val Thr Leu Asp Gly Gln Ser Ile Gly
245 250 255

Ser Gly Lys Pro Gly Pro Val Thr Lys Gln Leu Gln Ala Ala Phe Gln
260 265 270

Glu Ser Ile Gln Gln Ala Ala Ser Ile Ser
275 280

<210> 108
<211> 283
<212> PRT
<213> Bacillus lichenifomis

<400> 108

Met Lys Val Leu Phe Asn Gly Arg Leu Met Glu Arg Ser Glu Cys Ala
1 5 10 15

Val Asp Ile Glu Asp Arg Gly Tyr Gln Phe Gly Asp Gly Val Tyr Glu
20 25 30

Val Ile Arg Ile Tyr Asn Gly Ile Leu Phe Thr Leu Asp Glu His Ile
35 40 45

Ala Arg Leu Tyr Lys Ser Ala Ala Glu Ile Gly Ile Asp Leu Ser Phe
50 55 60

Ser Glu Ala Glu Leu Lys Ser Gln Leu Lys Glu Leu Val Asp Ile Asp
65 70 75 80

Gln Arg Arg Asp Gly Gly Leu Tyr Leu Gln Val Thr Arg Gly Lys Ala
85 90 95

Pro Arg Lys His Gln Tyr Gly Ala Gly Leu Thr Pro Gln Val Thr Ala
100 105 110

Tyr Thr Phe Pro Ile Gln Lys Pro Glu Lys Glu Gln Gln Asp Gly Val
115 120 125

Ser Ala Ile Thr Ala Asp Asp Met Arg Trp Leu Arg Cys Asp Ile Lys
130 135 140

Ser Leu Asn Leu Leu Tyr Asn Val Met Ile Lys Gln Lys Ala Gln Glu
145 150 155 160

Ala Ser Ala Phe Glu Ala Ile Leu Ile Arg Asp Gly Leu Val Thr Glu
165 170 175

Gly Thr Ser Ser Asn Val Tyr Val Ala Lys Gln Asn Val Ile Tyr Thr
180 185 190

His Pro Val Thr Thr Leu Ile Leu Asn Gly Ile Thr Arg Met Lys Val
195 200 205

Leu Gln Leu Cys Glu Glu Asn Gly Leu Asn Tyr Glu Glu Lys Ala Val
210 215 220

Thr Lys Asp Glu Leu Leu Asn Ala Asp Glu Val Phe Ile Thr Ser Thr
225 230 235 240

Thr Ala Glu Val Ile Pro Val Thr Ser Ile Asp Gly Gln Thr Ile Gly
245 250 255

Ser Gly Ala Pro Gly Pro Leu Thr Lys Asn Val Gln Thr Ala Leu Gln
260 265 270

Asn Ser Ile Leu Ser Glu Thr Ala Lys Thr Val
275 280

--.

In column 145, line 8, in Claim 1, delete “lichenformis” and insert -- licheniformis --, therefor.

In column 146, line 8, in Claim 3, delete “lichenformis” and insert -- licheniformis --, therefor.

In column 146, line 13, in Claim 3, delete “lichenformis” and insert -- licheniformis --, therefor.

In column 146, line 14, in Claim 3, after “wherein” delete “and”.